US007611717B2

(12) United States Patent
Murtaugh et al.

(10) Patent No.: US 7,611,717 B2
(45) Date of Patent: Nov. 3, 2009

(54) IDENTIFYING VIRALLY INFECTED AND VACCINATED ORGANISMS

(75) Inventors: Michael P. Murtaugh, Shoreview, MN (US); Craig R. Johnson, Lakeville, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 123 days.

(21) Appl. No.: 11/155,830

(22) Filed: Jun. 17, 2005

(65) Prior Publication Data

US 2007/0003570 A1 Jan. 4, 2007

Related U.S. Application Data

(60) Provisional application No. 60/656,192, filed on Feb. 25, 2005, provisional application No. 60/581,325, filed on Jun. 18, 2004.

(51) Int. Cl.
*A61K 39/12* (2006.01)

(52) U.S. Cl. ........................................ 424/204.1; 435/6

(58) Field of Classification Search ............. 424/204.1; 435/6, 69.1

See application file for complete search history.

(56) References Cited

U.S. PATENT DOCUMENTS

| | | | | |
|---|---|---|---|---|
| 4,683,195 | A | 7/1987 | Mullis et al. | |
| 4,908,305 | A | 3/1990 | Snyder | |
| 5,143,825 | A | 9/1992 | Chacko et al. | |
| 5,374,530 | A | 12/1994 | Nuzzolo et al. | |
| 5,498,551 | A | 3/1996 | de Jaeger et al. | |
| 5,683,865 | A | 11/1997 | Collins et al. | |
| 5,846,805 | A | 12/1998 | Collins et al. | |
| 5,888,513 | A | 3/1999 | Plana Duran et al. | |
| 6,015,663 | A * | 1/2000 | Wesley et al. | 435/5 |
| 2002/0012670 | A1 | 1/2002 | Elbers et al. | |

FOREIGN PATENT DOCUMENTS

| | | |
|---|---|---|
| CA | 2 410 694 | 12/1999 |
| WO | WO 93/07898 | 4/1993 |
| WO | WO 96/04010 | 2/1996 |

OTHER PUBLICATIONS

GenBank Accession No. AF046869 dated Mar. 17, 1999, 8 pages.
GenBank Accession No. AF066183 dated May 26, 2005, 8 pages.
GenBank Accession No. AF176348 dated Sep. 3, 2002, 8 pages.
GenBank Accession No. AF184212 dated Sep. 28, 2000, 8 pages.
GenBank Accession No. AF325691 dated Feb. 11, 2001, 8 pages.
GenBank Accession No. AF494042 dated Jun. 19, 2002, 8 pages.
GenBank Accession No. AY032626 dated May 30, 2001, 9 pages.
GenBank Accession No. AY424271 dated Mar. 17, 2004, 9 pages.
GenBank Accession No. AY545985 dated Jul. 9, 2004, 8 pages.
GenBank Accession No. AY585241 dated Jul. 13, 2004, 8 pages.
GenBank Accession No. M96292 dated Aug. 2, 1993, 1 page.
GenBank Accession No. U87392 dated Nov. 17, 2000, 9 pages.

"Porcine Reproductive and Respiratory Syndrome Virus Antibody Test Kit," 1997, IDEXX Laboratories, 4 pages.
Ausubel et al. (eds.), "Purification of Proteins by Precipitation, " *Short Protocols in Molecular Biology*, 1992, Chapter 10, Section VI, Greene Publishing Associates and John Wiley & Sons.
Bierk et al., "Diagnostic investigation of chronic porcine reproductive and respiratory syndrome virus in a breeding herd of pigs," *Vet. Rec.*, 2001, 148:687-690.
Buchner et al., "A Method for Increasing the Yield of Properly Folded Recombinant Fusion Proteins: Single-Chain Immunotoxins from Renaturation of Bacterial Inclusion Bodies," *Anal. Biochem.*, 1992, 205(2):263-270.
Cavanagh, "*Nidovirales*: a new order comprising *Coronaviridae* and *Arteriviridae*," *Arch. Virol.*, 1997, 142:629-633.
Christopher-Hennings et al., "Persistence of porcine reproductive and respiratory syndrome virus in serum and semen of adult boars," *J. Vet. Diag. Invest.*, 1995, 7:456-464.
Clark, "Refolding of recombinant proteins," *Curr. Opin. Biotechnol.*, 1998, 9(2):157-163.
Collins et al., "Isolation of swine infertility and respiratory syndrome virus (isolate ATCC VR-2332) in North America and experimental reproduction of the disease in gnotobiotic pigs," *J. Vet. Diagn. Invest.*, 1992, 4:117-126.
den Boon et al., "Equine Arteritis Virus Is Not a Togavirus but Belongs to the Coronaviruslike Superfamily," *J. Virol.*, 1991, 65(6):2910-2920.
Diamond, "Real-space Refinement of the Structure of Hen Egg-white Lysozyme," *J. Mol. Biol.*, 1974, 82:371-391.
Godeny et al., "Simian Hemorrhagic Fever Virus: Another Member of the Coronavirus-Like Superfamily," *Proceedings of the 9th International Congress of Virology*, Aug. 8-13, 1993, Glasgow, Scotland, p. 22, Abstract No. W4-8.
Hill, "Overview and History of Mystery Swine Disease (Swine Infertility and Respiratory Syndrome)," *Proceedings of the Mystery Swine Disease Committee Meeting*, Oct. 6, Denver CO, Livestock Conservation Institute, Madison, WI, 1990, pp. 29-30.
Imoto et al., "Vertebrate Lysozymes," *The Enzymes* 1972, Chapter 21, 7:665-868, Academic Press, NY.
Johnson et al., "Pathogenic and humoral immune responses to porcine reproductive and respiratory syndrome virus (PRRSV) are related to viral load in acute infection," *Vet. Immunol. Immunopathol.*, 2004, 102:233-247.
Keffaber, "Reproductive Failure of Unknown Etiology," *Am. Assoc. Swine Pract. News1.*, 1989, 1:1-9.
Laemmli, "Cleavage of Structural Proteins during the Assembly of the Head of Bacteriophage T4," *Nature*, 1974, 227:680-684.
Lawson et al., "Porcine reproductive and respiratory syndrome virus infection of gnotobiotic pigs: sites of virus replication and co-localization with MAC-387 staining at 21 days post-infection," *Virus Res.*, 1997, 51:105-113.

(Continued)

*Primary Examiner*—Ali R. Salimi
(74) *Attorney, Agent, or Firm*—Fish & Richardson P.C.

(57) ABSTRACT

This document provides methods and materials related to assessing organisms for the presence or absence of anti-virus antibodies. For example, this document provides methods and materials that can be used to determine whether or not an organism (e.g., a member of a swine species such as a pig) contains anti-PRRS virus antibodies. In other embodiments, this document provides methods and materials that can be used to determine if a particular organism received a vaccine version of a virus, was infected with a naturally-occurring version of the virus, or is naive with respect to the virus.

7 Claims, 50 Drawing Sheets

OTHER PUBLICATIONS

Nelsen et al., "Porcine Reproductive and Respiratory Syndrome Virus Comparison: Divergent Evolution of Two Continents," *J. Virol.*, 1999, 73:270-280.

Paton et al., "'Blue ear' disease of pigs," *Vet. Rec.*, 1991, 128:617.

Plagemann and Moennig, "Lactate Dehydrogenase-Elevating Virus, Equine Arteritis Virus, and Simian Hemorrhagic Fever Virus: A New Group of Positive-Strand RNA Viruses," *Adv. Vir. Res.*, 1992, 41:99-192.

Plagemann, "Lactate Dehydrogenase-Elevating Virus and Related Viruses," *Fields Virology*, 1996, 3rd ed., Fields et al. (eds.), Philadelphia, Lippincott-Raven, pp. 1105-1120.

Prager et al., "Widespread Distribution of Lysozyme *g* in Egg White of Birds," *J. Biol. Chem.*, 1974, 249(22):7295-7297.

Roberts and Bazer, "The functions of uterine secretions," *J. Reprod. Fert.*, 1988, 82:875-892.

Wensvoort et al., "Mystery swine disease in the Netherlands: the isolation of Lelystad virus," *Vet Q.*, 1991, 13(3):121-130.

Yoon et al., "Characterization of the humoral immune response to porcine reproductive and respiratory syndrome (PRRS) virus infection," *J. Vet. Diagn. Invest.*, 1995, 7:305-312.

Allende et al., "Mutations in the genome of porcine reproductive and respiratory syndrome virus responsible for the attenuation phenotype," *Arch. Virol.*, 2000, 145(6):1149-1161.

Baldo et al., "Comparison of different blocking agents and nitrocelluloses in the solid phase detection of proteins by labelled antisera and protein A," *J. Biochem. Biophys. Meth.*, 1986, 12:271-279.

Oleksiewicz, M.B., et al., Epitope Mapping Porcine Reproductive and Respiratory Syndrome Virus by Phage Display: the nsp2 Fragment of the Replicase Polyprotein Contains a Cluster of b-Cell Epitopes, J. Virology, 75(7):3277-3290 (2001).

Olelcsiewicz, M.B., et al., "Semen from boars infected with porcine reproductcive and respiratory syndrome virus (PRRSV) contains antibodies against structural as well as nonstructural viral proteins," Veterinary Microbiology, 81:109-125 (2001).

U.S. Examiner A.R. Salimi, USPTO Non-Final Office Action from U.S. Appl. No. 12/138,156, dated May 6, 2009, 16 pages.

* cited by examiner pET 24b myc-NSP 1-His (VR-2332)

Bgl II, T7 Promoter

AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator, Xba 1, RBS, Nde 1, Myc Tag

ATAGGGGAATTGTGAGCGGATAACAATTCCCCTCTAGAAATAATTTTGTTTAACTTTAAGAAGGAGATATACATATGGAACAAAAACTCATCTCAGAAGA 200

Start M E Q K L I S E E

EcoR 1, BamH I, NSP 1 (underlined)

GGATCTGAATCGATCCATGAATTCTAGTGGATCCTCTGGGATACTTGATCGGTGCACGTGTACCCCCAATGCCAGGGTGTTTATGGCGGAGGGCCAAGTC 300

D L N R S M N S S G S

TACTGCACACGATGCCTCAGTGCACGGTCTCTCCTTCCCCTGAACCTCCAAGTTTCTGAGCTCGGGGTGCTAGGCCTATTCTACAGGCCCGAAGAGCCAC 400

TCCGGTGGACGTTGCCACGTGCATTCCCCACTGTTGAGTGCTCCCCCGCCGGGGCCTGCTGGCTTTCTGCAATCTTTCCAATCGCACGAATGACCAGTGG 500

AAACCTGAACTTCCAACAAAGAATGGTACGGGTCGCAGCTGAGCTTTACAGAGCCGGCCAGCTCACCCCTGCAGTCTTGAAGGCTCTACAAGTTTATGAA 600

CGGGGTTGCCGCTGGTACCCCATTGTTGGACCTGTCCCTGGAGTGGCCGTTTTCGCCAATTCCCTACATGTGAGTGATAAACCTTTCCCGGGAGCAACTC 700

ACGTGTTGACCAACCTGCCGCTCCCGCAGAGACCCAAGCCTGAAGACTTTTGCCCCTTTGAGTGTGCTATGGCTACTGTCTATGACATTGGTCATGACGC 800

CGTCATGTATGTGGCCGAAAGGAAAGTCTCCTGGGCCCCTCGTGGCGGGGATGAAGTGAAATTTGAAGCTGTCCCCGGGGAGTTGAAGTTGATTGCGAAC 900

CGGCTCCGCACCTCCTTCCCGCCCCACCACACAGTGGACATGTCTAAGTTCGCCTTCACAGCCCCTGGGTGTGGTGTTTCTATGCGGGTCGAACGCCAAC 1000

ACGGCTGCCTTCCCGCTGACACTGTCCCTGAAGGCAACTGCTGGTGGAGCTTGTTTGACTTGCTTCCACTGGAAGTTCAGAACAAAGAAATTCGCCATGC 1100

TAACCAATTTGGCTACCAGACCAAGCATGGTGTCTCTGGCAAGTACCTACAGCGGAGGCTGCAAGTTAATGGTCTCCGAGCAGTAACTGACCTAAACGGA 1200

CCTATCGTCGTACAGTACTTCTCCGTTAAGGAGAGTTGGATCCGCCATTTGAAACTGGCGGGAGAACCCAGCTACTCTGGGTTTGAGGACCTCCTCAGAA 1300

Xho I, His Tag

TAAGGGTTGAGCCTAACACGTCGCCATTGGCTGACAAGGAAGAAAAAATTTTCCGGTTTGGCAGTCACAAGTGGTACGGCGCTCTCGAGCACCACCACCA 1400

Stop, Bpu1102 I, T7 Terminator

CCACCACTGAGATCCGGCTGCTAACAAAGCCCGAAAGGAAGCTGAGTTGGCTGCTGCCACCGCTGAGCAATAACTAGCATAACCCCTTGGGGCCTCTAA 1500

ACGGGTCTTGAGGGGTTTTTTGCTGAAAGGAGGAACTATATCCGGATTGGCGAATGGGACGCGCCCTGTAGCGGCGCATTAAGCGCG 1587

FIG. 2 pET 24b myc-NSP 2P-His

Bgl II — T7 Promoter

AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator — Xba 1 — Ribz — Nde 1 — Myc Tag

ATAGGGGAATTGTGAGCGGATAACAATTCCCCTCTAGAAATAATTTTGTTTAACTTTAAGAAGGAGATATACATATGGAACAAAAACTCATCTCAGAAGA 200

Start M E Q K L I S E E

Ecor 1 — BamH I — NSP 2 (underline)

GGATCTGAATCGATCCATGAATTCTAGTGGATCC

GCTGGAAAGAGAGCAAGAAAAGCACGCTCTTGTGCGACTGCTACAGTCGCTGGCCGCGCTTTGTCCGTTCGTGAAACCCGGCAGGCCAAGGAGCACGAGGTTGCCGGCCAACAAGGCTGAGCACCTCAAACACT
ACTCCCCGCCTGCCGAAGGGAATTGTGGTTGGCACTGCATTTCCGCCATCGCCAACCGGATGGTGAATTCCAAATTTGAAACCACCCTTCCCGAAAGAGTGAGACCTCCAGATGACTGGGCTACTGACGAGGAT
CTTGTGAATGCCATCCAAATCCTCAGACTCCCTGCGGCCTTAGACAGGAACGGTGCTTGTACTAGCGCCAAGTACGTACTTAAGCTGGAAGGTGAGCATTGGACTGTCACTGTGACCCCTGGGATGTCCCCTTC
TTTGCTCCCTCTTGAATGTGTTCAGGGCTGTTGTGGGCACAAGGGCGGTTTGGTTCCCCAGATGCAGTCGAGGTCTCCGGATTTGACCCTGCCTGCCTTGACCGGCTGGCTGAGGTGATGCACCTGCCTAGCA
GTGCTATCCCAGCCGCTCTGGCCGAAATGTCTGGCGATTCCGATCGTTCGGCTTCTCCGGTCACCACCGTGTGGACTGTTTCGCAGTTCTTTGCCCGTCACAGCGGAGGGAATCACCCTGACCAAGTGCGCTTA
GGGAAAATTATCAGCCTTTGTCAGGTGATTGAGGACTGCTGCTGTTCCCAGAACAAAACCAACCGGGTCACCCCGGAGGAGGTCGCAGCAAAGATTGACCTGTACCTCCGTGGTGCAACAAATCTTGAAGAATG
CTTGGCCAGGCTTGAGAAAGCGCGCCCGCCACGCGTAATCGACACCTCCTTTGATTGGGATGTTGTGCTCCCTGGGGTTGAGGCGGCAACCCAGACGATCAAGCTGCCCCAGGTCAACCAGTGTCGTGCTCTGG
TCCCTGTTGTGACTCAAAAGTCCTTGGACAACAACTCGGTCCCCCTGACCGCCTTTTCACTGGCTAACTACTACTACCGTGCGCAAGGTGACGAAGTTCGTCACCGTGAAAGACTAACCGCCGTGCTCTCCAAG
TTGGAAAAGGTTGTTCGAGAAGAATATGGGCTCATGCCAACCGAGCCTGGTCCACGGCCCACACTGCCACGCGGGCTCGACGAACTCAAAGACCAGATGGAGGAGGACTTGCTGAAACTGGCTAACGCCCAGAC
GACTTCGGACATGATGGCCTGGGCAGTCGAGCAGGTTGACCTAAAAACTTGGGTCAAGAACTACCCGCGGTGGACACCACCACCCCCTCCGCCAAAAGTTCAGCCTCGAAAAACGAAGCCTGTCAAGAGCTTGC
CGGAGAGAAAGCCTGTCCCCGCCCCGCGCAGGAAGGTTGGGTCCGATTGTGGCAGCCCGGTTTCATTAGGCGGCGATGTCCCTAACAGTTGGGAAGATTTGGCTGTTAGTAGCCCCTTTGATCTCCCGACCCCA
CCTGAGCCGGCAACACCTTCAAGTGAGCTGGTGATTGTGTCCTCACCGCAATGCATCTTCAGGCCGGCGACACCCTTGAGTGAGCCGGCTCCAATTCCCGCACCTCGCGGAACTGTGTCTCGACCGGTGACACC
CTTGAGTGAGCCGATCCCTGTGCCCGCACCGCGGCGTAAGTTTCAGCAGGTGAAAAGATTGAGTTCGGCGGCGGCAATCCCACCGTACCAGGACGAGCCCCTGGATTTGTCTGCTTCCTCACAGACTGAATATG
AGGCCTCTCCCCCAGCACCGCCGCAGAGCGGGGGCGTTCTGGGAGTAGAGGGGCATGAAGCTGAGGAAACCCTGAGTGAAATCTCGGACATGTCGGGTAACATTAAACCTGCGTCCGTGTCATCAAGCAGCTCC
TTGTCCAGCGTGAGAATCACACGCCCAAAATACTCAGCTCAAGCCATCATCGACTCGGGCGGGCCCTGCAGTGGGCATCTCCAAGAGGTAAAGGAAACATGCCTTAGTGTCATGCGCGAGGCATGTGATGCCAC
TAAGCTTGATGACCCTGCTACGCAGGATGGCTTTCTCGCATGTGGGATCGGGTGGACATGCTGACTTGGCGCAACACGTCTGTTTACCAGGCGATTTGCACCTTAGATGGCAGGTTAAAGTTCCTCCCAAAAA
TGATACTCGAGACACCGCCGCCCTATCCGTGTGAGTTTGTGATGATGCCTCACACGCCTGCACCTTCCGTAGGTGCGGAGAGCGACCTTACCATTGGCTCAGTTGCTACTGAAGATGTTCCACGCATCCTCGAG
AAAATAGAAAATGTCGGCGAGATGGCCAACCAGGGACCCTTGGCCTTCTCCGAGGATAAACCGGTAGATGACCAACTTGTCAACGACCCCCGGATATCGTCGCGGAGGCCTGACGAGAGCACATCAGCTCCGTC
CGCAGGCACAGGTGGCGCCGGCTCTTTTACCGATTTGCCGCCTTCAGATGGCGCGGATGCGGACGGGGGGGGGCCGTTTCGGACGGTAAAAAGAAAAGCTGAAAGGCTCTTTGACCAACTGAGCCGTCAGGTTT
TTGACCTCGTCTCCCATCTCCCTGTTTTCTTCTCACGCCTTTTCTACCCTGGCGGTGGTTATTCTCCGGGTGATTGGGGTTTTGCAGCTTTTACTCTATTGTGCCTCTTTTTATGTTACAGTTACCCAGCCTTT
GGTATTGCTCCCCTCTTGGGTGTGTTTTCTGGGTCTTCTCGGCGCGTTCGAATGGGGGTTTTTGGCTGCTGGTTGGCTTTTGCTGTTGGTCTGTTCAAGCCTGTGTCCGACCCAGTCGGCGCTGCTTGTGAGTT
TGACTCGCCAGAGTGTAGAAACATCCTTCATTCTTTTGAGCTTCTCAAACCTTGGGACCCTGTTCGCAGCCTTGTTGTGGGCCCCGTCGGTCTCGGTCTTGCCATTCTTGGCAGGTTACTGGGCGGGGCACGCT
GCATCTGGCACTTTTTGCTTAGGCTTGGCATTGTTGCAGACTGTATCTTGGCTGGAGCTTACGTGCTTTCTCAAGGTAGGTGTAAAAAGTGCTGGGGATCTTGTATAAGAACTGCTCCTAATGAGGTCGCTTTT
AACGTGTTTCCTTTCACACGTGCGACCAGGTCGTCACTTATCGACCTGTGCGATCGGTTTTGTGCGCCAAAAGGAATGGACCCCATTTTTCTCGCCACTGGGTGGCGCGGGTGCTGGGCCGGCCGAAGCCCCAT
TGAGCAACCCTCTGAAAAACCCATCGCGTTTGCCCAATTGGATGAAAAGAAGATTACGGCTAGGACTGTGGTCGCCCAGCCTTATGACCCCAACCAAGCCGTAAAGTGCTTGCGGGTATTGCAGTCGGGTGGGG
CGATGGTGGCTAAGGCGGTCCCAAAAGTGGTCAAGGTTTCCGCTGTTCCATTCCGAGCCCCCTTCTTTCCCACTGGAGTGAAAGTTGACCCTGATTGCAGGGTCGTGGTTGACCCTGACACTTTCACTGCAGCT
CTCCGGTCTGGCTACTCCACCACAAACCTCGTCCTTGGTGTAGGGGACTTTGCCCAGCTGAATGGATTAAAAATCAGGCAAATTTCCAAGCCTTCAGGG

CTCGAGCACCACCACCACCACCACTGAGATCCGGCTGCTAACAAAGCCCGAAAGGAAGCTGAGTTGGCTGCTGCCACCGCTGAGCAATAACTAGCATAACC

L E H H H H H H Stop

CCTTGGGGCCTCTAAACGGGTCTTGAGGGGTTTTTTGCTGAAAGGAGGAACTATATCCGGATTGGCGAATGGGACGCGCCCTGTAGCGGCGCATTAAGCGCG

T7 Terminator

FIG. 3

```
pET  24b  myc-NSP  4-His
                                                                     Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100

         lac  operator        Xba 1                    RBS          Nde  1    Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                         Start  M  E  Q  K  L  I  S  E  E

                     EcoR 1   Bamh I      NSP  4  (underlined)
GGATCTGAATCGATCCATGAATTCTAGTGGATCCGGTGCTTTCAGAACTCGAAAGCCCTCACTGAACACCGTCAATGTGATCGGGTCCTCCATGGGCTCT  300
 D  L  N  R  S  M  N  S  S  G  S  G  A  F  R  T  R  K  P  S  L  N  T  V  N  V  I  G  S  S  M  G  S

GGCGGGGTGTTTACCATCGACGGGAAAGTCAAGTGCGTAACTGCCGCACATGTCCTTACGGGCAATTCAGCTCGGGTTTCCGGGGTCGGCTTCAATCAAA  400
 G  G  V  F  T  I  D  G  K  V  K  C  V  T  A  A  H  V  L  T  G  N  S  A  R  V  S  G  V  G  F  N  Q

TGCTTGACTTTGACGTAAAGGGAGATTTCGCTATAGCTGATTGCCCGAATTGGCAAGGGGCTGCCCCCAAGACCCAATTCTGCACGGATGGATGGACTGG  500
M  L  D  F  D  V  K  G  D  F  A  I  A  D  C  P  N  W  Q  G  A  A  P  K  T  Q  F  C  T  D  G  W  T  G

CCGTGCCTATTGGCTAACATCCTCTGGCGTCGAACCCGGCGTCATTGGAAAAGGATTCGCCTTCTGCTTCACCGCATGTGGCGATTCCGGGTCCCCAGTG  600
 R  A  Y  W  L  T  S  S  G  V  E  P  G  V  I  G  K  G  F  A  F  C  F  T  A  C  G  D  S  G  S  P  V

ATCACCGAGGCCGGTGAGCTTGTCGGCGTTCACACGGGATCGAATAAACAAGGGGGGGGCATTGTTACGCGCCCCTCAGGCCAGTTTTGTAATGTGGCAC  700
I  T  E  A  G  E  L  V  G  V  H  T  G  S  N  K  Q  G  G  G  I  V  T  R  P  S  G  Q  F  C  N  V  A

CCATCAAGCTAAGCGAATTAAGTGAATTCTTTGCTGGGCCTAAGGTCCCGCTCGGTGATGTGAAGGTCGGCAGCCACATAATTAAAGACATAAGCGAGCT  800
P  I  K  L  S  E  L  S   E  F  F  A  G  P  K  V  P  L  G  D  V  K  V  G  S  H  I  I  K  D  I  S  E  V

                                                 Xho  I   His  Tag
GCCTTCAGATCTTTGTGCCTTGCTTGCTGCCAAACCTGAACTGGAACTCGAGCACCACCACCACCACCACTGAGATCCGGCTGCTAACAAAGCCCGAAAG  900
 P  S  D  L  C  A  L  L  A  A  K  P  E  L  E  L  E  H  H  H  H  H  H  Stop

                   Bpu1102 I                   T7 Terminator
GAAGCTGAGTTGGCTGCTGCCACCGCTGAGCAATAACTAGCATAACCCCTTGGGGCCTCTAAACGGGTCTTGAGGGGTTTTTTGCTGAAAGGAGGAACTA  1000

TATCCGGATTGGCGAATGGGACGCGCCCTGTAGCGGCGCATTAAGCGCG                                                     1049
```

FIG. 4

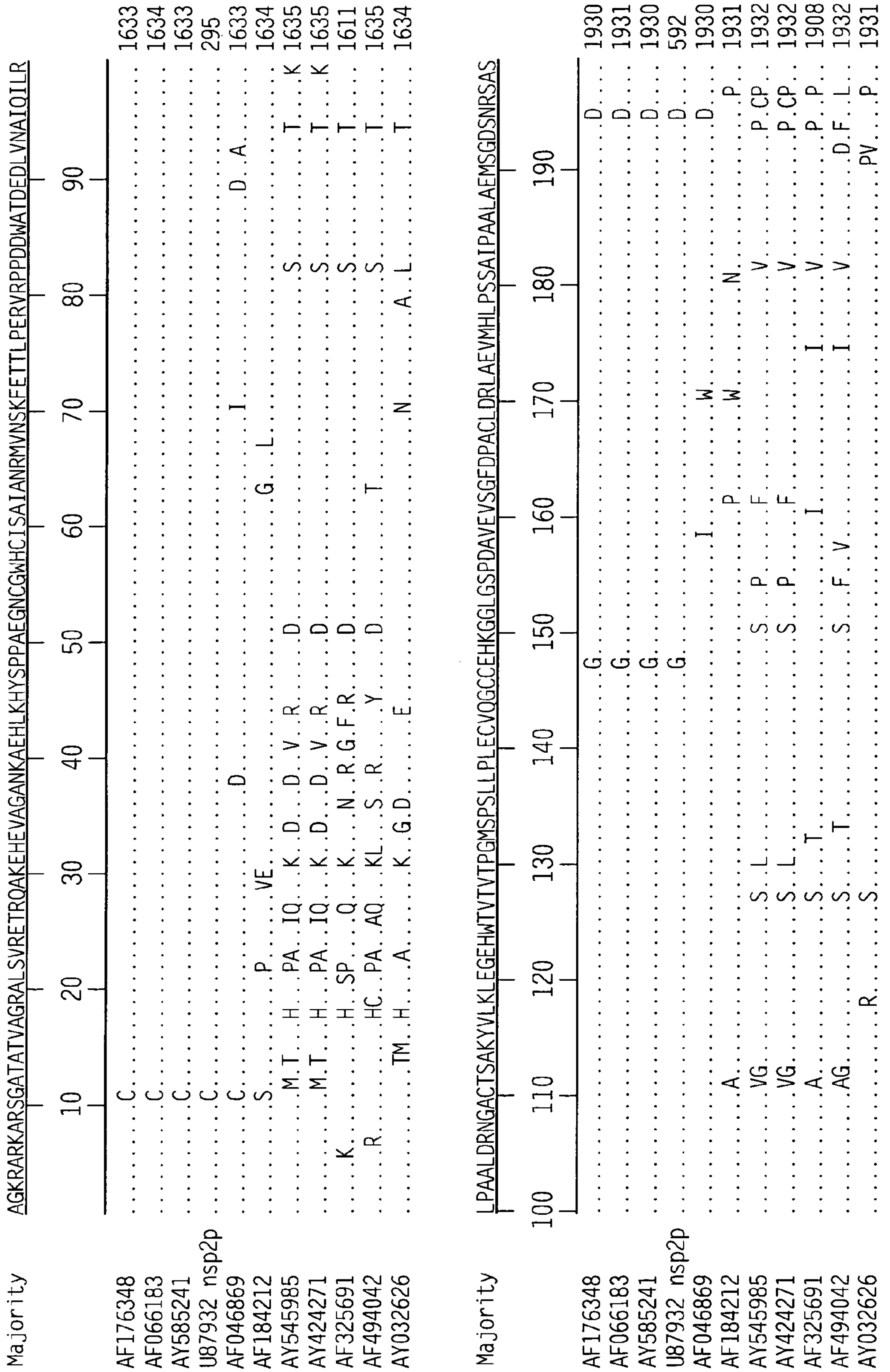
FIG. 14 (Page 1 of 4)

```
Majority       PVTTVWTVSQFFARHSGGNHPDQVRLGKIISLCQVIEDCCCSQNKTNRVTPEEVAAKIDLYLRGATNLEECLARLEKARPPRVIDTSFDWDVVLPGVEA
                200       210       220       230       240       250       260       270       280       290

AF176348       ........................................................F.............................P............ 2227
AF066183       .......................................................................................F............ 2228
AY585241       .......................................................................................F............ 2227
U87932 nsp2p   .................................................................................................... 889
AF046869       .................................................................................................... 2227
AF184212       ...........L...N.......I............................................................M............... 2228
AY545985       ...............R..E................V.E...H......A.......R..Q..H...S.....I...RVC..SAA...F...N......G. 2229
AY424271       ...............R..E................V.E...H......A.......R..Q..H...S.....I...RVC..SAA...F...N......G. 2229
AF325691       ...............R..E..................E...R..D..........V..NQ............T...R.C..SAA.......N.....I.. 2205
AF494042       .AA............R..E.....C.....N......E....R..A..A........V.Q.....AS.G....K..R....SAM.......N.......T 2229
AY032626       ....A......Y...R....R...C................H......A..........Q......S.....IK..RVS..SAA.......N........ 2228

Majority       ATQTTKLPQVNQCRALVPVVTQKSLDNNSVPLTAFSLANYYYRAQGDEVRHRERLTAVLSKLEGVVREEYGLMPTEPGPRPTLPRGLDELKDQMEEDLL
                300       310       320       330       340       350       360       370       380       390

AF176348       ....I..........................................................K...........K........................ 2524
AF066183       ....I..........................................................k.................................... 2525
AY585241       ....I..................................H....................N..K.................................... 2524
U87932 nsp2p   ....I..........................................................K.................................... 1186
AF046869       ....N..........................................................E.................................... 2524
AF184212       .....E.....................................................................G....................V... 2525
AY545985       S.....QLH.............EP..KD.........S.C..P............NS................T........A..N..V........... 2526
AY424271       S.....QLH.............EP..KD.........S.C..P............NS................T........A..N..V........... 2526
AF325691       ......QLH.............EP..KD.........S.C..P............NS................T........A..N.............. 2502
AF494042       .D....QLH.............EP..RD.........S.C..P............NS................T..G.....A..N.............. 2526
AY032626       .N....QLH.............EP..KD.........S.C..P............NS........L.......S.GL.....V..S.............. 2525
```

FIG. 14 (Page 2 of 4)

```
Majority     KLANAQATSDMMAWAAEQVDLKTWVKNYPRWTPPPPPPKVQPRKTKPVKSLPERKPVPAPRRKVGSDCGSPVLLGGNVPNSWEDLAVGGPLDLPTPPEP
                 400       410       420       430       440       450       460       470       480       490

AF176348     ......T.............................S....L..........K....................S...D..........SS.F........ 2821
AF066183     ......T........V.........................................................S...D..........SS.F........ 2822
AY585241     ......T........V.........................................................S...D..........SS.F........ 2821
U87932 nsp2p ......T........V.........................................................S...D..........SS.F........ 1483
AF046869     R..............V..................................................P......S...D..........SS.......... 2821
AF184212     ......M........V.......................I.......L......S..........R..DC.T.S.N.L.D.........C.S....S... 2822
AY545985     ..V......E............A................R.......S.....GN..........R......I.M.D...DGR...T.......S.S... 2823
AY424271     ..V......E............A................R.......S.....GN..........R......I.M.D...DGR...T.......S.S... 2823
AF325691     ..V......E............A................R.......S.....GD..........R......I.M.D.D..GR...T.D.....S.S... 2799
AF494042     ..V......E............A................R.......S....L.N..........R..Y...I.M.D....G...ST.......SA.S.. 2823
AY032626     .........E............A...S............R..............N.................I.M.D....G...F.......F..S... 2822

Majority     ATPLSEPVLVSAPQCIFRPVTPLSEPAPVPAPRGTVSRPVTPLSEPIPVPAPRRKFQQVERANSAAATPTYQDEPLDLSASSQTEYEASPLAPPQNGGV
                 500       510       520       530       540       550       560       570       580       590

AF176348     .I.S..L.I..S.......A........I...............................K.LS....I.P..N.................P....S... 3118
AF066183     ...S..L.I..S.......A........I...............................K.LS....I.P..N.................P....S... 3119
AY585241     ...S..L.I..S.......A........I...............................K.LS....I.P..N.................P....S... 3118
U87932 nsp2p ...S..L.I..S.......A........I...............................K.LS....I.P....................P....S... 1780
AF046869     ..LS..L.I..S.......A........I...............................K.LS....V.LH.N.................S....S... 3118
AF184212     V......AS....RRS....K......V.....K.....A....................KV.P....LGC...FP.......H........VL....D. 3119
AY545985     M......A.MP.L.Y.S....S..VL.......F.............F.S...H......E.L..T.L.H......................T.L..M.I 3120
AY424271     M......A.MP.L.Y.S....S..VL.......R.............F.S...H......E.L..T.L.H......................T.L..M.I 3120
AF325691     M...G..A.LP.L.H.S....S..V........RA............FES...H.L....E.LV.T.L.H.........................L..M.. 3096
AF494042     M...............S....S..V........RA....M..S....F.S.L.H......K.L...A.M..................G....T....V.I 3102
AY032626     M........MP.S.H.P.......G........R.....M.......F.S...H......E.P..T.L.............F....C.......L..M.I 3119
```

FIG. 14 (Page 3 of 4)

```
Majority     LEVEGQEAEEVLSEISDMLGDIKPASVSSSSSLSSVRITRPKYSAQAIIDSGGPCSGHLQEVKEACLSIMREACDATKLDDPATQEWLSRMWDRVDMLT
                   600       610       620       630       640       650       660       670       680       690

AF176348     .G...H....T.......S.N............................................T...V.............................. 3415
AF066183     .G...H....T.......S.N............................................T...V.............................. 3416
AY585241     .G...H....T.......S.N................................................V.............................. 3415
U87932 nsp2p .G...H....T.......S.N............................................T...V.............................. 2077
AF046869     .G...H....T.......S.N...............E........................G...T...V.............................. 3415
AF184212     ....ER....I..G...I.DA.....A.........A..................Y.........T.....S....V....................... 3416
AY545985     ...G.............T.N..N..P..........K.....H.................RRE..............A..S................... 3417
AY424271     ...G.............T.N..N..P..........K.....H.................RRE..............A..S................... 3417
AF325691     ...G.............I.N..N..P..........K.......................RRE.........K....A..S................... 3393
AF494042     ...R.............I.N.TN..P.........................L.........RE.....R........A..S................... 3399
AY032626     ..AG.........G...I.N..N..P...................................RE..............A..S................... 3416

Majority     WRNTSVYQAIRTLDGRLKFLPKMILE------
                   700       710       720

AF176348     ........V.C....M..........                                                                          3493
AF066183     ..........C..N............                                                                          3494
AY585241     ..........C...............                                                                          3493
U87932 nsp2p ..........C...............                                                                          2155
AF046869     ......C...................                                                                          3493
AF184212     ......H..S....D.F.........                                                                          3494
AY545985     .....A...F.I....FE........                                                                          3495
AY424271     .....A...F.I....FE........                                                                          3495
AF325691     .....A...L.V....FG........                                                                          3471
AF494042     .....A...F......FG........TPPPYP                                                                    3495
AY032626     .....A...LH.....SG........                                                                          3494
```

FIG. 14 (Page 4 of 4)

```
Majority MLGKCLTAGCCSRLLSLWCIVPFCFAVLANASNSSSSHLQLIYNLTLCELNGTDWLANKFDWAVESFVIFPVLTHIVSYGALTTSHFLDTVGLVTVSTAGFV
                  10        20        30        40        50        60        70        80        90       100

AF176348 .........W..Q....G...............D....V....................................................A.......... 14091
AF066183 ..E.........Q....................D.........................................................A.......... 14092
AY585241 ..E.........Q....................D.........................................................A.......... 14091
PRU87392 ..E..............................D.........................................................A.......... 14091
AF046869 ..E.......................................................R................................A.......... 14091
AF184212 ................F...........V...Y....................................................................Y 14200
AY545985 ...R......................A.V..NSN......................KD.......T...................................Y 14093
AY424271 ...R......................A.V..NSN......................KD.......T...................................Y 14093
AF325691 ..E........L..P.............V..N......F.S............E..SE.......T...................................L 14069
AF494042 ............................GS.NS.....F..................E.......T...................................Y 14075
AY032626 .......T....................V..NSN....F..........................T...................................Y 14092

Majority HGRYVLSSIYAVCALAALICFVIRLAKNCMSWRYSCTRYTNFLLDTKGRLYRWRSPVIIEKGGKVEVEGHLIDLKRVVLDGSVATPLTRVSAEQWGRP-
                110       120       130       140       150       160       170       180       190       200

AF176348 ..................T.....F.........A..........................R........................I............ 14388
AF066183 ..................T.....F.........A.............G............R........................I............ 14389
AY585241 ..................T.....F.........A..........................R........................I............ 14388
PRU87392 ..................T.....F.........A..........................R........................I............ 14388
AF046869 ..................T.....F.........A..........................R........................I............ 14388
AF184212 ....................................................................S.............A................ 14497
AY545985 .................................................................................................L. 14390
AY424271 .................................................................................................L. 14390
AF325691 .R......V............I..........................K..............R..................A..............L. 14366
AF494042 .................................................................................................L. 14372
AY032626 .........................................................V.......................................L. 14389
```

FIG. 15

```
Majority MPNNNGKQQKKKKGDGQPVNQLCQMLGKIIAQQNQSRGKGPGKKNKKKNPEKPHFPLATEDDVRHHFTPSERQLCLSSIQTAFNQGAGTCTLSDSGRIS
                  10        20        30        40        50        60        70        80        90
AF176348 ..........R........................................................................................ 15183
AF066183 ..........R........................................................................................ 15184
AY585241 ..........R........................................................................................ 15183
PRU87392 ..........R........................................................................................ 15183
AF046869 ..........R........................................................................................ 15183
AF184212 .............................................................Y..................................... 15292
AY545985 ............R.N.............................I.N.................................................... 15185
AY424271 ............R.N.............................I.N.................................................... 15185
AF325691 ..............N.............................I...................................................... 15161
AF494042 ..............N.............................S.........................G............................ 15167
AY032626 ........R.....N.................................S.................................................. 15184

Majority YTVEFSLPTHHTVRLIRVTASPSA-
         100       110       120
AF176348 .........................                                                                          15258
AF066183 .........................                                                                          15259
AY585241 .........................                                                                          15258
PRU87392 .........................                                                                          15258
AF046869 .........................                                                                          15258
AF184212 .........................                                                                          15367
AY545985 ...................PS....                                                                          15260
AY424271 ...................PS....                                                                          15260
AF325691 ...................P.....                                                                          15236
AF494042 .........................                                                                          15242
AY032626 .........................                                                                          15259
```

FIG. 16

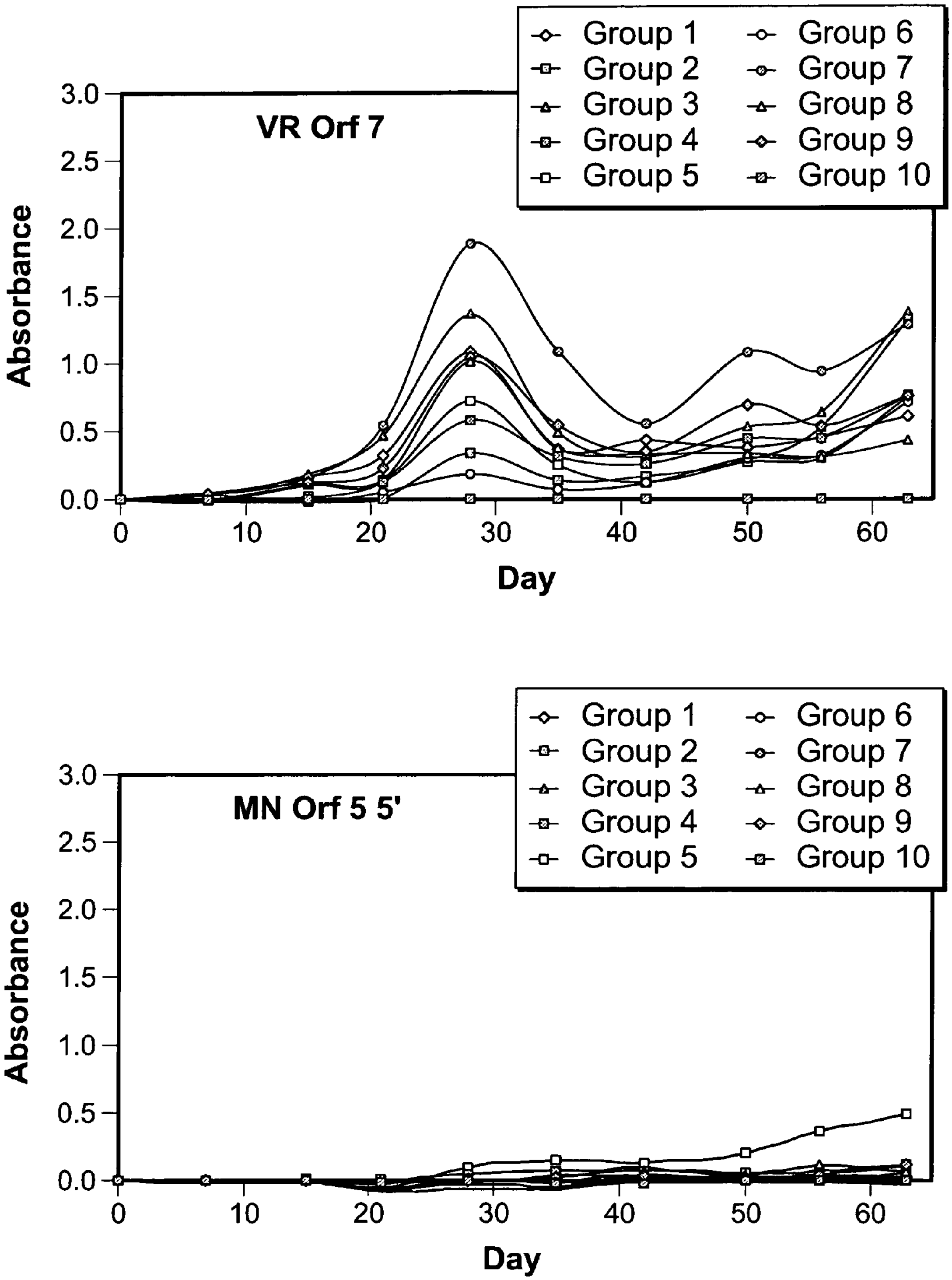
FIG. 18 (Page 1 of 5)

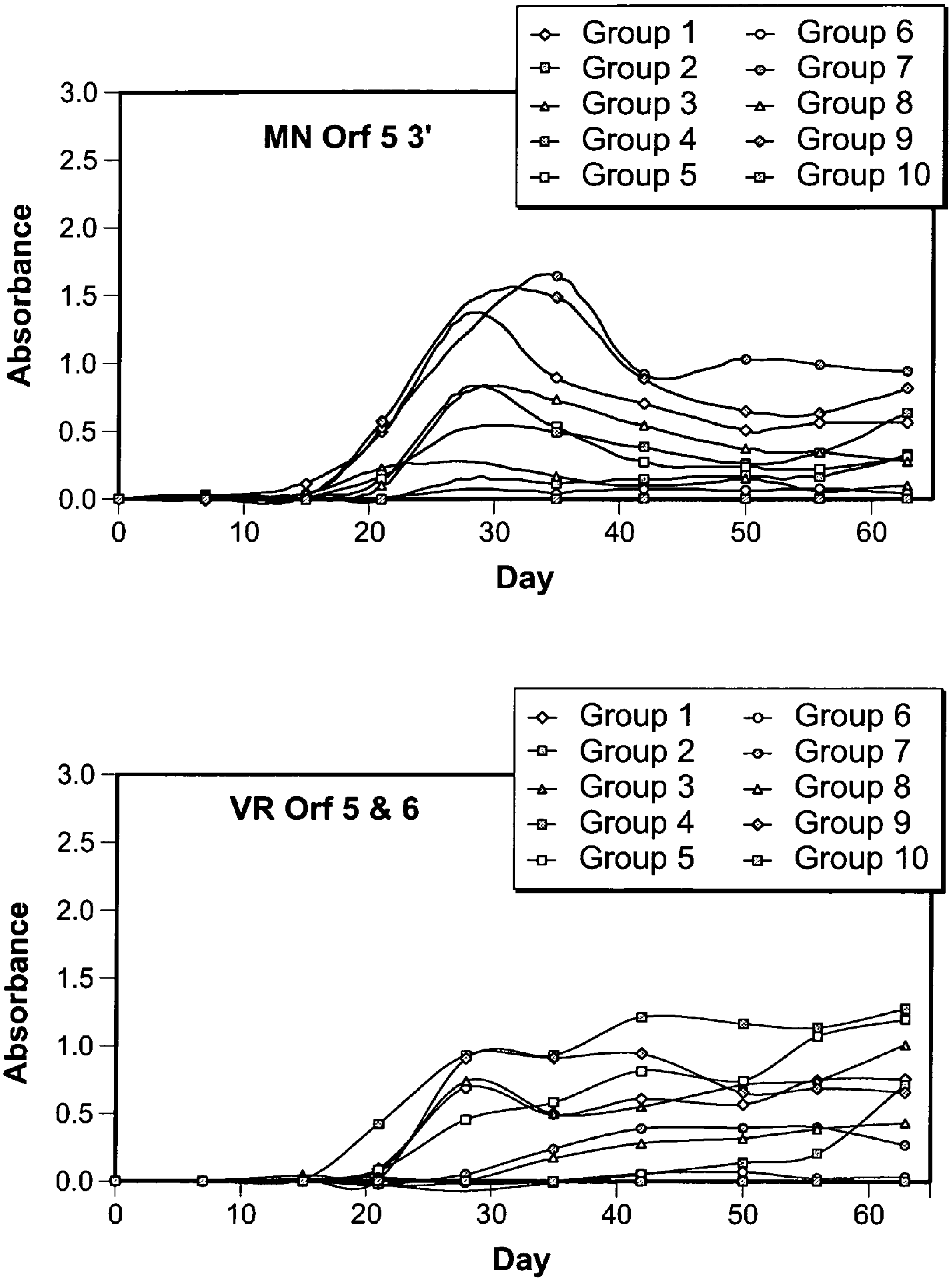
FIG. 18 (Page 2 of 5)

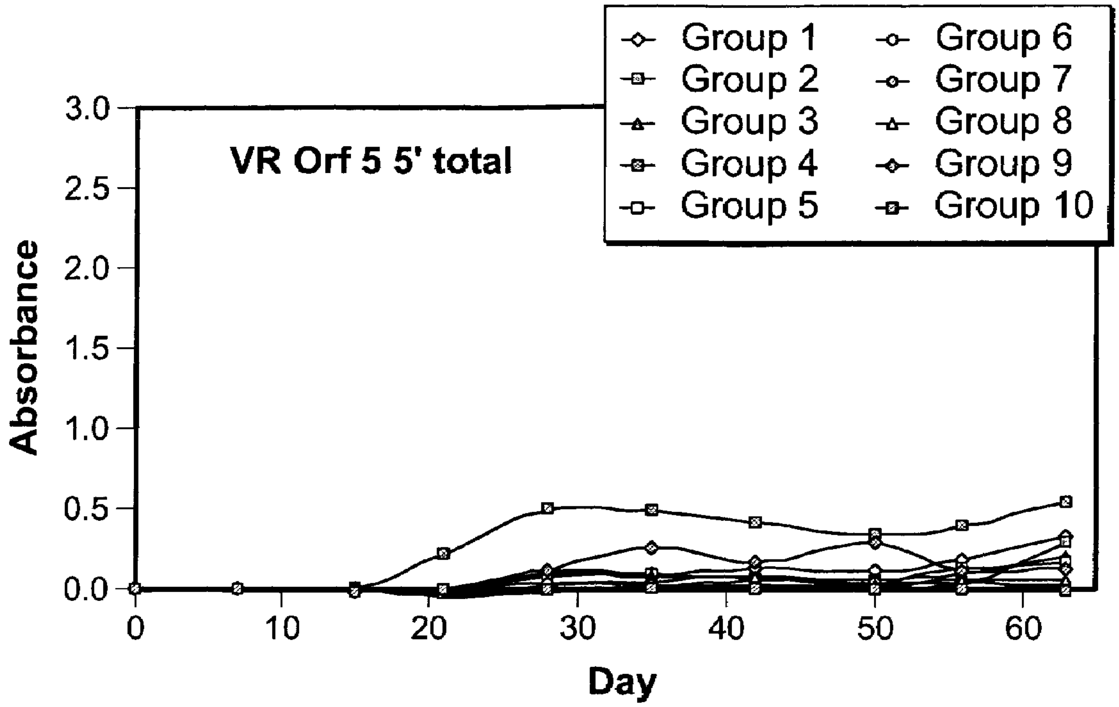
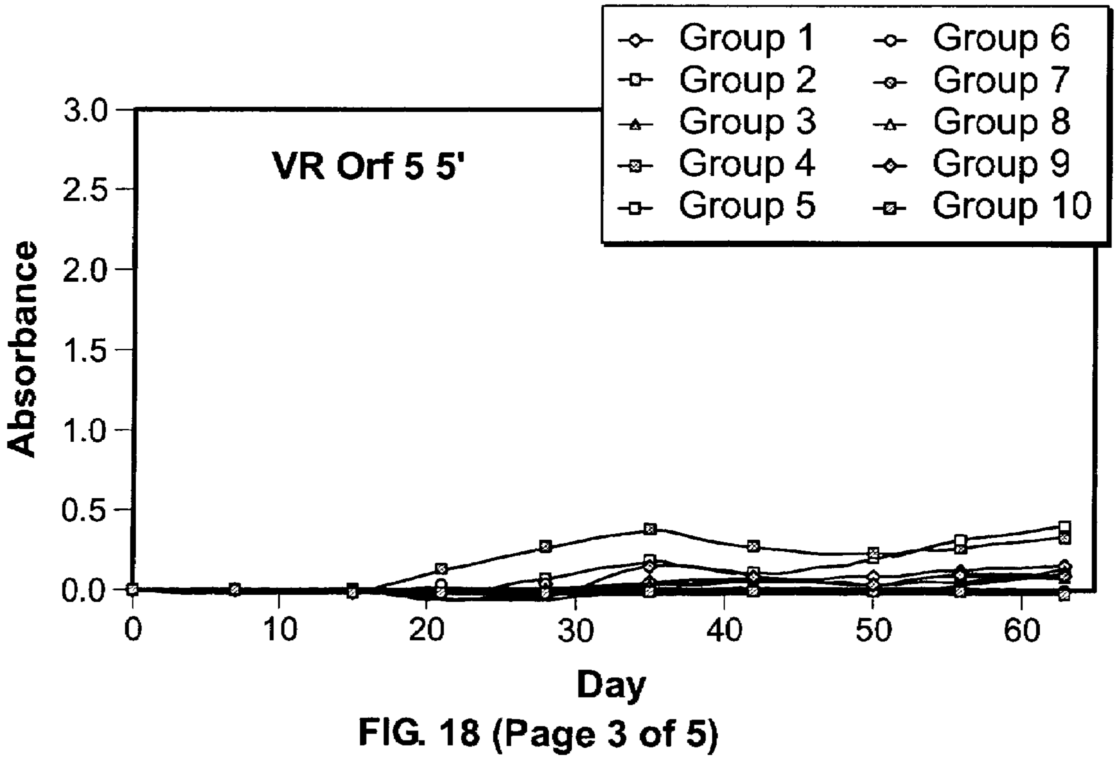
FIG. 18 (Page 3 of 5)

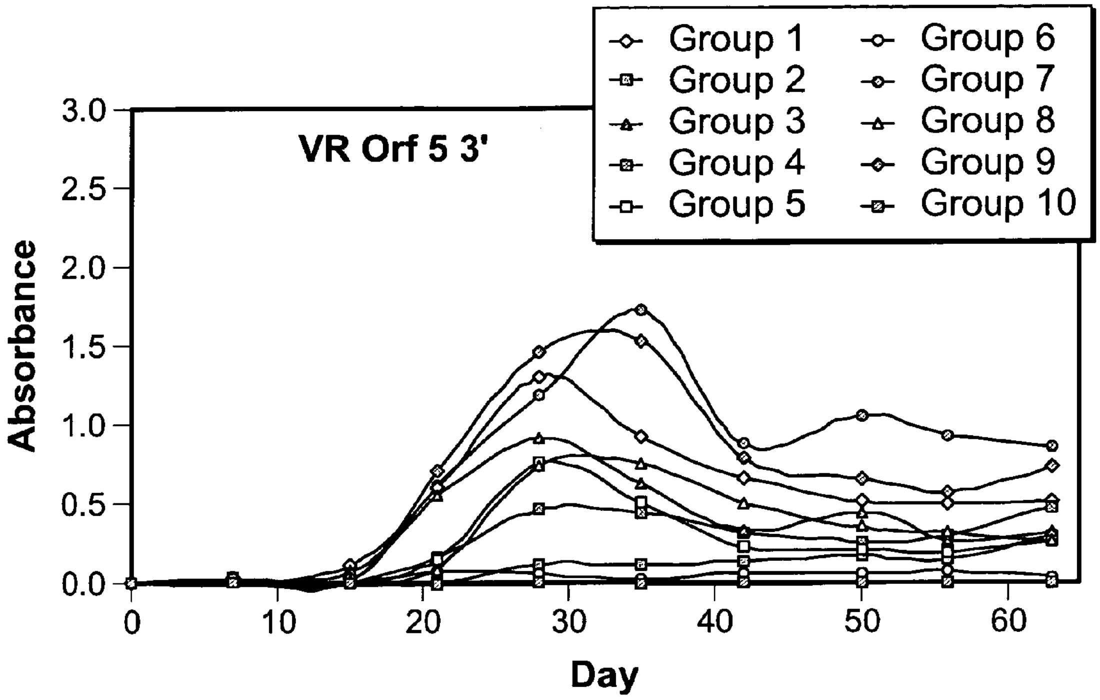
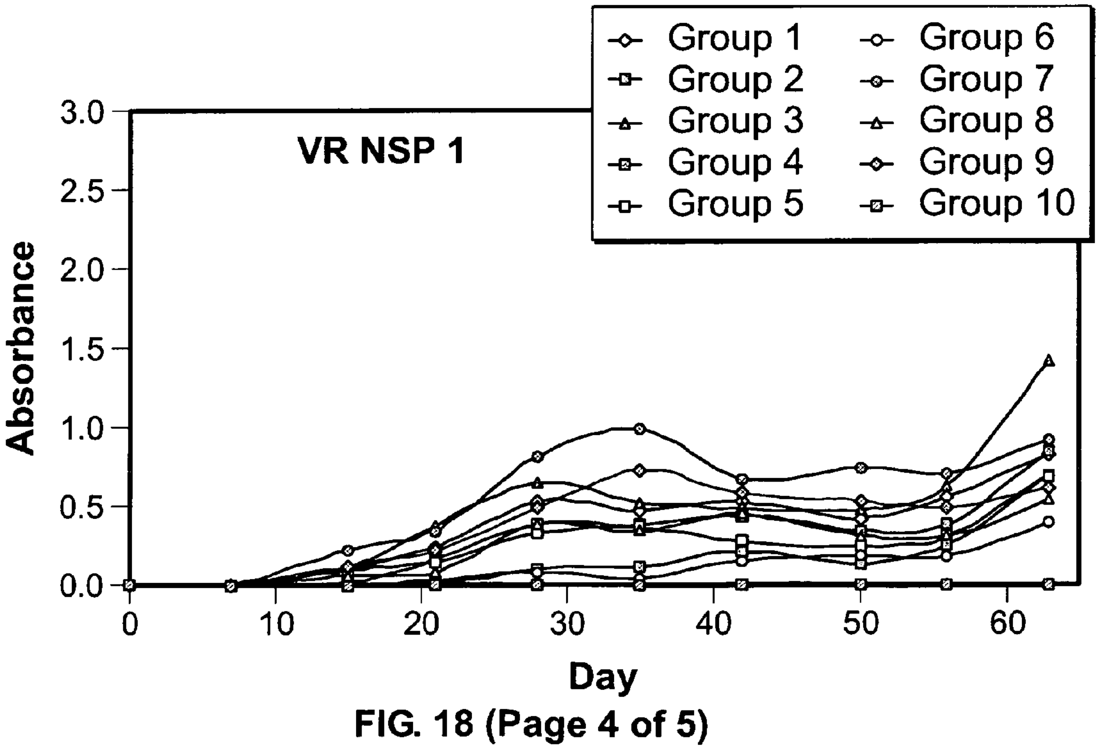
FIG. 18 (Page 4 of 5)

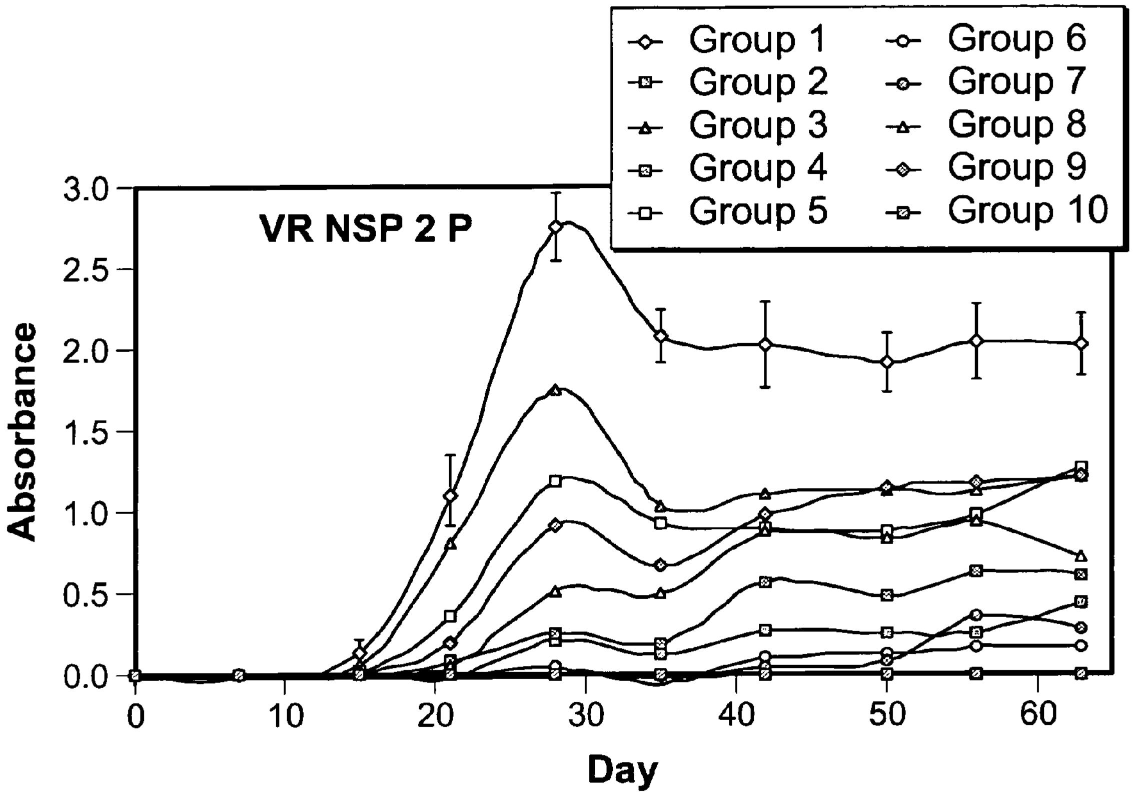
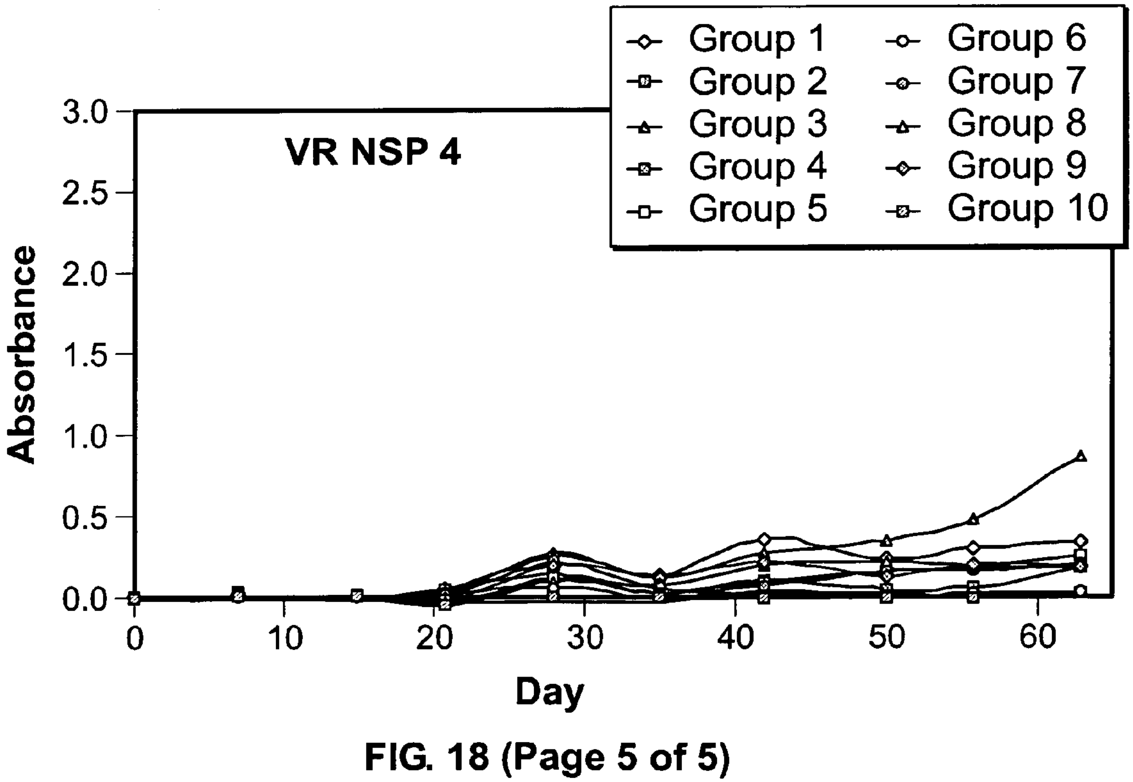
FIG. 18 (Page 5 of 5)

pET 24b myc-NSP 2P-His

Bgl II / T7 Promoter

AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator / Xba 1 / RBS / Nde 1 / Myc Tag

ATAGGGGAATTGTGAGCGGATAACAATTCCCCTCTAGAAATAATTTTGTTTAACTTTAAGAAGGAGATATACATATGGAACAAAAACTCATCTCAGAAGA 200

Start M E Q K L I S E E

EcoR 1 / BamH I

GGATCTGAATCGATCCATGAATTCTAGTGGATCC

D L N R S M N S S G S

NSP 2P (underlined)

GCTGGAAAGAGAGCAAGAAAAGCACGCTCTTGTGCGACTGCTACAGTCGCTGGCCGCGCTTTGTCCGTTCGTGAAACCCGGCAGGCCAAGGAGCACGAGGTTGCCGG
CGCCAACAAGGCTGAGCACCTCAAACACTACTCCCCGCCTGCCGAAGGGAATTGTGGTTGGCACTGCATTTCCGCCATCGCCAACCGGATGGTGAATTCCAAATTTG
AAACCACCCTTCCCGAAAGAGTGAGACCTCCAGATGACTGGGCTACTGACGAGGATCTTGTGAATGCCATCCAAATCCTCAGACTCCCTGCGGCCTTAGACAGGAAC
GGTGCTTGTACTAGCGCCAAGTACGTACTTAAGCTGGAAGGTGAGCATTGGACTGTCACTGTGACCCCTGGGATGTCCCCTTCTTTGCTCCCTCTTGAATGTGTTCA
GGGCTGTTGTGGGCACAAGGGCGGTCTTGGTTCCCCAGATGCAGTCGAGGTCTCCGGATTTGACCCTGCCTGCCTTGACCGGCTGGCTGAGGTGATGCACCTGCCTA
GCAGTGCTATCCCAGCCGCTCTGGCCGAAATGTCTGGCGATTCCGATCGTTCGGCTTCTCCGGTCACCACCGTGTGGACTGTTTCGCAGTTCTTTGCCCGTCACAGC
GGAGGGAATCACCCTGACCAAGTGCGCTTAGGGAAAATTATCAGCCTTTGTCAGGTGATTGAGGACTGCTGCTGTTCCCAGAACAAAACCAACCGGGTCACCCCGGA
GGAGGTCGCAGCAAAGATTGACCTGTACCTCCGTGGTGCAACAAATCTTGAAGAATGCTTGGCCAGGCTTGAGAAAGCGCGCCCGCCACGCGTAATCGACACCTCCT
TTGATTGGGATGTTGTGCTCCCTGGGGTTGAGGCGGCAACCCAGACGATCAAGCTGCCCCAGGTCAACCAGTGTCGTGCTCTGGTCCCTGTTGTGACTCAAAAGTCC
TTGGACAACAACTCGGTCCCCCTGACCGCCTTTTCACTGGCTAACTACTACTACCGTGCGCAAGGTGACGAAGTTCGTCACCGTGAAAGACTAACCGCCGTGCTCTC
CAAGTTGGAAAAGGTTGTTCGAGAAGAATATGGGCTCATGCCAACCGAGCCTGGTCCACGGCCCACACTGCCACGCGGGCTCGACGAACTCAAAGACCAGATGGAGG
AGGACTTGCTGAAACTGGCTAACGCCCAGACGACTTCGGACATGATGGCCTGGGCAGTCGAGCAGGTTGACCTAAAAACTTGGGTCAAGAACTACCCGCGGTGGACA
CCACCACCCCCTCCGCCAAAAGTTCAGCCTCGAAAAACGAAGCCTGTCAAGAGCTTGCCGGAGAGAAAGCCTGTCCCCGCCCCGCGCAGGAAGGTTGGGTCCGATTG
TGGCAGCCCGGTTTCATTAGGCGGCGATGTCCCTAACAGTTGGGAAGATTTGGCTGTTAGTAGCCCCTTTGATCTCCCGACCCCACCTGAGCCGGCAACACCTTCAA
GTGAGCTGGTGATTGTGTCCTCACCGCAATGCATCTTCAGGCCGGCGACACCCTTGAGTGAGCCGGCTCCAATTCCCGCACCTCGCGGAACTGTGTCTCGACCGGTG
ACACCCTTGAGTGAGCCGATCCCTGTGCCCGCACCGCGGCGTAAGTTTCAGCAGGTGAAAAGATTGAGTTCGGCGGCGGCAATCCCACCGTACCAGGACGAGCCCCT
GGATTTGTCTGCTTCCTCACAGACTGAATATGAGGCCTCTCCCCCAGCACCGCCGCAGAGCGGGGGCGTTCTGGGAGTAGAGGGGCATGAAGCTGAGGAAACCCTGA
GTGAAATCTCGGACATGTCGGGTAACATTAAACCTGCGTCCGTGTCATCAAGCAGCTCCTTGTCCAGCGTGAGAATCACACGCCCAAAATACTCAGCTCAAGCCATC
ATCGACTCGGGCGGGCCCTGCAGTGGGCATCTCCAAGAGGTAAAGGAAACATGCCTTAGTGTCATGCGCGAGGCATGTGATGCGACTAAGCTTGATGACCCTGCTAC
GCAGGAATGGCTTTCTCGCATGTGGGATCGGGTGGACATGCTGACTTGGCGCAACACGTCTGTTTACCAGGCGATTTGCACCTTAGATGGCAGGTTAAAGTTCCTCC
CAAAAATGATA

Xho I / His Tag / Bpu1102 I

CTCGAGCACCACCACCACCACCACTGAGATCCGGCTGCTAACAAAGCCCGAAAGGAAGCTGAGTTGGCTGCTGCCACCGCTGAGCAATAACTAGCATAACC

L E H H H H H H Stop

T7 Terminator

CCTTGGGGCCTCTAAACGGGTCTTGAGGGGTTTTTTGCTGAAAGGAGGAACTATATCCGGATTGGCGAATGGGACGCGCCCTGTAGCGGCGCATTAAGCGCG

FIG. 19 pET 24b myc-ORF 5 5'-His (MN30100)

```
                                                                     Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT   100

      lac operator            Xba 1                    RBS             Nde 1       Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA   200
                                                                Start  M  E  Q  K  L  I  S  E  E

               Ecor 1    BamH I        MN ORF5 5' (underlined)
GGATCTGAATCGATCCATGAATTCTAGTGGATCCATGAACGCCAACAGCACCAGCAGCTCACATTTTCAGTTGATTTATAACTTGACGCTATGCGAGCTG   300
  D  L  N  R  S  M  N  S  S  G  S  M  N  A  N  S  T  S  S  S  H  F  Q  L  I  Y  N  L  T  L  C  E  L

                                        Xho I       His Tag
AATGGCACAGATTGGCTGGCTGGAAAGTTTGATTGGGCAGTGCTCGAGCACCACCACCACCACCACTGAGATCCGGCTGCTAACAAAGCCCGAAAGGAAG   400
 N  G  T  D  W  L  A  G  K  F  D  W  A  V  L  E  H  H  H  H  H  H Stop

               Bpu1102 I                 T7 Terminator
CTGAGTTGGCTGCTGCCACCGCTGAGCAATAACTAGCATAACCCCTTGGGGCCTCTAAACGGGTCTTGAGGGGTTTTTTGCTGAAAGGAGGAACTATATC   500

CGGATTGGCGAATGGGACGCGCCCTGTAGCGGCGCATTAAGCGCG                                                         545
```

FIG. 20 pET 24b myc-ORF 5 5'-His (VR-2332)

```
                                                              Bgl II                 T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

      lac operator         Xba 1                     RBS          Nde 1     Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                  Start  M  E  Q  K  L  I  S  E  E

             Ecor 1  BamH I     ORF5 5' (underlined)
GGATCTGAATCGATCCATGAATTCTAGTGGATCCATGAACGCCAGCAACGACAGCAGCTCCCATCTACAGCTGATTTACAACTTGACGCTATGTGAGCTG 300
 D  L  N  R  S  M  N  S  S  G  S  M  N  A  S  N  D  S  S  S  H  L  Q  L  I  Y  N  L  T  L  C  E  L

                                       Xho 1       His Tag
AATGGCACAGATTGGCTAGCTAACAAATTTGATTGGGCAGTGCTCGAGCACCACCACCACCACCACTGAGATCCGGCTGCTAACAAAGCCCGAAAGGAAG 400
N  G  T  D  W  L  A  N  K  F  D  W  A  V  L  E  H  H  H  H  H  H Stop

             Bpu1102 I                   T7 Terminator
CTGAGTTGGCTGCTGCCACCGCTGAGCAATAACTAGCATAACCCCTTGGGGCCTCTAAACGGGTCTTGAGGGGTTTTTTGCTGAAAGGAGGAACTATATC 500

CGGATTGGCGAATGGGACGCGCCCTGTAGCGGCGCATTAAGCGCG 545
```

FIG. 21 pET 24b myc-ORF 5 total-His (VR-2332)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 RBS Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 BamH I ORF5 5' Ectodomain 1
GGATCTGAATCGATCCATGAATTCTAGTGGATCCATGAACGCCAGCAACGACAGCAGCTCCCATCTACAGCTGATTTACAACTTGACGCTATGTGAGCTG 300
D L N R S M N S S G S M N A S N D S S S H L Q L I Y N L T L C E L Xho 1 GGGGS Linker ORF5 5' Ectodomain 2 Xho 1
AATGGCACAGATTGGCTAGCTAACAAATTTGATTGGGCAGTGCTCGAGGGAGGAGGCGGCAGCGGGTTTGTTCACGGGCGGTATGTCCTAAGTCTCGAGC 400
N G T D W L A N K F D W A V L E G G G G S G F V H G R Y V L S L E His Tag Bpu1102 I T7 Terminator
ACCACCACCACCACCACTGAGATCCGGCTGCTAACAAAGCCCGAAAGGAAGCTGAGTTGGCTGCTGCCACCGCTGAGCAATAACTAGCATAACCCCTTGG 500
H H H H H H Stop T7 Terminator
GGCCTCTAAACGGGTCTTGAGGGGTTTTTTGCTGAAAGGAGGAACTATATCCGGATTGGCGAATGGGACGCGCCCTGTAGCGGCGCATTAAGCGCG 500

FIG. 22 pET 24b myc-ORF 5 3'-His (VR-2332)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 RBS Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 BamH I ORF5 3'fragment (underlined)
GGATCTGAATCGATCCATGAATTCTAGTGGATCCATGAAGAATTGCATGTCCTGGCGCTACGCGTGTACCAGATATACCAACTTTCTTCTGGACACTAAG 300
D L N R S M N S S G S M K N C M S W R Y A C T R Y T N F L L D T K GGCAGACTCTATCGTTGGCGGTCGCCTGTCATCATAGAGAAAAGGGGCAAAGTTGAGGTCGAAGGTCATCTGATCGACCTCAAAAGAGTTGTGCTTGATG 400
G R L Y R W R S P V I I E K R G K V E V E G H L I D L K R V V L D Xho 1 His Tag
GTTCCGTGGCAACCCCTATAACCAGAGTTTCAGCGGAACAATGGGGTCGTCCTCTCGAGCACCACCACCACCACCACTGAGATCCGGCTGCTAACAAAGC 500
G S V A T P I T R V S A E Q W G R P L E H H H H H H Stop

Bpu1102 I T7 Terminator
CCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGA 600

GGAACTATATCCGGATTGGCGAATGGGACGCGCCCTGTAGCGGCGCATTAAGCGCG 656

FIG. 23 pET 24b myc-ORF 5 3'-His (MN30100)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 RBS Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 BamH I MN ORF5 3' Endodomain (underlined)
GGATCTGAATCGATCCATGAATTCTAGTGGATCCATGAAGAACTGCATGTCCTGGCGCTATTCATGTACCAGATACACCAACTTCCTCCTAGACACTAAG 600
D L N R S M N S S G S M K N C M S W R Y S C T R Y T N F L L D T K GGCAGACTCTATCGTTGGCGGTCGCCTGTCATTATAGAGAAAGGGGGTAAGGTTGAGGTCGAAGGCCACCTGATCGACCTCAAAAGAGTTGTGCTTGATG 700
G R L Y R W R S P V I I E K G G K V E V E G H L I D L K R V V L D Xho 1 His Tag
GTTCCGTGGCAACACCTTTAACCAGAGTTTCAGCGGAACAATGGGGTCGTCCTCTCGAGCACCACCACCACCACCACTGAGATCCGGCTGCTAACAAAGC 500
G S V A T P L T R V S A E Q W G R P L E H H H H H H Stop

Bpu1102 I T7 Terminator
CCGAAAGGAAGCTGAGTTGGCTGCTGCCACCGCTGAGCAATAACTAGCATAACCCCTTGGGGCCTCTAAACGGGTCTTGAGGGGTTTTTTGCTGAAAGGA 600

GGAACTATATCCGGATTGGCGAATGGGACGCGCCCTGTAGCGGCGCATTAAGCGCG 656

FIG. 24 pET 24b myc-ORF 5+6-His (VR-2332)

```
                                                                                                                Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100

           lac operator            Xba 1                      RBS                Nde 1        Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                               Start   M  E  Q  K  L  I  S  E  E

                EcoR 1    BamH I                        ORF5 5' Ectodomain 1
GGATCTGAATCGATCCATGAATTCTAGTGGATCCATGAACGCCAGCAACGACAGCAGCTCCCATCTACAGCTGATTTACAACTTGACGCTATGTGAGCTG  300
  D  L  N  R  S  M  N  S  S  G  S  M  N  A  S  N  D  S  S  S  H  L  Q  L  I  Y  N  L  T  L  C  E  L

                                         Xho 1 GGGGS Linker     ORF5 5' Ectodomain 2        GGGGS Linker
AATGGCACAGATTGGCTAGCTAACAAATTTGATTGGGCAGTGCTCGAGGGAGGAGGCGGCAGCGGGTTTGTTCACGGGCGGTATGTCCTAAGTGGAGGAG  400
 N  G  T  D  W  L  A  N  K  F  D  W  A  V  L  E  G  G  G  G  S  G  F  V  H  G  R  Y  V  L  S  G  G

                    ORF6  Ectodomain  2                              GGGGS  Linker   ORF6   Ectodomain  2
GCGGCAGCATGGGGTCGTCCTTAGATGACTTCTGTCATGATAGCACGGCTCCACAAAAGGTGCTTGGAGGAGGCGGCAGCGCGCACTTTCAGAGTACAAA  500
G  G  S  M  G  S  S  L  D  D  F  C  H  D  S  T  A  P  Q  K  V  L  G  G  G  G  S  A  H  F  Q  S  T  N

   Xho  1    His Tag                                                                 Bpu1102 I
TAAGCTCGAGCACCACCACCACCACCACTGAGATCCGGCTGCTAACAAAGCCCGAAAGGAAGCTGAGTTGGCTGCTGCCACCGCTGAGCAATAACTAGCA  400
  K  L  E  H  H  H  H  H  H  Stop

          T7 Terminator
TAACCCCTTGGGGCCTCTAAACGGGTCTTGAGGGGTTTTTTGCTGAAAGGAGGAACTATATCCGGATTGGCGAATGGGACGCGCCCTGTAGCGGCGCATT  500
```

FIG. 25 pET 24b myc-ORF 7-His (VR-2332)

```
                                                                Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

       lac operator         Xba 1                        Ribz       Nde 1    Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                  Start  M  E  Q  K  L  I  S  E  E

               Ecor 1    BamH I     ORF 7 (underline)
GGATCTGAATCGATCCATGAATTCTAGTGGATCCATGCCAAATAACAACGGCAAGCAGCAGAAGAGAAAGAAGGGGGATGGCCAGCCAGTCAATCAGCTG 300
 D  L  N  R  S  M  N  S  S  G  S  M  P  N  N  N  G  K  Q  Q  K  R  K  K  G  D  G  Q  P  V  N  Q  L

TGCCAGATGCTGGGTAAGATCATCGCTCAGCAAAACCAGTCCAGAGGCAAGGGACCGGGAAAGAAAAATAAGAAGAAAAACCCGGAGAAGCCCCATTTTC 400
 C  Q  M  L  G  K  I  I  A  Q  Q  N  Q  S  R  G  K  G  P  G  K  K  N  K  K  K  N  P  E  K  P  H  F

CTCTAGCGACTGAAGATGATGTCAGACATCACTTTACCCCTAGTGAGCGGCAATTGTGTCTGTCGTCAATCCAGACCGCCTTTAATCAAGGCGCTGGGAC 500
P  L  A  T  E  D  D  V  R  H  H  F  T  P  S  E  R  Q  L  C  L  S  S  I  Q  T  A  F  N  Q  G  A  G  T

TTGCACCCTGTCAGATTCAGGGAGGATAAGTTACACTGTGGAGTTTAGTTTGCCTACGCATCATACTGTGCGCCTGATCCGCGTCACAGCATCACCCTCA 600
  C  T  L  S  D  S  G  R  I  S  Y  T  V  E  F  S  L  P  T  H  H  T  V  R  L  I  R  V  T  A  S  P  S

  Xho I     His Tag                                                               Bpu1102 I
GCACTCGAGCACCACCACCACCACCACTGAGATCCGGCTGCTAACAAAGCCCGAAAGGAAGCTGAGTTGGCTGCTGCCACCGCTGAGCAATAACTAGCAT 700
 A  L  E  H  H  H  H  H  H  Stop

          T7 Terminator
AACCCCTTGGGGCCTCTAAACGGGTCTTGAGGGGTTTTTTGCTGAAAGGAGGAACTATATCCGGATTGGCGAATGGGACGCGCCCTGTAGCGGCGCATTA 800

AGCGCG                                                                                               806
```

FIG. 26 pET 24b myc-NSP 2HP-His (VR-2332)

```
                                                               Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

       lac operator         Xba 1                   RBS           Nde 1      Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                  Start M  E  Q  K  L  I  S  E  E

           Ecor 1  BamH I                   NSP 2HP (underlined)
GGATCTGAATCGATCCATGAATTCTAGTGGATCCGGCAGCCCGGTTTCATTAGGCGGCGATGTCCCTAACAGTTGGGAAGATTTGGCTGTTAGTAGCCCC 300
 D  L  N  R  S  M  N  S  S  G  S  G  S  P  V  S  L  G  G  D  V  P  N  S  W  E  D  L  A  V  S  S  P

TTTGATCTCCCGACCCCACCTGAGCCGGCAACACCTTCAAGTGAGCTGGTGATTGTGTCCTCACCGCAATGCATCTTCAGGCCGGCGACACCCTTGAGTG 400
 F  D  L  P  T  P  P  E  P  A  T  P  S  S  E  L  V  I  V  S  S  P  Q  C  I  F  R  P  A  T  P  L  S

AGCCGGCTCCAATTCCCGCACCTCGCGGAACTGTGTCTCGACCGGTGACACCCTTGAGTGAGCCGATCCCTGTGCCCGCACCGCGGCGTAAGTTTCAGCA 500
E  P  A  P  I  P  A  P  R  G  T  V  S  R  P  V  T  P  L  S  E  P  I  P  V  P  A  P  R  R  K  F  Q  Q

GGTGAAAAGATTGAGTTCGGCGGCGGCAATCCCACCGTACCAGGACGAGCCCCTGGATTTGTCTGCTTCCTCACAGGCTGAATATGAGGCCTCTCCCCCA 600
 V  K  R  L  S  S  A  A  A  I  P  P  Y  Q  D  E  P  L  D  L  S  A  S  S  Q  A  E  Y  E  A  S  P  P

GCACCGCCGCAGAGCGGGGGCGTTCTGGGAGTAGAGGGGCATGAAGCTGAGGAAACCCTGAGTGAAATCTCGGACATGTCGGGTAACATTAAACCTGCGT 700
 A  P  P  Q  S  G  G  V  L  G  V  E  G  H  E  A  E  E  T  L  S  E  I  S  D  M  S  G  N  I  K  P  A

           Xho I  His Tag                                                            Bpu1102 I
CCGTGTCATCACTCGAGCACCACCACCACCACCACTGAGATCCGGCTGCTAACAAAGCCCGAAAGGAAGCTGAGTTGGCTGCTGCCACCGCTGAGCAATA 800
S  V  S  S  L  E  H  H  H  H  H  H  Stop

                T7 Terminator
ACTAGCATAACCCCTTGGGGCCTCTAAACGGGTCTTGAGGGGTTTTTTGCTGAAAGGAGGAACTATATCCGGATTGGCGAATGGGACGCGCCCTGTAGCG 900

GCGCATT                                                                                              907
```

FIG. 27 pET 24b myc-NSP 2 S1 HP-His (VR-2332)

```
                                                                Bgl II            T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

          lac operator      Xba 1                    RBS          Nde 1    Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                     Start M  E  Q  K  L  I  S  E  E

                   Ecor 1   BamH I                 NSP 2 S1 HP (underlined)
GGATCTGAATCGATCCATGAATTCTAGTGGATCCGCGACTGCTACAGTCGCTGGCCGCGCTTTGTCCGTTCGTGAAACCCGGCAGGCCAAGGAGCACGAG 300
  D  L  N  R  S  M  N  S  S  G  S  A  T  A  T  V  A  G  R  A  L  S  V  R  E  T  R  Q  A  K  E  H  E

                                    Xho 1       His Tag
GTTGCCGGCGCCAACAAGGCTGAGCACCTCAAACACCTCGAGCACCACCACCACCACCACTGAGATCCGGCTGCTAACAAAGCCCGAAAGGAAGCTGAGT 400
 V  A  G  A  N  K  A  E  H  L  K  H  L  E  H  H  H  H  H  H Stop

              Bpu1102 I                T7 Terminator
TGGCTGCTGCCACCGCTGAGCAATAACTAGCATAACCCCTTGGGGCCTCTAAACGGGTCTTGAGGGGTTTTTTGCTGAAAGGAGGAACTATATCCGGATT 500

GGCGAATGGGACGCGCCCTGTAGCGGCGCATT                                                                     532
```

FIG. 28 pET 24b myc-NSP 2 S2 HP-His (VR-2332)

Bgl II … T7 Promoter

AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator … Xba 1 … RBS … Nde 1 … Myc Tag

ATAGGGGAATTGTGAGCGGATAACAATTCCCCTCTAGAAATAATTTTGTTTAACTTTAAGAAGGAGATATACATATGGAACAAAAACTCATCTCAGAAGA 200

Start M E Q K L I S E E

Ecor 1 … BamH I … NSP 2 S2 HP (underlined)

GGATCTGAATCGATCCATGAATTCTAGTGGATCCGCAAAGATTGACCTGTACCTCCGTGGTGCAACAAATCTTGAAGAATGCTTGGCCAGGCTTGAGAAA 300

D L N R S M N S S G S A K I D L Y L R G A T N L E E C L A R L E K

Xho 1 … His Tag

GCGCGCCCGCCACGCGTAATCGACACCTCCTTTGATTGGGATCTCGAGCACCACCACCACCACCACTGAGATCCGGCTGCTAACAAAGCCCGAAAGGAAG 400

A R P P R V I D T S F D W D L E H H H H H H Stop

Bpu1102 I … T7 Terminator

CTGAGTTGGCTGCTGCCACCGCTGAGCAATAACTAGCATAACCCCTTGGGGCCTCTAAACGGGTCTTGAGGGGTTTTTTGCTGAAAGGAGGAACTATATC 500

CGGATTGGCGAATGGGACGCGCCCTGTAGCGGCGCATT 538

FIG. 29 pET 24b myc-ORF 6 5' total-His (VR-2332)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 RBS Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 BamH I 5' ORF6 Ectodomain 1 GGGGS Linker
GGATCTGAATCGATCCATGAATTCTAGTGGATCCATGGGGTCGTCCTTAGATGACTTCTGTCATGATAGCACGGCTCCACAAAAGGTGCTTGGAGGAGGC 300
D L N R S M N S S G S M G S S L D D F C H D S T A P Q K V L G G G

3' ORF6 Ectodomain 2 Xho 1 His Tag
GGCAGCGCGCACTTTCAGAGTACAAATAAGCTCGAGCACCACCACCACCACCACTGAGATCCGGCTGCTAACAAAGCCCGAAAGGAAGCTGAGTTGGCTG 400
G S A H F Q S T N K L E H H H H H H Stop Bpu1102 I T7 Terminator
CTGCCACCGCTGAGCAATAACTAGCATAACCCCTTGGGGCCTCTAAACGGGTCTTGAGGGGTTTTTTGCTGAAAGGAGGAACTATATCCGGATTGGCGAA 500

TGGGACGCGCCCTGTAGCGGCGCATT 526

FIG. 30 pET 24b myc-ORF 6 3'-His (VR-2332)

```
                                                                     Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

      lac operator          Xba 1                       RBS              Nde 1       Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                        Start  M  E  Q  K  L  I  S  E  E

                  EcoR 1   BamH I                      ORF 6 3'  (underline)
GGATCTGAATCGATCCATGAATTCTAGTGGATCCTCAGCCATAGAAACCTGGAAATTCATCACCTCCAGATGCCGTTTGTGCTTGCTAGGCCGCAAGTAC 300
  D  L  N  R  S  M  N  S  S  G  S  S  A  I  E  T  W  K  F  I  T  S  R  C  R  L  C  L  L  G  R  K  Y

ATTCTGGCCCCTGCCCACCACGTTGAAAGTGCCGCACGGTTTCATCCGATTGCGGCAAATGATAACCACGCATTTGTCGTCCGGCGTCCCGGCTCCACTA 400
 I  L  A  P  A  H  H  V  E  S  A  A  R  F  H  P  I  A  A  N  D  N  H  A  F  V  V  R  R  P  G  S  T

CGGTCAACGGCACATTGGTGCCCGGGTTAAAAAGCCTCGTGTTGGGTGGCAGAAAAGCTGTTAAACAGGGAGTGGTAAACCTTGTCAAATATGCCAAACT 500
T  V  N  G  T  L  V  P  G  L  K  S  L  V  L  G  G  R  K  A  V  K  Q  G  V  V  N  L  V  K  Y  A  K  L

Xho 1   His Tag                                                          Bpu1102 I
CGAGCACCACCACCACCACCACTGAGATCCGGCTGCTAACAAAGCCCGAAAGGAAGCTGAGTTGGCTGCTGCCACCGCTGAGCAATAACTAGCATAACCC 600
  E  H  H  H  H  H  H Stop

    T7 Terminator
CTTGGGGCCTCTAAACGGGTCTTGAGGGGTTTTTTGCTGAAAGGAGGAACTATATCCGGATTGGCGAATGGGACGCGCCCTGTAGCGGCGCATT 694
```

FIG. 31 pET 24b myc-ORF 7-His (Lelystad)

```
                                                    Bgl II               T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

       lac operator          Xba 1                Ribz          Nde 1    Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                     Start  M E Q K L I S E E

                EcoR 1   BamH I      ORF 7 (underline)
GGATCTGAATCGATCCATGAATTCTAGTGGATCCATGGCCGGTAAAAACCAGAGCCAGAAGAAAAAGAAAAGTACAGCTCCGATGGGGAATGGCCAGCCA 300
 D L N R S M N S S G S M A G K N Q S Q K K K K S T A P M G N G Q P

GTCAATCAACTGTGCCAGTTGCTGGGTGCAATGATAAAGTCCCAGCGCCAGCAACCTAGGGGAGGACAGGCCAAAAAGAAAAAGCCTGAGAAGCCACATT 400
 V N Q L C Q L L G A M I K S Q R Q Q P R G G Q A K K K K P E K P H

TTCCCCTGGCTGCTGAAGATGACATCCGGCACCACCTCACCCAGACTGAACGCTCCCTCTGCTTGCAATCGATCCAGACGGCTTTCAATCAAGGCGCAGG 500
F P L A A E D D I R H H L T Q T E R S L C L Q S I Q T A F N Q G A G

AACTGCGTCGCTTTCATCCAGCGGGAAGGTCAGTTTTCAGGTTGAGTTTATGCTGCCGGTTGCTCATACAGTGCGCCTGATTCGCGTGACTTCTACATCC 600
 T A S L S S S G K V S F Q V E F M L P V A H T V R L I R V T S T S

                Xho I    His Tag                                                           Bpu1102 I
GCCAGTCAGGGTGCAAGTCTCGAGCACCACCACCACCACCACTGAGATCCGGCTGCTAACAAAGCCCGAAAGGAAGCTGAGTTGGCTGCTGCCACCGCTG 700
 A S Q G A S L E H H H H H H Stop

                      T7 Terminator
AGCAATAACTAGCATAACCCCTTGGGGCCTCTAAACGGGTCTTGAGGGGTTTTTTGCTGAAAGGAGGAACTATATCCGGATTGGCGAATGGGACGCGCCC 800

                                  TGTAGCGGCGCATTAAGCGCG 821
```

FIG. 36 pET 24b myc-NSP 2P-His (Lelystad)

Bgl II | T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator | Xba 1 | Ribz | Nde 1 | Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 | BamH I
GGATCTGAATCGATCCATGAATTCTAGTGGATCC
D L N R S M N S S G S NSP 2P (1899 bps underline)

GCTGCCGGCAAACGGGCTCGTGCTAAGCGTGCCGCTAAAAGTGAGAAGGATTCGGCTCCCACCCCCAAGGTTGCCCTGCCGGTCCCCACCTGTGGAATTACCACCTACTCTCCACCGACAGACGGGTCTTGTGGTTGGCATGTCC
TTGCCGCCATAATGAACCGGATGATAAATGGTGACTTCACGTCCCCTCTGACTCAGTACAACAGACCAGAGGATGATTGGGCTTCTGATTATGATCTTGTTCAGGCGATTCAATGTCTACGACTGCCTGCTACCGTGGTTCGGAA
TCGCGCCTGTCCTAACGCCAAGTACCTTATAAAACTTAACGGAGTTCACTGGGAGGTAGAGGTGAGGTCTGGAATGGCTCCTCGCTCCCTTTCTCGTGAATGTGTGGTTGGCGTTTGCTCTGAAGGCTGTGTCGCACCGCCTTAT
CCAGCAGACGGGCTACCTAAACGTGCACTCGAGGCCTTGGCGTCTGCTTACAGACTACCCTCCGATTGTGTTAGCTCTGGTATTGCTGACTTTCTTGCTAATCCACCTCCTCAGGAATTCTGGACCCTCGACAAAATGTTGACCT
CCCCGTCACCAGAGCGGTCCGGCTTCTCTAGTTTGTATAAATTACTATTAGAGGTTGTTCCGCAAAAATGCGGTGCCACGGAAGGGGCTTTCATCTATGCTGTTGAGAGGATGTTGAAGGATTGTCCGAGCTCCAAACAGGCCAT
GGCCCTTCTGGCAAAAATTAAAGTTCCATCCTCAAAGGCCCCGTCTGTGTCCCTGGACGAGTGTTTCCCTACGGATGTTTTAGCCGACTTCGAGCCAGCATCTCAGGAAAGGCCCCAAAGTTCCGGCGCTGCTGTTGTCCTGTGT
TCACCGGATGCAAAAGAGTTCGAGGAAGCAGCCCCGGAAGAAGTTCAAGAGAGTGGCCACAAGGCCGTCCACTCTGCACTCCTTGCCGAGGGTCCTAACAATGAGCAGGTACAGGTGGTTGCCGGTGAGCAACTGAAGCTCGGCG
GTTGTGGTTTGGCAGTCGGGAATGCTCATGAAGGTGCTCTGGTCTCAGCTGGTCTAATTAACCTGGTAGGCGGGAATTTGTCCCCCTCAGACCCCATGAAAGAAAACATGCTCAATAGCCGGGAAGACGAACCACTGGATTTGTC
CCAACCAGCACCAGCTTCCACAACGACCCTTGTGAGAGAGCAAACACCCGACAACCCAGGTTCTGATGCCGGTGCCCTCCCCGTCACCGTTCGAGAATTTGTCCCGACGGGGCCTATACTCTGTCATGTTGAGCACTGCGGCACG
GAGTCGGGCGACAGCAGTTCGCCTTTGGATCTATCTGATGCGCAAACCCTGGACCAGCCTTTAAATCTATCCCTGGCCGCTTGGCCAGTGAGGGCCACCGCGTCTGACCCTGGCTGGGTCCACGGTAGGCGCGAGCCTGTCTTTG
TAAAGCCTCGAAATGCTTTCTCTGATGGCGATTCAGCCCTTCAGTTCGGGGAGCTTTCTGAATCCAGCTCTGTCATCGAGTTTGACCGGACAAAAGATGCTCCGGTGGTTGACGCCCCTGTCGACTTGACGACTTCGAACGAGGC
CCTCTCTGTAGTCGATCCTTTCGAATTTGCCGAACTCAAGCGCCCGCGTTTCTCCGCACAAGCCTTAATTGACCGAGGCGGTCCACTTGCCGATGTCCATGCAAAAATAAAGAACCGGGTATATGAACAGTGCCTCCAAGCTTGT
GAGCCCGGTAGTCGTGCAACCCCAGCCACCAGGGAGTGGCTCGACAAAATGTGGGATAGGGTGGACATGAAAACTTGGCGCTGCACCTCGCAGTTCCAAGCTGGTCGCATTCTTGCGTCCCTCAAATTCCTCCCTGACATGATTC
AAGACACACCGCCT

Xho I | His Tag | Bpu1102 I
CTCGAGCACCACCACCACCACCACTGAGATCCGGCTGCTAACAAAGCCCGAAAGGAAGCTGAGTTGGCTGCTGCCACCGCTGAGCAATAACTAGCATAACC
L E H H H H H H Stop T7 Terminator
CCTTGGGGCCTCTAAACGGGTCTTGAGGGGTTTTTTGCTGAAAGGAGGAACTATATCCGGATTGGCGAATGGGACGCGCCCTGTAGCGGCGCATTAAGCGCG

FIG. 37 pET 24b myc-NSP 2P-His (JA 142)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 Ribz Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E EcoR 1 BamH I
GGATCTGAATCGATCCATGAATTCTAGTGGATCC
D L N R S M N S S G S

NSP 2P (2151 bps underline)

GCTGGAAAGAGAGCAAGGAAAGCACGCTCTGGTATGACCACCACAGTCGCTCACCGCGCCTTGCCCGCTCGTGAAATCCAGCAAGCCAAAAAGCACGAGGATGCCGGCGCTGATAAGGCTGTGCATCTCAGGCACTATTCTCCGC
CTGCCGACGGGAACTGTCCTTGGCACTGCATTTCCGCCATCGCCAACCGAATGGTGAATTCCAAATTTGAAACTACTCTTCCCGAGAGGGTGAGACCTTCAGATGACTGGGCTACTGACGAGGACCTTGTGAACACCATCCAAAT
TCTCAAGCTCCCTGCGGCCTTGGACAGGAACGGTGCTTGTGTTGGCGCCAAATACGTGCTTAAGCTGGAAGGCGAGCATTGGACTGTCTCTGTGACCCTTGGGATGTCCCCTTCTTTGCTCCCCCTTGAATGTGTTCAGGGCTGT
TGTGAGCATAAGAGCGGACTTGGTCCCCCAGATGCGGTCGAAGTTTTCGGATTTGACCCTGCCTGCCTTGACCGACTGGCTGAGGTAATGCACTTGCCTAGCAGTGTCATCCCAGCTGCTCTGGCCGAAATGTCCGGCGACCCCA
ACTGTCCGGCTTCCCCGGTCACTACTGTGTGGACTGTTTCACAATTCTTTGCCCGCCACAGAGGAGGAGAGCACCCTGATCAGGTGCGCTTAGGAAAAATCATCAGCCTTTGTCAAGTTGTTGAGGAATGCTGTTGCCATCAGAA
TAAAACCAACCGGGCCACCCCGGAAGAGGTTGCGGCAAGGATTGATCAGTACCTCCATGGTGCAACAAGTCTTGAAGAATGCTTGATTAGGCTTGAGAGGGTTTGCCCGCCGAGCGCTGCGGACACCTTCTTTGATTGGAATGTT
GTGCTCCCTGGGGTTGGGGCTTCAACTCAGACAACCAAACAGCTCCATGTCAACCAGTGCCGCGCTCTGGTTCCTGTCGTGACTCAAGAGCCTTTGGACAAAGACTCAGTCCCTCTGACCGCCTTCTCGCTGTCCAATTGCTACT
ATCCTGCACAAGGTGACGAGGTTCGTCACCGTGAGAGGCTAAACTCCGTACTCTCTAAGCTGGAGGGGGTTGTTCGTGAGGAATATGGGCTCACGCCAACTGAACCTGGCCCGCGACCCGCACTACCGAACGGGCTCGTCGAACT
TAAAGACCAGATGGAGGAGGATCTGCTGAAACTAGTCAACGCCCAGGCAACTTCAGAAATGATGGCCTGGGCAGCCGAGCAGGTTGATCTGAAAGCTTGGGTCAAAAACTACCCACGGTGGACACCGCCACCCCCTCCACCAAGA
GTTCAGCCTCGAAAAACAAAGTCTGTCAAGAGCTTGCCAGGGAACAAACCTGTCCCCGCTCCACGCAGGAAGGTCAGATCTGATTGTGGCAGCCCGATTTTGATGGGCGACAATGTTCCTGACGGTCGGGAAGATTTGACTGTTG
GTGGCCCCCTTGATCTTTCGACACCATCCGAGCCGATGACACCTCTGAGTGAGCCTGCACTTATGCCCGCGTTGCAATATATTTCTAGGCCAGTGACATCTTTGAGTGTGCTGGCCCCAGTTCCTGCACCGCGTAGAACTGTGTC
CCGACCGGTGACGCCCTTGAGTGAGCCAATTTTTGTGTCTGCACCGCGACACAAATTTCAGCAGGTGGAAGAAGCGAATCTGGCGGCAACAACGCTGACGCACCAGGACGAACCTCTAGATTTGTCTGCATCCTCACAGACTGAA
TATGAGGCTTCTCCCCTAACACCACTGCAGAACATGGGTATTCTGGAGGTGGGGGGCAAGAAGCTGAGGAAGTTCTGAGTGAAATCTCGGATACACTGAATGACATCAACCCTGCACCTGTGTCATCAAGCAGCTCCCTGTCAA
GTGTTAAGATCACACGCCCAAAACACTCTGCTCAAGCCATCATTGACTCGGGCGGGCCCTGCAGTGGGCATCTCCGAAGGGAAAAAGAAGCATGCCTCAGCATCATGCGTGAGGCTTGTGATGCGGCTAAGCTTAGTGACCCTGC
CACGCAGGAATGGCTTTCTCGCATGTGGGATAGGGTTGACATGCTGACTTGGCGCAACACGTCTGCTTACCAGGCGTTCCGCATCTTAGATGGTAGGTTTGATTTCTCCCAAAGATGATA

Xho I His Tag Bpu1102 I
CTCGAGCACCACCACCACCACCACTGAGATCCGGCTGCTAACAAAGCCCGAAAGGAAGCTGAGTTGGCTGCTGCCACCGCTGAGCAATAACTAGCATAACC
L E H H H H H H Stop

T7 Terminator
CCTTGGGGCCTCTAAACGGGTCTTGAGGGGTTTTTTGCTGAAAGGAGGAACTATATCCGGATTGGCGAATGGGACGCGCCCTGTAGCGGCGCATTAAGCGCG

FIG. 38 pET 24b myc-NSP 2HP-His (ATP)

```
                                                                Bgl II                    T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

         lac operator       Xba 1                      RBS           Nde 1      Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                   Start   M  E  Q  K  L  I  S  E  E

                EcoR 1   BamH I                    NSP 2HP (underlined)
GGATCTGAATCGATCCATGAATTCTAGTGGATCCGGCAGCCCGATTTTGATGGGCGACAATGTTCCTGACGGTCGGGAAGATTTGCCTGTTGGTGGCCCC 300
  D  L  N  R  S  M  N  S  S  G  S  G  S  P  I  L  M  G  D  N  V  P  D  G  R  E  D  L  P  V  G  G  P

CTTGATCTTTCGACACCATCCGAGCCGATGACACCTCTGAGTGAGCCTGCACCTATGCCCGCGTTGCAATATATTTCTAGGCCAGTGACACCTTTGAGTG 400
 L  D  L  S  T  P  S  E  P  M  T  P  L  S  E  P  A  P  M  P  A  L  Q  Y  I  S  R  P  V  T  P  L  S

AGCTGGCCCCAGTACCTGCACCGCGTAGAACTGTGTCCCGACCGGTGACGCCCTTGAGTGAGCCAATTTTTGTGTCTGCACCGCGACACAAATTTCGGCA 500
E  L  A  P  V  P  A  P  R  R  T  V  S  R  P  V  T  P  L  S  E  P  I  F  V  S  A  P  R  H  K  F  R  Q

GGTGGAAGAAGCGAATCTGGCGGCAACAATGCTGACGCACCAGGACGAACCTCTAGATTTGTCTGCATCCTCACAGACTGAATATGAGGCTTCTCCCCTA 600
 V  E  E  A  N  L  A  A  T  M  L  T  H  Q  D  E  P  L  D  L  S  A  S  S  Q  T  E  Y  E  A  S  P  L

ACACCACTGCAGAACATGGGTATTCTTGAGGTGGGGGGGCAAGAAGCTGAGGAAGTTCTGAGTGAAAACTCGGATACACTGAATGACATCAACCCTGCAC 700
 T  P  L  Q  N  M  G  I  L  E  V  G  G  Q  E  A  E  E  V  L  S  E  N  S  D  T  L  N  D  I  N  P  A

           Xho 1     His Tag                                                             Bpu1102 I
CTGTGTCATCACTCGAGCACCACCACCACCACCACTGAGATCCGGCTGCTAACAAAGCCCGAAAGGAAGCTGAGTTGGCTGCTGCCACCGCTGAGCAAT 800
P  V  S  S  L  E  H  H  H  H  H  H  Stop

           T7 Terminator
AACTAGCATAACCCCTTGGGGCCTCTAAACGGGTCTTGAGGGGTTTTTTGCTGAAAGGAGGAACTATATCCGGATTGGCGAATGGGACGCGCCCTGTAG 900

                                     CGGCGCATT 909
```

FIG. 39 pET 24b myc-ORF 5 3'-His (Lelystad)

```
                                                                    Bgl II                 T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100

      lac operator         Xba 1                    RBS          Nde 1     Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                 Start  M  E  Q  K  L  I  S  E  E

                   Ecor 1   BamH I        ORF 5 3' (underline)
GGATCTGAATCGATCCATGAATTCTAGTGGATCCTGCATGGCCTGCCGCTATGCCCGTACCCGGTTTACCAACTTCATTGTGGACGACCGGGGGAGAGTT 300
  D  L  N  R  S  M  N  S  S  G  S  C  M  A  C  R  Y  A  R  T  R  F  T  N  F  I  V  D  D  R  G  R  V

CATCGATGGAAGTCTCCAATAGTGGTAGAAAAATTGGGCAAAGCCGAAGTCGATGGCAACCTCGTCACCATCAAACATGTCGTCCTCGAAGGGGTTAAAG 400
 H  R  W  K  S  P  I  V  V  E  K  L  G  K  A  E  V  D  G  N  L  V  T  I  K  H  V  V  L  E  G  V  K

                                            Xho I    His Tag
CTCAACCCTTGACGAGGACTTCGGCTGAGCAATGGGAGGCCCTCGAGCACCACCACCACCACCACTGAGATCCGGCTGCTAACAAAGCCCGAAAGGAAGC 500
 A  Q  P  L  T  R  T  S  A  E  Q  W  E  A  L  E  H  H  H  H  H  H Stop

                   Bpu1102 I                   T7 Terminator
TGAGTTGGCTGCTGCCACCGCTGAGCAATAACTAGCATAACCCCTTGGGGCCTCTAAACGGGTCTTGAGGGGTTTTTTGCTGAAAGGAGGAACTATATC 600

CGGATTGGCGAATGGGACGCGCCCTGTAGCGGCGCATTAAGCGCG 645
```

FIG. 40 pET 24b myc-Orf 6 3'-His (Lelystad)

```
                                                                                           Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100

      lac operator           Xba 1                     RBS          Nde 1     Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                             Start   M  E  Q  K  L  I  S  E  E

                  EcoR 1   BamH I             ORF 6 3' (underline)
GGATCTGAATCGATCCATGAATTCTAGTGGATCCAGCTTCACAGAGTCATGGAAGTTTATCACTTCCAGATGCAGATTGTGTTGCCTTGGCCGGCGATAC  300
  D  L  N  R  S  M  N  S  S  G  S  S  F  T  E  S  W  K  F  I  T  S  R  C  R  L  C  C  L  G  R  R  Y

ATTCTGGCCCCTGCCCATCACGTAGAAAGTGCTGCAGGTCTCCATTCAATCTCAGCGTCTGGTAACCGAGCATACGCTGTGAGAAAGCCCGGACTAACAT  400
 I  L  A  P  A  H  H  V  E  S  A  A  G  L  H  S  I  S  A  S  G  N  R  A  Y  A  V  R  K  P  G  L  T

CAGTGAACGGCACTCTAGTACCAGGACTTCGGAGCCTCGTGCTGGGCGGCAAACGAGCTGTTAAACGAGGAGTGGTTAACCTCGTCAAGTATGGCCGGCT  500
S  V  N  G  T  L  V  P  G  L  R  S  L  V  L  G  G  K  R  A  V  K  R  G  V  V  N  L  V  K  Y  G  R  L

Xho 1   His Tag                                                             Bpu1102 I
CGAGCACCACCACCACCACCACTGAGATCCGGCTGCTAACAAAGCCCGAAAGGAAGCTGAGTTGGCTGCTGCCACCGCTGAGCAATAACTAGCATAACCC  600
 E  H  H  H  H  H  H  Stop

    T7 Terminator
CTTGGGGCCTCTAAACGGGTCTTGAGGGGTTTTTTGCTGAAAGGAGGAACTATATCCGGATTGGCGAATGGGACGCGCCCTGTAGCGGCGCATT        694
```

FIG. 41

| Linear Equation | Standard Deviation of the Residuals | | |
|---|---|---|---|
| y = -0.065x + 1.066 | 0.19 | ◇ | VR 3 Protein Combination |
| y = -0.100x + 1.592 | 0.18 | ▨ | VR ORF 5+6 chimera |
| y = -0.062x + 0.969 | 0.25 | ◇ | VR NSP 1 |
| y = -0.073x + 1.157 | 0.37 | ○ | VR NSP 2P |
| y = -0.033x + 0.532 | 0.17 | ⊘ | LV NSP 2P |
| y = -0.140x + 2.542 | 0.55 | □ | IDEXX (S/P) |

IDENTIFYING VIRALLY INFECTED AND VACCINATED ORGANISMS

CROSS-REFERENCE TO RELATED APPLICATIONS

This application claims the benefit of U.S. Provisional Application Ser. No. 60/656,192, filed on Feb. 25, 2005, and U.S. Provisional Application Ser. No. 60/581,325, filed on Jun. 18, 2004.

BACKGROUND

1. Technical Field

This document relates to methods and materials involved in identifying virally infected or vaccinated organisms (e.g., vertebrates and mammals). For example, this document relates to methods and material for identifying a mammal (e.g., a pig) having antibodies against a virus such as a porcine reproductive and respiratory syndrome (PRRS) virus.

2. Background Information

Organisms infected with a virus can mount an immune response against that infecting virus. Such an immune response can include the production of antibodies that bind to the virus. The presence of antibodies against a virus can indicate that the organism was exposed to that virus. For example, pigs infected with a PRRS virus can contain pig antibodies that bind PRRS virus.

PRRS is a viral disease of pigs, characterized by reproductive failure in sows (e.g., late-term abortions and stillbirths in sows) and respiratory difficulties in piglets (e.g., interstitial pneumonia in nursery pigs) (Collins et al., *J. Vet. Diagn. Invest.,* 4:117-126 (1992) and Wensvoort et al., *Vet Q.,* 13:121-130 (1991)). It was detected in North America in 1987 (Keffaber, *Am. Assoc. Swine Pract. Newsl.,* 1:1-9 (1989) and Hill, Overview and History of Mystery Swine Disease (Swine Infertility and Respiratory syndrome). In: Proceedings of the Mystery Swine Disease Committee Meeting, October 6, Denver Colo., pp. 29-30. Livestock Conservation Institute, Madison, Wis. (1990)) and in Europe in 1990 (Paton et al., *Vet Rec.,* 128:617 (1991)). The causative agent is a small, enveloped positive-stranded RNA virus that is recovered primarily from alveolar macrophages and blood of infected swine. It is a member of the Arteriviridae, which includes equine arteritis virus (EAV; den Boon et al., *J. Virol.,* 65:2910-2920 (1991)), lactate dehydrogenase elevating virus of mice (LDV; Plagemann and Moennig, *Adv. Vir. Res.,* 41:99-192 (1992)), and simian hemorrhagic fever virus (SHFV; Godeny et al., In Proceedings of the 9th International Congress of Virology, p 22, August 8-13, Glasgow, Scotland (1993) and Plagemann, In Fields Virology, 3$^{rd}$ ed., pp. 1105-1120. Edited by B. N. Fields, D. M. Knipe and P. M. Howley. Philadelphia: Lippincott-Raven (1996)), in the Order Nidovirales (Cavanagh, *Arch. Virol.,* 142:629-633 (1997)). Like other arteriviruses, PRRS virus infects predominantly macrophages and establishes a persistent infection in resident macrophages of numerous tissues (Lawson et al., *Virus Res.,* 51:105-113 (1997) and Christopher-Hennings et al., *J. Vet. Diag. Invest.,* 7:456-464 (1995)).

SUMMARY

This document involves methods and materials related to assessing organisms to determine whether or not the organisms were exposed to a viral vaccine or viral infection. For example, this document provides methods and materials that can be used to determine whether or not an organism (e.g., a member of a swine species such as a pig) contains anti-PRRS virus antibodies. Determining whether or not, for example, pigs contain anti-PRRS virus antibodies can allow pig farmers to identify pigs that can be infected with PRRS virus. This can allow the farmer to separate pigs suspected to be infected with a PRRS virus from those pigs believed to be uninfected. Also, identifying pigs that do not contain anti-PRRS virus antibodies can allow pig farmers to vaccinate the previously uninfected population of pigs as opposed to an entire herd, which could include many previously infected pigs.

In one embodiment, this document provides methods and materials that can be used to determine if a particular organism received a vaccine version of a virus, was infected with a naturally-occurring version of the virus, or is naive with respect to the virus. Differentiating between vaccinated organisms and organisms infected with a naturally-occurring version of the virus can allow clinicians, in the case of humans, and farmers, in the case of farm animals, to determine the immunological origin of each organism's immunity to the virus. For example, a farmer receiving a herd of pigs can determine if the pigs of the herd received a PRRS virus vaccine, were infected with a naturally-occurring version of the virus (e.g., a field isolate of PRRS virus), or are naive with respect to the virus. With this information, the farmer can determine whether the herd need not be vaccinated or whether any uninfected pigs are at risk of being infected from, for example, pigs that were infected with a naturally-occurring version of the virus.

In general, this document features a kit for detecting a swine anti-PRRS virus antibody. The kit includes (a) a polypeptide having an amino acid sequence present in a PRRS virus polypeptide selected from the group consisting of NSP 2 polypeptides and ORF 5 polypeptides, wherein the polypeptide contains an epitope for the swine anti-PRRS virus antibody; and (b) an anti-swine Ig antibody. The polypeptide can be at least eight amino acid residues in length. The polypeptide can contain an amino acid sequence at least 100 amino acids in length that is at least about 80 percent identical to an amino acid sequence encoded by the nucleic acid sequence set forth in SEQ ID NO:5 over the length. The polypeptide can contain an amino acid sequence at least 100 amino acids in length that is at least about 90 percent identical to an amino acid sequence encoded by the nucleic acid sequence set forth in SEQ ID NO:5 over the length. The polypeptide can contain an amino acid sequence at least 20 amino acids in length that is at least about 80 percent identical to a sequence set forth in SEQ ID NO:22 over the length. The polypeptide can contain an amino acid sequence at least 20 amino acids in length that is at least about 90 percent identical to a sequence set forth in SEQ ID NO:22 over the length. The polypeptide can contain the amino acid sequence encoded by the nucleic acid sequence set forth in SEQ ID NO:11. The polypeptide can contain an amino acid sequence of SEQ ID NO:32. The polypeptide can contain an amino acid sequence of SEQ ID NO: 16, 19, 22, 26, 29, 32, 39, 45, 61, or 64. The polypeptide can be a recombinant polypeptide produced in cells not infected with a PRRS virus. The anti-swine Ig antibody can be an anti-swine IgG or IgM antibody. The anti-swine Ig antibody can be a goat anti-swine Ig antibody. The kit can contain a polypeptide having an amino acid sequence present in a PRRS virus NSP 2 polypeptide and a polypeptide having an amino acid sequence present in a PRRS virus ORF 5 polypeptide. The kit can contain a polypeptide having an amino acid sequence present in a PRRS virus ORF 7 polypeptide (e.g., a polypeptide containing an amino acid sequence of SEQ ID NO:36 or 54). The kit can contain a polypeptide having an amino acid sequence present in a PRRS virus ORF 6 polypeptide (e.g., a polypeptide containing an amino acid sequence of SEQ ID NO:32, 48, 51, or 67). The anti-swine Ig antibody can contain an enzyme. The kit can contain a polypeptide having an amino acid sequence present in a PRRS virus NSP 1 polypeptide. The kit can contain a control sample containing swine anti-PRRS virus antibody. The kit can contain a control sample containing swine serum lacking swine anti-PRRS virus antibodies.

In another embodiment, this document features a method for determining whether or not a sample contains a swine anti-PRRS virus antibody. The method includes (a) contacting a polypeptide with the sample under conditions wherein the polypeptide forms a polypeptide:swine anti-PRRS virus antibody complex with an antibody, if present, within the sample, wherein the polypeptide contains an amino acid sequence present in a PRRS virus polypeptide selected from the group consisting of NSP 2 polypeptides and ORF 5 polypeptides, wherein the polypeptide contains an epitope for the swine anti-PRRS virus antibody; and (b) detecting the presence or absence of the complex, wherein the presence of the complex indicates that the sample contains the swine anti-PRRS virus antibody. The sample can be a pig serum sample. The polypeptide can be at least eight amino acid residues in length. The polypeptide can contain an amino acid sequence at least 100 amino acids in length that is at least about 80 percent identical to an amino acid sequence encoded by the nucleic acid sequence set forth in SEQ ID NO:5 over the length. The polypeptide can contain an amino acid sequence at least 20 amino acids in length that is at least about 80 percent identical to a sequence set forth in SEQ ID NO:22 over the length. The polypeptide can contain the amino acid sequence encoded by the nucleic acid sequence set forth in SEQ ID NO:11. The polypeptide can contain an amino acid sequence of SEQ ID NO:32. The polypeptide can contain an amino acid sequence of SEQ ID NO: 16, 19, 22, 26, 29, 32, 39, 45, 61, or 64. The polypeptide can be a recombinant polypeptide produced by cells not infected with a PRRS virus. The step (b) can include contacting the complex with an anti-swine Ig antibody. The anti-swine Ig antibody can contain an enzyme. The step (a) can include contacting the sample with polypeptides within a kit, wherein the kit contains a polypeptide having an amino acid sequence present in a PRRS virus NSP 2 polypeptide and a polypeptide having an amino acid sequence present in a PRRS virus ORF 5 polypeptide. The kit can contain a polypeptide containing an amino acid sequence present in a PRRS virus ORF 7 polypeptide (e.g., a polypeptide containing an amino acid sequence of SEQ ID NO:36 or 54), a polypeptide containing an amino acid sequence present in a PRRS virus ORF 6 polypeptide (e.g., a polypeptide containing an amino acid sequence of SEQ ID NO:32, 48, 51, or 67), and a polypeptide containing an amino acid sequence present in a PRRS virus NSP 1 polypeptide. The method can include contacting the sample with an additional polypeptide to form a polypeptide:swine anti-PRRS virus antibody complex, wherein the additional polypeptide contains an amino acid sequence present in a PRRS virus ORF 7 polypeptide, a PRRS virus ORF 6 polypeptide, or a PRRS virus NSP 1 polypeptide.

In another aspect, this document features a kit for determining whether an animal received a vaccine version of a virus or was infected with a naturally-occurring version of the virus. The kit includes (a) a first polypeptide having an amino acid sequence such that antibodies made against the vaccine version of the virus bind the first polypeptide and antibodies made against the naturally-occurring version of the virus bind the first polypeptide, and (b) a second polypeptide having an amino acid sequence such that antibodies made against the vaccine version of the virus bind the second polypeptide and antibodies made against the naturally-occurring version of the virus do not bind the second polypeptide. The animal can be a vertebrate (e.g., an avian or mammalian species). The animal can be a pig or a human. The virus can be a PRRS virus. The vaccine version can be an attenuated PRRS virus. The vaccine version can be the RespPRRS vaccine. The first polypeptide can contain an amino acid sequence present in a C-terminal portion of an ORF 5 polypeptide of a VR2332 or RespPRRS PRRS virus. The second polypeptide can contain an amino acid sequence present in the N-terminal half of an ORF 5 polypeptide of a VR2332 or RespPRRS PRRS virus.

In another embodiment, this document features a method for determining the immunological state of an animal with respect to a virus, wherein the immunological state is that (1) the animal received a vaccine version of the virus, (2) the animal was infected with a naturally-occurring version of the virus, or (3) the animal is immunologically naive with respect to the virus. The method includes (a) contacting a first sample from the animal with a first polypeptide under conditions wherein the first polypeptide forms a first polypeptide:antibody complex with an antibody, if present, within the first sample, wherein the first polypeptide contains an amino acid sequence such that antibodies made against the vaccine version of the virus bind the first polypeptide and antibodies made against the naturally-occurring version of the virus bind the first polypeptide; (b) contacting a second sample from the animal with a second polypeptide under conditions wherein the second polypeptide forms a second polypeptide:antibody complex with an antibody, if present, within the second sample, wherein the second polypeptide contains an amino acid sequence such that antibodies made against the vaccine version of the virus bind the second polypeptide and antibodies made against the naturally-occurring version of the virus do not bind the second polypeptide; and (c) detecting the presence or absence of the first polypeptide:antibody complex and the presence or absence of the second polypeptide:antibody complex, wherein the presence of the first polypeptide:antibody complex and the presence of the second polypeptide:antibody complex indicates that the animal received the vaccine version of the virus, wherein the presence of the first polypeptide:antibody complex and the absence of the second polypeptide:antibody complex indicates that the animal was infected with the naturally-occurring version of the virus, and wherein the absence of the first polypeptide:antibody complex and the absence of the second polypeptide:antibody complex indicates that the animal is immunologically naive with respect to the virus. The animal can be a vertebrate (e.g., an avian or mammalian species). The animal can be a pig or a human. The virus can be a PRRS virus. The vaccine version can be an attenuated PRRS virus. The vaccine version can be the RespPRRS vaccine. The first polypeptide can contain an amino acid sequence present in a C-terminal portion of an ORF 5 polypeptide of a VR2332 or RespPRRS PRRS virus. The second polypeptide can contain an amino acid sequence present in the N-terminal half of an ORF 5 polypeptide of a VR2332 or RespPRRS PRRS virus.

Another aspect of this document features a substantially pure polypeptide having the amino acid sequence of a PRRS virus NSP 2 polypeptide or a fragment of the PRRS virus NSP 2 polypeptide, wherein the fragment is greater than 20 amino acid residues in length.

Another aspect of this document features a substantially pure polypeptide having the amino acid sequence of a PRRS virus NSP 4 polypeptide or a fragment of the PRRS virus NSP 4 polypeptide, wherein the fragment is greater than 20 amino acid residues in length.

Another aspect of this document features a host cell that expresses a PRRS virus NSP 1, NSP 2, or NSP 4 polypeptide. The cell can be a prokaryotic cell (e.g., a bacterial cell).

Another aspect of this document features a method of reducing background signals in an assay capable of detecting PRRS virus antibodies in a swine sample. The assay includes contacting a solid support containing PRRS virus polypeptides with the swine sample. The method includes treating the solid support with a blocking solution at a pH value greater than 8.0 (e.g., greater than 8.5, 9.0, 9.5, 10.0, or 10.5). The blocking solution can be milk (e.g., nonfat dry milk in PBS), protein solutions, or animal serum.

Another aspect of this document features a solid support containing PRRS virus polypeptides. The solid support was treated with a blocking solution at a pH value greater than 8.0 (e.g., greater than 8.5, 9.0, 9.5, 10.0, or 10.5). The blocking solution can be milk 10 (e.g., nonfat dry milk in PBS), protein solutions, or animal serum. The solid support can be a plastic plate (e.g., a 96 well plate), a glass slide, glass or plastic beads, or the like.

Another aspect of this document features a method of increasing the ability of a polypeptide attached to a solid support to react with an antibody that binds the polypeptide. The method includes contacting the solid support with the polypeptide and a lysozyme. The polypeptide can be a PRRS virus polyp eptide. The polyp eptide can be a PRRS virus ORF 7 polypeptide. The polypeptide can be a recombinant polypeptide produced by cells not infected with a PRRS virus. The antibody can be an anti-PRRS virus polypeptide antibody. The lysozyme can be a chicken egg lysozyme. The polypeptide and the lysozyme c an be contacted with the solid support at a ratio of at least 4 ng of the polypeptide per 1 ng of the lysozyme. The lysozyme and the polypeptide can be contacted with the solid support at a ratio of at least 1 ng of the lysozyme per 1 ng of the polypeptide.

Another aspect of this document features a solid support that was treated with a PRRS virus polypeptide and a lysozyme. The polypeptide can be a PRRS virus ORF 7 polypeptide. The polypeptide can be a recombinant polypeptide produced by cells not infected with a PRRS virus. The lysozyme can be a chicken egg lysozyme. The polypeptide and the lysozyme can be contacted with the solid support at a ratio of at least 4 ng of the polyp eptide per 1 ng of the lysozyme. The lysozyme and the polypeptide can be contacted with the solid support at a ratio of at least 1 ng of the lysozyme per 1 ng of the polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is a listing of a nucleic acid sequence (SEQ ID NO:1) of a pET 24b myc-polypeptide-His construct with the polypeptide being an NSP 1 polypeptide from the VR-2332 strain of PRRS virus. The underlined nucleic acid sequence (SEQ ID NO:2) encodes an NSP 1 polypeptide from the VR-2332 strain of PRRS virus. The shown amino acid sequence (SEQ ID NO:3) is the amino acid sequence from the start site to the start of the NSP 1 polypeptide-encoding region.

FIG. 3 is a listing of a nucleic acid sequence (SEQ ID NO:4) of a pET 24b myc-polypeptide-His construct with the polypeptide being an NSP 2 polypeptide from the VR-2332 strain of PRRS virus. The underlined nucleic acid sequence (SEQ ID NO:5) encodes an NSP 2 polypeptide. The shown amino acid sequence (SEQ ID NO:6) is the amino acid sequence from the start site into the myc tag-encoding region. The LEHHHHHH sequence (SEQ ID NO:13) includes a his tag.

FIG. 4 is a listing of a nucleic acid sequence (SEQ ID NO:7) of a pET 24b myc-polypeptide-His construct with the polypeptide being an NSP 4 polypeptide from the VR-2332 strain of PRRS virus. The underlined nucleic acid sequence (SEQ ID NO:8) encodes an NSP 4 polypeptide. The shown amino acid sequence (SEQ ID NO:9) is an amino acid sequence for a myc-NSP 4-His polypeptide.

FIG. 14 contains a sequence alignment of PRRS virus NSP 2 polypeptides (SEQ ID NOS: 70-81, respectively, in order of appearance). The nucleic acid encoding the NSP 2 polypeptide of VR-2332 PRRS virus was truncated using a naturally-occurring XhoI restriction site at nucleotides 3490-3495 to generate nucleic acid encoding a truncated NSP 2 polypeptide referred to as an NSP 2P polypeptide.

FIG. 15 contains a sequence alignment of PRRS virus ORF 5 polypeptides (SEQ ID NOS: 82-93, respectively, in order of appearance).

FIG. 16 contains a sequence alignment of PRRS virus ORF 7 polypeptides (SEQ ID NOS: 94-105, respectively, in order of appearance).

FIG. 18 contains graphs plotting the absorbance for ELISAs containing the indicated polypeptide. The groups are as set forth in Table 6.

FIG. 19 is a listing of a nucleic acid sequence (SEQ ID NO:10) of a pET 24b myc-polypeptide-His construct with the polypeptide being an NSP 2P polypeptide from the VR-2332 strain of PRRS virus. The underlined nucleic acid sequence (SEQ ID NO:11) encodes an NSP 2P polypeptide. The first amino acid sequence (SEQ ID NO:12) is an amino acid sequence of the myc tag region of a myc-NSP 2P-His polypeptide, while the second amino acid sequence (SEQ ID NO:13) is an amino acid sequence of the His tag region of a myc-NSP 2P-His polypeptide.

FIG. 20 is a listing of a nucleic acid sequence (SEQ ID NO:14) of a pET 24b myc-polypeptide-His construct with the polypeptide being an ORF 5 5' polypeptide from the MN30100 strain of PRRS virus. The underlined nucleic acid sequence (SEQ ID NO:15) encodes an ORF 5 5' polypeptide. The amino acid sequence (SEQ ID NO:16) is an amino acid sequence for a myc-ORF 5 5'-His polypeptide.

FIG. 21 is a listing of a nucleic acid sequence (SEQ ID NO:17) of a pET 24b myc-polypeptide-His construct with the polypeptide being an ORF 5 5' polypeptide from the VR-2332 strain of PRRS virus. The underlined nucleic acid sequence (SEQ ID NO:18) encodes an ORF 5 5' polypeptide. The amino acid sequence (SEQ ID NO:19) is an amino acid sequence for a myc-ORF 5 5'-His polypeptide.

FIG. 22 is a listing of a nucleic acid sequence (SEQ ID NO:20) of a pET 24b myc-polypeptide-His construct with the polypeptide being an ORF 5 5' total polypeptide from the VR-2332 strain of PRRS virus. The underlined nucleic acid sequence (SEQ ID NO:21) encodes an ORF 5 total polypeptide. The amino acid sequence (SEQ ID NO:22) is an amino acid sequence for a myc-ORF 5 total-His polypeptide. A linker amino acid sequence (GGGGS; SEQ ID NO:23) is located between the first and second ectodomains of the 5' region of the ORF 5 polypeptide.

FIG. 23 is a listing of a nucleic acid sequence (SEQ ID NO:24) of a pET 24b myc-polypeptide-His construct with the polypeptide being an ORF 5 3' polypeptide from the VR-2332 strain of PRRS virus. The underlined nucleic acid sequence (SEQ ID NO:25) encodes an ORF 5 3' polypeptide. The amino acid sequence (SEQ ID NO:26) is an amino acid sequence for a myc-ORF 5 3'-His polypeptide.

FIG. 24 is a listing of a nucleic acid sequence (SEQ ID NO:27) of a pET 24b myc-polypeptide-His construct with the polypeptide being an ORF 5 3' polypeptide from the MN30100 strain of PRRS virus. The underlined nucleic acid sequence (SEQ ID NO:28) encodes an ORF 5 3' polypeptide. The amino acid sequence (SEQ ID NO:29) is an amino acid sequence for a myc-ORF 5 3'-His polypeptide.

FIG. 25 is a listing of a nucleic acid sequence (SEQ ID NO:30) of a pET 24b myc-polypeptide-His construct with the polypeptide being an ORF 5+6 polypeptide from the VR-2332 strain of PRRS virus. The underlined nucleic acid sequence (SEQ ID NO:31) encodes an ORF 5+6 polypeptide. The amino acid sequence (SEQ ID NO:32) is an amino acid sequence for a myc-ORF 5+6-His polypeptide. A first linker amino acid sequence (GGGGS; SEQ ID NO:23) is located between the first and second ectodomains of the 5' region of the ORF 5 polypeptide. A second linker amino acid sequence is located between the second ectodomain of the 5' region of the ORF 5 polypeptide and the first ectodomain of the 5' region of the ORF 6 polypeptide. A third linker amino acid sequence is located between the first and second ectodomains of the 5' region of the ORF 6 polypeptide.

FIG. 26 is a listing of a nucleic acid sequence (SEQ ID NO:34) of a pET 24b myc-polypeptide-His construct with the polypeptide being an ORF 7 polypeptide from the VR-2332 strain of PRRS virus. The underlined nucleic acid sequence (SEQ ID NO:35) encodes an ORF 7 polypeptide. The amino acid sequence (SEQ ID NO:36) is an amino acid sequence for a myc-ORF 7-His polypeptide.

FIG. 27 is a listing of a nucleic acid sequence (SEQ ID NO:37) of a pET 24b myc-polypeptide-His construct with the polypeptide being an NSP 2HP polypeptide from the VR-2332 strain of PRRS virus. The underlined nucleic acid sequence (SEQ ID NO:38) encodes an NSP 2HP polypeptide. The amino acid sequence (SEQ ID NO:39) is an amino acid sequence for a myc-NSP 2HP-His polypeptide.

FIG. 28 is a listing of a nucleic acid sequence (SEQ ID NO:40) of a pET 24b myc-polypeptide-His construct with the polypeptide being an NSP 2 S1 HP polypeptide from the VR-2332 strain of PRRS virus. The underlined nucleic acid sequence (SEQ ID NO:41) encodes an NSP 2 S1 HP polypeptide. The amino acid sequence (SEQ ID NO:42) is an amino acid sequence for a myc-NSP 2 S1 HP-His polypeptide.

FIG. 29 is a listing of a nucleic acid sequence (SEQ ID NO:43) of a pET 24b myc-polypeptide-His construct with the polypeptide being an NSP 2 S2 HP polypeptide from the VR-2332 strain of PRRS virus. The underlined nucleic acid sequence (SEQ ID NO:44) encodes an NSP 2 S2 HP polypeptide. The amino acid sequence (SEQ ID NO:45) is an amino acid sequence for a myc-NSP 2 S2 HP-His polypeptide.

FIG. 30 is a listing of a nucleic acid sequence (SEQ ID NO:46) of a pET 24b myc-polypeptide-His construct with the polypeptide being an ORF 6 5' total polypeptide from the VR-2332 strain of PRRS virus. The underlined nucleic acid sequence (SEQ ID NO:47) encodes an ORF 6 5' total polypeptide. The amino acid sequence (SEQ ID NO:48) is an amino acid sequence for a myc-ORF 6 5' total-His polypeptide. A linker amino acid sequence (GGGGS; SEQ ID NO:23) is located between the first and second ectodomains of the 5' region of the ORF 5 polypeptide.

FIG. 31 is a listing of a nucleic acid sequence (SEQ ID NO:49) of a pET 24b myc-polypeptide-His construct with the polypeptide being an ORF 6 3' polypeptide from the VR-2332 strain of PRRS virus. The underlined nucleic acid sequence (SEQ ID NO:50) encodes an ORF 6 3' polypeptide. The amino acid sequence (SEQ ID NO:51) is an amino acid sequence for a myc-ORF 6 3'-His polypeptide.

FIG. 36 is a listing of a nucleic acid sequence (SEQ ID NO:52) of a pET 24b myc-polypeptide-His construct with the polypeptide being an ORF 7 polypeptide from the Lelystad virus strain of PRRS virus. The underlined nucleic acid sequence (SEQ ID NO:53) encodes an ORF 7 polypeptide. The amino acid sequence (SEQ ID NO:54) is an amino acid sequence for a myc-ORF 7-His polypeptide.

FIG. 37 is a listing of a nucleic acid sequence (SEQ ID NO:55) of a pET 24b myc-polypeptide-His construct with the polypeptide being an NSP 2P polypeptide from the Lelystad virus strain of PRRS virus. The underlined nucleic acid sequence (SEQ ID NO:56) encodes an NSP 2P polypeptide. The shown amino acid sequence is the amino acid sequence from the start site to the start of the NSP 2P polypeptide-encoding region (SEQ ID NO:3) and from the end of the NSP 2P polypeptide-encoding region through the his tag (SEQ ID NO:13).

FIG. 38 is a listing of a nucleic acid sequence (SEQ ID NO:57) of a pET 24b myc-polypeptide-His construct with the polypeptide being an NSP 2P polypeptide from the JA 142 virus strain of PRRS virus. The underlined nucleic acid sequence (SEQ ID NO:58) encodes an NSP 2P polypeptide. The shown amino acid sequence is the amino acid sequence from the start site to the start of the NSP 2P polypeptide-encoding region (SEQ ID NO:3) and from the end of the NSP 2P polypeptide-encoding region through the his tag (SEQ ID NO:13).

FIG. 39 is a listing of a nucleic acid sequence (SEQ ID NO:59) of a pET 24b myc-polypeptide-His construct with the polypeptide being an NSP 2HP polypeptide from the Boehringer Ingelheim Ingelvac ATP virus strain of PRRS virus. The underlined nucleic acid sequence (SEQ ID NO:60) encodes an NSP 2HP polypeptide. The amino acid sequence (SEQ ID NO:61) is an amino acid sequence for a myc-NSP 2HP-His polypeptide.

FIG. 40 is a listing of a nucleic acid sequence (SEQ ID NO:62) of a pET 24b myc-polypeptide-His construct with the polypeptide being an ORF 5 3' polypeptide from the Lelystad virus strain of PRRS virus. The underlined nucleic acid sequence (SEQ ID NO:63) encodes an ORF 5 3' polypeptide. The amino acid sequence (SEQ ID NO:64) is an amino acid sequence for a myc-ORF 5 3'-His polypeptide.

FIG. 41 is a listing of a nucleic acid sequence (SEQ ID NO:65) of a pET 24b myc-polypeptide-His construct with the polypeptide being an ORF 6 3' polypeptide from the Lelystad virus strain of PRRS virus. The underlined nucleic acid sequence (SEQ ID NO:66) encodes an ORF 6 3' polypeptide. The amino acid sequence (SEQ ID NO:67) is an amino acid sequence for a myc-ORF 6 3'-His polypeptide.

DETAILED DESCRIPTION

Figure 1:
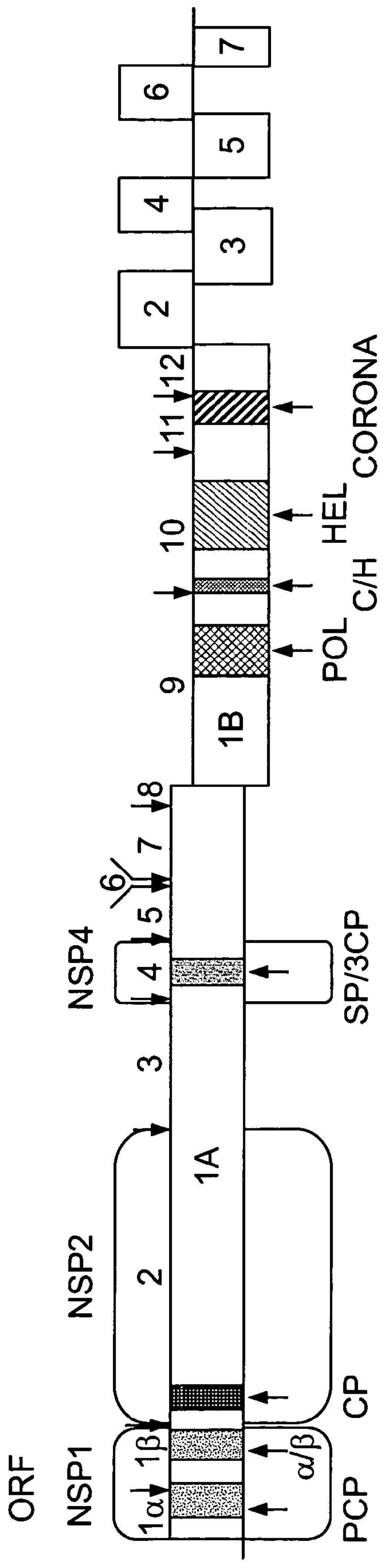
FIG. 1 is a diagram of a PRRS virus genome. Genomic regions shaded in gray were PCR amplified from VR2332 viral RNA, cloned, and expressed in *E. coli* BL21(DE3RP) cells.

This document provides methods and materials related to assessing organisms to determine whether or not the organisms were exposed to viral antigens via, for example, a viral vaccination (e.g., vaccination with a vaccine of recombinant viral polypeptides or a vaccine of attenuated virus) or a viral infection. For example, this document provides polypeptides, nucleic acid encoding such polypeptides, methods for making such polypeptides, host cells that express such polypeptides, methods for making such host cells, kits for detecting anti-PRRS virus antibodies, methods for detecting anti-PRRS virus antibodies, kits for assessing an organism's immunological state with respect to a virus, and methods for assessing an organism's immunological state.

Polypeptides

In one embodiment, this document provides polypeptides that can be used to detect anti-PRRS virus antibodies present in a sample from an organism (e.g., pigs). The anti-PRRS virus antibodies can be any type of anti-PRRS virus antibody. For example, the anti-PRRS virus antibodies can be IgA, IgD, IgE, IgG, or IgM antibodies. Such antibodies can be formed in an organism when that organism is exposed to a PRRS virus antigen such as a PRRS virus polypeptide, an attenuated PRRS virus vaccine, or a pathogenic PRRS virus. In addition, the anti-PRRS virus antibodies can be antibodies that bind to any type of PRRS virus including, without limitation, a VR-2332 PRRS virus (GenBank® Accession No. PRU87392; U.S. Pat. Nos. 5,846,805 and 5,683,865), an MN30100 PRRS virus (Bierk et al., *Vet. Rec.,* 148:687-690 (2001)), an attenuated PRRS virus such as a RespPRRS virus (GenBank® Accession No. AF066183), a 16244B PRRS virus (GenBank® Accession No. AF046869), a PA8 PRRS virus (GenBank® Accession No. AF176348), an SP PRRS virus (GenBank® Accession No. AF184212), an NVSL 97-7985 IA 1-4-2 PRRS virus (GenBank® Accession No. AF325691), a P129 PRRS virus (GenBank® Accession No. AF494042), a CH-1a PRRS virus (GenBank® Accession No. AY032626), a JA142 PRRS virus (GenBank® Accession No.

AY424271), an NVSL 97-7895 PRRS virus (GenBank® Accession No. AY545985), or a PL97-1 PRRS virus (GenBank® Accession No. AY585241). Likewise, the anti-PRRS virus antibodies can be antibodies that bind to field isolates or naturally-occurring versions of a PRRS virus including, without limitation, isolates and naturally-occurring versions of PRRS viruses from North America, Europe, or elsewhere (e.g., China).

The polypeptides provided herein can be used to detect anti-PRRS virus antibodies present in a sample from an organism that is susceptible to a PRRS virus infection. Such organisms include, without limitation, swine species such as domestic and feral pigs and wild boars. In some cases, the polypeptides provided herein can be used to detect anti-PRRS virus antibodies present in a sample from an organism that is not susceptible to a PRRS virus infection. For example, the polypeptides provided herein can be used to detect anti-PRRS virus antibodies present in a sample from a rabbit or mouse that was exposed to a PRRS virus antigen via, for example, injection of a PRRS virus polypeptide, an attenuated PRRS virus vaccine, or a pathogenic PRRS virus. When making anti-PRRS virus antibodies in a rabbit or mouse, detecting anti-PRRS virus antibodies in a rabbit or mouse serum sample can help scientists identify rabbits or mice that produce anti-PRRS virus antibodies.

Any sample can be obtained from an organism and assessed for the presence or absence of an anti-PRRS virus antibody. Such samples include, without limitation, blood samples, serum samples, tissue samples (e.g., lymph tissue, muscle tissue, and skin tissue). For example, blood samples can be obtained from pigs and assessed for the presence or absence of pig anti-PRRS virus antibodies.

The polypeptides provided herein can be any length (e.g., between 8 and 2500 amino acid residues). In some embodiments, the polypeptide can contain at least eight amino acid residues. For example, the length of a polypeptide can be greater than 8, 9, 10, 11, 12, 13, 14, 15, 20, 25, 30, 50, 75, 100, 150, 200, 250, 300, 400, 500, 600, 700, 800, 900, 1000, or more amino acid residues. In other embodiments, the length of the polypeptide can be between 25 and 800 amino acid residues, between 50 and 800 amino acid residues, between 50 and 450 amino acid residues, between 50 and 400 amino acid residues, between 50 and 300 amino acid residues, between 100 and 400 amino acid residues, or between 100 and 300 amino acid residues.

The polypeptides can have any amino acid sequence. For example, a polypeptide can contain an amino acid sequence present in a PRRS virus polypeptide (e.g., an NSP 1, NSP 2, NSP 3, NSP 4, NSP 5, NSP 6, pol, C/H, HEL, CORONA, ORF 2, ORF 2b, ORF 3, ORF 4, ORF 5, ORF 6, or ORF 7 polypeptide). In some embodiments, the polypeptide can be a PRRS virus NSP 2 polypeptide that lacks a hydrophobic region such as the region encoded by nucleotides 1339 to 3495 of the sequence set forth in GenBank accession number PRU87392. In other embodiments, the polypeptide can be an ectodomain of a PRRS virus ORF 5 or ORF 6 polypeptide. For example, a polypeptide can contain the first ectodomain from the 5' end of a PRRS virus ORF 5 polypeptide (ORF 5 5' ectodomain 1), the second ectodomain from the 5' end of a PRRS virus ORF 5 polypeptide (ORF 5 5' ectodomain 2), the first ectodomain from the 5' end of a PRRS virus ORF 6 polypeptide (ORF 6 5' ectodomain 1), the second ectodomain from the 5' end of a PRRS virus ORF 6 polypeptide (ORF 6 5' ectodomain 2), or combinations thereof. When a polypeptide contains more than one (e.g., two, three, four, five, six, or more) ectodomain, the ectodomains can be next to each other or separated by a linker sequence (e.g., a GGGGS (SEQ ID NO:23) amino acid linker sequence).

The polypeptides provided herein can contain additional amino acid sequences including those commonly used as tags (e.g., poly-histidine tags, myc tags, GFP tags, and GST tags). For example, a 50 amino acid fragment of a PRRS virus NSP 2 polypeptide can contain the amino acid sequence of a poly-histidine tag (e.g., HHHHHH, SEQ ID NO:33).

A polypeptide provided herein can contain an amino acid sequence having (1) a length, and (2) a percent identity to an identified amino acid sequence over that length. Likewise, an isolated nucleic acid provided herein can encode such a polypeptide or can contain a nucleic acid sequence having (1) a length, and (2) a percent identity to an identified nucleic acid sequence over that length. Typically, the identified nucleic acid or amino acid sequence is a sequence referenced by a particular sequence identification number or a particular GenBank accession number or is a particular PRRS virus nucleic acid or polypeptide (e.g., a PRRS virus NSP 2 polypeptide). The nucleic acid or amino acid sequence being compared to the identified sequence typically is referred to as the target sequence. For example, an identified sequence can be a PRRS virus ORF 5 polypeptide sequence set forth in SEQ ID NO:16, 19, or 22.

A length and percent identity over that length for any nucleic acid or amino acid sequence is determined as follows. First, a nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library (catalog number: QH 447.M6714) as well as from Fish & Richardson's web site ("fr" dot "com/blast/") or from the U.S. government's National Center for Biotechnology Information web site ("ncbi" dot "nlm" dot "nih" dot "gov"). Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); –j is set to a file containing the second nucleic acid sequence to be compared (e.g., C:\seq2.txt); –p is set to blastn; –o is set to any desired file name (e.g., C:\output.txt); –q is set to –1; –r is set to 2; and all other options are left at their default setting. For example, the following command can be used to generate an output file containing a comparison between two sequences: C:\B12seq –i c:\seq1.txt –j c:\seq2.txt –p blastn –o c:\output.txt –q –1 –r 2. To compare two amino acid sequences, the options of B12seq are set as follows: –i is set to a file containing the first amino acid sequence to be compared (e.g., C:\seq1.txt); –j is set to a file containing the second amino acid sequence to be compared (e.g., C:\seq2.txt); –p is set to blastp; –o is set to any desired file name (e.g., C:\output.txt); and all other options are left at their default setting. For example, the following command can be used to generate an output file containing a comparison between two amino acid sequences: C:\B12seq –i c:\seq1.txt –j c:\seq2.txt –p blastp –o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to a PRRS virus NSP 2 polypeptide sequence, (2) the B12seq program presents 200 nucleotides from the target sequence aligned with a region of the PRRS virus NSP 2 polypeptide sequence where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180÷200*100=90).

It will be appreciated that a single nucleic acid or amino acid target sequence that aligns with an identified sequence can have many different lengths with each length having its own percent identity. For example, a target sequence containing a 20 nucleotide region that aligns with an identified sequence as follows has many different lengths including those listed in Table A.

```
                     1                  20
Target Sequence:     AGGTCGTGTACTGTCAGTCA (SEQ ID
                     | || ||| |||| |||| |  NO:68)
Identified Sequenc:  ACGTGGTGAACTGCCAGTGA (SEQ ID
                                           NO:69)
```

TABLE A

| Starting Position | Ending Position | Length | Matched Positions | Percent Identity |
|---|---|---|---|---|
| 1 | 20 | 20 | 15 | 75.0 |
| 1 | 18 | 18 | 14 | 77.8 |
| 1 | 15 | 15 | 11 | 73.3 |
| 6 | 20 | 15 | 12 | 80.0 |
| 6 | 17 | 12 | 10 | 83.3 |
| 6 | 15 | 10 | 8 | 80.0 |
| 8 | 20 | 13 | 10 | 76.9 |
| 8 | 16 | 9 | 7 | 77.8 |

It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It is also noted that the length value will always be an integer.

In some embodiments, the polypeptide can have an amino acid sequence at least about 70 percent (e.g., at least about 75, 80, 85, 90, 95, or 99 percent) identical to the sequence set forth in SEQ ID NO:9, 16, 19, 22, 26, 29, 32, 36, 39, 42, 45, 48, 51, 54, 61, 64, or 67 over a length such as 20, 30, 40, 50, 60, 70, 80, 90, 100, 110, 120, 130, 140, 150, 160, 170, 180, 190, 200, or more amino acid residues.

The polypeptides provided herein can be substantially pure. The term "substantially pure" as used herein with reference to a polypeptide means the polypeptide is substantially free of other polypeptides, lipids, carbohydrates, and nucleic acid with which it is naturally associated. For example, a substantially pure polypeptide is any polypeptide that is removed from its natural environment and is at least 60 percent pure. The term "substantially pure" as used herein with reference to a polypeptide also includes chemically synthesized polypeptides. A substantially pure polypeptide can be at least about 65, 70, 75, 80, 85, 90, 95, or 99 percent pure. Typically, a substantially pure polypeptide will yield a single major band on a non-reducing polyacrylamide gel.

Any method can be used to obtain a polypeptide or a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, cultured cells engineered to over-express a particular polypeptide of interest can be used to obtain substantially pure polypeptide. Such cells can be prokaryotic cells (e.g. bacterial cells such as *E. coli* cells) or eukaryotic cells (e.g., yeast cells, insect cells, mammalian cells). A polypeptide can be designed to contain an amino acid sequence that allows the polypeptide to be captured onto an affinity matrix. For example, a tag such as c-myc, hemagglutinin, poly histidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

The polypeptides provided herein can be formulated into a polypeptide composition that contains additional ingredients. For example, a polypeptide provided herein can be combined with other polypeptides to form a composition that contains more than one different polypeptide (e.g., two, three, four, five, six, seven, eight, nine, ten, or more different polypeptides). For example, a composition can contain a PRRS virus NSP 2 polypeptide and a PRRS virus NSP 1 polypeptide. A composition containing one or more of the polypeptides provided herein can contain one or more carriers such as a solvent, suspending agent, or any other vehicle. Carriers can be liquid or solid, and can be selected with the desired use in mind so as to provide for the desired bulk, consistency, and other pertinent transport and chemical properties. Typical carriers include, without limitation, water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism or virus from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally occurring can be exogenous to a particular cell. For example, an entire chromosome isolated from a cell of person X is an exogenous nucleic acid with respect to a cell of person Y once that chromosome is introduced into Y's cell.

An isolated nucleic acid can encode any of the polypeptides provided herein. For example, an isolated nucleic acid can encode a PRRS virus NSP 2 polypeptide that lacks a hydrophobic region (e.g., amino acid residues 1 to 722 of a VR-2332 PRRS virus NSP 2 polypeptide) normally present in a PRRS virus NSP 2 polypeptide. In some embodiments, the nucleic acid can encode a polypeptide having an amino acid sequence at least about 70 percent (e.g., at least about 75, 80, 85, 90, 95, or 99 percent) identical to the sequence set forth in SEQ ID NO: 9, 16, 19, 22, 26, 29, 32, 36, 39, 42, 45, 48, 51, 54, 61, 64, or 67 over a length such as 20, 30, 40, 50, 60, 70, 80, 90, 100, 110, 120, 130, 140, 150, 160, 170, 180, 190, 200, or more amino acid residues. In other embodiments, the nucleic acid can have a nucleic acid sequence at least about 70 percent (e.g., at least about 75, 80, 85, 90, 95, or 99 percent) identical to the sequence set forth in SEQ ID NO:2, 5, 8, 11, 15, 18, 21, 25, 28, 31, 35, 38, 41, 44, 47, 50, 53, 56, 58, 60, 63, or 66 over a length such as 20, 30, 40, 50, 60, 70, 80, 90, 100, 110, 120, 130, 140, 150, 160, 170, 180, 190, 200, 250,300, 350, 400, 450, 500, 550, 600, 650, 700, 750, 800, 850, 900, 950, 1000, or more nucleotides.

The isolated nucleic acids provided herein can be at least about 5 bases in length (e.g., at least about 5, 6, 7, 8, 9, 10, 15, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid that encodes a polypeptide provided herein (e.g., a PRRS virus NSP 2P polypeptide or a PRRS virus ORF 5/ORF 6 chimeric polypeptide). The hybridization conditions can be moderately or highly stringent hybridization conditions.

For the purpose of this invention, moderately stringent hybridization conditions mean the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM KPO4 (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate.

Isolated nucleic acids can be obtained using any method including, without limitation, common molecular cloning and chemical nucleic acid synthesis techniques. For example, PCR can be used to obtain an isolated nucleic acid containing a nucleic acid sequence sharing similarity to a PRRS virus nucleic acid sequence provided, for example, in GenBank® (e.g., GenBank® Accession No. PRU87392). PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

In addition, nucleic acid and amino acid databases (e.g., GenBank®) can be used to obtain an isolated nucleic acid. For example, any nucleic acid sequence having some homology to a nucleic acid sequence that encodes a polypeptide provided herein can be used as a query to search GenBank®.

Host Cells

A host cell can be designed to contain an isolated nucleic acid described herein. Such cells can be prokaryotic cells (e.g., bacterial cells such as *E. coli, B. subtilis*, or *Agrobacterium tumifaciens, Streptomyces* species cells) or eukaryotic cells (e.g., fingal cells such as yeast cells including, without limitation, *Saccharomyces* species cells and *Pichia pastoris* cells; insect cells; or mammalian cells). Cells It is noted that cells containing an isolated nucleic acid provided herein are not required to express a polypeptide. In addition, the isolated nucleic acid can be integrated into the genome of the cell or maintained in an episomal state. Thus, host cells can be stably or transiently transfected with a construct containing an isolated nucleic acid provided herein. Typically, a host cell contains an exogenous nucleic acid molecule that encodes a polypeptide provided herein and expresses that encoded polypeptide.

Any methods can be used to introduce an isolated nucleic acid molecule into a cell. For example, calcium phosphate precipitation, electroporation, heat shock, lipofection, microinjection, and viral-mediated nucleic acid transfer are common methods that can be used to introduce an isolated nucleic acid molecule into a cell.

Detecting Anti-PRRS Virus Antibodies

The methods and materials provided herein can be used to detect anti-PRRS virus antibodies within an organism (e.g., a pig). In general, anti-PRRS virus antibodies are detected by contacting a PRRS virus polypeptide provide herein with a sample from an organism under conditions wherein the PRRS virus polypeptide can bind to an anti-PRRS virus antibody, if present within the sample, to form an antibody-polypeptide complex. Such complexes can be detected using, for example, labeled-antibodies that bind to that organism's antibodies.

Any of the PRRS virus polypeptides provided herein can be used to detect anti-PRRS virus antibodies. Furthermore, multiple different PRRS virus polypeptides provided herein can be used in combination to detect anti-PRRS virus antibodies. For example, a kit containing PRRS virus NSP 1, NSP 2, NSP 4, and ORF 7 polypeptides can be used to detect anti-PRRS virus antibodies.

Typically, the PRRS virus polypeptides are immobilized on solid substrates such as dipsticks, microtiter plates, particles (e.g., beads), affinity columns, and immunoblot membranes. See, U.S. Pat. Nos. 5,143,825; 5,374,530; 4,908,305; and 5,498,551 for exemplary descriptions of solid substrates and methods for their use. For example, PRRS virus polypeptides can be immobilized on a solid substrate, such as a 96-well plate, using known methodologies, then contacted with a sample from a pig under conditions such that anti-PRRS virus antibodies present within the sample can bind to the immobilized PRRS virus polypeptides to form antibody-polypeptide complexes. Suitable conditions include incubation in an appropriate buffer (e.g., sodium phosphate buffer, pH 7.2 to 7.4) at room temperature from about at least 10 minutes to about 10 hours (e.g., from about 1 to about 2.5 hours). Thereafter, unbound material is washed away, and antibody-polypeptide complexes can be detected.

Detecting the presence of such antibody-polypeptide complexes can be indicative of a PRRS virus infection. Any method can be used to detect the antibody-polypeptide complexes. For example, an indicator molecule having binding affinity for the antibody-polypeptide complex can be used to detect an antibody-polypeptide complex. As used herein, an "indicator molecule" is any molecule that allows the presence of a given polypeptide, antibody, or antibody-polypeptide complex to be visualized, either with the naked eye or an appropriate instrument. Typically, the indicator molecule is an antibody having binding affinity for antibodies from the organism (e.g., a pig) from which the sample was obtained, e.g., anti-pig IgG antibodies. Indicator molecules can be detected either directly or indirectly by standard methodologies. See, e.g., *Current Protocols in Immunology*, Chapters 2 and 8, Coligan et al., (eds.), John Wiley & Sons (1996). For direct detection, the indicator molecule can be labeled with a radioisotope, fluorochrome, other non-radioactive label, or any other suitable chromophore. For indirect detection methods, enzymes such as horseradish peroxidase (HRP) and alkaline phosphatase (AP) can be attached to the indicator molecule, and the presence of the antibody-polypeptide complex can be detected using standard assays for HRP or AP. Alternatively, the indicator molecule can be attached to avidin or streptavidin, and the presence of the antibody-polypeptide complex can be detected with biotin conjugated to, for example, a fluorochrome, or vice versa. Thus, assay formats for detecting antibody-polypeptide complexes can include enzyme-linked immunoassays (ELISA) such as competitive ELISAs, radioimmunoassays (RIA), fluorescence assays, chemiluminescent assays, immunoblot assays (Western blots), particulate-based assays, and other known techniques. In some embodiments, antibody-polypeptide complexes are formed in solution. Such complexes can be detected by immunoprecipitation. See, e.g., *Short Protocols in Molecular Biology*, Chapter 10, Section VI, Ausubel et al., (eds.), Green Publishing Associates and John Wiley & Sons (1992).

Kits for Detecting Anti-PRRS Virus Antibodies

The PRRS virus polypeptides provided herein can be used to make kits for detecting anti-PRRS virus antibodies. Such kits can contain one, two, three, four, five, six, seven, eight, nine, ten, or more different PRRS virus polypeptides. For example, a kit can contain a PRRS virus NSP 1 polypeptide, a PRRS virus NSP 2 polypeptide, a PRRS virus NSP 4 polypeptide, a PRRS virus ORF 5 polypeptide, a PRRS virus ORF 6 polypeptide, a PRRS virus ORF 7 polypeptide, or any combination thereof. In some embodiments, the kit can contain a PRRS virus NSP 2P polypeptide and an ORF 7 polypeptide.

The kit containing PRRS virus polypeptides can contain other components including, without limitation, packaging materials (e.g., written instructions), indicator molecules (e.g., anti-swine Ig antibodies), buffers, positive control samples (e.g., a sample containing swine anti-PRRS virus antibodies), and negative control samples (e.g., a sample containing swine serum lacking swine anti-PRRS virus antibodies).

Assessing an Organism's Immunological State

The methods and materials provided herein can be used to determine an organism's immunological state with respect to a virus. Such methods and materials can be used to determine an immunological state in any organism. For example, the immunological state of a pig, dog, cat, bird (e.g., chicken, turkey, or duck), sheep, cow, horse, goat, monkey, or human can be determined using the methods and materials provided herein. In addition, an organism's immunological state with respect to any virus can be determined. For example, an organism's immunological state with respect to a PRRS virus, a circovirus, an influenza virus, a herpes virus, an adenovirus, a parvovirus, a coronavirus, a picomavirus, a parainfluenza virus, or a filovirus can be determined.

In one embodiment, the methods and materials provided herein can be used to determine whether an organism's immunological state is such that (1) the organism received a vaccine version of a virus, (2) the organism was infected with a naturally-occurring version of the virus, or (3) the organism is immunologically naive with respect to the virus. In some cases, the methods and materials provided herein can be used to differentiate between organisms having either an immunological state such that (1) the organism received a vaccine version of a virus or (2) the organism was infected with a naturally-occurring version of the virus.

In general, at least two polypeptides are used to assess an organism's immunological state. The first polypeptide can be a polypeptide having an amino acid sequence that is conserved (e.g., highly conserved or, in some cases, completely conserved) between a vaccine version of a virus and naturally-occurring versions of the virus. For example, the first polypeptide can have an amino acid sequence such that antibodies made against a vaccine version of the virus bind the first polypeptide and antibodies made against naturally-occurring versions of the virus bind the first polypeptide. When assessing the immunological state of a pig with respect to a PRRS virus, the first polypeptide can be a polypeptide having an amino acid sequence that is conserved among vaccine and naturally-occurring versions of PRRS viruses such as a C-terminal region of a PRRS ORF 5 polypeptide. Other amino acid sequences conserved among vaccine and naturally-occurring versions of PRRS viruses can be obtained from standard sequence alignments (FIGS. 14-16).

The second polypeptide can be a polypeptide having an amino acid sequence that is not well conserved (e.g., a variable sequence) between a vaccine version of a virus and naturally-occurring versions of the virus. The second polypeptide can have a sequence that is similar or identical to a sequence present in a vaccine version of the virus. For example, the second polypeptide can have an amino acid sequence such that antibodies made against a vaccine version of the virus bind the second polypeptide and antibodies made against naturally-occurring versions of the virus do not bind the second polypeptide. When assessing the immunological state of a pig with respect to a PRRS virus, the second polypeptide can be a polypeptide having an amino acid sequence that is variable among vaccine and naturally-occurring versions of PRRS viruses such as an N-terminal region of a PRRS ORF 5 polypeptide. The amino acid sequence of such a second polypeptide can be from a VR-2332 or RespPRRS PRRS virus. Other amino acid sequences not conserved among vaccine and naturally-occurring versions of PRRS viruses can be obtained from standard sequence alignments (FIGS. 14-16).

To assess an organism's immunological state with respect to a virus, the first and second polypeptides can be contacted with a sample from the organism under conditions such that the first and second polypeptides can bind to anti-virus antibodies, if present within the sample, to form either (1) first polypeptide-antibody complexes or (2) first polypeptide-antibody complexes and second polypeptide-antibody complexes. The formation of first polypeptide-antibody complexes and not second polypeptide-antibody complexes can indicate that the sample is from an organism that was exposed to a naturally-occurring version of the virus. The formation of both first polypeptide-antibody complexes and second polypeptide-antibody complexes can indicate that the sample is from an organism that was exposed to a vaccine version of the virus. The failure to detect either first polypeptide-antibody complexes or second polypeptide-antibody complexes can indicate that the sample is from an organism that is naive with respect to the virus.

In the case of assessing a pig's immunological state with respect to PRRS virus, the first and second polypeptides can be contacted with a blood sample from the pig under conditions such that the first and second polypeptides can bind to anti-PRRS virus antibodies, if present within the blood sample, to form either (1) first polypeptide-antibody complexes or (2) first polypeptide-antibody complexes and second polypeptide-antibody complexes. The formation of first polypeptide-antibody complexes and not second polypeptide-antibody complexes can indicate that the sample is from a pig that was exposed to a naturally-occurring version of PRRS virus. The formation of both first polypeptide-antibody complexes and second polypeptide-antibody complexes can indicate that the sample is from a pig that was exposed to a vaccine version of PRRS virus. The failure to detect either first polypeptide-antibody complexes or second polypeptide-antibody complexes can indicate that the sample is from a pig that is naive with respect to the virus.

Typically, the virus polypeptides are immobilized on solid substrates such as dipsticks, microtiter plates, particles (e.g., beads), affinity columns, and immunoblot membranes. See, U.S. Pat. Nos. 5,143,825; 5,374,530; 4,908,305; and 5,498,551 for exemplary descriptions of solid substrates and methods for their use. For example, PRRS virus polypeptides (e.g., one polypeptide with a PRRS virus sequence limited to a conserved PRRS virus amino acid sequence and another polypeptide with a PRRS virus sequence limited to a divergent PRRS virus amino acid sequence) can be immobilized on a solid substrate, such as a 96-well plate, using known methodologies, then contacted with a sample for a pig under conditions such that anti-PRRS virus antibodies present within the sample can bind to the immobilized PRRS virus polypeptides to form polypeptide-antibody complexes. Suitable conditions include incubation in an appropriate buffer (e.g., sodium phosphate buffer, pH 7.2 to 7.4) at room temperature from about at least 10 minutes to about 10 hours (e.g., from about 1 to about 2.5 hours). Thereafter, unbound material is washed away, and polypeptide-antibody complexes can be detected as described herein.

Kits for Assessing an Organism's Immunological State

A first polypeptide having an amino acid sequence such that antibodies made against a vaccine version of the virus can bind that first polypeptide and antibodies made against naturally-occurring versions of the virus can bind that first polypeptide can be combined with a second polypeptide to make a kit for assessing an organism's immunological state. The second polypeptide can have a sequence that is similar or identical to a sequence present in a vaccine version of the virus. In addition, the second polypeptide can have an amino acid sequence such that antibodies made against a vaccine version of the virus bind that second polypeptide and antibodies made against naturally-occurring versions of the virus do not bind that second polypeptide. Such kits can contain additional polypeptides. For example, a kit can contain two, three, four, five, six, seven, eight, nine, ten, or more different polypeptides with each having a different sequence that is conserved among vaccine and naturally-occurring versions of the virus. Likewise, a kit can contain two, three, four, five, six, seven, eight, nine, ten, or more different polypeptides with each having a different viral sequence that is not conserved among vaccine and naturally-occurring versions of the virus.

The kit can contain other components including, without limitation, packaging materials (e.g., written instructions), indicator molecules (e.g., anti-organism Ig antibodies), buffers, positive control samples, and negative control samples.

In some cases, a solid support can be contacted with a polypeptide and a lysozyme to increase the ability of the polypeptide attached to the solid support to react with an antibody that binds the polypeptide. Any polypeptide can be attached to a solid support including, without limitation, the PRRS virus polypeptides provided herein (e.g., a PRRS virus ORF 7 polypeptide). Any lysozyme can be used. Typically, a lysozyme can be a hydrolytic enzyme that degrades β-1,4 glucosidic linkages between N-acetylmuramic acid and N-acetylglucosamine in cell walls of certain bacteria, particularly Gram-positive bacteria. A lysozyme can be found in animal secretions and tissues, including, without limitation, saliva, tears, milk, urine, cervical mucus, leucocytes, and kidneys. For example, a lysozyme can be found in uterine secretions of the pig (Roberts and Bazer, *J. Reprod. Fertil.,* 82:875-892 (1988)). Lysozyme from chicken egg white has been extensively studied, and was the first enzyme for which a crystal structure was solved (Diamond, *J. Mol. Biol.,* 82:371-391 (1974)). Lysozyme is widely distributed in egg white of birds (Prager et al., *J. Biol. Chem.,* 249:7295-7297 (1974)). Structure-function relationships of lysozymes are described elsewhere (Imoto et al., *J. Vertebrate Lysozymes, The Enzymes* 7, P. Boyer, Academic Press, NY, 1972)).

Any ratio of polypeptide to lysozyme can be used. For example, a polypeptide and a lysozyme can be contacted with a solid support at a ratio of at least 4 ng of the polypeptide per 1 ng of the lysozyme (e.g., 4:1, 5:1, 6:1, 7:1, or more). In some cases, a lysozyme and a polypeptide can be contacted with a solid support at a ratio of at least 1 ng of the lysozyme per 1 ng of the polypeptide (e.g., 1:1, 2:1, 3:1, 4:1, 5:1, or more).

The solid support can be any type of solid support including, without limitation, glass slides, plastic plates, 96-well plates, beads, and the like.

The invention will be further described in the following examples, which do not limit the scope of the invention described in the claims.

EXAMPLES

Example 1

Production of Recombinant PRRS Virus Polypeptides

Methods and Materials

Plasmid cloning vectors pET24b, pET25b, and pETBlue2 were obtained from Novagen (Madison, Wis.) and pGEM-T was obtained from Promega (Madison, Wis.). *E. coli* BL21 (DE3) cells were obtained from Novagen. *E. coli* BL21(DE3) strains Tuner, R P, and ABLE-K were obtained from Stratagene (La Jolla, Calif.). DH5α cells were obtained from Invitrogen (Carlsbad, Calif.). Plasmid and DNA purification kits were obtained from Qiagen (Valencia, Calif.). PCR reagents were obtained from Applied Biosystems (Roche Molecular Systems, Branchburg, N.J.). Standard lab supplies, bacterial growth media, and electrophoresis chemicals were obtained from Sigma Chemical Co. (St. Louis, Mo.). PRRS virus cDNA fragments for cloning were obtained by reverse transcriptase-PCR amplification of regions of VR-2332 genomic RNA encoding NSP 1α and 1β, NSP 2, and NSP 4.

PCR Amplification, Cloning of DNA Fragments, and Restriction Analysis

Primers for PCR were designed using Primer3 (Whitehead Institute for Biomedical Research, Cambridge, Mass.) and PRRS virus strain VR2332 sequence (GenBank accession number U87392 or PRU87392) (Table 1). Primers were synthesized, purified, and quantified by Integrated DNA Technologies, Inc. (Coralville, Iowa). PCR reactions used the Applied Biosystems heat activated AmpliTaq Gold® kit (Roche Molecular Systems, Branchburg, N.J.). The reaction mixtures (50 μL total volume) contained 10× Buffer II (1× concentration), 1.5 mM $MgCl_2$, 200 μM each of dATP, dCTP, dGTP, dTTP; 0.2 μM each primer pair (Table 1); 1.0 U AmpliTaq Gold®, and the appropriate cDNA. Upon mixing, the solutions were immediately placed in the thermocycler (GeneAmp PCR system 2400, Perkin Elmer, Shelton, Conn.). Temperature cycle: 1 cycle (95° C. for 10 minutes); 35 cycles (94° C. for 30 seconds, 55° C. for 30 seconds, 72° C. for 45 seconds); 1 cycle (72° C. for 7 minutes, 4° C. hold). The resulting amplified DNA was then separated using an agarose gel. Bands corresponding to the predicted product sizes were gel extracted (Gel Extraction Kit, Qiagen) and then further purified using a PCR Purification Kit. The isolated products were then cloned into pGEM-T vector and transformed into DH5α cells, which were spread on LB 100 μg/mL ampicillin (Amp) agar plates with IPTG and X-Gal. White colonies were selected and grown. The nucleic acid from the selected colonies was sequenced using the standard T7 and SP6 primers (Advanced Genetic Analysis Center, University of Minnesota, St, Paul Minn.). After an initial BLAST search screening (GeneBank NCBI, Bethesda, Md.), trace files were edited to remove vector sequence (Seqman, DNASTAR, Inc., Madison, Wis.) and aligned (Megalign, DNASTAR).

A specialized vector based on pET 24b (Novagen, Madison, Wis.) containing a myc tag 5' leader sequence and a terminal 3' His tag was engineered for high efficiency polypeptide expression and isolation. This plasmid (pET 24b myc His) contains a Bam HI site immediately 3' to the myc tag and a Xho I site preceding the terminal 6X His tag. The vector was prepared for insertion by digestion with BamHI and Xho I, followed by dephosphorylation with calf intestinal alkaline phosphatase (CIAP) (Promega). PCR conditions, insert isolation, and purification were as described above followed by restriction digestion (BamHI, Xho I) to prepare the insert for ligation. Ligation reactions typically contained 100 ng of dephosphorylated vector, 20 ng insert, IX ligation buffer, and 400 Units T4 ligase (New England Biolabs, Beverly, Mass.), total volume 10 μL. The ligation reaction was placed at 16° C. for 16 hours before transformation into DH5α cells. Colonies were selected as previously described and grown. The nucleic acid from the selected colonies was sequenced and analyzed (yielding plasmid pET 24b myc-polypeptide-His).

Test Protein Expression

To test polypeptide expression, recombinant plasmids were transformed into BL21 (DE3)-RP cells, which contain eukaryotic tRNA's for arginine and proline and are chloramphenicol (cam) resistant. Transformed cells were spread on kanamycin 30 μg/mL (kan 30), chloramphenicol 35 μg/mL (cam 35) LB plates and screened by colony PCR using the T7 and SP6 primers for the pET 24b plasmid. Ten positive colonies were grown overnight at 30° C. in 2 mL of 2×YT media (kan 30, cam 35). 200 μL of each of the overnight cultures were used to inoculate ten temperature equilibrated (30° C.)

10 mL aliquots of 2×YT (kan 30). These cultures were grown at 30° C. to an $OD_{600}$ of 0.4, 200 μL was remove for SDS-PAGE analysis, and IPTG was added to a final concentration of 1.0 mM. The induced samples were allowed to grow at 30° C. for 4 hours, and then 200 μL were removed for SDS-PAGE analysis.

Large Scale Polypeptide Expression and Purification

Polypeptides were purified using a modification of the Qiagen Ni-NTA agarose affinity isolation procedure for native His tagged proteins. Briefly, the induced bacterial cells from a 1-liter culture were pelleted at 4000 g for 20 minutes at 4° C., and supernatant was decanted. The pellet was resuspended in 30 mL of lysis buffer (50 mM $NaH_2PO_4$, 300 mM NaCl, 10 mM imidazole, 1μM pepstatin A, 1 μM leupeptin, and 1 mM PMSF, at pH 8.0), and then lysozyme was added to a final concentration of 1.0 mg/mL. The solution was incubated on ice for 60 minutes, followed by sonication on ice using six 10-second bursts of 250 W at 10-second intervals. RNAse A (10 Ig/mL final) and DNAse I (5 μg/mL final) were then added, and the solution was incubated on ice for an additional 15 minutes to further degrade nucleic acids. The lysate was then centrifuged (4° C.) for 30 minutes at 10,000×g to pellet the insoluble aggregates and cellular debris. The pellet contained the majority of expressed recombinant polypeptide in the form of inclusion bodies and was isolated in the denatured form to be refolded later. Immediately following centrifugation, this pellet was resuspended in 30 mL of a solution containing 100 mM $NaH_2PO_4$, 10 mM Tris-HCl, and 8 M urea, at pH 8.0. The resuspended pellet was rotated (200 rpm) at room temperature for 30 minutes and then placed at 4° C. for later processing.

The supernatant containing various levels of soluble polypeptide was decanted into 6 mL of 50% Ni-NTA slurry and gently rotated (200 rpm) for 1 hour at 4° C. The supernatant-Ni-NTA mixture was then poured into a 1.5×30 cm column and drained by gravity. The column was washed twice with 20 mL of a solution containing 50 mM $NaH_2PO_4$, 300 mM NaCl, 20 mM imidazole, 1μM pepstatin A, 1 μM leupeptin, and 1 mM PMSF at pH 8.0. The polypeptide was eluted with four 3-mL aliquots of elution buffer containing 50 mM $NaH_2PO_4$, 300 mM NaCl, 250 mM imidazole, 1 μM pepstatin A, 1 μM leupeptin, and 1 mM PMSF at pH 8.0. Purified polypeptides were concentrated by either tangential flow filtration cassette (Pellicon XL Ultracel PLC 5 kD, Millipore, Bedford Mass.) or a YM-3 Amicon Centriprep® centrifugal filter device (Millipore Corp. Bedford, Mass.), followed by dialysis (Spectra/Por MWCO® 6-8,000, Spectrum Laboratories, Rancho Dominguez, Calif.) against 50% glycerol and 20 mM Tris HCl, pH 7.5. Polypeptide concentrations were determined using the Bio-Rad RC DC protein assay kit (Bio-Rad, Hercules, Calif.). Purified polypeptide solutions were stored at −20° C.

The denatured insoluble recombinant polypeptide mixture stored at 4° C. was centrifuged at 4° C. for 30 minutes at 10,000×g to pellet cellular debris. The supernatant contained high levels of previously insoluble denatured recombinant polypeptide and was decanted into 6 mL of 50% Ni-NTA slurry and gently rotated (200 rpm) for 1 hour at 4° C. The supernatant-Ni-NTA mixture was then poured into a 1.5×30 cm column and allowed to drain. The column was washed twice with 20 mL of a solution containing 100 mM $NaH_2PO_4$, 10 mM Tris-HCl, and 8 M urea, at pH 6.3. The polypeptide was then eluted 4 times with 3 mL aliquots of elution buffer containing 100 mM $NaH_2PO_4$, 10 mM Tris-HCl, and 8 M urea, pH 5.9. SDS gel analysis, concentration of the polypeptide, dialysis into PBS, and the concentration determinations were done as described above.

Polypeptide Refolding

Refolding of the denatured recombinant polypeptide was performed using a variation of the methods described elsewhere (Buchner et al., *Anal. Biochem.,* 205:263-270 (1992) and Clark, Curr. *Opin. Biotechnol.,* 9:157-163 (1998)). Briefly, denatured polypeptide solutions containing purified polypeptide were pooled and dialyzed (Spectra/Por MWCO® 6-8,000, Spectrum Laboratories, Rancho Dominguez, Calif.) for 4 hours at 4° C. against 500 mL of 0.1 M Tris, pH 8.0, 6 M guanidine-HCl, and 2 mM EDTA. The dialysis was then repeated with fresh buffer for an additional 4 hours. After adjusting the polypeptide concentration to 3 mg/mL (concentration determined with the Bio-Rad RC DC protein assay kit, Bio-Rad, Hercules, Calif.), dithiothreitol (DTT) was added to a final concentration of 300 mM DTT. The resulting 5-mL solution was stirred at room temperature for 2 hours followed by filtration using a 0.45 μm filter (Syringe Filter, Fisher Scientific, Pittsburgh, Pa.). The reduced polypeptide solution was then added rapidly at 4° C. with moderate stirring into 500 mL of refolding buffer (100 mM Tris HCl, pH 8.0, 0.5 M L-arginine, 8 mM oxidized glutathione, 2 mM EDTA, 10 μM pepstatin A, 10 μM leupeptin, and 1 mM PMSF) corresponding to a final dilution of about 1:100. The resulting solution was then filtered through a 0.22 μm membrane (Steritop, Millipore, Bedford Mass.) to remove particulates and stirred overnight. Purified polypeptide was concentrated by tangential flow filtration cassette (Pellicon XL Ultracel PLC 5 kD, Millipore, Bedford Mass.) to a volume of 10 mL followed by dialysis (Spectra/Por MWCO® 6-8,000, Spectrum Laboratories) against 50% glycerol and 20 mM Tris HCl, pH 7.5. Polypeptide concentrations were determined using the Bio-Rad RC DC protein assay kit (Bio-Rad, Hercules, Calif.). Purified polypeptide solutions were stored at −20° C.

Gel Electrophoresis and Immunoblotting

Bacterial lysates, purification fractions, and purified polypeptides were analyzed on SDS-polyacrylamide gels with the Laemmli buffer system (Laemmli, *Nature,* 227:680-684 (1974). Protein bands were visualized by staining with 0.025% Coomassie blue. For immunoblotting, gels were electroblotted onto supported nitrocellulose membranes (MSI Separations, Westbrook Mass.). Membranes were incubated with anti-myc monoclonal antibody 9E10 for 1 hour at room temperature. Antibody binding was detected using alkaline phosphatase-conjugated goat-anti-mouse IgG and visualized with the ECL Western Blotting system (Amersham Pharmaciea Biotech, Piscataway, N.J.).

ELISA

ELISA plates were coated with individual PRRS virus polypeptides in 100 μL carbonate buffer (15 mM $Na_2CO_3$ and 35 mM $NaHCO_3$), pH 9.6, or buffer alone overnight and washed 6 times with PBS-Tween (0.1% Tween-20). Two hundred AL of PBS-Tween containing 2.5% nonfat dried milk was added for 1 hour at room temperature to block previously unbound sites, and the plates were washed 5 times. One hundred μL of pig serum at various dilutions was added in duplicate for 2 hours at room temperature, and plates were washed 4 times with PBS-Tween. Levels of specific antibody were determined by incubation of wells in horseradish peroxidase-conjugated goat-anti swine IgG (heavy+light chains) (KPL, Gaithersburg Md.) diluted 1:5000 for 1 hour. Wells were washed 5 times, and color was developed with 100 μL of TMB substrate (KPL). Reactions were stopped after 15 minutes with 100 μL 1 M phosphoric acid, and the plates read at 450 nm.

pETBlue2 (Novagen)

Clones in pGEM-T were transformed into DH5α cells. Colonies were grown overnight, and plasmids were isolated with Qiagen Miniprep Purification Kits. The purified plasmids and 2 μg of pETBlue2 were digested individually with Nco I and Not I for 4 hours. pETBlue2 was dephosphorylated with CIAP for the last 20 minutes of digestion. Insert fragments and linearized pETBlue2 were gel purified with the Qiagen Gel Purification Kit and then ligated in an about 1:2 ratio of vector to insert.

The ligations were transformed into DH5α cells. Two colonies per plate were cultured overnight, and a plasmid preparation was performed on the cultures to isolate the plasmids. The purified plasmids were then transformed into BL-21 (DE3) RP cells. Two colonies per clone were cultured and induced with 400 μM of IPTG for 4 hours at 30° C. A subsequent SDS-PAGE gel of the whole cell lysates showed no evidence of specific polypeptide induction. Similarly, ELISA tests of induced cell lysates coated on microtiter plates and reacted with $PRRS^+$ and $PRRS^-$ swine sera did not reveal evidence of PRRS virus polypeptide. Evaluation of pETBlue2 for PRRS virus polypeptide expression was stopped at this point.

pET24d/pET25b (Novagen)

2 μg of pET24d was digested with Nco I and Not I and dephosphorylated with CIAP. The fragment was then purified with a Qiagen PCR Purification Kit. An agarose gel was used to further purify the fragment, and a QIAquick Gel Extraction Kit was used to extract the vector fragment from the gel. The pET24d fragment was then ligated to the clone fragments in an about 2:1 insert to vector ratio. Transformation of these plasmids into DH5α cells did not result in colony growth. Similar results were obtained after cloning into pET24d vector that was not dephosphorylated or into pET25d that was or was not dephosphorylated.

Cloning

PCR was used to amplify the three PRRS virus proteases that were identified by their active sites, at the following amino acid positions in ORF 1a of PRRS virus strain VR2332: papain-like cysteine protease α and β (PCP α/β) (amino acids 74-146 and 268-339), unusual cysteine protease (amino acids 435-506), and the poliovirus 3C-like serine protease (amino acids 1840-1946). The location of these functional protease domains in the PRRS virus genome is shown graphically in FIG. 1. Table 1 lists the nucleotide sequence regions of PRRS virus strain VR2332 that were PCR amplified and summarizes the overall results.

TABLE 1

PRRS virus NSP fragments cloned.

| Nonstructural protein (NSP) | Region Amplified | Restriction Sites | Results |
|---|---|---|---|
| 1 (PCPα/β) | 174-1322 | AccIII, BamHI NdeI, XhoI XhoI, NcoI | PCR band, digestion product, transformed bacterial colonies positive by PCR screening, no plasmid |
| 2 (unusual cysteine protease) | 1339-4922 | BamHI, NcoI NdeI, XhoI | PCR band, digestion product, PCR-positive colonies, no plasmid |
| 4 (poliovirus 3C-like serine protease) | 5598-6209 | NdeI, XhoI | PCR band, digestion product, transformed bacterial colony, plasmid with insert, point mutation in protein |

Nonstructural Protein 1 (NSP 1)

Ligation products of this fragment and pET24b yielded colonies following transformation of *E. coli* DH5α cells. Colonies grew slowly and typically required 48 hours at 37° C. to be visible. Screening of colonies by PCR gave positive results consistent with the presence of a cloned fragment. Efforts to recover recombinant plasmid from bacteria grown in broth were unsuccessful. It appeared that recombinant plasmids were unstable. To overcome this problem, a variety of *E. coli* strains were used as plasmid recipients: DH5α, JM109, HB101, SURE (Stratagene), and ABLE (Stratagene). Transformation plates and broth cultures were incubated at 37°, 30°, and 22° C. Culture volumes of 1, 2, 5, 10, and 25 mL were performed. Various methods of plasmid purification were attempted, including Qiagen miniprep, standard alkaline lysis with phenol/chloroform extraction, and boiling lysis with lithium chloride/isopropanol precipitation. None of these conditions and treatments resulted in the recovery of recombinant plasmid. In all, 353 transformants were screened by colony PCR, with about 70 reactions yielding bands. Plasmid purifications yielded no visible bands or a high molecular weight band, which upon diagnostic restriction digestion disappeared from the gel. This result is consistent with the behavior of genomic DNA.

Nonstructural Protein 2 (NSP 2)

The same results were obtained as with NSP 1. Transformed colonies were obtained on LB agar plates that were positive by PCR, but attempts to isolate plasmid DNA were unsuccessful.

Nonstructural Protein 4 (NSP 4)

The results with NSP 4 were identical to the experiences with NSP 1 and NSP 2 with one exception. Plasmid DNA was successfully recovered from a clone and was shown by DNA sequencing to contain the predicted NSP 4. A point mutation was noted that changed amino acid 16 from isoleucine to threonine.

Cloning of NSP Fragments in pET24bmycHis

DNA fragments corresponding to NSP 1, NSP 2, and NSP 4 were amplified by PCR and cloned into pET24b-mycHis (FIGS. 2, 3, and 4). Functionally positive clones were identified by small-scale test induction of individual colonies, and a single, high expressing clone was picked, grown, purified, and sequenced. Each clone contained EcoRI and BamHI sites at the 5'-end and an XhoI site at the 3'-end. The encoded polypeptides contained an amino terminal myc tag and a carboxyl terminal 6×His tag.

Recombinant NSP Expression and Purification

Figure 5:
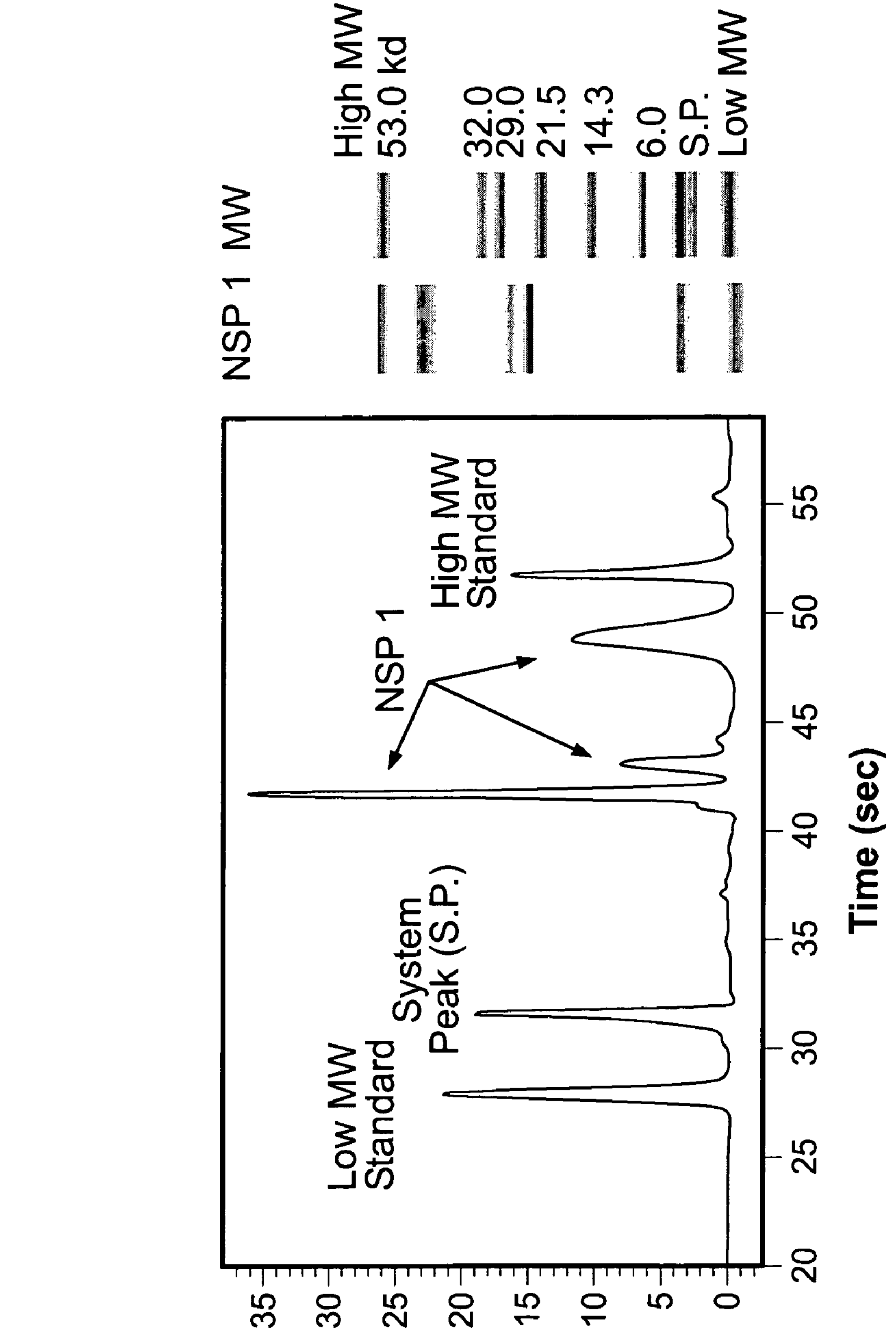
FIG. 5 is a graph plotting the fluorescence level of refolded NSP 1 polypeptides detected using an Agilent bioanalyzer. Purified and refolded NSP 1 polypeptide was applied to an Agilent 2100 Bioanalyzer (Agilent Technologies, Palo Alto, Calif.) and analyzed according to the standard protocol on the Protein 50 Assay LabChip kit. The NSP 1 polypeptide resulted in peaks corresponded to 46 kD (intact polypeptide) and 24 and 22 kD PCP1α and PCP1β, respectively.
Figure 6:
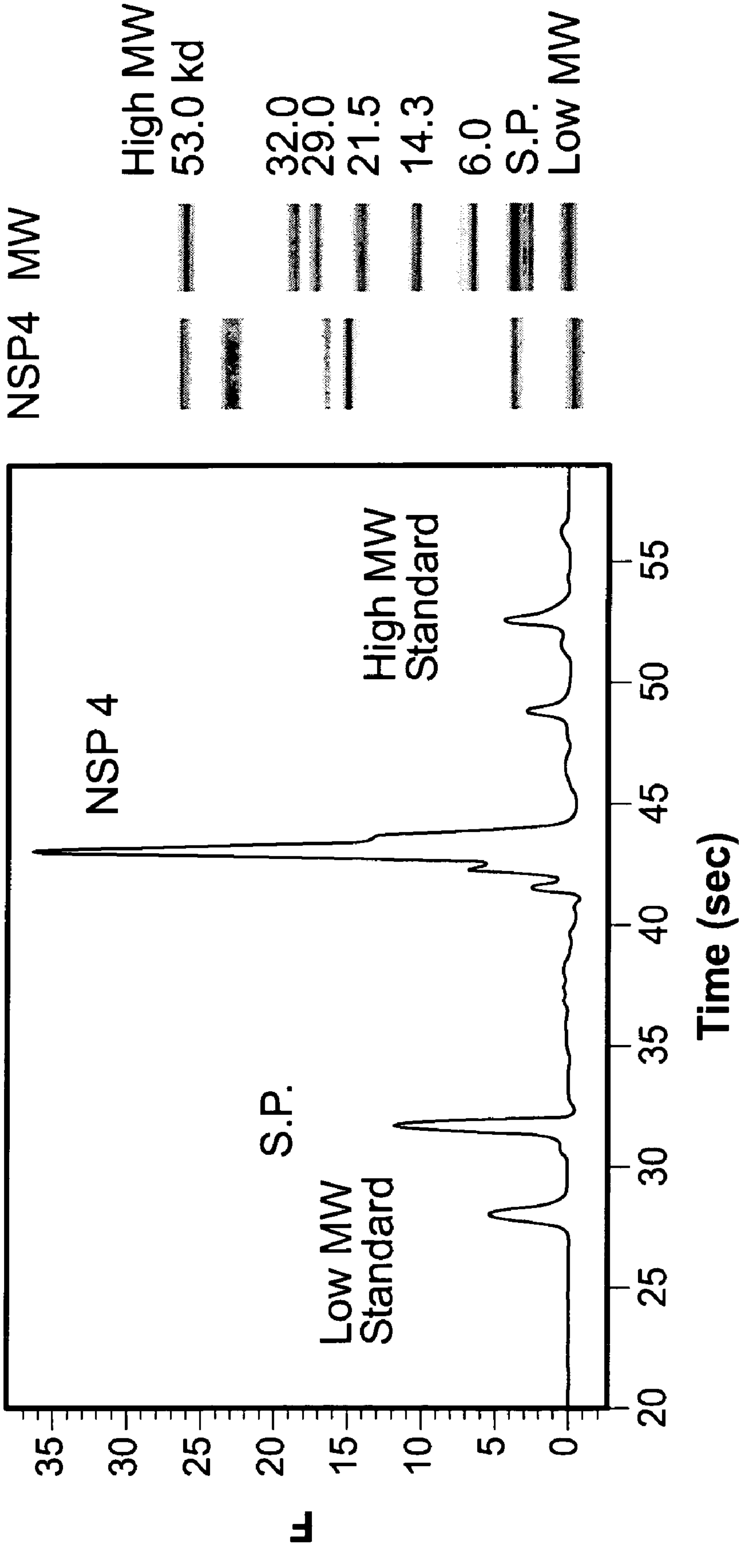
FIG. 6 is a graph plotting the fluorescence level of refolded NSP 4 polypeptides detected using an Agilent bioanalyzer. Purified and refolded NSP 4 polypeptide was applied to an Agilent 2100 Bioanalyzer (Agilent Technologies, Palo Alto, Calif.) and analyzed according to the standard protocol on the Protein 50 Assay LabChip kit. The NSP 4 polypeptide resulted in a single peak at 26 kD.

Individual colonies were grown and induced for polypeptide expression as described herein. Polypeptides were purified by Ni-NTA immobilized metal affinity chromatography. Recombinant NSP 1 and NSP 4 were readily expressed at mg/L levels in shake flasks under the described conditions, and about 50% of the polypeptide was recovered following affinity chromatography and refolding (Table 2). The purified and refolded polypeptides were homogeneous and contained fragment sizes consistent with predicted protease activities. The NSP 1 and NSP 4 polypeptides consisted of homogeneous polypeptides in which the NSP 1 preparation contain intact polypeptide and two fragments autoproteolytically cleaved into PCP1α and PCP1β, whereas the NSP 4 preparation was a single band (FIGS. 5 and 6).

TABLE 2

Polypeptide expression yields.

| Nonstructural protein (NSP) | Total expressed (mg/L culture) | Ni-NTA purified (mg/L culture) | After Refolding (mg/L culture) |
|---|---|---|---|
| NSP 1 (pcpα/pcpβ) | 20 | 10 | 9 |
| NSP 4 | 25 | 14 | 13 |

The NSP 2 polypeptide was expressed at low levels that could not be visualized in whole cell lysates on SDS polyacrylamide gels stained with Coomassie blue, but it was observed by western blot detection with anti-myc antibody. The presence of multiple bands at sizes lower than the encoded polypeptide sequence of 132 kD indicated that proteolytic degradation had occurred either during bacterial growth and polypeptide expression or during cell lysis and sample handling. Further evidence that the western blot band contained PRRS virus NSP 2 was obtained from test ELISA results in which microtiter plate wells were coated with induced bacterial lysates from clones expressing NSP 1, NSP 2, or NSP 4. Wells containing NSP 2 polypeptide reacted strongly and in a specific and dilution-dependent fashion. The low level of expression of NSP 2 polypeptide may be due to the presence of a hydrophobic region toward the carboxyl end of the polypeptide.

Effect of Refolding on ELISA Reactivity

Apparent differences in antibody reactivity among the three NSP polypeptides were observed in the preliminary test ELISA, raising the possibility that the conformation of the purified, recombinant polypeptides might be variable and might affect immunoreactivity. Recombinant nucleocapsid (N) varied in immunoreactivity depending on the conditions of expression, purification, and refolding. Therefore, the immunoreactivity of NSP 1 and NSP 4 was evaluated before and after refolding.

Figure 7:
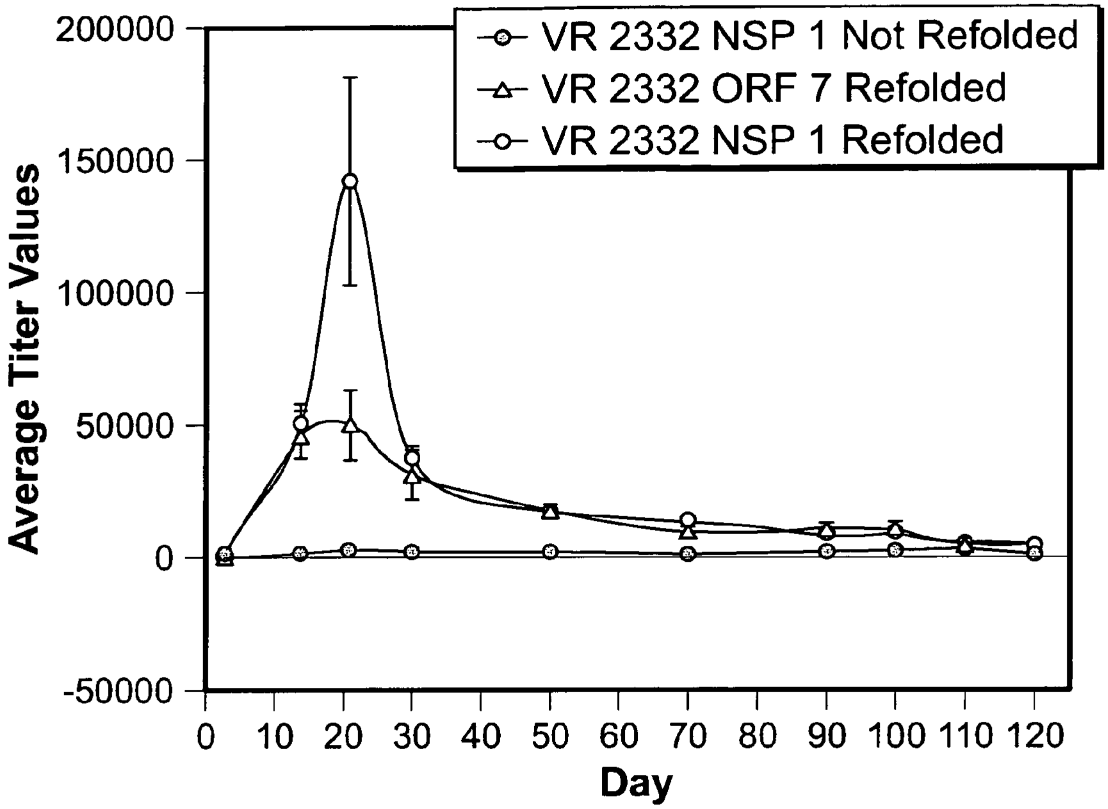
FIG. 7 is a graph plotting the average titer values for antibodies reactive against NSP1 polypeptides (not refolded), NSP 1 polypeptides (refolded), and nucleocapsid (ORF 7) polypeptides (refolded). The time course of anti-NSP 1 or anti-N antibody response was performed using a cohort of 14 pigs that were infected with PRRS virus strain MN30100 and bled at the indicated times.

Refolding had an effect on the immunoreactivity of NSP 1 (FIG. 7). Affinity purified NSP 1 polypeptide that was not refolded was essentially non-reactive to serum obtained from pigs during a 120 day period after PRRS virus infection.

Figure 8:
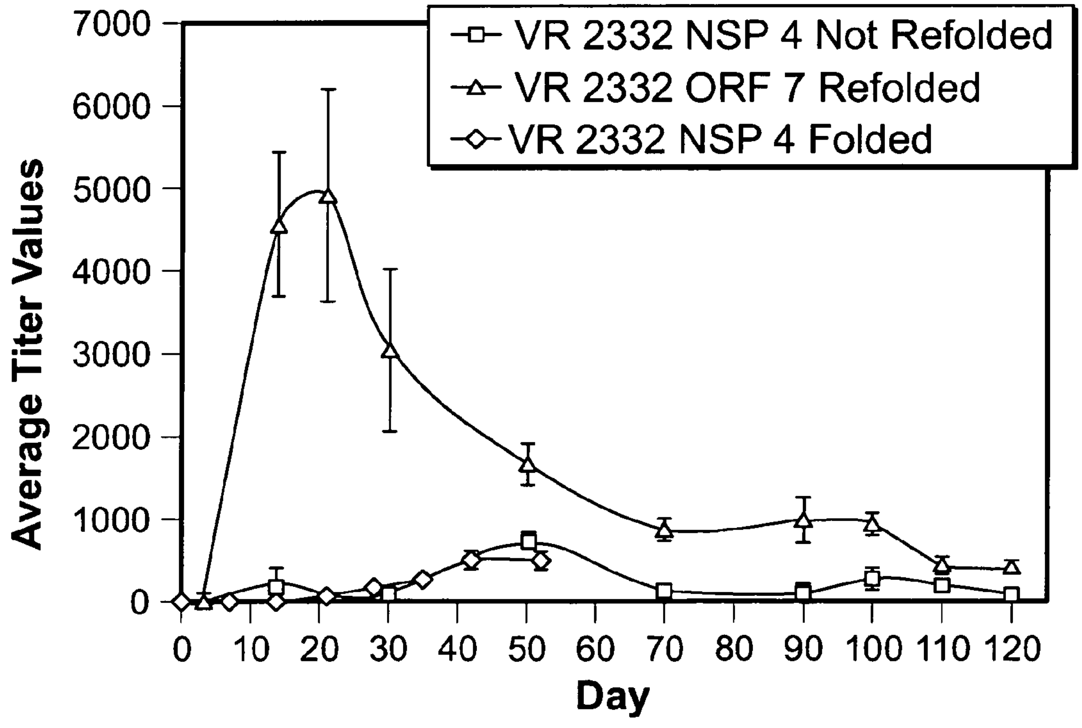
FIG. 8 is a graph plotting the average titer values for antibodies reactive against NSP 4 polypeptides (not refolded), NSP 4 polypeptides (folded), and nucleocapsid (ORF 7) polypeptides (refolded). The time course of anti-NSP 4 (not refolded) and anti-ORF 7 antibody responses were performed using a cohort of 14 pigs that were infected with PRRS virus strain MN30100, while the anti-NSP 4 (folded) responses were performed in pigs immunized with Ingelac MLV vaccine.

By contrast, there was no substantial difference in anti-NSP 4 antibody titers against non-refolded or refolded NSP 4 polypeptides (FIG. 8). The analysis of refolded polypeptide reactivity was terminated at 52 days since it was apparent that there was no difference in the two forms for NSP 4. The lack of effect of refolding was further emphasized by the choice of serum samples for analysis. The maximum antibody response was predicted to occur in animals immunized with homologous virus (VR2332 is the parental strain to Ingelvac MLV vaccine) and tested with refolded, presumably native, polypeptide. The minimum response was predicted to occur in animals infected with a heterologous strain (MN30100) and tested with non-refolded polypeptide. Under these conditions, no differences were observed.

These results demonstrate that polypeptide refolding affects immunoreactivity in the case of NSP 1 and is insignificant for NSP 4. Each recombinant NSP polypeptide, however, is routinely refolded and stored in soluble form in glycerol to maintain a uniform product.

Induction and Duration of Antibody Responses to NSP Recombinant Polypeptide

Figure 9:
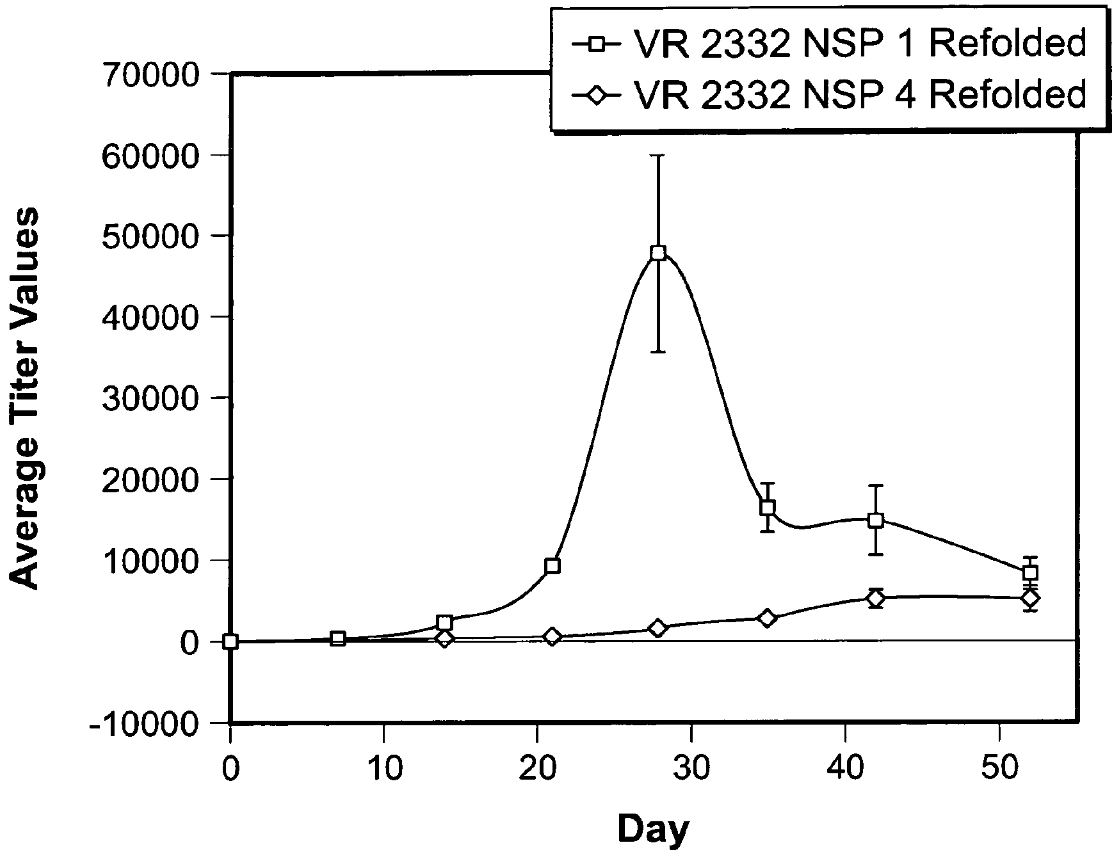
FIG. 9 is a graph plotting the average titer values for antibodies reactive against refolded NSP 1 and NSP 4 polypeptides in pigs immunized with Ingelvac MLV.

The kinetics of anti-NSP 1 antibody response were similar to the response to N in 4-month old gilts. The anti-NSP 1 titer was about 1/50,000 at 14 days after infection and peaked at 21 days after infection at about 1/140,000. Antibody levels declined rapidly and were equivalent to N (ORF 7) from 28-120 days after infection. In a small group of young pigs (4-6 weeks of age) immunized with Ingelvac MLV, antibody titers to NSP 1 showed a similar sharp peak and rapid decline, but the peak occurred at 28 days instead of 21 days after infection (FIG. 9).

In gilts, the antibody response to NSP 4 was weak in comparison to N and to NSP 1. There was evidence of an increase in titer at 40-55 days after infection, and again, possibly at 100-110 days after infection. In young pigs, there was a similar late and modest increase in anti-NSP 4 titers starting at about 28-35 days after immunization (FIG. 9). This time frame corresponds to the period in which acute infection is resolved.

Cross-reactivity of Swine Anti-NSP Antibodies to VR2332 NSP Recombinant Polypeptide Purified and refolded NSP 1 and 4 polypeptides, derived from the VR2332 strain of PRRS virus and expressed in bacteria, reacted equivalently with antiserum from pigs exposed to a homologous strain (Ingelvac MLV) and a heterologous strain (MN30100) of PRRS virus.

Example 2

Production of Additional Recombinant PRRS Virus Polypeptides

The following polypeptides were produced: a PRRS virus NSP 2P polypeptide (FIG. 19), a PRRS virus first N-terminal ectodomain ORF 5 polypeptide (ORF 5 5'; FIGS. 20 and 21), a PRRS virus first and second N-terminal ectodomains ORF 5 polypeptide (ORF 5' total; FIG. 22), a PRRS virus endodomain ORF 5 polypeptide (ORF 5 3'; FIGS. 23 and 24), a chimeric polypeptide combining a PRRS virus first and second N-terminal ectodomains ORF 5 polypeptide with a PRRS virus first and second N-terminal ectodomains ORF 6 polypeptide (ORF 5+6; FIG. 25), and a PRRS virus ORF 7 polypeptide. The nucleic acid encoding the polypeptides were from the nucleotide sequences in the VR-2332 strain of PRRS virus (GenBank® Accession No. PRU87392) or the MN30100 strain of PRRS virus.

PCR Amplification and Cloning

Fragments for cloning were obtained from plasmids prepared as described elsewhere (Nelsen et al., *J. Virol.,* 73:270-280 (1999)). The desired fragments were isolated with appropriate cloning sites by PCR. Primers were designed using Primer3 (Whitehead Institute for Biomedical Research, Cambridge, Mass.). The oligonucleotide primers were obtained from IDT (Coralville, Iowa). The nucleic acid encoding the ORF 7, ORF 5 5', and ORF 5 3' polypeptides were PCR amplified in separate reactions using the AmpliTaq Gold® kit (Roche Molecular Systems, Branchburg, N.J.). The nucleic acid encoding the ORF 5 5' total and ORF 5+6 polypeptide were constructed both by PCR of cDNA and subsequent oligo annealing, PCR amplification, and ligation. The reaction mixtures (50 μL total volume) contained 10× Buffer II (1× concentration), 1.5 mM $MgCl_2$, 200 μM each of dATP, dCTP, dGTP, and dTTP; 0.2 μM each primer pair; 1.0 U AmpliTaq Gold®, and the appropriate serially diluted (1:10 . . . 1:10,000) MRNA derived cDNA. Upon mixing, the solutions were immediately placed in the thermocycler (GeneAmp PCR system 2400, Perkin Elmer, Shelton, Conn.). Temperature cycle; 1 cycle (95° C. for 10 min); 35 cycles (94° C. for 30 sec, 55° C. for 30 sec, 72° C. for 45 sec); 1 cycle (72° C. for 7 min, 4° C. hold). The resulting amplified DNAs were then separated on an agarose gel. Bands corresponding to the predicted product sizes were gel extracted (Gel Extraction Kit®, Qiagen, Valencia, Calif.) then further purified using the Qiagen PCR Purification Kit® (Qiagen, Valencia, Calif.). The isolated products were then cloned into pGEM®T vector (Promega, Madison, Wis.) transformed into DH5α cells (Invitrogen Corp., Carlsbad, Calif.), which were spread on LB 100 mg/mL ampicillin (Amp) agar plates with IPTG and X-Gal. Colonies were color-selected and grown, and the nucleic acid sequenced (Advanced Genetic Analysis Center, University of Minnesota, St, Paul Minn.). After an initial BLAST search screening (GeneBank NCBI, Bethesda, Md.), trace files were edited to remove vector sequence (Seqman® DNASTAR, Inc., Madison, Wis.), and overlapping sequences were aligned (Megalign® DNASTAR, Inc., Madison, Wis.). The nucleic acid encoding the NSP 2P polypeptide was obtained by digesting the clone pET 24b myc-NSP 2-His (FIG. 3) with XhoI and religating the vector.

Sub-cloning into the Expression Plasmid

Clones were amplified using the appropriate pGEM®T constructs as templates for primers having terminal BaniHI and Xho I sites. The PCR conditions and the insert isolation and purification were standard, followed by restriction digestion (BamHI, XhoI) to prepare the insert for ligation. Ligation conditions were: 100 ng of dephosphorylated vector, 20 ng insert, 1× ligation buffer, and 400 U T4 ligase (New England Biolabs), total volume 10 μL. The ligation reaction was placed at 16° C. for 16 hours before transformation into DH5α cells (Invitrogen Corp., Carlsbad, Calif.). Colonies were selected as previously described and grown, and the nucleic acid sequenced and analyzed (yielding plasmid pET 24b myc-polypeptide-His).

Nucleic acid constructs encoding polypeptides similar to ORF 5 5' and ORF 5 3' were also made from MN30100 PRRS virus sequences (Bierk et al., *Vet. Rec.,* 148:687-690 (2001)) starting from cell culture supernatants containing the virus. Viral RNA was obtained from the media by standard procedures. Viral RNA was isolated using the QIAamp viral RNA kit (Qiagen) and stored at −80° C. Purified RNA was converted to cDNA with random hexamers using the GeneAmp RNA PCR kit (Applied Biosystems, Roche Molecular Systems, Branchburg, N.J.). Briefly, 1 μL of a 50 μM solution of random hexamers was combined with 3.0 μg of total RNA to a total volume of 4 μL. The solution was heated at 68° C. for 10 minutes, then quick chilled on ice. 16 μL of a master mix solution was added for a final concentration that contained 10× Buffer II (1× concentration final); 5 mM $MgCl_2$, 1.0 mM each of dATP, dCTP, dGTP, and dTTP; 20 U/μL Rnase inhibitor, and 25 U/μL reverse transcriptase. This solution was immediately incubated at 25° C. for 10 minutes, 42° C. for 30 minutes, 99° C. for 5 minutes, then 4° C. for 5 minutes. The resulting cDNA was stored at −20° C. and used for PCR amplification.

Protein Expression

Plasmids pET 24b myc-polypeptide-His were transformed into BL21™ (DE3)-RP cells (Stratagene, River Creek, Tex.), which contain eukaryotic tRNA's for arginine and proline as well as chloramphenicol (cam) resistance. Transformed cells were spread on Kanamycin 30 μg/mL (kan 30), chloramphenicol 35 μg/mL (cam 35) LB plates and screened by colony PCR using the T7, T7 termination primers for the pET 24b plasmid. Ten positive colonies each were grown overnight at 30° C. in 2 mL of 2×YT media (kan 30, cam 35). 200 μL of each of the overnight cultures were used to inoculate ten temperature equilibrated (30° C.) 10 mL aliquots of 2×YT (kan 30). These cultures were grown at 30° C. to an $OD_{\lambda=600}$ of 0.3; 200 μL was remove for SDS-PAGE analysis; and IPTG was added to a final concentration of 1.0 mM. The induced samples were allowed to grow at 30° C. for 4 hours, then 200 μL was removed for SDS-PAGE analysis. SDS-PAGE gels indicated that all of the colonies expressed polypeptides of the predicted size at high levels (>2 mg/liter media). Expression on a larger scale was done in the same manner scaling up by 100× for a total of 1 liter of media.

Polypeptide Purification

Figure 17:
FIG. 17 contains photographs of gels of the indicated purified PRRS virus polypeptides.

The polypeptides were purified using a modification of the Qiagen Ni-NTA agarose affinity isolation procedure for denatured His tagged polypeptides (Qiagen, Valencia, Calif.). Briefly, 1 liter of induced plasmid containing bacterial cells was pelleted at 4000 g for 20 minutes at 4° C., and the supernatant was decanted off. Immediately following centrifugation, the pellet was resuspended in 30 mL of a solution containing 100 mM $NaH_2PO_4$, 10 mM Tris-HCl, 8 M Urea, at pH 8.0, and rotated gently at room temperature for 30 minutes. The resulting suspensions were then centrifuged (4° C.) for 30 minutes at 10,000 g to pellet the cellular debris. The supernatant contained high levels of denatured polypeptide and was decanted into 6 mL of 50% Ni-NTA slurry and gently rotated for 1 hour at 4° C. The supernatant-Ni-NTA mixture was then poured into a 1.5 cm ID×30 cm length column and allowed to drain. The column was then washed twice with 20 mL of a solution containing 100 mM $NaH_2PO_4$, 10 mM Tris-HCl, 8 M Urea, at pH 6.3. The polypeptide was then eluted 4 times with 3 mL aliquots of elution buffer containing 100 mM $NaH_2PO_4$, 10 mM Tris-HCl, 8 M Urea, at pH 5.9. SDS gel analysis and protein concentration were determined as described above (FIG. 17).

Polypeptide Refolding

Refolding of the denatured recombinant polypeptides was performed using a variation of the method described elsewhere (Buchner et al., *Anal. Biochem.,* 205(2):263-70 (1992) and Clark, *Curr. Opin. Biotechnol.,* 9(2):157-63 (1998)). First, denatured polypeptide solutions containing pure polypeptide were pooled and dialyzed (Spectra/Por MWCO® 6-8,000, Spectrum Laboratories, Rancho Dominguez, Calif.) for 4 hours at 4° C. against 500 mL of 0.1 M Tris, pH 8.0, 6 M guanidine-HCl, and 2 mM EDTA. The dialysis was then repeated with fresh buffer for an additional 4 hours. After adjusting the polypeptide concentration to 3 mg/mL (concentration determination using the Bio-Rad RC DC protein assay kit, Bio-Rad, Hercules, Calif.), dithiothreitol (DTT) was added yielding a final concentration of 300 mM DTT. This solution (5 mL) was allowed to stir at room temperature for 2 hours followed by filtration using a 0.45 μm filter (Syringe Filter, Fisher Scientific, Pittsburgh, Pa.). The reduced polypeptide solution was then added rapidly at 4° C. with moderate stirring into 500 mL of refolding buffer (100 mM Tris at pH 8.0, 0.5 M L-Arginine, 8 mM oxidized glutathione, 2 mM EDTA,10 μM pepstatin A, 10 μM leupeptin, 1 mM PMSF) corresponding to a final dilution of about 1:100. The resulting solution was then filtered through a 0.22 μm membrane (Steritop, Millipore, Bedford Mass.) to remove particulates and left to stir overnight. The purified polypeptide was concentrated by tangential flow filtration cassette (Pellicon XL Ultracel PLC 5 kd, Millipore, Bedford Mass.) to a volume of 10 mL followed by dialysis (Spectra/Por MWCO® 6-8,000, Spectrum Laboratories, Rancho Dominguez, Calif.) against 20 mM Tris HCl, at pH 8.0. Polypeptide concentrations were determined using the Bio-Rad RC DC protein assay kit (Bio-Rad, Hercules, Calif.), quantitative SDS gel, and the Agilent 2100 bioanalyzer (Protein LabChip® Kit, Agilent Technologies, Palo Alto, Calif.). Purified polypeptide solutions were stored at −80° C. The polypeptides ORF 5 5', ORF 5 3', and ORF 5 total were not routinely refolded because refolding did not affect ELISA reactivity.

ELISA

Polypeptides were diluted in carbonate buffer (15 mM $Na_2CO_3$, 35 mM $NaHCO_3$, pH 9.6) to a concentration of 1 μg/mL. Each of the ELISA plate wells (COSTAR 3590, 96 Well ELA/RIA plate, Corning Inc., Corning, N.Y.) was then coated with 100 μL of the appropriate polypeptide carbonate solution (providing 100 ng of polypeptide per well), then incubated at 4° C. overnight. Samples were run in duplicate. A set of wells was left uncoated for determination of serum and secondary antibody background effects (found to be less that 0.005 Absorbance units). The plates were then washed (EL-404 Microplate Washer, Bio-Tek Instruments Inc. Winooski, Vt.) six times with PBS-Tween-20 (0.1%) at room temperature. Non-specific binding sites were blocked with 300 μL/well of PBS-Tween (0.1%) containing 3% nonfat dried milk (NFDM) for 2 hour at room temperature. The plates were then washed as described above. Serum samples were then diluted 1:2000 with PBS-Tween-20 (0.1%) containing 3% NFDM, then 100 μL was added to the appropriate wells, and the plates equilibrated at room temperature for 2 hours. The titer values using serial dilution indicated that 1:2000 serum dilutions demonstrated similar data trends (within error). The wells were then washed as before. Secondary detection antibody (peroxidase labeled goat anti-swine IgG (H+L), Kirkegaard & Perry Laboratories Inc. (KPL) Gaithersburg, Md.) was diluted 1:5000 in PBS-Tween (0.1%) containing 3% NFDM, 100 μL of the diluted solution was added to each well. After incubating for 1 hour at room temperature, the plates were again washed. Tetra methyl benzidine (TMB cat #50-76-00 Kirkegaard & Perry Laboratories Inc. (KPL) Gaithersburg, Md.) was used to perform the calorimetric analysis. Equal volumes of TMB peroxidase (solution A) and peroxidase (solution B) were mixed together, and 100 μL was added to each well. The solution was allowed to develop for 15 minutes at room temperature (blue color). The reactions were then quenched by adding 100 μL of 1 M phosphoric acid (yellow color). Plates were read at 450 nm (Thermo Max microplate reader, Molecular Devices, Sunnyvale, Calif.).

Example 3

PRRS Virus Antibody Responses Following Repeated Homologous Wild-type Virus Challenges Serology has been the cornerstone of veterinary disease monitoring and control. The presence of specific antibodies in serum indicates prior exposure to disease, and may also confirm that the animal possesses protective immunity. Currently available PRRS virus ELISA antibody tests may not be sensitive for all possible situations found in infected groups of pigs, particularly re-infected animals. Many animals return to seronegative status within 4 to 6 months after initial infection (Yoon et al., *J. Vet. Diagn. Invest.,* 7:305-312 (1995)). In addition, there have been reports of animals returning to and remaining ELISA antibody negative during multiple repeated vaccinations with a modified live PRRS virus vaccine (Baker et al., Proc. Allen D. Leman Swine Conference, vol. 26 (suppl.) p. 31 (1999)). If loss of ELISA antibody response were to occur after repeated frequent exposures to the same wild-type PRRS virus, it might alter the way veterinarians interpret PRRS virus ELISA test results for their clients when monitoring herds for continued virus circulation.

The following experiment was performed to (1) determine whether PRRS virus ELISA seronegative animals can be induced by multiple low-dose immunizations with wild-type virus and (2) characterize the expression timeline for PRRS virus serum neutralizing antibodies and antibodies to individual recombinant ORF polypeptides.

Sixty-eight PRRS virus-negative 6 month old barrows were injected twice, one month apart, and then every other month approximating a 6/60 type schedule for a total of 6 immunizations using $10^{2.5}$ field strain SD 28983 PRRS viruses per dose. The animals were bled 3 weeks following each immunization, and the samples tested for PRRS virus ELISA and serum neutralizing antibodies. Four months after the last immunization (12 months after initial exposure), the animals were challenged again with SD 28983.

The blood samples were tested for serum neutralization antibodies by fluorescent focus neutralization (strain 23983 virus as assay inoculum) and for antibodies to recombinant PRRS virus polypeptides obtained as described herein. Briefly, PRRS virus rORF polypeptides were produced by inserting the desired cDNA nucleic acid fragments into *E. coli* for expression. The polypeptides produced included nucleocapsid (an ORF 7 polypeptide) and a chimera polypeptide fragment that contained the ectodomain regions of both an ORF 5 envelope polypeptide and an ORF 6 matrix polypeptide, which co-localize within the viral envelope. ELISA plates were coated with each polypeptide and serum samples were tested by limiting dilution. Results were recorded as titers rather than optical density ratios. The blood samples also were tested using a commercially available PRRS virus ELISA (2×R PRRS virus antibody test kit; IDEXX Laboratories).

The PRRS virus 2×R ELISA antibody levels dropped sharply after initial sero-conversion, even in the face of repeated injections with virulent 28983 strain PRRS virus. Nearly all animals developed solidly positive antibody responses initially. 75 percent of these animals, however, returned to sero-negative status 4 months after the 6th injection with live virus. This is similar to that observed in sows following multiple vaccinations with MLV PRRS virus vaccine (Baker et al., Proc. Allen D. Leman Swine Conference, vol. 26 (suppl.) p. 31 (1999)). Conversely, the serum neutralization test detected antibody later following initial infection, and all animals remained serum neutralization antibody positive at the end of the experiment.

The rORF ELISAs revealed temporal antibody curves. The assay using recombinant nucleocapsid polypeptides resulted in a curve that followed the IDEXX 2×R ELISA response curve closely, falling to low levels at 4 months. Conversely, the envelope chimera ORF 5 and ORF 6 polypeptide ELISA followed a temporal pattern nearly identical to the PRRS serum neutralization antibody response curve. Thus, it appears that pigs initially produce strong antibody responses directed predominantly against nucleocapsid polypeptides, but over time the antibody response is redirected to the envelope polypeptides. It appears that the immune response to PRRS virus is slow to shift to immunologically protective serum neutralization antibodies.

These results demonstrate that an effective diagnostic kit can include ORF 5 polypeptides and ORF 6 polypeptides. These results also demonstrate that a weak IDEXX PRRS virus ELISA antibody response following vaccination or re-exposure may paradoxically indicate that the animal has a protective immune response against that vaccine or virus, since the IDEXX PRRS virus ELISA kit appears to be limited to detecting antibodies that bind PRRS virus nucleocapsid polypeptides.

Example 4

Comparative Antibody Responses to Virulent and Attenuated Strains of PRRS Virus The following experiment was performed to (1) characterize the antibody response of pigs to individual PRRS virus polypeptides, (2) determine the antibody responses to viral isolates that vary in virulence, and (3) determine the relationship between antibody response and protection to challenge.

One hundred PRRS-negative 3-4 week-old piglets were divided into groups. Ten pigs per group were inoculated intranasally with $2\times10^3$ $TCID_{50}$ PRRS virus strains characterized as highly or moderately virulent (SDSU73, MN 184, JA 142, and 17198-6), low virulent (VR2332 and ABST-1), or avirulent (Ingelvac PRRS and Ingelvac ATP). One group of ten pigs received a cocktail containing equal amounts of all viruses, and ten control pigs received no virus. After animals were fully recovered from acute infection, they were challenged with MN 184. Clinical signs were recorded throughout the experiment and necropsies were performed 14 days after challenge. Animals were bled weekly, and antibody levels were determined by ELISA to purified nonstructural and structural polypeptides that were produced by inserting the desired cDNA fragments into *E. coli* for expression and purification. The polypeptides included a VR2332 PRRS virus ORF 7 polypeptide (a nucleocapsid polypeptide), a VR2332 PRRS virus NSP 1 polypeptide, a VR2332 PRRS virus NSP 2P polypeptide, a VR2332 PRRS virus NSP 4 polypeptide, a VR2332 ORF 5 5' ectodomain 1 polypeptide, an MN30100 VR2332 ORF 5 5' ectodomain 1 polypeptide, a VR2332 ORF 5 3' endodomain polypeptide, an MN30100 ORF 5 3' endodomain polypeptide, a VR2332 ORF 5 5' ectodomains 1 and 2 polypeptide, and a VR2332 ORF 5/ORF 6 chimeric polypeptide (ORF 5 5' ectodomains 1 and 2 plus ORF 6 5' ectodomains 1 and 2; also referred to as a GP5-M chimeric ectodomain polypeptide). ELISA plates were coated with each polypeptide, and the serum samples were tested at a dilution of 1/2000. Specific antibody levels were expressed as background-corrected optical density values.

Clinical responses to PRRS virus inoculation ranged from no or minimal observed effects in animals given avirulent or lowly virulent strains, to death in about 50 percent of animals administered MN 184. Antibody responses to animals inoculated with highly and moderately virulent strains were pronounced. Antibodies usually first appeared at 21 days and peaked at 28 days after infection. The level of antibodies to nucleocapsid declined dramatically after day 28, whereas the response to other viral polypeptides tended to be maintained at high levels to the end of the experiment. Antibody responses to nonstructural polypeptides NSP 1 and NSP 2 were as high or higher than the response to nucleocapsid, but the response to NSP 4, encoding a viral protease, was low at all time points.

Although the humoral response to viral administration was IDEXX-positive in all treatment groups, marked variations in the intensity of antibody responses were apparent. Avirulent and lowly virulent strains elicited less robust antibody responses as compared to moderate or highly virulent strains. These differences were present across all antigens tested. However, response to challenge was similar among all treatment groups.

In summary, differences in antibody response to various structural and nonstructural PRRS virus polypeptides were observed. In addition, variation in antibody responses to virulent strains of PRRS virus as compared to their attenuated forms were observed. The differences in antibody responses, however, were not associated with protection against re-infection with a heterologous, highly virulent challenge strain. These findings are the first characterization of antibody responses to individual PRRS virus polypeptides throughout acute infection and following virulent challenge.

Example 5

Detecting Antibodies to PRRS Virus Using Individual PRRS Virus Polypeptides Versus a Commercially Available ELISA Kit The following experiment was performed to determine whether particular polypeptide ELISAs can detect PRRS virus positive samples under conditions of multiple exposure and extended time periods in which the IDEXX ELISA changes from positive to negative. PRRS-negative 6 month old barrows were injected with $10^{2.5}$ tissue culture infective dose 50% ($TCID_{50}$) of field strain SD 28983 PRRS virus initially, then at one, two, four, six, and eight months for a total of 6 inoculations. Animals were bled preceding each inoculation, and serum was collected. The blood samples were tested using (1) a commercially available PRRS virus ELISA (2×R PRRS virus antibody test kit; IDEXX Laboratories) or (2) an ELISA containing particular PRRS virus polypeptides. The IDEXX 2×R HerdChek® ELISA was performed according to the manufacturer's directions on serum samples diluted 1/40. Data are presented as means and standard deviation of all samples in each group. Group size varied from 19-23 samples from 23 pigs per group.

Figure 10:
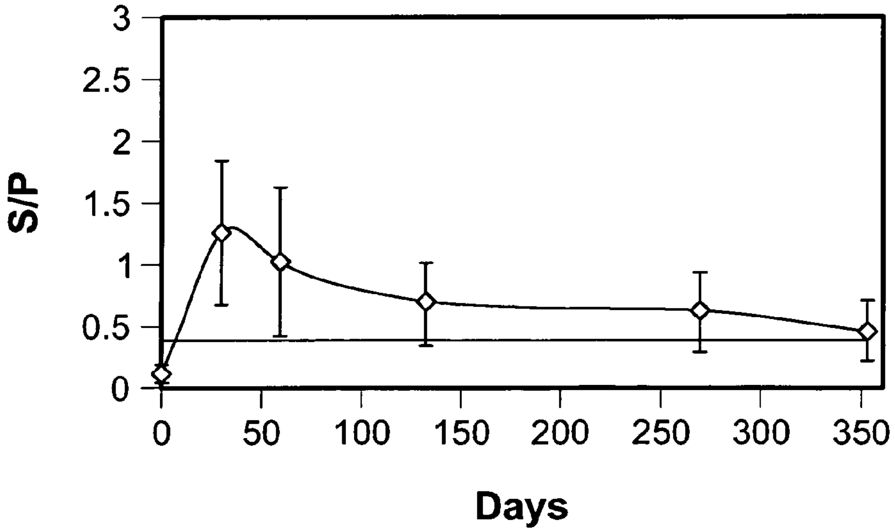
FIG. 10 is a graph plotting the sample/positive ratio (S/P ratio) for samples analyzed using a commercially available ELISA kit (IDEXX 2XR kit). The horizontal line intersecting the Y-axis at 0.4 shows the cutoff value for a positive result.

About half the animals analyzed using the IDEXX kit were found to be negative at the 353 day time point (Table 3 and FIG. 10). An S/P ratio greater than 0.4 indicated that the sample was positive for antibodies to PRRS virus, while an S/P ratio less than 0.4 indicated that the sample was negative for antibodies to PRRS virus.

TABLE 3

Analysis of samples using the IDEXX kit.

| Days | Average S/P | Number Samples Positive | Number Samples Negative |
|---|---|---|---|
| 0 | 0.124 | 0 | 22 |
| 29 | 1.273 | 22 | 1 |
| 59 | 1.033 | 20 | 1 |
| 132 | 0.697 | 17 | 2 |
| 270 | 0.629 | 18 | 4 |
| 353 | 0.480 | 11 | 11 |

The same samples were analyzed using either recombinant GP5 endodomain polypeptides or recombinant GP5-M chimeric polypeptides in ELISAs. Briefly, plates were coated with 100 ng polypeptide per well in carbonate pH 9.6 overnight. Sera were diluted 1/1000 and tested in duplicate. For the GP5 endodomain polypeptide ELISAs, data are presented as the sample/positive ratio of unadjusted OD values of all samples in each group and the number of samples with a mean greater than (Positive) or less than (Negative) 0.21. For the GP5-M chimeric polypeptide ELISAs, data are presented as the sample/positive ratio of unadjusted OD values of all samples in each group and the number of samples with a mean greater than (Positive) or less than (Negative) 0.5. The sample/positive ratio was determined as the sample OD minus OD of control wells without antigen/positive control OD minus OD of control wells without antigen.

Figure 11:
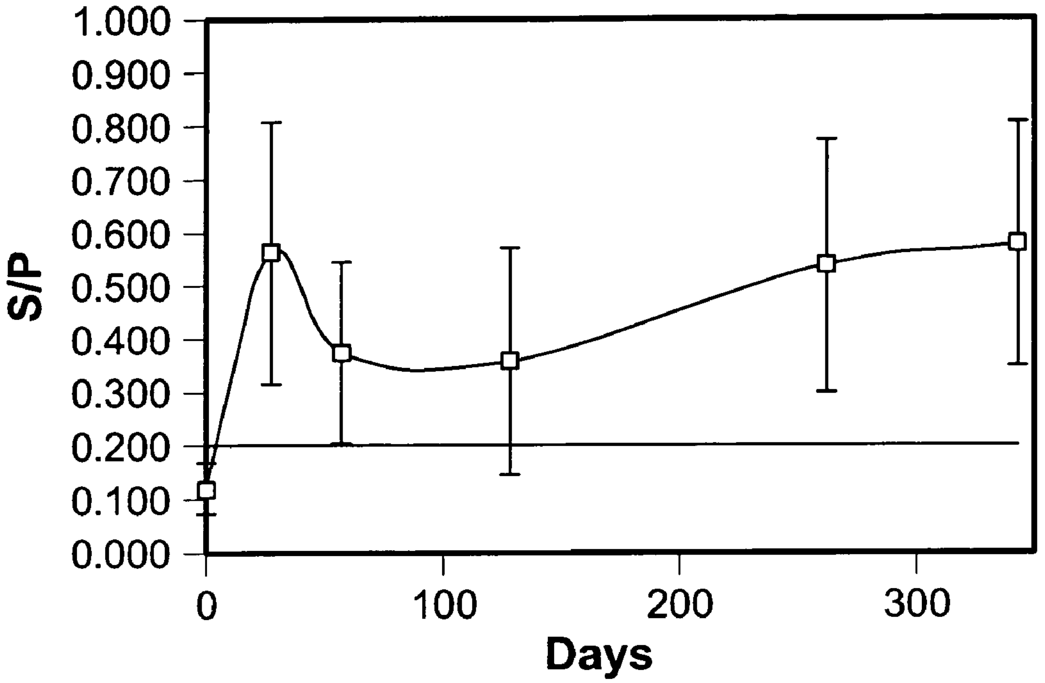
FIG. 11 is a graph plotting the S/P ratios for samples analyzed using a 3' polypeptide fragment of PRRS virus ORF 5 in an ELISA. The horizontal line intersecting the Y-axis at 0.21 shows the cutoff value for a positive result.
Figure 12:
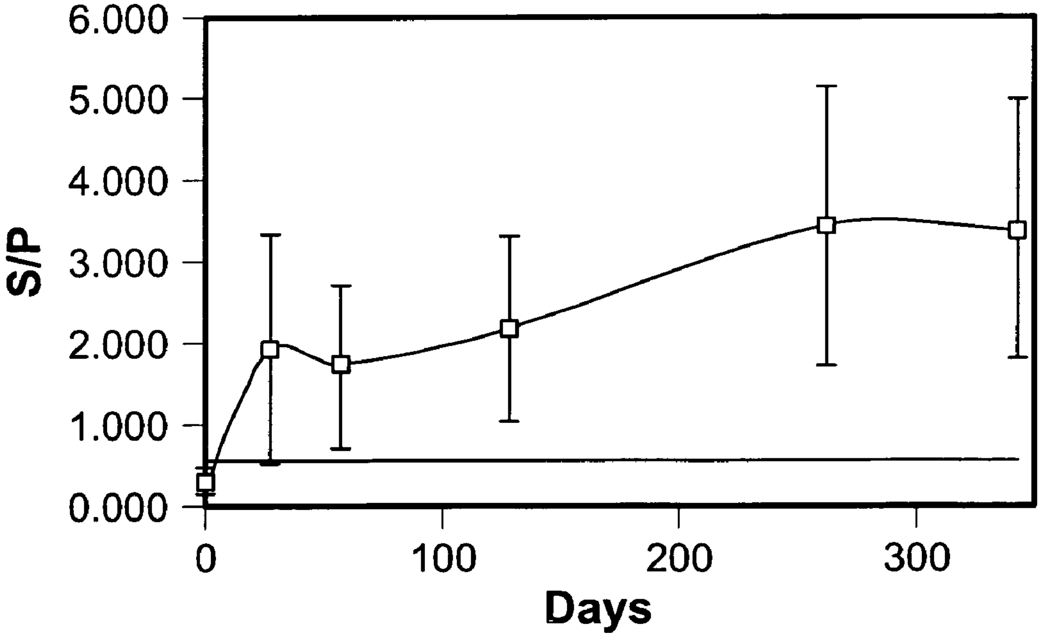
FIG. 12 is a graph plotting the S/P ratios for samples analyzed using a GP5-M chimeric polypeptide in an ELISA. The horizontal line intersecting the Y-axis at 0.5 shows the cutoff value for a positive result.

Two samples were found to be negative for antibodies to the tested PRRS virus GP5 endodomain polypeptide at the 353-day time point (Table 4 and FIG. 11). When the GP5-M chimeric polypeptide was used, all the tested samples were found to be positive at the 353-day time point (Table 5 and FIG. 12). These results demonstrate that assays using GP5 polypeptides can detect anti-PRRS virus antibodies in situations where the commercially available IDEXX kit can not.

TABLE 4

Analysis of samples using a GP5 endodomain polypeptide in an ELISA.

| Days | Months | Average S/P | Number Samples Positive | Number Samples Negative |
|---|---|---|---|---|
| 0 | 0.000 | 0.123 | 0 | 22 |
| 29 | 1.000 | 0.565 | 23 | 0 |
| 59 | 2.000 | 0.374 | 19 | 2 |
| 132 | 4.400 | 0.360 | 15 | 4 |
| 270 | 9.000 | 0.537 | 23 | 0 |
| 353 | 11.800 | 0.576 | 20 | 2 |

TABLE 5

Analysis of samples using a GP5-M chimeric polypeptide in an ELISA.

| Days | Months | Average S/P | Number Samples Positive | Number Samples Negative |
|---|---|---|---|---|
| 0 | 0.000 | 0.333 | 0 | 22 |
| 29 | 1.000 | 1.929 | 21 | 2 |
| 59 | 2.000 | 1.722 | 20 | 1 |
| 132 | 4.400 | 2.157 | 19 | 0 |
| 270 | 9.000 | 3.378 | 23 | 0 |
| 353 | 11.800 | 3.318 | 22 | 0 |

Example 6

Detecting Antibodies to PRRS Virus Using a Mixture of PRRS Virus Polypeptides Versus a Commercially Available ELISA Kit Ten weaned pigs per group were each inoculated intranasally with 2 mL of tissue culture media containing 3.0 $Log_{10}$ $TCID_{50}$/mL of the virus isolates listed in Table 6. The pool was a mixture of equal portions of each of the eight isolates. The control was tissue culture media alone.

TABLE 6

PRRS virus isolates.

| Isolate | Group number | Virulence |
|---|---|---|
| VR 2332 | 1 | Moderate |
| Ingelvac ® PRRS MLV* | 2 | Attenuated VR2332 |
| JA 142 | 3 | High |
| Ingelvac ® PRRS ATP* | 4 | Attenuated JA 142 |
| SDSU 73 | 5 | High |
| Abst-1* | 6 | Attenuated SDSU 73 |
| MN 184 | 7 | High |
| 17198 | 8 | High |
| Pool** | 9 | High |
| Control | 10 | N/A |

*Attenuated PRRS virus isolates.
**Mixture containing all of the eight isolates.

To compare the IDEXX ELISA kit with a recombinant polypeptide ELISA, sera were selected blindly from five pigs per group at day 7 after inoculation. Four of the five samples were also tested on day 14. For the IDEXX ELISA kit, an S/P ratio ≧0.4 indicated that the sample was positive, while an S/P ratio <0.4 indicated that the sample was negative. The same samples were analyzed using the IDEXX ELISA kit and the recombinant polypeptide ELISA.

For the recombinant polypeptide ELISA, the following polypeptides were expressed and purified as described herein: an ORF 7 polypeptide, a ORF 5+6 chimeric ectodomains polypeptide, an NSP 2P polypeptide, and an ORF 5 3' endodomain polypeptide. The purified polypeptide concentrations were determined by agreement among $OD_{280}$ absorbance, Agilent bioanalyzer analysis, SDS PAGE, and RC DC Lowry protein assay. Microtiter plates were coated with 150 ng of each polypeptide for a total of 600 ng in 100 μL carbonate, pH 9.6, coating buffer. ELISAs were performed on serum samples at a 1/500 dilution. The day 7 and day 14 samples are the identical samples as were analyzed by IDEXX ELISA. In addition, 7 animals per group (5 in the MN184 and pool groups) were analyzed at day 50. Control animals were negative at all times. Seven pigs in group 10 were tested and were negative at all tested days.

Only one of the tested samples collected on day 7 was positive when analyzed using the IDEXX kit (Table 7). In addition, thirteen samples collected on day 14 were negative for PRRS virus antibodies. Twenty-three of the 36 samples collected on day 14 were positive for PRRS virus antibodies.

TABLE 7

Results with IDEXX ELISA kit.

| Day | Average S/P | Number Samples Positive | Number Samples Negative |
|---|---|---|---|
| 7 | 0.116374 | 1 | 44 |
| 14 | 0.753558 | 23 | 13 |

In contrast, 14 of the tested 45 samples collected on day 7 were positive when analyzed using the ELISA containing the mixture of PRRS virus polypeptides (Table 8). In addition, only eight of the 36 samples collected on day 14 were negative for PRRS virus antibodies. Twenty-eight of the 36 samples collected on day 14 were positive for PRRS virus antibodies. Further, 54 of the 59 samples collected on day 50 were positive for PRRS virus antibodies (Table 8).

TABLE 8

| Results with ELISA containing the mixture of PRRS virus polypeptides. | | | | |
|---|---|---|---|---|
| Days | Average S/P | Number Samples Positive | Number Samples Negative | Cutoff value |
| 7 | 0.558178 | 14 | 31 | 0.4 |
| 14 | 1.549222 | 28 | 8 | 0.4 |
| 50 | 3.024511 | 54 | 5 | 0.55 |

These results demonstrate that mixtures of PRRS virus polypeptides can be used to detect PRRS virus antibodies in animals exposed to PRRS virus at time points that are not only early but also late with respect to the time of PRRS virus exposure. For example, positive samples were detected at day 7, 14, and 50 following PRRS virus exposure.

The samples for each group were also tested using ELISAs with an individual PRRS virus polypeptide obtained as described herein (FIG. 18).

Example 7

Differentiating between Animals Exposed to Vaccine or Field Strains of PRRS Virus Twenty-eight days after vaccination with the Ingelvac MLV (also referred to as RespPRRS; GenBank® Accession Number AF066183), serum samples were obtained from 5 pigs, diluted 1/300, and analyzed in duplicate on ELISA plates coated with 200 ng of a 5' ectodomain ORF 5 polypeptide from PRRS virus strain VR2332, a 5' ectodomain ORF 5 polypeptide from PRRS virus isolate MN30100, a 3' endodomain ORF 5 polypeptide from PRRS virus strain VR2332, or a 3' endodomain ORF 5 polypeptide from PRRS virus isolate MN30100. Twenty-eight days after inoculation with PRRS virus isolate MN30100, serum samples were obtained from 5 pigs and analyzed in the same manner. The 5' ectodomain of PRRS virus ORF 5 polypeptides contains an amino acid sequence that is variable among PRRS virus isolates, while the 3' endodomain of PRRS virus ORF 5 polypeptides contains an amino acid sequence that is conserved among PRRS virus isolates.

Figure 13:
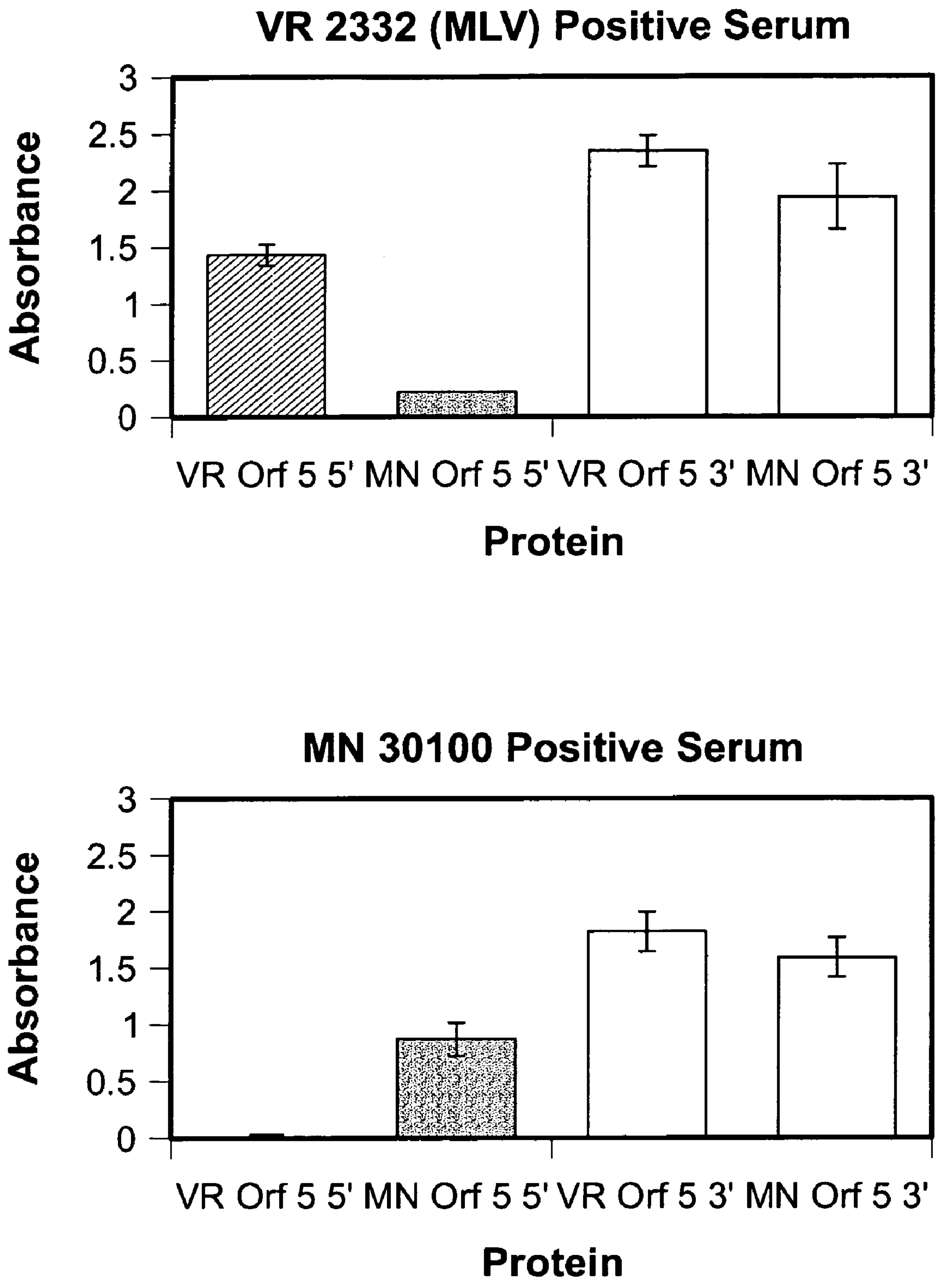
FIG. 13 contains two bar graphs plotting the absorbance for samples obtained from animals exposed to MLV or MN30100 PRRS viruses. The absorbance values were detected using an ELISA with the indicated polypeptide.

The ELISAs containing the 3' endodomain ORF 5 polypeptides (either the 3' endodomain ORF 5 polypeptide from VR2332 or the 3' endodomain ORF 5 polypeptide from MN30100) detected PRRS virus antibodies in samples obtained from animals exposed to either the vaccine strain (Ingelvac MLV) or the field isolate (MN30100) of PRRS virus (Table 9 and FIG. 13). These results demonstrate that a polypeptide limited to a PRRS virus sequence that is conserved among PRRS viruses, whether from a vaccine version or a wild-type version of PRRS virus, can be used to detected animals exposed to any type of PRRS virus (e.g., a vaccine version or wild-type version of PRRS virus).

TABLE 9

ELISA results of serum samples obtained from pigs exposed to PRRS virus Ingelvac MLV or MN30100 and reacted with polypeptide fragments from either PRRS virus Ingelvac MLV or MN30100.

| Polypeptide for ELISA: | Virus animal exposed to: | Average* | Standard Deviation | SEM |
|---|---|---|---|---|
| 5' ORF 5 (VR2332) | MN30100 | 0.009 | 0.05303 | 0.037 |
| | MLV | 1.443 | 0.11172 | 0.079 |
| 5' ORF 5 (MN30100) | MN30100 | 0.946 | 0.22273 | 0.157 |
| | MLV | 0.193 | 0.00636 | 0.004 |
| 3' ORF 5 (VR2332) | MN30100 | 1.985 | 0.26269 | 0.185 |
| | MLV | 2.336 | 0.19940 | 0.141 |
| 3' ORF 5 (MN30100) | MN30100 | 1.726 | 0.27930 | 0.197 |
| | MLV | 1.932 | 0.42426 | 0.300 |

*The data are specific OD values after subtraction of background.

The ELISAs containing the 5' ectodomain ORF 5 polypeptide from VR2332 detected PRRS virus antibodies in samples obtained from animals exposed to the vaccine strain (Ingelvac MLV) and did not detect PRRS virus antibodies in samples obtained from animals exposed to the field isolate (MN30100) of PRRS virus (Table 9 and FIG. 13). Likewise, the ELISAs containing the 5' ectodomain ORF 5 polypeptide from MN30100 detected PRRS virus antibodies in samples obtained from animals exposed to the field isolate (MN30100) of PRRS virus and did not detect PRRS virus antibodies in samples obtained from animals exposed to the vaccine strain (Ingelvac MLV)(Table 9). These results demonstrate that a polypeptide limited to a PRRS virus sequence from a vaccine version of a PRRS virus that is variable among PRRS viruses can be used to identify animals exposed to the vaccine version of PRRS virus as opposed to animals exposed to a wild-type version of PRRS virus.

Example 8

Producing Additional Recombinant PRRS Virus Polypeptides from Vaccine Strains and Field Isolates The following polypeptides were produced: a PRRS virus ORF 7 polypeptide (FIG. 26), a PRRS virus NSP 2HP polypeptide (FIG. 27), a PRRS virus NSP 2 S1 HP polypeptide (FIG. 28), a PRRS virus NSP 2 S2 HP polypeptide (FIG. 29), a PRRS virus first and second N-terminal ectodomains ORF 6 polypeptide (ORF 6 5' total; FIG. 30), and a PRRS virus endodomain ORF 6 polypeptide (ORF 6 3'; FIG. 31). In each case, the polypeptides contained a myc sequence followed by the PRRS virus sequence followed by a polyhistidine sequence. The nucleic acid encoding the PRRS virus sequence of these polypeptides was from the nucleotide sequence in the VR-2332 strain of PRRS virus (GenBank® Accession No. PRU87392). In addition, a myc-ORF 7-His polypeptide, a myc-ORF 5 3'-His polypeptide, a myc-ORF 6 3'-His polypeptide, and a myc-NSP 2-His polypeptide was produced. The nucleic acid encoding the PRRS virus sequence of these polypeptides were from the nucleotide sequence in the Lelystad Virus (LV) strain of PRRS virus (GenBank® Accession No. M96292). A myc-NSP 2 HP-His polypeptide also was produced. The nucleic acid encoding the PRRS virus sequence of this polypeptide was from the nucleotide sequence in the Boehringer Ingelheim vaccine strain ATP. GenBank® Accession No. AY424271 for PRRS virus strain JA142 was used to obtain the ATP sequences since PRRS virus strain JA142 is the parental virus strain of the Boehringer Ingelheim vaccine strain ATP.

The polypeptides containing a PRRS sequence of VR-2332 were constructed as described in Example 2. For plasmids containing sequences of PRRS virus strains LV or ATP, viruses were isolated from cell culture lysates by centrifugation through a sucrose cushion. Viral RNA was extracted with a Qiagen kit. Primers were designed to amplify the desired sequences and to contain necessary restriction sites. PCR products were cleaned up with the Qiagen PCR Purification kit and ligated into pGEM-T vector. Plasmids were amplified in *E. coli* DH5α, purified, and digested with BamHI and XhoI. The insert was purified and recloned into the pET 24b myc His vector.

Recombinant polypeptides were expressed from plasmids in BL21 (DE3)-RP cells. After transformation, cells were spread on LB agar plates containing kanamycin (30 μg/mL) and chloramphenicol (35 μg/mL) and incubated overnight at 37° C. A single colony was picked and grown in 20 mL 2×YT medium containing kanamycin and chloramphenicol as above and grown overnight with shaking at 225 rpm. The 20 mL culture was transferred to 1 liter of 2×YT medium with antibiotics at 30° C. with shaking until the $OD_{600}$ reached 0.3. IPTG was added to 1 mM, and the flask agitated for 4 to 5 hours at 30° C. Two hundred μL of culture was removed for gel analysis.

The remaining culture was centrifuged at 4000×g for 20 minutes at 4° C. to pellet bacteria. The pellet was resuspended in 30 mL of 100 mM $NaH_2PO_4$, 10 mM Tris HCl, 8 M urea, pH 8.0. PMSF was added to 1 mM, and the mixture was rotated gently at room temperature for 2 hours. The mixture was centrifuged at 10,000×g for 30 minutes at 4° C. to pellet cellular debris. Six mL of a 50% slurry of Ni-NTA agarose (Qiagen, Valencia Calif.) was added to the supernatant containing denatured protein and rotated gently for 1 hour at room temperature. The mixture was then placed in a glass column 1.5 cm ID×40 cm and allowed to drain. The column was washed twice with 20 mL of 100 mM $NaH_2PO_4$, 10 mM Tris HCl, 8 M urea, pH 6.3. Recombinant protein was eluted with three to four 4-mL aliquots of 100 mM $NaH_2PO_4$, 10 mM Tris HCl, 8 M urea, pH 5.5-5.7. Proteins were stored at −20° C. until refolding.

Proteins were refolded by adding 231.3 mg of dithiothreitol to the pooled protein solution and stirring gently for 2 hours. Then, the solution was rapidly diluted into 500 mL of refolding buffer (100 mM Tris HCl, pH 8.0, 0.5 M L-arginine, 8 mM oxidized glutathione, 2 mM EDTA, 10 μM pepstatin A, 10 μM leupeptin, 1 mM PMSF) and stirred gently overnight at 4° C. Protein was reconcentrated by tangential flow filtration (Pellicon XL Ultracel PLC 5 kd, Millipore, Bedford Mass.) and dialyzed (Spectra/Por MWCO 3,000) overnight at 4° C. against 10 mM Na phosphate, pH 8.0. Solutions were concentrated by centrifugation (Centriprep, Millipore) at 3,800 rpm for 30 minutes at 4° C. as needed. Proteins were stored in aliquots at −80° C. Protein concentrations and purity were assessed by SDS-polyacrylamide gel electrophoresis.

Example 9

Detecting Antibodies to North American and European genotype PRRS Viruses Using Mixtures of PRRS Virus Polypeptides from Either or Both Genotypes The following experiments were performed to (1) determine if ELISAs using polypeptides from a North American type PRRS virus (e.g., VR-2332) are capable of detecting PRRS virus positive samples from pigs inoculated with a European type PRRS virus (e.g., Lelystad virus) and (2) determine if ELISAs using polypeptides from a European type PRRS virus (e.g., Lelystad virus) are capable of detecting PRRS virus positive samples from pigs inoculated with a North American type PRRS virus (e.g., VR-2332). The following experiments also were performed to determine if ELISAs using a combination of polypeptides from both North American and European type viruses are capable of detecting PRRS virus positive samples from pigs infected with either type of virus.

The following polypeptides in 15 mM $Na_2CO_3$, 35 mM $NaHCO_3$, pH 9.6, were used to coat ELISA plates (COSTAR 3590, 96 well EIA/RIA plate, Coming NY): myc-ORF 7-His (VR-2332), myc-ORF 6 3'-His (VR-2332), myc-ORF 5 3'-His (VR-2332), myc-ORF 7-His (LV), myc-ORF 6 3'-His (LV), and myc-ORF 5 3'-His (LV). These polypeptides were expressed from the respective plasmids containing all or portions of ORF 7 (N), ORF 6 (M), or ORF 5 (GP5). Wells were coated with solutions containing either 100 ng each of the three VR-2332 polypeptides/100 μL, or 100 ng each of the three LV polypeptides/100 μL, or 50 ng each of all six polypeptides/100 μL. Thus, all wells contained 300 ng of polypeptide.

Plates were incubated with coating solution overnight at 4° C. Plate wells were washed one time with PBS, 0.05% Tween 20, pH 7.3-7.5 and blocked with 300 μL of 5% nonfat dry milk in PBS, 0.05% Tween 20, pH 9.4-9.6, per well for 2 hours. Plates were washed 5 times in PBS, 0.05% Tween 20, pH 7.3-7.5, and 100 μL of test serum diluted 1/500 in PBS, 0.05% Tween 20, 5% nonfat dry milk was added to duplicate wells for 1 hour. Plates were washed 5 times, and 100 μL of peroxidase-labeled affinity purified antibody to swine IgG (H+L) (KPL, Gaithersburg Md.) diluted 1/5000 in PBS, 0.05% Tween 20, 5% nonfat dry milk was added for 1 hour. Plates were washed 5 times, and enzyme substrate was added for 5 minutes. Enzyme substrate consisted of 100 μL per well of equal portions of TMB peroxidase substrate solution A and peroxidase $H_2O_2$ substrate solution B (TMB Peroxidase Substrate System, KPL, Gaithersburg Md.) mixed together. Reactions were stopped with 100 μL of 2 M phosphoric acid, and results were read at 450 nm in a Thermo Max Microplate Reader, Molecular Devices, Sunnyvale Calif.

Figure 32A:
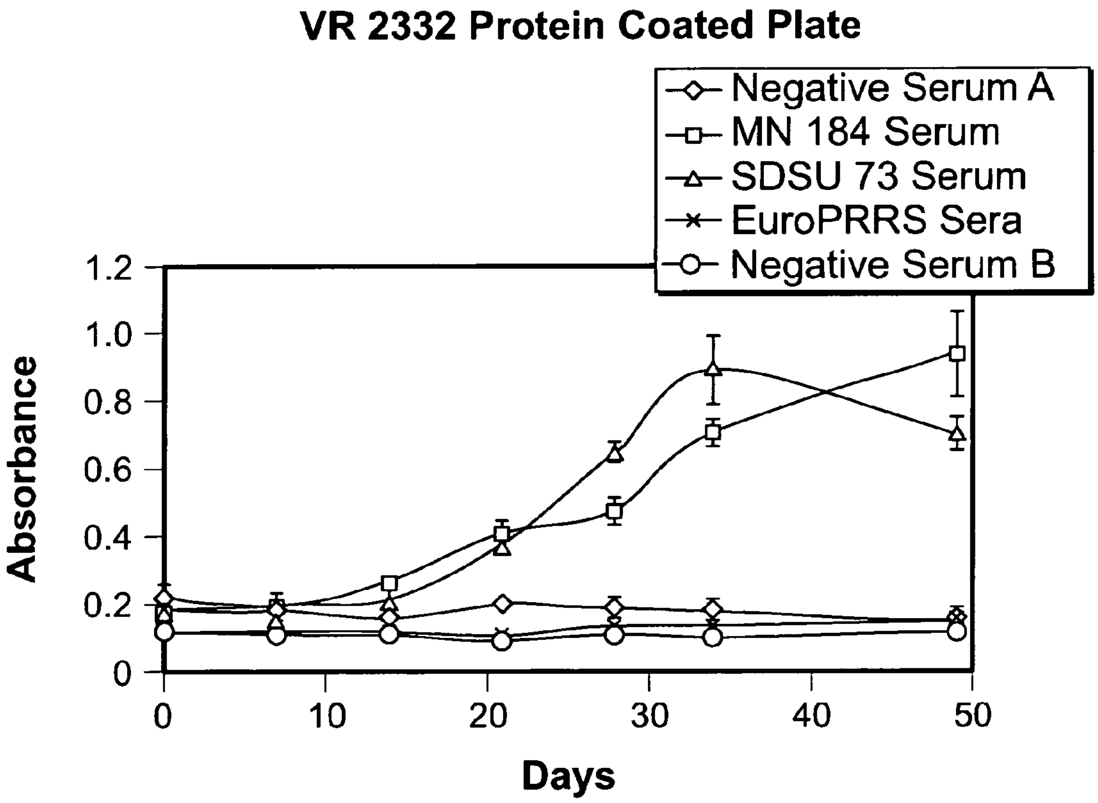
FIG. 32 contains three graphs plotting the absorbance for samples obtained from animals exposed to MN 184, SDSU 73, or EuroPRRS as well as two controls. The absorbance values were detected using an ELISA of VR-2332 polypeptides (A), LV polypeptides (B), or a mixture of both (C).
Figure 32B:
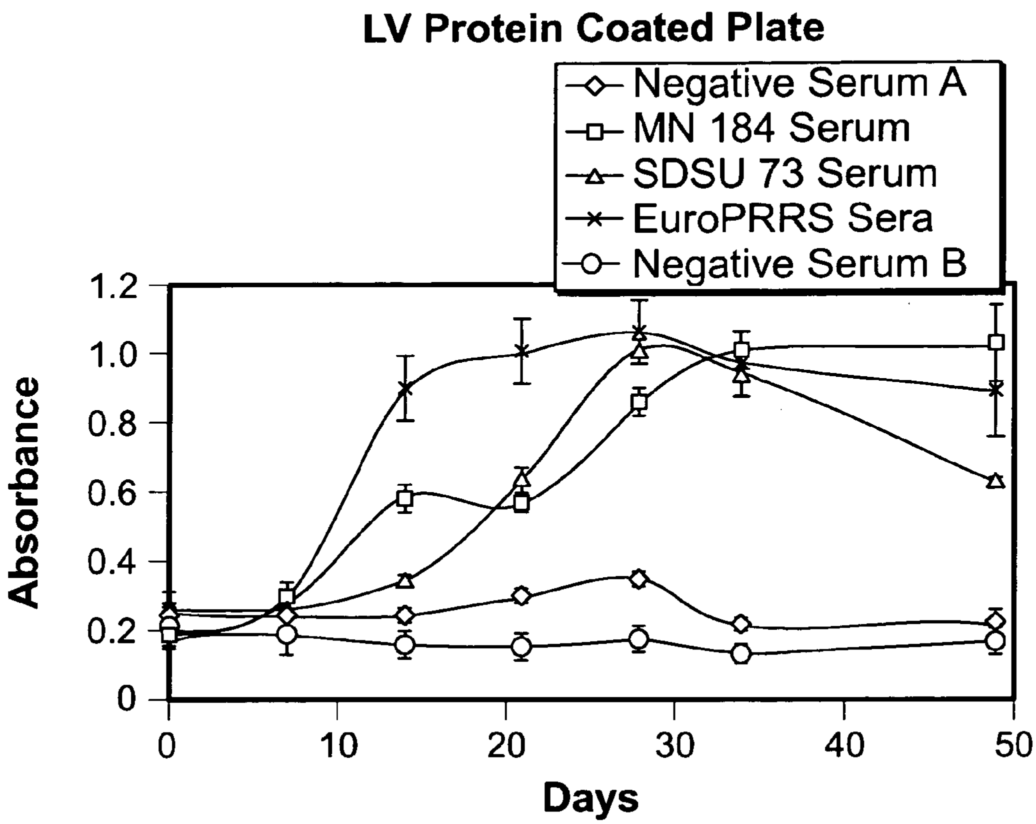
Figure 32C:
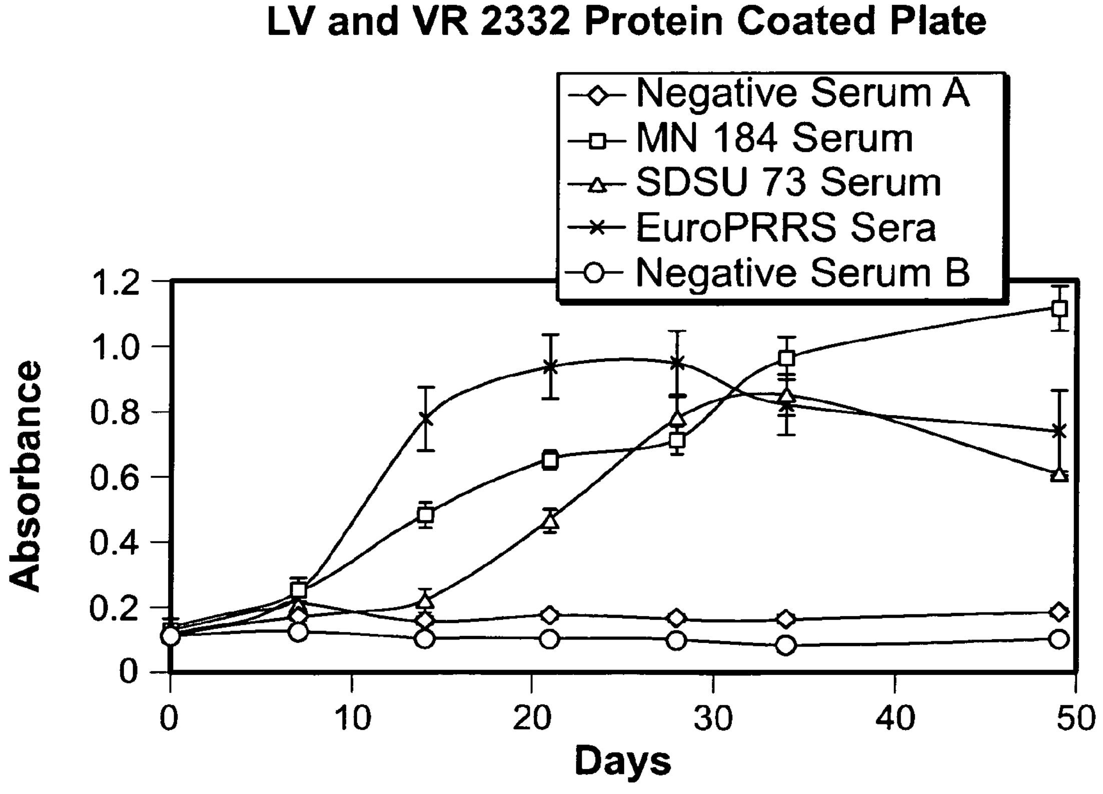

Serum samples were obtained from pigs that were uninfected (negative sera A and negative serum B), infected with a European type PRRS virus (n=9), and either of two North American PRRS virus strains, MN 184 or SDSU 73 (Johnson et al., *Vet. Immunol. Immunopathol.,* 102:233-247 (2004)) (n=1 each). Samples were obtained at approximately 0, 7, 14, 21, 28, 35, and 49 days after infection. The mixture of VR-2332 polypeptides detected anti-PRRS virus antibodies in sera of pigs exposed to MN1 84 or SDSU 73 at 14 days after infection and at all time points thereafter (FIG. 32; panel A). The VR-2332 polypeptides did not detect anti-PRRS virus antibodies in sera of pigs infected with a European PRRS virus.

The mixture of LV polypeptides detected antibodies in sera of pigs exposed to a European genotype PRRS virus at 7 days of infection and at high levels at all time points thereafter (FIG. 32; panel B). The LV polypeptides also detected antibodies in pigs exposed to North American PRRS viruses at day 14 and later (FIG. 32; panel B). The combination of LV and VR-2332 polypeptides detected anti-PRRS virus antibodies in sera of exposed pigs similarly to LV polypeptides alone except that there was a tendency to higher values in the animal exposed to MN 184 (FIG. 32; panel C).

These results indicate that LV polypeptides, such as the mixture of ORF 5 3', ORF 6 3', and ORF 7 polypeptides, can detect an antibody response in pigs exposed to European and North American genotype PRRS viruses as early as 7 days after infection. VR-2332 polypeptides specifically recognized sera of pigs exposed to North American type PRRS viruses, and not to sera from pigs exposed to the European type virus. Thus, with the appropriate mixtures of polypeptides, one can detect serological responses to all PRRS viruses and can differentiate between responses to European and North American types.

Example 10

Figure 33A:
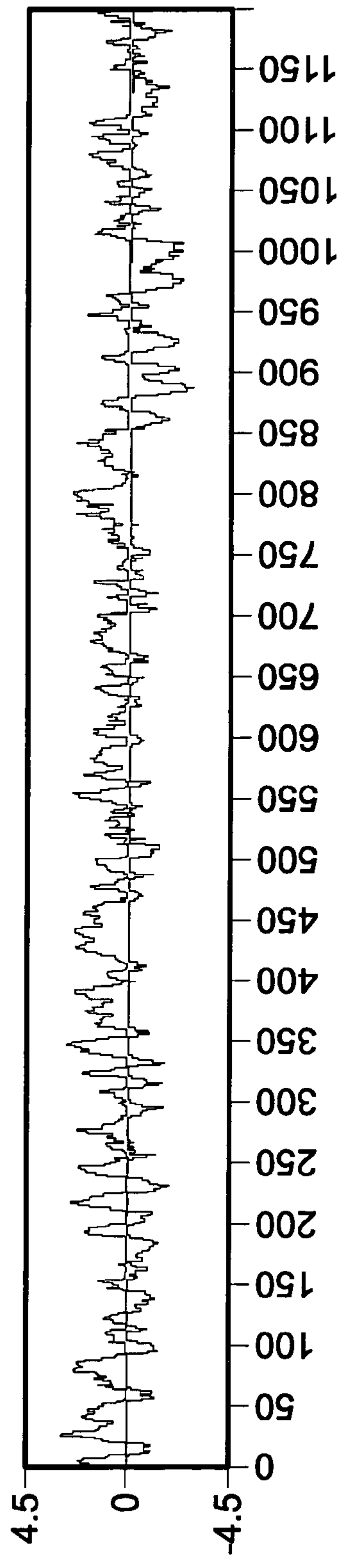
FIG. 33A contains a Kyte-Doolittle hydrophilicity profile of an NSP 2 polypeptide.
Figure 33B:
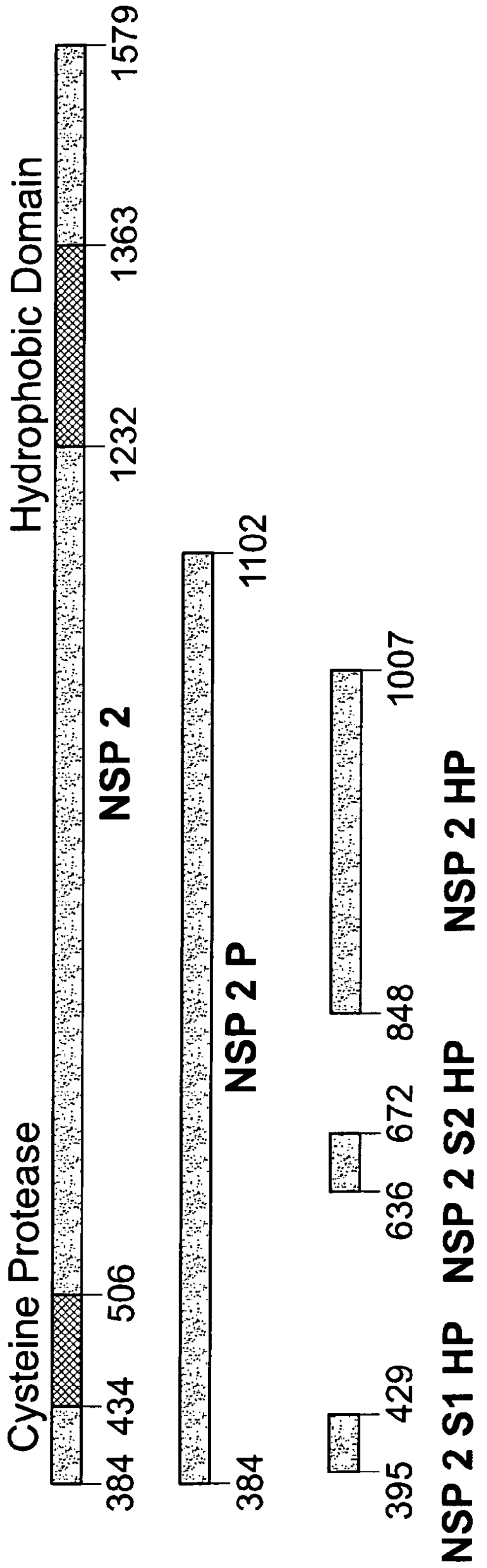
FIG. 33B is a diagram of NSP 2 and fragments of NSP 2. The amino acid numbering is according to VR-2332 orf 1 (GenBank® accession number U87392). The cysteine protease catalytic site and the hydrophobic domain are labeled.

Differentiating Between Animals Exposed to a Vaccine or Field Strains of PRRS Virus Using Nonstructural Protein Polypeptides Example 4 demonstrated that swine antibody responses to PRRS viruses can be greater to the nonstructural proteins than to structural proteins such as N. Since detection of NSP's might result in a more sensitive assay, the following experiments were performed to determine if ELISAs comprised of polypeptides derived from a nonstructural protein from VR-2332 or the Ingelvac ATP vaccine strain of PRRS virus would differentiate pigs vaccinated with the Ingelvac MLV or Ingelvac ATP strains from pigs exposed to field strains of PRRS virus. Various polypeptides were produced containing portions of NSP 2 (FIG. 33).

In the first experiment, serum samples from pigs exposed to field viruses or the Ingelvac MLV vaccine virus for 28 days were incubated in microtiter plates coated with myc-NSP 2 P-His (VR-2332) or myc-NSP 2HP-His (VR-2332) polypeptides. Serum from pigs inoculated with MLV vaccine, which was derived from the VR-2332 strain, reacted strongly with both myc-NSP 2P-His and myc-NSP 2 HP-His polypeptides. Positive signals in serum samples diluted 1/1000 from seven pigs ranged from 0.8 to 3.6 OD units against NSP 2P and from 0.7 to 3.1 OD units against NSP 2HP. The relative percent difference ($1-(OD_{NSP\ 2HP}/OD_{NSP\ 2P})$) after background subtraction, ranged from 9.9 to 23.2 percent. By contrast, serum from pigs inoculated with any of five different wild-type field viruses reacted more strongly with myc-NSP 2P-His polypeptides than with myc-NSP 2HP-His polypeptides. Positive signals among 35 pigs exposed to five different viruses ranged from 0.54 to 3.3 OD units against NSP 2P and from 0.22 to 1.9 OD units against NSP 2HP. The relative percent difference ranged from 36.6 to 85.1 percent.

These results indicate that the NSP 2HP (VR-2332) polypeptide is different from other PRRS virus NSP 2HP polypeptides such that its derived vaccine virus, MLV, elicits antibodies in pigs that react selectively with the NSP 2HP (VR-2332) polypeptide. In addition, the pronounced reactivity of serum samples from field virus-exposed pigs with NSP 2P (VR-2332) indicates that this polypeptide can be used as a diagnostic polypeptide. The relative specificity of the NSP 2 HP polypeptide for the MLV vaccine indicates that a test that compares the relative serological reactivity of a test serum to both VR-2332 NSP 2P and NSP 2HP can differentiate swine vaccinated with Ingelvac MLV from pigs that were exposed to field viruses.

In a second experiment, additional portions from the NSP 2 (VR-2332) polypeptide that showed variation in amino acid sequence among the PRRS virus sequences in GenBank were evaluated for specific reactivity with serum from pigs exposed to Ingelvac MLV vaccine or field viruses as in the previous experiment. ELISA plates were coated with myc-NSP 2P-His (VR-2332) polypeptides or with myc-NSP 2 SI HP-His (VR-2332) or myc-NSP 2 S2 HP-His (VR-2332) polypeptides.

All pig sera, both from vaccinated and field virus-exposed animals and diluted 1/1000 (n=42), reacted with NSP 2P with high OD values as in the previous experiment. However, the sera reacted weakly with both NSP 2 S1 HP and NSP 2 S2 HP. The OD values of more than 90 percent of the samples were below 0.1. These results indicate that polypeptides of about 30 to 40 amino acids may not encompass sufficient immunoreactivity to discriminate different serological reactivities to a viral infection even though the amino acid sequence variability in the polypeptide is high.

Figure 34A:
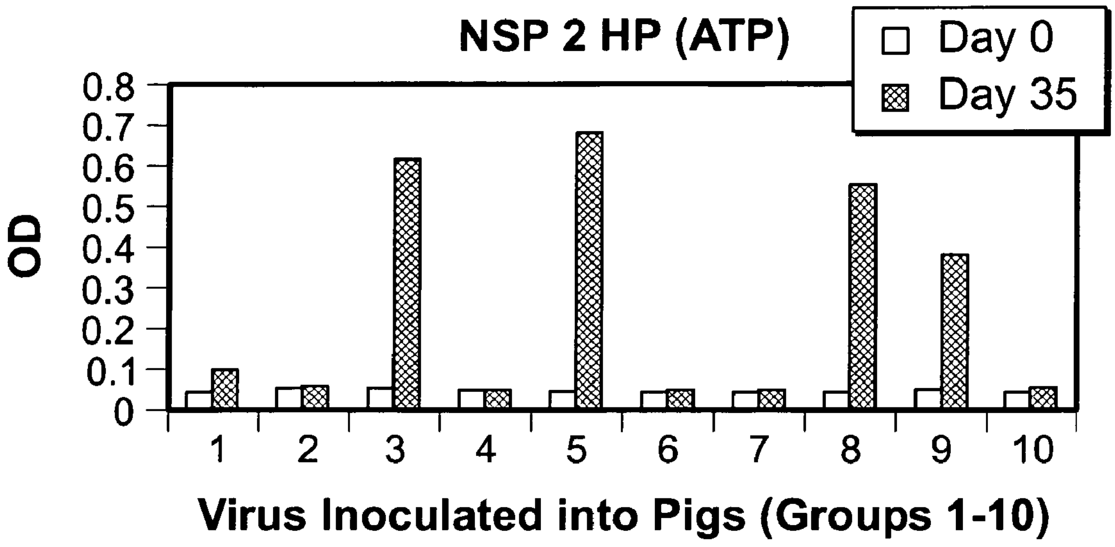
FIG. 34 contains two graphs plotting the absorbance for samples obtained from animals treated as indicated. The absorbance values were detected using an ELISA of NSP 2 HP (ATP) polypeptides (A) or NSP 2P (VR-2332) polypeptides (B).
Figure 34B:
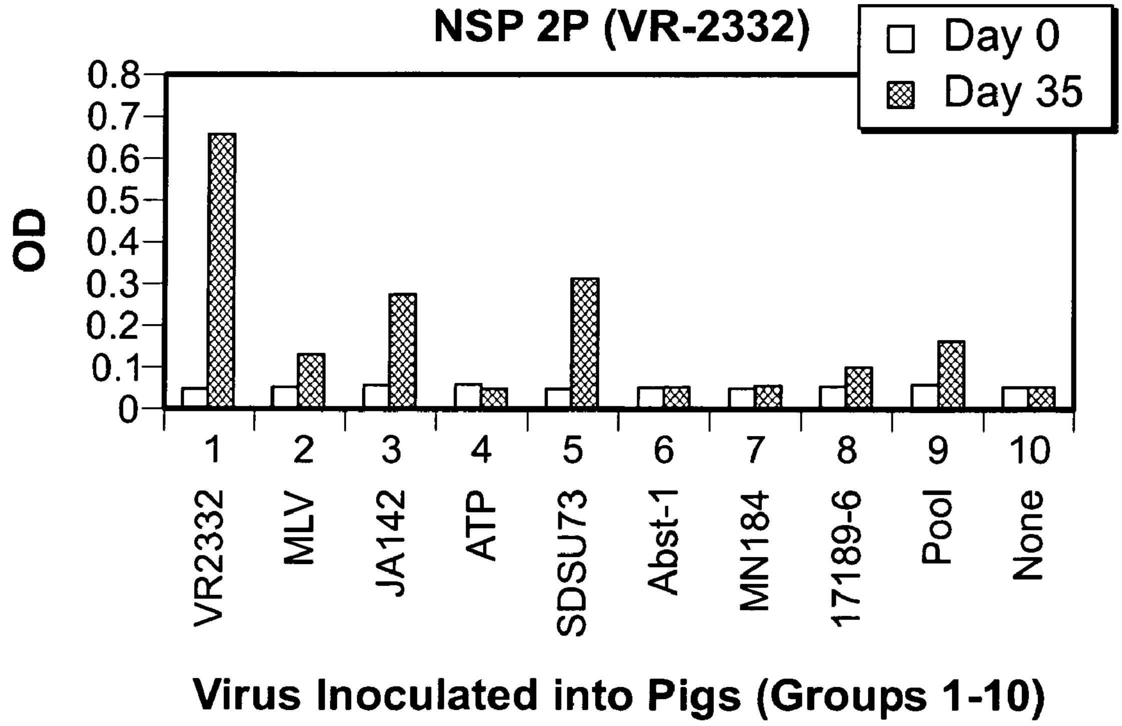

In a third experiment, microtiter plates were coated as described in Example 9 with myc-NSP 2HP-His (ATP) or myc-NSP 2P-His (VR-2332) polypeptides. ELISA assays were performed with serum samples from pigs exposed to vaccine and field viruses as described in Example 4. The assay was performed as described in Example 9 with the exception that serum samples were diluted 1/1000, and color development reactions were stopped after 3 minutes. As shown herein, serum samples from pigs exposed to field viruses or the MLV vaccine react positively with NSP 2P (VR-2332) (FIG. 34). Serum from pigs exposed to Abst-1 or the vaccine strain ATP did not react positively, due to use at doses that elicited a low or negligible immune response. The NSP 2HP (ATP) polypeptide reacted strongly with serum from a pig exposed to JA142, the parental virus of the vaccine, but also to serum from pigs exposed to field viruses SDSU73 and 17198-6. These results demonstrate that the use of nonstructural polypeptides such as NSP 2HP and NSP 2 P from different PRRS virus strains such as Ingelvac ATP and VR-2332 did not result in a serological test that was specific for exposure of swine to a particular strain or isolate. The NSP 2HP (ATP) polypeptide may not be uniquely different from other PRRS virus NSP 2 HP polypeptides in the way that NSP 2HP (VR-2332) is.

Example 11

Increasing pH During the Blocking Step Reduces Background Signals

High nonspecific backgrounds in ELISA tests is a commonly encountered problem in swine serology, especially with serum at low dilutions and from older animals such as six months and above. The levels of specific and nonspecific reactivity of positive and negative swine sera were determined on ELISA plates that were blocked at pH 7.4 or 9.6. Wells were coated with equal amounts of N, ORF 5 and ORF 6 ectodomains, and ORF 5 endodomain (all from VR-2332) at zero to 300 ng/well, and positive or negative sera were applied at dilutions of 1/40 to 1/4000. The positive serum samples were obtained from a 7 week-old pig at 3 weeks after exposure to VR-2332. The negative serum samples were obtained from a 6 month-old pig. Blocking was performed with 5% nonfat dry milk in PBS, 0.05% Tween 20 at pH 7.4 or 9.6.

Figure 35A:
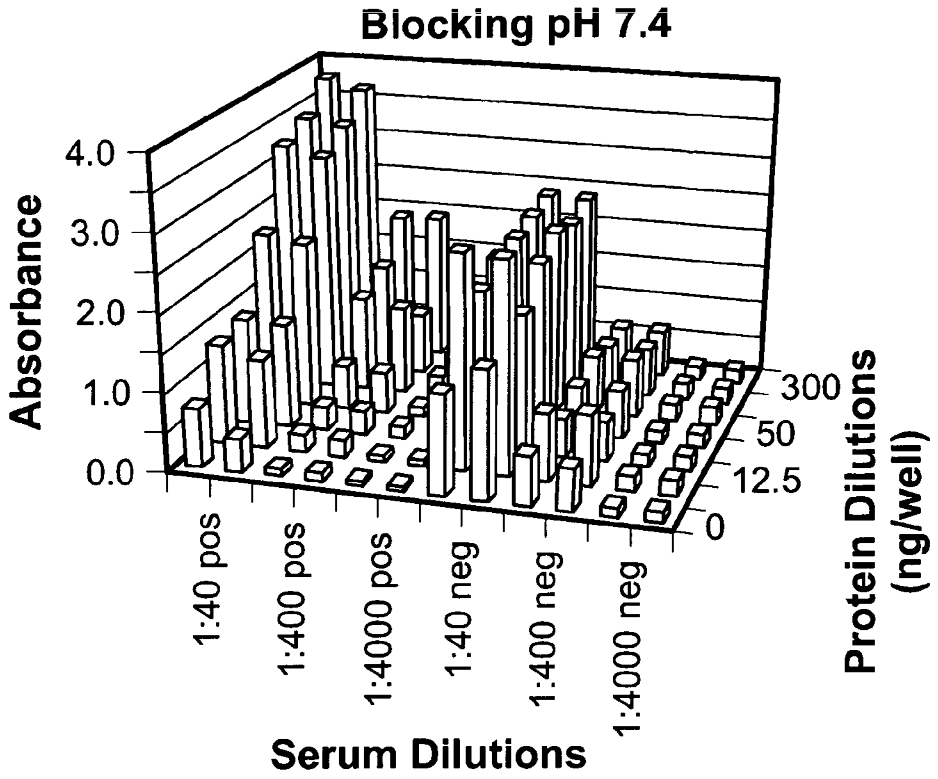
FIG. 35 contains two 3D graphs plotting the absorbance for positive and negative samples diluted as indicated and assessed with wells having the indicated amount of polypeptide. The pH during the blocking step was either 7.4 (A) or 9.6 (B).
Figure 35B:
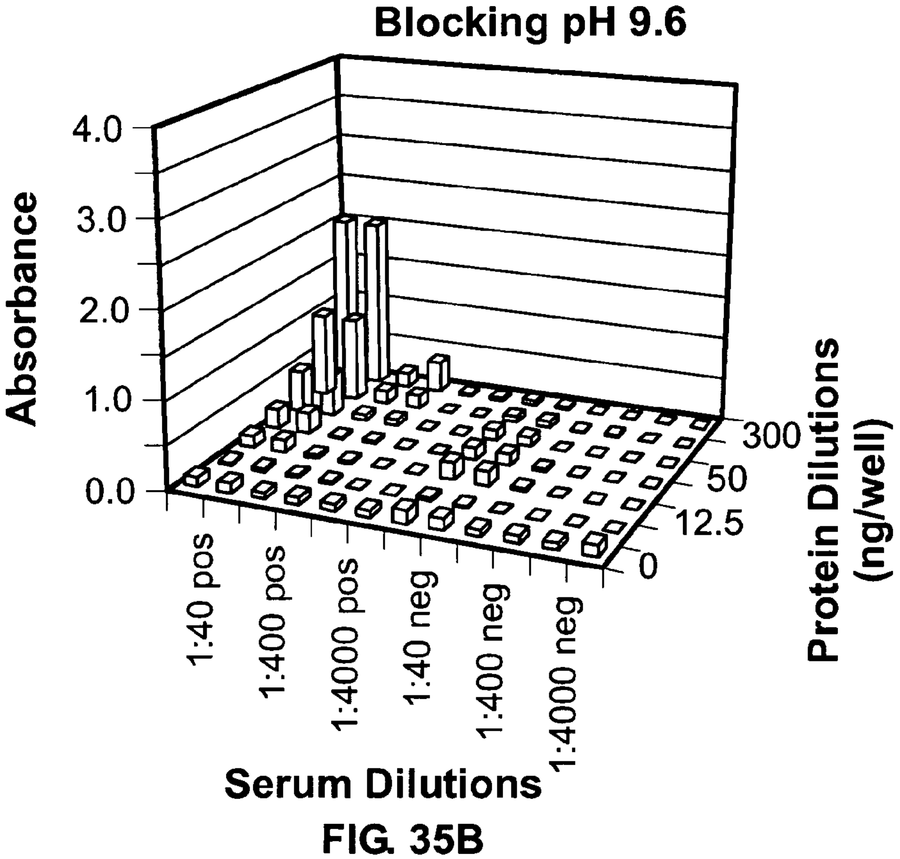

Serum concentration-dependent color development was observed in PRRS virus-positive serum at pH 7.4, but nonspecific color development in PRRS virus-negative serum wells was even higher than specific reactivity at moderate and low levels of antigen on the plate (FIG. 35). At a blocking pH value of 9.6, the nonspecific reactivity was nearly completely abolished. Specific reactivity was reduced by about 50 percent, but the overall signal-to-noise ratio was greatly increased (FIG. 35).

These results indicate that blocking solutions (e.g., protein solutions) applied to ELISA plates at neutral pH do not completely neutralize the protein-binding capacity, resulting in nonspecific binding of swine immunoglobulins and high OD values. The problem is exacerbated at low serum dilutions which would otherwise increase assay sensitivity. Increasing the pH of the blocking solution above 7.4 (e.g., greater than 9) reduced or abolished nonspecific reactivity across a wide range of antigen coating amounts and serum dilutions.

Example 12

Producing Recombinant PRRS Virus Polypeptides

The following polypeptides were produced using methods and materials similar to those described in Example 2: a PRRS virus (Lelystad strain) ORF 7 polypeptide (FIG. 36), a PRRS virus (Lelystad strain) NSP 2P polypeptide (FIG. 37), a PRRS virus (JA 142 strain) NSP 2P polypeptide (FIG. 38), a PRRS virus (ATP strain) NSP 2HP polypeptide (FIG. 39), a PRRS virus (Lelystad strain) endodomain ORF 5 polypeptide (ORF 5 3'; FIG. 40), and a PRRS virus (Lelystad strain) endodomain ORF 6 (ORF 6 3'; FIG. 41) polypeptide.

Example 13

Adding Lysozyme to Coating Buffer Increases Reactivity to Nucleocapsid

Lysozyme was included as a control in coating of wells with recombinant polypeptides. Briefly, ELISA wells were coated with 100 ng of polypeptides (e.g., refolded myc-ORF 7-His polypeptide) alone or with various amounts of chicken egg lysozyme (Sigma) in 100 μL carbonate buffer. ELISA was performed with serum samples from two pigs 21 days after infection with PRRS virus strain VR2332 or two uninfected control pig serum.

Figure 42:
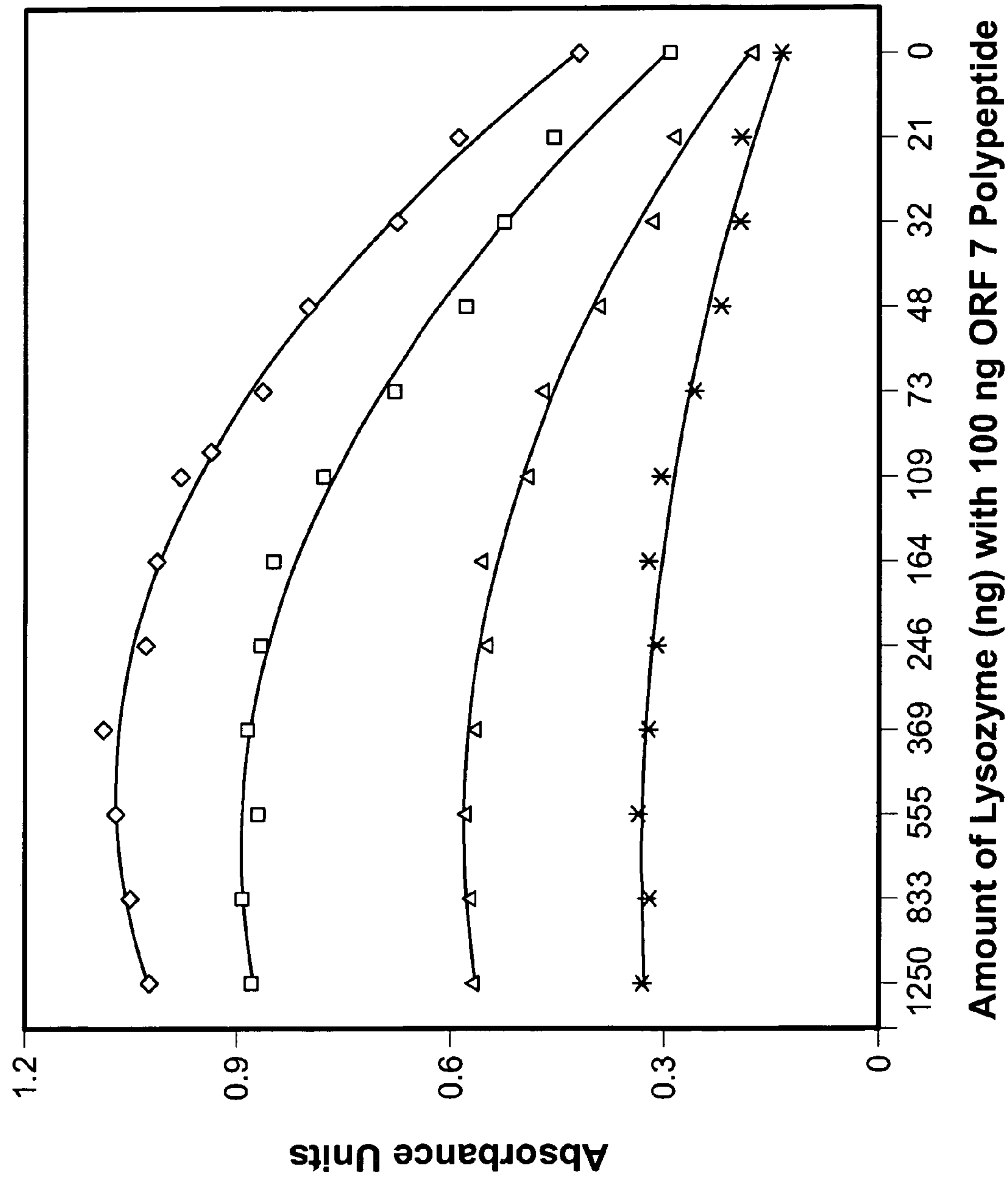
FIG. 42 is a graph plotting the absorbance versus the amount of chicken egg lysozyme added to 100 ng of refolded myc-ORF 7-His polypeptide. Values are the specific anti-ORF 7 polypeptide means after subtraction of negative serum backgrounds. Data points are from sera diluted 1/300 (diamond), 1/600 (square), 1/1200 (triangle), and 1/2400 (cross-x).

No difference was observed in the intensity of color reactions when plates were coated with various recombinant polypeptides, including myc-ORF 5-3'-His polypeptide and non-refolded myc-ORF 7-His polypeptide, in the presence or absence of lysozyme at various concentrations. Similarly, no reactivity was observed to lysozyme alone. Refolded myc-ORF 7-His polypeptide reactivity, however, was substantially increased in the presence of lysozyme. Moreover, the degree of enhancement was proportional to the amount of lysozyme added (FIG. 42). Inclusion of lysozyme in the coating step increased the specific reactivity of immune PRRS virus serum in a dose-dependent manner up to a maximum of about 200 ng of lysozyme per well (FIG. 42).

The effect was observed at all dilutions of serum examined with greater effects observed with less dilute sera. At a 1/300 dilution of serum, the average specific absorbance was about 0.42 in the absence of lysozyme, but it was greater than 1.0 in the presence of 164 ng or greater of lysozyme. The enhancing effect of lysozyme also was observed with a wide range of coating amounts, including the range of 20 to 500 ng, of refolded myc-ORF 7-His polypeptide per well. About 100 ng of lysozyme per well provided enhanced results under a variety of conditions including, for example, dilution of test serum from 1:40 to 1:5000, incubation of test serum with antigen for 45 minutes to 90 minutes, dilution of second antibody conjugate from 1:500 to 1:5000, and color development reaction time from 2 minutes to 20 minutes. The finding that lysozyme enhances the specific anti-PRRS serological reactivity to the ORF 7 polypeptide is useful since the ORF 7 polypeptide is a major antigen of the PRRS virus and is widely used in serological testing. Conditions that increase the sensitivity of detection of anti-ORF 7 polypeptide antibodies can increase the sensitivity of a diagnostic assay to early infection or exposure to PRRS virus, can increase the duration of detection following exposure or seroconversion, and can provide a basis for a more robust test since the difference between positive and negative results can be increased.

Example 14

Increased Stability of Recombinant Viral Protein-Based ELISAs

Figure 43:
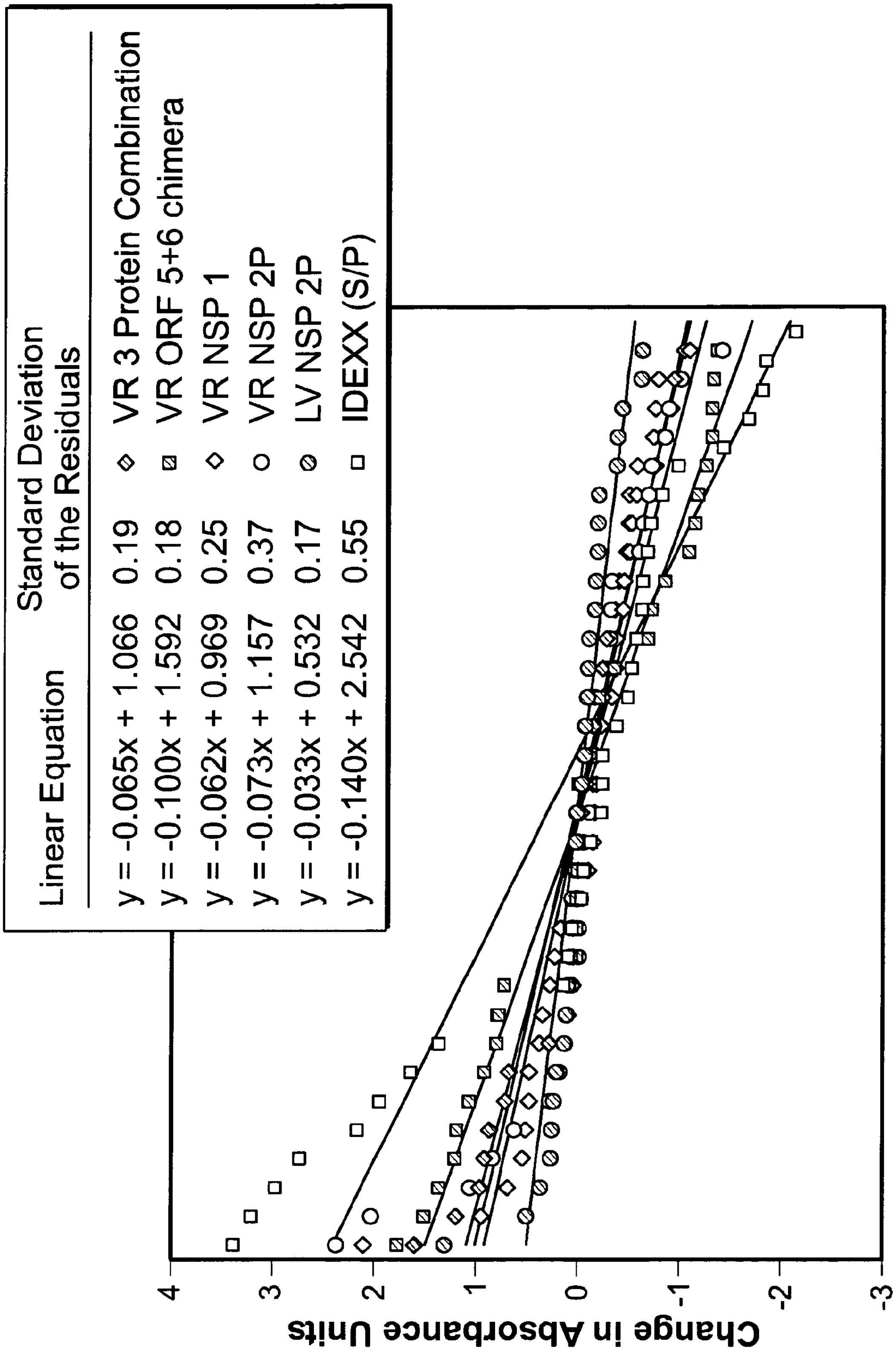
FIG. 43 is a graph plotting the change in absorbance detected in animals using the indicated ELISAs. VR indicates the polypeptide is from strain VR2332. LV indicates the polypeptide is from Lelystad virus. Standard deviation of the residuals is a measure of goodness-of-fit of the data to the equation determined by linear regression.

The ability of recombinant polypeptides to detect previous exposure to PRRS virus in pregnant sows in a commercial pig-rearing operation was evaluated in comparison to the IDEXX 2XR ELISA. Sera from 32 pregnant sows in an endemically infected herd were obtained at 35 day intervals and tested for anti-PRRS virus antibodies by IDEXX 2XR ELISA and by ELISA reactivity to a combination of three recombinant PRRS virus polypeptides (ORF 7, ORF 5-3', and ORF 6-3', all strain VR2332), or individual PRRS virus polypeptides from strain VR2332 (ORF 5+6 ectodomain chimera, NSP 1, and NSP 2P) or an individual PRRS virus polypeptide from the Lelystad virus strain (NSP 2P; FIG. 37). Briefly, serum samples diluted 1/500 were run in duplicate on ELISA plates coated with 50 ng of ORF 5+6 chimera alone, or 100 ng of a combination of ORF 7, ORF 5-3' and ORF 6-3' (33 ng each), or 100 ng of NSP 1, or 100 ng of NSP 2P. The serum samples were also analyzed by IDEXX 2×R ELISA. For each ELISA assay, the difference in average absorbance value (day 35-day 0) was calculated for all 32 pigs and ordered from positive to negative. For each set of data, a hypothetical linear regression equation and regression coefficient was calculated. The resulting values were ordered from highest to lowest value for all 32 animals for each recombinant polypeptide preparation (FIG. 43).

In each instance, a range of values from positive (higher value at interval day 35 than interval day 0) to negative (lower value at interval day 35 than interval day 0) was obtained. The greatest variation (standard deviation of the residuals=0.55) among animals in antibody levels, both positive and negative, occurred in the IDEXX 2×R ELISA test (FIG. 43). The recombinant polypeptide ELISAs exhibited more uniform results in that a hypothetical regression analysis indicated a line with a slope closer to zero, and reduced variation in the highest and lowest responses (FIG. 43). These results were on average more uniform, as indicated by the linear regression equation slope that was closer to zero and the smaller standard deviation of the residuals in each case as compared to IDEXX 2×R ELISA. The most consistent result was obtained with NSP2P derived from Lelystad virus.

Large differences in assay results in a 35 day period can be interpreted as a loss of immunity in animals that exhibit a large decrease in reactivity, and as new infection of susceptible animals in cases of large increases in reactivity. The consequence can be a potential increase in false positive and false negative interpretations of the PRRS virus status of individual animals and of commercial swine populations. The recombinant polypeptide ELISA assays exhibited less variation in animal responses, consistent with exposure of the animals to PRRS virus, the presence of an immune response in the animals, and little change in antibody status of the animals in a 35 day period. These results indicate that the recombinant polypeptide ELISAs, based on individual polypeptides or combinations of polypeptides, can provide a more uniform assessment of herd exposure to PRRS virus and can have a reduced likelihood of false positive and false negative interpretations.

Example 15

Figure 44A:
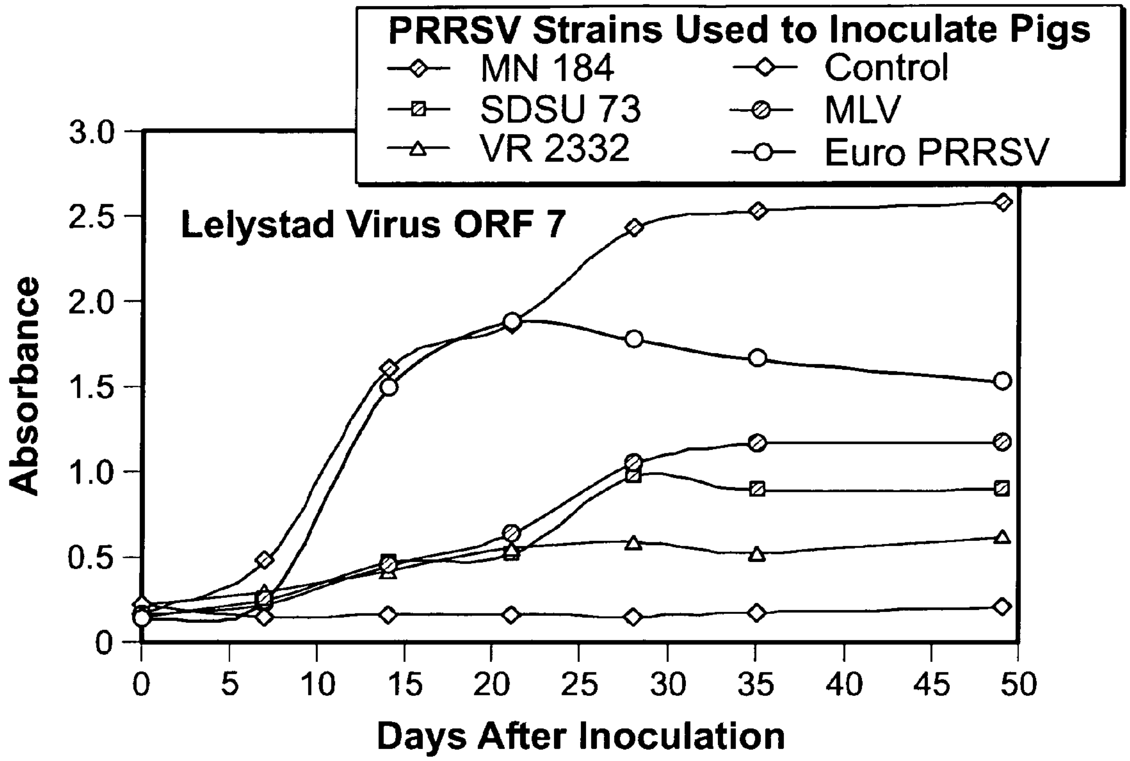
FIG. 44 contains graphs plotting the absorbance observed with samples inoculated with the indicated PRRS virus using ELISAs containing the indicated polypeptide.
Figure 44B:
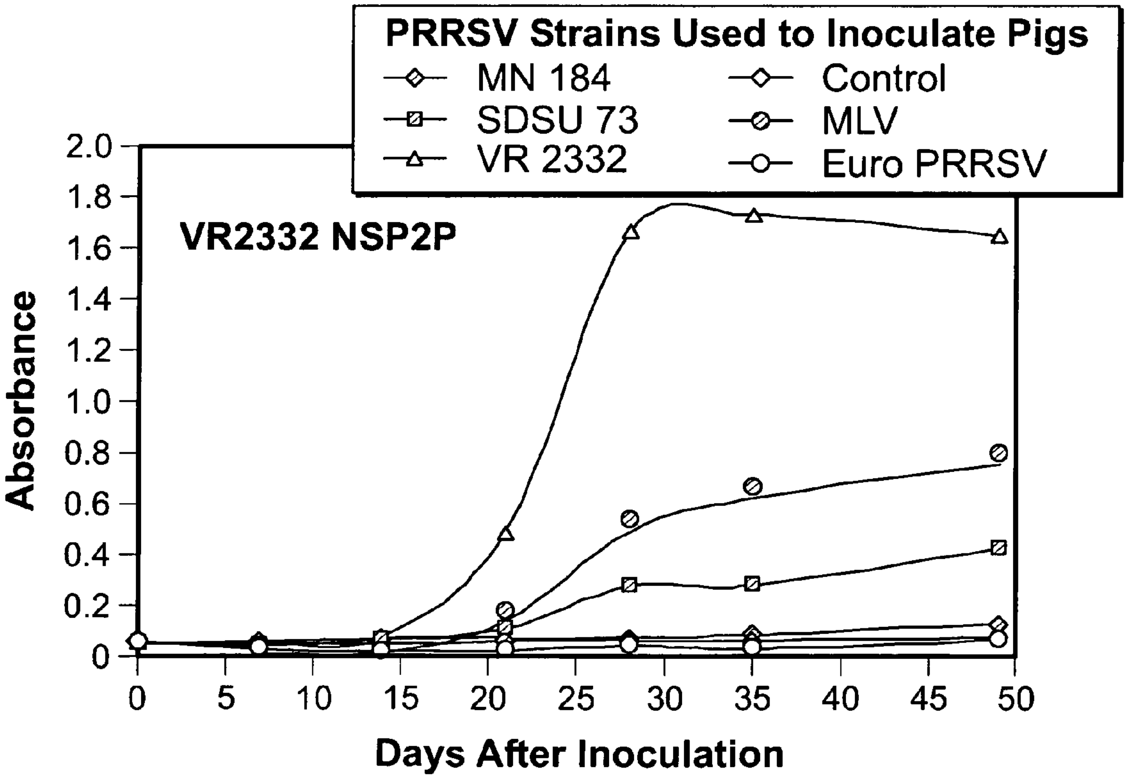
Figure 44C:
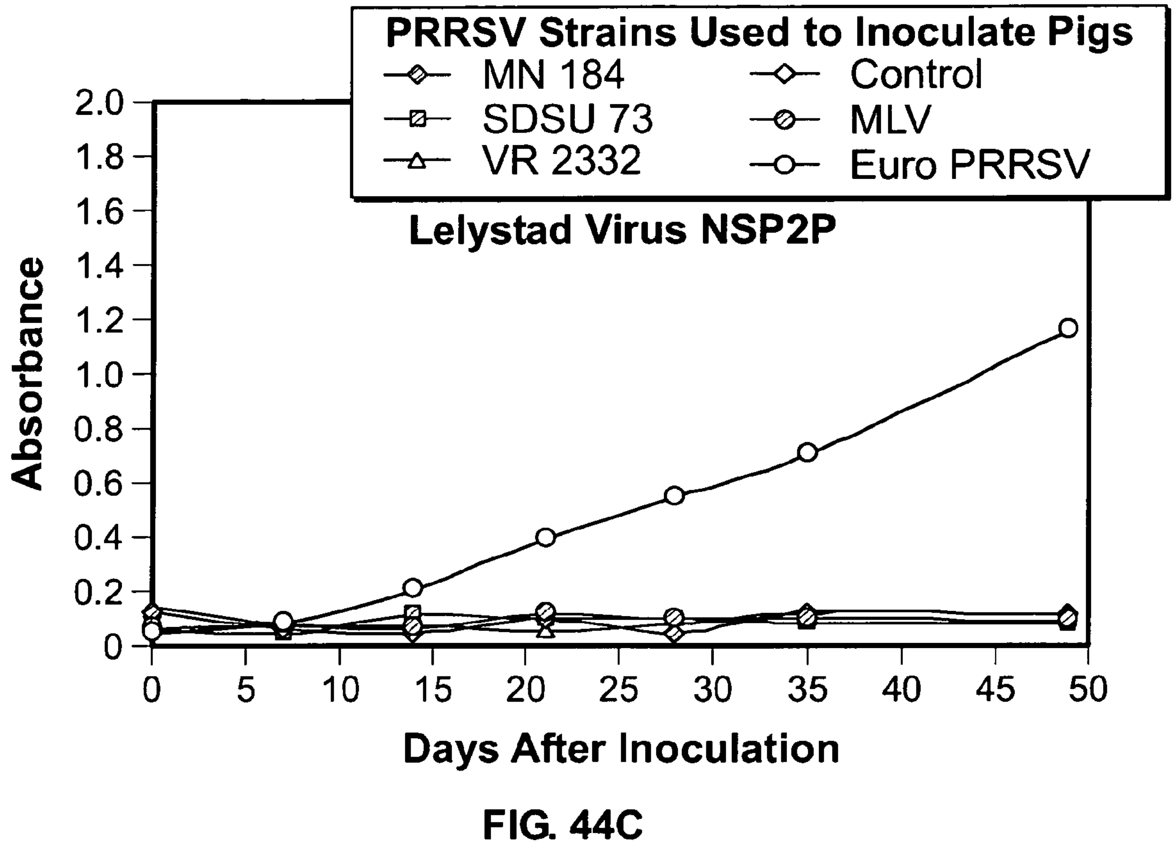

Detecting Antibodies to North American and European Genotype PRRS Viruses Using Individual PRRS Virus Polypeptides from Either Genotvpe The serum samples described in Example 9 as well as recombinant PRRS virus ORF 7 (from Lelystad virus, a European genotype; FIG. 36) and NSP2P (from VR2332, a North American genotype; or Lelystad virus, FIG. 37) polypeptides were used to examine the specificity of reaction for individual PRRS virus polypeptides. Serum samples from pigs inoculated with a European genotype PRRS virus and with the North American genotype virus, MN184, reacted strongly with Lelystad virus ORF 7 polypeptides, while North American genotype strains SDSU73, VR2332, and Ingelvac MLV reacted weakly (FIG. 44). These results indicate that ORF 7 polypeptides of Lelystad virus can be used to discriminate serological responses to a subset of North American PRRS viruses as well as to European PRRS virus strains. Serum samples from pigs inoculated with a European genotype PRRS virus reacted exclusively with LV NSP 2P polypeptides and not at all with VR2332 NSP 2P polypeptides (FIG. 44, panels B and C). The VR2332 NSP 2P polypeptide reacted strongly with sera from pigs exposed to VR2332 and positively, but less strongly, with sera of pigs exposed to Ingelvac MLV and SDSU73. It appeared not to react at all with sera from pigs exposed to MN184. These findings indicate that individual PRRS virus polypeptides can detect serological responses to pigs exposed to subsets of PRRS viruses.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit for determining whether an animal received a vaccine version of a PRRS virus or was infected with a naturally-occurring version of said PRRS virus, said kit comprising:

(a) a first PRRS polypeptide having an amino acid sequence such that antibodies made against said vaccine version of said PRRS virus bind said first PRRS polypeptide and antibodies made against said naturally-occurring version of said PRRS virus bind said first PRRS polypeptide, and (b) a second PRRS polypeptide having an amino acid sequence such that antibodies made against said vaccine version of said PRRS virus bind said second PRRS polypeptide and antibodies made against said naturally-occurring version of said PRRS virus do not bind said second PRRS polypeptide.

2. The kit of claim 1, wherein said animal is a vertebrate.

3. The kit of claim 1, wherein said animal is a pig.

4. The kit of claim 1, wherein said vaccine version is an attenuated PRRS virus.

5. The kit of claim 1, wherein said vaccine version having the sequence set forth in SEQ ID NO:106.

6. The kit of claim 1, wherein said first PRRS polypeptide comprises an amino acid sequence present in a C-terminal portion of an ORF 5 polypeptide of a VR2332 virus or a virus having the sequence set forth in SEQ ID NO:106.

7. The kit of claim 1, wherein said second PRRS polypeptide comprises an amino acid sequence present in the N-terminal half of an ORF 5 polypeptide of a VR2332 virus or a virus having the sequence set forth in SEQ ID NO:106.

* * * * *

UNITED STATES PATENT AND TRADEMARK OFFICE

CERTIFICATE OF CORRECTION

PATENT NO. : 7,611,717 B2

APPLICATION NO. : 11/155830
DATED : November 3, 2009
INVENTOR(S) : Murtaugh et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 123 days.

Delete the phrase "by 123 days" and insert -- by 290 days --

Signed and Sealed this

Tenth Day of August, 2010

David J. Kappos

*Director of the United States Patent and Trademark Office*

```
                          SEQUENCE LISTING

<160> NUMBER OF SEQ ID NOS: 105

<210> SEQ ID NO 1
<211> LENGTH: 1586
<212> TYPE: DNA
<213> ORGANISM: Porcine reproductive and respiratory syndrome virus
<220> FEATURE:
<221> NAME/KEY: CDS
<222> LOCATION: (175)..(234)

<400> SEQUENCE: 1

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
            5                  10                  15

agt gga tcc tctgggatac ttgatcggtg cacgtgtacc cccaatgcca               274
Ser Gly Ser
        20

gggtgtttat ggcggagggc caagtctact gcacacgatg cctcagtgca cggtctctcc     334

ttcccctgaa cctccaagtt tctgagctcg gggtgctagg cctattctac aggcccgaag     394

agccactccg gtggacgttg ccacgtgcat tccccactgt tgagtgctcc cccgccgggg     454

cctgctggct ttctgcaatc tttccaatcg cacgaatgac cagtggaaac ctgaacttcc     514

aacaaagaat ggtacgggtc gcagctgagc tttacagagc cggccagctc acccctgcag     574

tcttgaaggc tctacaagtt tatgaacggg gttgccgctg gtaccccatt gttggacctg     634

tccctggagt ggccgttttc gccaattccc tacatgtgag tgataaacct ttcccgggag     694

caactcacgt gttgaccaac ctgccgctcc cgcagagacc caagcctgaa gacttttgcc     754

cctttgagtg tgctatggct actgtctatg acattggtca tgacgccgtc atgtatgtgg     814

ccgaaaggaa agtctcctgg gcccctcgtg gcggggatga agtgaaattt gaagctgtcc     874
```

-continued

```
ccggggagtt gaagttgatt gcgaaccggc tccgcacctc cttcccgccc caccacacag    934

tggacatgtc taagttcgcc ttcacagccc ctgggtgtgg tgtttctatg cgggtcgaac    994

gccaacacgg ctgccttccc gctgacactg tccctgaagg caactgctgg tggagcttgt   1054

ttgacttgct tccactggaa gttcagaaca aagaaattcg ccatgctaac caatttggct   1114

accagaccaa gcatggtgtc tctggcaagt acctacagcg gaggctgcaa gttaatggtc   1174

tccgagcagt aactgaccta aacggaccta tcgtcgtaca gtacttctcc gttaaggaga   1234

gttggatccg ccatttgaaa ctggcgggag aacccagcta ctctgggttt gaggacctcc   1294

tcagaataag ggttgagcct aacacgtcgc cattggctga caaggaagaa aaaattttcc   1354

ggtttggcag tcacaagtgg tacggcgctc tcgagcacca ccaccaccac cactgagatc   1414

cggctgctaa caaagcccga aaggaagctg agttggctgc tgccaccgct gagcaataac   1474

tagcataacc ccttggggcc tctaaacggg tcttgagggg ttttttgctg aaaggaggaa   1534

ctatatccgg attggcgaat gggacgcgcc ctgtagcggc gcattaagcg cg           1586
```

<210> SEQ ID NO 2
<211> LENGTH: 1149
<212> TYPE: DNA
<213> ORGANISM: Porcine reproductive and respiratory syndrome virus

<400> SEQUENCE: 2

```
tctgggatac ttgatcggtg cacgtgtacc cccaatgcca gggtgtttat ggcggagggc     60

caagtctact gcacacgatg cctcagtgca cggtctctcc ttcccctgaa cctccaagtt    120

tctgagctcg ggtgctaggg cctattctac aggcccgaag agccactccg gtggacgttg    180

ccacgtgcat tccccactgt tgagtgctcc cccgccgggg cctgctggct ttctgcaatc    240

tttccaatcg cacgaatgac cagtggaaac ctgaacttcc aacaaagaat ggtacgggtc    300

gcagctgagc tttacagagc cggccagctc accccctgcag tcttgaaggc tctacaagtt    360

tatgaacggg gttgccgctg gtaccccatt gttggacctg tccctggagt ggccgttttc    420

gccaattccc tacatgtgag tgataaacct ttcccgggag caactcacgt gttgaccaac    480

ctgccgctcc cgcagagacc caagcctgaa gacttttgcc cctttgagtg tgctatggct    540

actgtctatg acattggtca tgacgccgtc atgtatgtgg ccgaaaggaa agtctcctgg    600

gcccctcgtg gcggggatga agtgaaattt gaagctgtcc ccggggagtt gaagttgatt    660

gcgaaccggc tccgcacctc cttcccgccc caccacacag tggacatgtc taagttcgcc    720

ttcacagccc ctgggtgtgg tgtttctatg cgggtcgaac gccaacacgg ctgccttccc    780

gctgacactg tccctgaagg caactgctgg tggagcttgt ttgacttgct tccactggaa    840

gttcagaaca aagaaattcg ccatgctaac caatttggct accagaccaa gcatggtgtc    900

tctggcaagt acctacagcg gaggctgcaa gttaatggtc tccgagcagt aactgaccta    960

aacggaccta tcgtcgtaca gtacttctcc gttaaggaga gttggatccg ccatttgaaa   1020

ctggcgggag aacccagcta ctctgggttt gaggacctcc tcagaataag ggttgagcct   1080

aacacgtcgc cattggctga caaggaagaa aaaattttcc ggtttggcag tcacaagtgg   1140

tacggcgct                                                           1149
```

<210> SEQ ID NO 3
<211> LENGTH: 20
<212> TYPE: PRT
<213> ORGANISM: Porcine reproductive and respiratory syndrome virus

<400> SEQUENCE: 3

-continued

```
Met Glu Gln Lys Leu Ile Ser Glu Glu Asp Leu Asn Arg Ser Met Asn
  1               5                  10                  15

Ser Ser Gly Ser
             20


<210> SEQ ID NO 4
<211> LENGTH: 3968
<212> TYPE: DNA
<213> ORGANISM: Porcine reproductive and respiratory syndrome virus
<220> FEATURE:
<221> NAME/KEY: CDS
<222> LOCATION: (175)..(201)
<220> FEATURE:
<221> NAME/KEY: CDS
<222> LOCATION: (3766)..(3789)

<400> SEQUENCE: 4

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gatctgaatc gatccatgaa ttctagtgga     231
Glu Gln Lys Leu Ile Ser Glu Glu
              5

tccgccgcgc tttgtccgtt cgtgaaaccc ggcaggccaa ggagcacgag gttgccggcc    291

aacaaggctg agcacctcaa acactactcc ccgcctgccg aagggaattg tggttggcac    351

tgcatttccg ccatcgccaa ccggatggtg aattccaaat ttgaaaccac ccttcccgaa    411

agagtgagac ctccagatga ctgggctact gacgaggatc ttgtgaatgc catccaaatc    471

ctcagactcc ctgcggcctt agacaggaac ggtgcttgta ctagcgccaa gtacgtactt    531

aagctggaag gtgagcattg gactgtcact gtgacccctg ggatgtcccc ttctttgctc    591

cctcttgaat gtgttcaggg ctgttgtggg cacaagggcg gtcttggttc cccagatgca    651

gtcgaggtct ccggatttga ccctgcctgc cttgaccggc tggctgaggt gatgcacctg    711

cctagcagtg ctatcccagc cgctctggcc gaaatgtctg gcgattccga tcgttcggct    771

tctccggtca ccaccgtgtg gactgtttcg cagttctttg cccgtcacag cggagggaat    831

caccctgacc aagtgcgctt agggaaaatt atcagccttt gtcaggtgat tgaggactgc    891

tgctgttccc agaacaaaac caaccgggtc accccggagg aggtcgcagc aaagattgac    951

ctgtacctcc gtggtgcaac aaatcttgaa gaatgcttgg ccaggcttga gaaagcgcgc   1011

ccgccacgcg taatcgacac ctcctttgat tgggatgttg tgctccctgg ggttgaggcg   1071

gcaacccaga cgatcaagct gccccaggtc aaccagtgtc gtgctctggt ccctgttgtg   1131

actcaaaagt ccttggacaa caactcggtc cccctgaccg cctttttcact ggctaactac   1191

tactaccgtg cgcaaggtga cgaagttcgt caccgtgaaa gactaaccgc cgtgctctcc   1251

aagttggaaa aggttgttcg agaagaatat gggctcatgc caaccgagcc tggtccacgg   1311

cccacactgc cacgcgggct cgacgaactc aaagaccaga tggaggagga cttgctgaaa   1371

ctggctaacg cccagacgac ttcggacatg atggcctggg cagtcgagca ggttgaccta   1431

aaaacttggg tcaagaacta cccgcggtgg acaccaccac cccctccgcc aaaagttcag   1491

cctcgaaaaa cgaagcctgt caagagcttg ccggagagaa agcctgtccc cgccccgcgc   1551

aggaaggttg ggtccgattg tggcagcccg gtttcattag gcggcgatgt ccctaacagt   1611
```

-continued

```
tgggaagatt tggctgttag tagccccttt gatctcccga ccccacctga gccggcaaca   1671

ccttcaagtg agctggtgat tgtgtcctca ccgcaatgca tcttcaggcc ggcgacaccc   1731

ttgagtgagc cggctccaat tcccgcacct cgcggaactg tgtctcgacc ggtgacaccc   1791

ttgagtgagc cgatccctgt gcccgcaccg cggcgtaagt ttcagcaggt gaaaagattg   1851

agttcggcgg cggcaatccc accgtaccag gacgagcccc tggatttgtc tgcttcctca   1911

cagactgaat atgaggcctc tcccccagca ccgccgcaga gcgggggcgt tctgggagta   1971

gaggggcatg aagctgagga aaccctgagt gaaatctcgg acatgtcggg taacattaaa   2031

cctgcgtccg tgtcatcaag cagctccttg tccagcgtga gaatcacacg cccaaaatac   2091

tcagctcaag ccatcatcga ctcgggcggg ccctgcagtg ggcatctcca agaggtaaag   2151

gaaacatgcc ttagtgtcat gcgcgaggca tgtgatgcga ctaagcttga tgaccctgct   2211

acgcaggaat ggctttctcg catgtgggat cgggtggaca tgctgacttg gcgcaacacg   2271

tctgtttacc aggcgatttg caccttagat ggcaggttaa agttcctccc aaaaatgata   2331

ctcgagacac cgccgcccta tccgtgtgag tttgtgatga tgcctcacac gcctgcacct   2391

tccgtaggtg cggagagcga ccttaccatt ggctcagttg ctactgaaga tgttccacgc   2451

atcctcgaga aaatagaaaa tgtcggcgag atggccaacc agggaccctt ggccttctcc   2511

gaggataaac cggtagatga ccaacttgtc aacgaccccc ggatatcgtc gcggaggcct   2571

gacgagagca catcagctcc gtccgcaggc acaggtggcg ccggctcttt taccgatttg   2631

ccgccttcag atggcgcgga tgcggacggg ggggggccgt ttcggacggt aaaaagaaaa   2691

gctgaaaggc tctttgacca actgagccgt caggtttttg acctcgtctc ccatctccct   2751

gttttcttct cacgcctttt ctaccctggc ggtggttatt ctccgggtga ttggggtttt   2811

gcagctttta ctctattgtg cctcttttta tgttacagtt acccagcctt tggtattgct   2871

cccctcttgg gtgtgtttttc tgggtcttct cggcgcgttc gaatgggggt ttttggctgc   2931

tggttggctt ttgctgttgg tctgttcaag cctgtgtccg acccagtcgg cgctgcttgt   2991

gagtttgact cgccagagtg tagaaacatc cttcattctt ttgagcttct caaaccttgg   3051

gaccctgttc gcagccttgt tgtgggcccc gtcggtctcg gtcttgccat tcttggcagg   3111

ttactgggcg gggcacgctg catctggcac tttttgctta ggcttggcat tgttgcagac   3171

tgtatcttgg ctggagctta cgtgctttct caaggtaggt gtaaaaagtg ctggggatct   3231

tgtataagaa ctgctcctaa tgaggtcgct tttaacgtgt ttcctttcac acgtgcgacc   3291

aggtcgtcac ttatcgacct gtgcgatcgg ttttgtgcgc caaaaggaat ggaccccatt   3351

tttctcgcca ctgggtggcg cgggtgctgg gccggccgaa gccccattga gcaaccctct   3411

gaaaaaccca tcgcgtttgc ccaattggat gaaaagaaga ttacggctag gactgtggtc   3471

gcccagcctt atgaccccaa ccaagccgta aagtgcttgc gggtattgca gtcgggtggg   3531

gcgatggtgg ctaaggcggt cccaaaagtg gtcaaggttt ccgctgttcc attccgagcc   3591

cccttctttc ccactggagt gaaagttgac cctgattgca gggtcgtggt tgaccctgac   3651

actttcactg cagctctccg gtctggctac tccaccacaa acctcgtcct tggtgtaggg   3711

gactttgccc agctgaatgg attaaaaatc aggcaaattt ccaagccttc aggg ctc     3768
                                                            Leu
                                                             10

gag cac cac cac cac cac cac tgagatccgg ctgctaacaa agcccgaaag        3819
Glu His His His His His His
                15

gaagctgagt tggctgctgc caccgctgag caataactag cataacccct tggggcctct   3879
```

-continued aaacgggtct tgaggggttt tttgctgaaa ggaggaacta tatccggatt ggcgaatggg 3939 acgcgccctg tagcggcgca ttaagcgcg 3968

<210> SEQ ID NO 5
<211> LENGTH: 3583
<212> TYPE: DNA
<213> ORGANISM: Porcine reproductive and respiratory syndrome virus

<400> SEQUENCE: 5
gctggaaaga gagcaagaaa agcacgctct tgtgcgactg ctacagtcgc tggccgcgct 60
ttgtccgttc gtgaaacccg gcaggccaag gagcacgagg ttgccggcca acaaggctga 120
gcacctcaaa cactactccc cgcctgccga agggaattgt ggttggcact gcatttccgc 180
catcgccaac cggatggtga attccaaatt tgaaaccacc cttcccgaaa gagtgagacc 240
tccagatgac tgggctactg acgaggatct tgtgaatgcc atccaaatcc tcagactccc 300
tgcggcctta gacaggaacg gtgcttgtac tagcgccaag tacgtactta agctggaagg 360
tgagcattgg actgtcactg tgacccctgg gatgtcccct tctttgctcc ctcttgaatg 420
tgttcagggc tgttgtgggc acaagggcgg tcttggttcc ccagatgcag tcgaggtctc 480
cggatttgac cctgcctgcc ttgaccggct ggctgaggtg atgcacctgc ctagcagtgc 540
tatcccagcc gctctggccg aaatgtctgg cgattccgat cgttcggctt ctccggtcac 600
caccgtgtgg actgtttcgc agttctttgc ccgtcacagc ggagggaatc accctgacca 660
agtgcgctta gggaaaatta tcagcctttg tcaggtgatt gaggactgct gctgttccca 720
gaacaaaacc aaccgggtca ccccggagga ggtcgcagca aagattgacc tgtacctccg 780
tggtgcaaca aatcttgaag aatgcttggc caggcttgag aaagcgcgcc cgccacgcgt 840
aatcgacacc tcctttgatt gggatgttgt gctccctggg gttgaggcgg caacccagac 900
gatcaagctg ccccaggtca accagtgtcg tgctctggtc cctgttgtga ctcaaaagtc 960
cttggacaac aactcggtcc ccctgaccgc cttttcactg gctaactact actaccgtgc 1020
gcaaggtgac gaagttcgtc accgtgaaag actaaccgcc gtgctctcca agttggaaaa 1080
ggttgttcga gaagaatatg ggctcatgcc aaccgagcct ggtccacggc ccacactgcc 1140
acgcgggctc gacgaactca aagaccagat ggaggaggac ttgctgaaac tggctaacgc 1200
ccagacgact tcggacatga tggcctgggc agtcgagcag gttgacctaa aaacttgggt 1260
caagaactac ccgcggtgga caccaccacc ccctccgcca aaagttcagc ctcgaaaaac 1320
gaagcctgtc aagagcttgc cggagagaaa gcctgtcccc gccccgcgca ggaaggttgg 1380
gtccgattgt ggcagcccgg tttcattagg cggcgatgtc cctaacagtt gggaagattt 1440
ggctgttagt agcccctttg atctcccgac cccacctgag ccggcaacac cttcaagtga 1500
gctggtgatt gtgtcctcac cgcaatgcat cttcaggccg gcgacaccct tgagtgagcc 1560
ggctccaatt cccgcacctc gcggaactgt gtctcgaccg gtgacaccct tgagtgagcc 1620
gatccctgtg cccgcaccgc ggcgtaagtt tcagcaggtg aaaagattga gttcggcggc 1680
ggcaatccca ccgtaccagg acgagcccct ggatttgtct gcttcctcac agactgaata 1740
tgaggcctct cccccagcac cgccgcagag cgggggcgtt ctgggagtag aggggcatga 1800
agctgaggaa accctgagtg aaatctcgga catgtcgggt aacattaaac ctgcgtccgt 1860
gtcatcaagc agctccttgt ccagcgtgag aatcacacgc ccaaaatact cagctcaagc 1920
catcatcgac tcgggcgggc cctgcagtgg gcatctccaa gaggtaaagg aaacatgcct 1980

-continued

```
tagtgtcatg cgcgaggcat gtgatgcgac taagcttgat gaccctgcta cgcaggaatg   2040

gctttctcgc atgtgggatc gggtggacat gctgacttgg cgcaacacgt ctgtttacca   2100

ggcgatttgc accttagatg gcaggttaaa gttcctccca aaaatgatac tcgagacacc   2160

gccgccctat ccgtgtgagt ttgtgatgat gcctcacacg cctgcacctt ccgtaggtgc   2220

ggagagcgac cttaccattg gctcagttgc tactgaagat gttccacgca tcctcgagaa   2280

aatagaaaat gtcggcgaga tggccaacca gggacccttg gccttctccg aggataaacc   2340

ggtagatgac caacttgtca acgacccccg gatatcgtcg cggaggcctg acgagagcac   2400

atcagctccg tccgcaggca caggtggcgc cggctctttt accgatttgc cgccttcaga   2460

tggcgcggat gcggacgggg gggggccgtt tcggacggta aaaagaaaag ctgaaaggct   2520

ctttgaccaa ctgagccgtc aggtttttga cctcgtctcc catctccctg ttttcttctc   2580

acgccttttc taccctggcg gtggttattc tccgggtgat tggggttttg cagcttttac   2640

tctattgtgc ctctttttat gttacagtta cccagccttt ggtattgctc ccctcttggg   2700

tgtgttttct gggtcttctc ggcgcgttcg aatgggggtt tttggctgct ggttggcttt   2760

tgctgttggt ctgttcaagc ctgtgtccga cccagtcggc gctgcttgtg agtttgactc   2820

gccagagtgt agaaacatcc ttcattcttt tgagcttctc aaaccttggg accctgttcg   2880

cagccttgtt gtgggccccg tcggtctcgg tcttgccatt cttggcaggt tactgggcgg   2940

ggcacgctgc atctggcact tttgcttag  gcttggcatt gttgcagact gtatcttggc   3000

tggagcttac gtgctttctc aaggtaggtg taaaaagtgc tggggatctt gtataagaac   3060

tgctcctaat gaggtcgctt ttaacgtgtt tcctttcaca cgtgcgacca ggtcgtcact   3120

tatcgacctg tgcgatcggt tttgtgcgcc aaaaggaatg gaccccattt ttctcgccac   3180

tgggtggcgc gggtgctggg ccggccgaag ccccattgag caaccctctg aaaaacccat   3240

cgcgtttgcc caattggatg aaaagaagat tacggctagg actgtggtcg cccagcctta   3300

tgaccccaac caagccgtaa agtgcttgcg ggtattgcag tcgggtgggg cgatggtggc   3360

taaggcggtc ccaaaagtgg tcaaggtttc cgctgttcca ttccgagccc ccttctttcc   3420

cactggagtg aaagttgacc ctgattgcag ggtcgtggtt gaccctgaca ctttcactgc   3480

agctctccgg tctggctact ccaccacaaa cctcgtcctt ggtgtagggg actttgccca   3540

gctgaatgga ttaaaaatca ggcaaatttc caagccttca ggg                      3583
```

<210> SEQ ID NO 6
<211> LENGTH: 9
<212> TYPE: PRT
<213> ORGANISM: Porcine reproductive and respiratory syndrome virus

<400> SEQUENCE: 6

```
Met Glu Gln Lys Leu Ile Ser Glu Glu
  1               5
```

<210> SEQ ID NO 7
<211> LENGTH: 1049
<212> TYPE: DNA
<213> ORGANISM: Porcine reproductive and respiratory syndrome virus
<220> FEATURE:
<221> NAME/KEY: CDS
<222> LOCATION: (175)..(870)

<400> SEQUENCE: 7

```
aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120
```

-continued

```
taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc ggt gct ttc aga act cga aag ccc tca ctg aac acc gtc      273
Ser Gly Ser Gly Ala Phe Arg Thr Arg Lys Pro Ser Leu Asn Thr Val
         20                  25                  30

aat gtg atc ggg tcc tcc atg ggc tct ggc ggg gtg ttt acc atc gac      321
Asn Val Ile Gly Ser Ser Met Gly Ser Gly Gly Val Phe Thr Ile Asp
     35                  40                  45

ggg aaa gtc aag tgc gta act gcc gca cat gtc ctt acg ggc aat tca      369
Gly Lys Val Lys Cys Val Thr Ala Ala His Val Leu Thr Gly Asn Ser
 50                  55                  60                  65

gct cgg gtt tcc ggg gtc ggc ttc aat caa atg ctt gac ttt gac gta      417
Ala Arg Val Ser Gly Val Gly Phe Asn Gln Met Leu Asp Phe Asp Val
                 70                  75                  80

aag gga gat ttc gct ata gct gat tgc ccg aat tgg caa ggg gct gcc      465
Lys Gly Asp Phe Ala Ile Ala Asp Cys Pro Asn Trp Gln Gly Ala Ala
             85                  90                  95

ccc aag acc caa ttc tgc acg gat gga tgg act ggc cgt gcc tat tgg      513
Pro Lys Thr Gln Phe Cys Thr Asp Gly Trp Thr Gly Arg Ala Tyr Trp
        100                 105                 110

cta aca tcc tct ggc gtc gaa ccc ggc gtc att gga aaa gga ttc gcc      561
Leu Thr Ser Ser Gly Val Glu Pro Gly Val Ile Gly Lys Gly Phe Ala
    115                 120                 125

ttc tgc ttc acc gca tgt ggc gat tcc ggg tcc cca gtg atc acc gag      609
Phe Cys Phe Thr Ala Cys Gly Asp Ser Gly Ser Pro Val Ile Thr Glu
130                 135                 140                 145

gcc ggt gag ctt gtc ggc gtt cac acg gga tcg aat aaa caa ggg ggg      657
Ala Gly Glu Leu Val Gly Val His Thr Gly Ser Asn Lys Gln Gly Gly
                150                 155                 160

ggc att gtt acg cgc ccc tca ggc cag ttt tgt aat gtg gca ccc atc      705
Gly Ile Val Thr Arg Pro Ser Gly Gln Phe Cys Asn Val Ala Pro Ile
            165                 170                 175

aag cta agc gaa tta agt gaa ttc ttt gct ggg cct aag gtc ccg ctc      753
Lys Leu Ser Glu Leu Ser Glu Phe Phe Ala Gly Pro Lys Val Pro Leu
        180                 185                 190

ggt gat gtg aag gtc ggc agc cac ata att aaa gac ata agc gag gtg      801
Gly Asp Val Lys Val Gly Ser His Ile Ile Lys Asp Ile Ser Glu Val
    195                 200                 205

cct tca gat ctt tgt gcc ttg ctt gct gcc aaa cct gaa ctg gaa ctc      849
Pro Ser Asp Leu Cys Ala Leu Leu Ala Ala Lys Pro Glu Leu Glu Leu
210                 215                 220                 225

gag cac cac cac cac cac cac tgagatccgg ctgctaacaa agcccgaaag         900
Glu His His His His His His
                230

gaagctgagt tggctgctgc caccgctgag caataactag cataacccct tggggcctct    960

aaacgggtct tgaggggttt tttgctgaaa ggaggaacta tatccggatt ggcgaatggg   1020

acgcgccctg tagcggcgca ttaagcgcg                                     1049
```

<210> SEQ ID NO 8
<211> LENGTH: 611
<212> TYPE: DNA
<213> ORGANISM: Porcine reproductive and respiratory syndrome virus

<400> SEQUENCE: 8

-continued

```
ggtgctttca gaactcgaaa gccctcactg aacaccgtca atgtgatcgg gtcctccatg      60

ggctctggcg gggtgtttac catcgacggg aaagtcaagt gcgtaactgc cgcacatgtc     120

cttacgggca attcagctcg ggtttccggg gtcggcttca atcaaatgct tgactttgac     180

gtaaagggag atttcgctat agctgattgc ccgaattggc aaggggctgc ccccaagacc     240

caattctgca cggatggatg gactggccgt gcctattggc taacatcctc tggcgtcgaa     300

cccggcgtca ttggaaaagg attcgccttc tgcttcaccg catgtggcga ttccgggtcc     360

ccagtgtcac cgaggccggt gagcttgtcg gcgttcacac gggatcgaat aaacaagggg     420

ggggcattgt tacgcgcccc tcaggccagt tttgtaatgt ggcacccatc aagctaagcg     480

aattaagtga attctttgct gggcctaagg tcccgctcgg tgatgtgaag gtcggcagcc     540

acataattaa agacataagc gaggtgcctt cagatctttg tgccttgctt gctgccaaac     600

ctgaactgga a                                                          611
```

```
<210> SEQ ID NO 9
<211> LENGTH: 232
<212> TYPE: PRT
<213> ORGANISM: Porcine reproductive and respiratory syndrome virus

<400> SEQUENCE: 9

Met Glu Gln Lys Leu Ile Ser Glu Glu Asp Leu Asn Arg Ser Met Asn
  1               5                  10                  15

Ser Ser Gly Ser Gly Ala Phe Arg Thr Arg Lys Pro Ser Leu Asn Thr
             20                  25                  30

Val Asn Val Ile Gly Ser Ser Met Gly Ser Gly Gly Val Phe Thr Ile
         35                  40                  45

Asp Gly Lys Val Lys Cys Val Thr Ala Ala His Val Leu Thr Gly Asn
     50                  55                  60

Ser Ala Arg Val Ser Gly Val Gly Phe Asn Gln Met Leu Asp Phe Asp
 65                  70                  75                  80

Val Lys Gly Asp Phe Ala Ile Ala Asp Cys Pro Asn Trp Gln Gly Ala
                 85                  90                  95

Ala Pro Lys Thr Gln Phe Cys Thr Asp Gly Trp Thr Gly Arg Ala Tyr
            100                 105                 110

Trp Leu Thr Ser Ser Gly Val Glu Pro Gly Val Ile Gly Lys Gly Phe
        115                 120                 125

Ala Phe Cys Phe Thr Ala Cys Gly Asp Ser Gly Ser Pro Val Ile Thr
    130                 135                 140

Glu Ala Gly Glu Leu Val Gly Val His Thr Gly Ser Asn Lys Gln Gly
145                 150                 155                 160

Gly Gly Ile Val Thr Arg Pro Ser Gly Gln Phe Cys Asn Val Ala Pro
                165                 170                 175

Ile Lys Leu Ser Glu Leu Ser Glu Phe Phe Ala Gly Pro Lys Val Pro
            180                 185                 190

Leu Gly Asp Val Lys Val Gly Ser His Ile Ile Lys Asp Ile Ser Glu
        195                 200                 205

Val Pro Ser Asp Leu Cys Ala Leu Leu Ala Ala Lys Pro Glu Leu Glu
    210                 215                 220

Leu Glu His His His His His His
225                 230

<210> SEQ ID NO 10
<211> LENGTH: 2588
<212> TYPE: DNA
```

-continued

```
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2386)..(2409)

<400> SEQUENCE: 10

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc gctggaaaga gagcaagaaa agcacgctct tgtgcgactg              274
Ser Gly Ser
         20

ctacagtcgc tggccgcgct ttgtccgttc gtgaaacccg gcaggccaag gagcacgagg    334

ttgccggcgc caacaaggct gagcacctca aacactactc cccgcctgcc gaagggaatt    394

gtggttggca ctgcatttcc gccatcgcca accggatggt gaattccaaa tttgaaacca    454

cccttcccga aagagtgaga cctccagatg actgggctac tgacgaggat cttgtgaatg    514

ccatccaaat cctcagactc cctgcggcct tagacaggaa cggtgcttgt actagcgcca    574

agtacgtact taagctggaa ggtgagcatt ggactgtcac tgtgacccct gggatgtccc    634

cttctttgct ccctcttgaa tgtgttcagg gctgttgtgg gcacaagggc ggtcttggtt    694

ccccagatgc agtcgaggtc tccggatttg accctgcctg ccttgaccgg ctggctgagg    754

tgatgcacct gcctagcagt gctatcccag ccgctctggc cgaaatgtct ggcgattccg    814

atcgttcggc ttctccggtc accaccgtgt ggactgtttc gcagttcttt gcccgtcaca    874

gcggagggaa tcaccctgac caagtgcgct tagggaaaat tatcagcctt tgtcaggtga    934

ttgaggactg ctgctgttcc cagaacaaaa ccaaccgggt caccccggag gaggtcgcag    994

caaagattga cctgtacctc cgtggtgcaa caaatcttga agaatgcttg gccaggcttg   1054

agaaagcgcg cccgccacgc gtaatcgaca cctcctttga ttgggatgtt gtgctccctg   1114

gggttgaggc ggcaacccag acgatcaagc tgccccaggt caaccagtgt cgtgctctgg   1174

tccctgttgt gactcaaaag tccttggaca acaactcggt cccccctgacc gccttttcac  1234

tggctaacta ctactaccgt gcgcaaggtg acgaagttcg tcaccgtgaa agactaaccg   1294

ccgtgctctc caagttggaa aaggttgttc gagaagaata tgggctcatg ccaaccgagc   1354

ctggtccacg gcccacactg ccacgcgggc tcgacgaact caaagaccag atggaggagg   1414

acttgctgaa actggctaac gcccagacga cttcggacat gatggcctgg gcagtcgagc   1474

aggttgacct aaaaacttgg gtcaagaact acccgcggtg gacaccacca ccccctccgc   1534

caaaagttca gcctcgaaaa acgaagcctg tcaagagctt gccggagaga aagcctgtcc   1594

ccgccccgcg caggaaggtt gggtccgatt gtggcagccc ggtttcatta ggcggcgatg   1654

tccctaacag ttgggaagat ttggctgtta gtagcccctt tgatctcccg accccacctg   1714

agccggcaac accttcaagt gagctggtga ttgtgtcctc accgcaatgc atcttcaggc   1774

cggcgacacc cttgagtgag ccggctccaa ttcccgcacc tcgcggaact gtgtctcgac   1834

cggtgacacc cttgagtgag ccgatccctg tgcccgcacc gcggcgtaag tttcagcagg   1894
```

-continued

```
tgaaaagatt gagttcggcg gcggcaatcc caccgtacca ggacgagccc ctggatttgt   1954

ctgcttcctc acagactgaa tatgaggcct ctcccccagc accgccgcag agcgggggcg   2014

ttctgggagt agaggggcat gaagctgagg aaaccctgag tgaaatctcg gacatgtcgg   2074

gtaacattaa acctgcgtcc gtgtcatcaa gcagctcctt gtccagcgtg agaatcacac   2134

gcccaaaata ctcagctcaa gccatcatcg actcgggcgg gccctgcagt gggcatctcc   2194

aagaggtaaa ggaaacatgc cttagtgtca tgcgcgaggc atgtgatgcg actaagcttg   2254

atgaccctgc tacgcaggaa tggctttctc gcatgtggga tcgggtggac atgctgactt   2314

ggcgcaacac gtctgtttac caggcgattt gcaccttaga tggcaggtta aagttcctcc   2374

caaaaatgat a ctc gag cac cac cac cac cac cac tgagatccgg             2419
             Leu Glu His His His His His His
                                 25

ctgctaacaa agcccgaaag gaagctgagt tggctgctgc caccgctgag caataactag   2479

cataacccct tggggcctct aaacgggtct tgaggggttt tttgctgaaa ggaggaacta   2539

tatccggatt ggcgaatggg acgcgccctg tagcggcgca ttaagcgcg               2588


<210> SEQ ID NO 11
<211> LENGTH: 2151
<212> TYPE: DNA
<213> ORGANISM: Porcine reproductive and respiratory syndrome virus

<400> SEQUENCE: 11

gctggaaaga gagcaagaaa agcacgctct tgtgcgactg ctacagtcgc tggccgcgct     60

ttgtccgttc gtgaaacccg gcaggccaag gagcacgagg ttgccggcgc caacaaggct    120

gagcacctca aacactactc cccgcctgcc gaagggaatt gtggttggca ctgcatttcc    180

gccatcgcca accggatggt gaattccaaa tttgaaacca cccttcccga aagagtgaga    240

cctccagatg actgggctac tgacgaggat cttgtgaatg ccatccaaat cctcagactc    300

cctgcggcct tagacaggaa cggtgcttgt actagcgcca agtacgtact taagctggaa    360

ggtgagcatt ggactgtcac tgtgacccct gggatgtccc cttctttgct ccctcttgaa    420

tgtgttcagg gctgttgtgg gcacaagggc ggtcttggtt ccccagatgc agtcgaggtc    480

tccggatttg accctgcctg ccttgaccgg ctggctgagg tgatgcacct gcctagcagt    540

gctatcccag ccgctctggc cgaaatgtct ggcgattccg atcgttcggc ttctccggtc    600

accaccgtgt ggactgtttc gcagttcttt gcccgtcaca gcggagggaa tcaccctgac    660

caagtgcgct tagggaaaat tatcagcctt tgtcaggtga ttgaggactg ctgctgttcc    720

cagaacaaaa ccaaccgggt caccccggag gaggtcgcag caaagattga cctgtacctc    780

cgtggtgcaa caaatcttga agaatgcttg gccaggcttg agaaagcgcg cccgccacgc    840

gtaatcgaca cctcctttga ttgggatgtt gtgctccctg ggggttgaggc ggcaacccag    900

acgatcaagc tgccccaggt caaccagtgt cgtgctctgg tccctgttgt gactcaaaag    960

tccttggaca acaactcggt ccccctgacc gccttttcac tggctaacta ctactaccgt   1020

gcgcaaggtg acgaagttcg tcaccgtgaa agactaaccg ccgtgctctc caagttggaa   1080

aaggttgttc gagaagaata tgggctcatg ccaaccgagc ctggtccacg gcccacactg   1140

ccacgcgggc tcgacgaact caaagaccag atggaggagg acttgctgaa actggctaac   1200

gcccagacga cttcggacat gatggcctgg gcagtcgagc aggttgacct aaaaacttgg   1260

gtcaagaact acccgcggtg gacaccacca cccccctccgc caaaagttca gcctcgaaaa   1320
```

-continued

```
acgaagcctg tcaagagctt gccggagaga aagcctgtcc ccgccccgcg caggaaggtt   1380

gggtccgatt gtggcagccc ggtttcatta ggcggcgatg tccctaacag ttgggaagat   1440

ttggctgtta gtagcccctt tgatctcccg accccacctg agccggcaac accttcaagt   1500

gagctggtga ttgtgtcctc accgcaatgc atcttcaggc cggcgacacc cttgagtgag   1560

ccggctccaa ttcccgcacc tcgcggaact gtgtctcgac cggtgacacc cttgagtgag   1620

ccgatccctg tgcccgcacc gcggcgtaag tttcagcagg tgaaaagatt gagttcggcg   1680

gcggcaatcc caccgtacca ggacgagccc ctggatttgt ctgcttcctc acagactgaa   1740

tatgaggcct ctcccccagc accgccgcag agcgggggcg ttctgggagt agaggggcat   1800

gaagctgagg aaaccctgag tgaaatctcg gacatgtcgg gtaacattaa acctgcgtcc   1860

gtgtcatcaa gcagctcctt gtccagcgtg agaatcacac gcccaaaata ctcagctcaa   1920

gccatcatcg actcgggcgg gccctgcagt gggcatctcc aagaggtaaa ggaaacatgc   1980

cttagtgtca tgcgcgaggc atgtgatgcg actaagcttg atgaccctgc tacgcaggaa   2040

tggctttctc gcatgtggga tcgggtggac atgctgactt ggcgcaacac gtctgtttac   2100

caggcgattt gcaccttaga tggcaggtta aagttcctcc caaaaatgat a            2151


<210> SEQ ID NO 12
<211> LENGTH: 20
<212> TYPE: PRT
<213> ORGANISM: Porcine reproductive and respiratory syndrome virus

<400> SEQUENCE: 12

Met Glu Gln Lys Leu Ile Ser Glu Glu Asp Leu Asn Arg Ser Met Asn
  1               5                  10                  15

Ser Ser Gly Ser
             20


<210> SEQ ID NO 13
<211> LENGTH: 8
<212> TYPE: PRT
<213> ORGANISM: Porcine reproductive and respiratory syndrome virus

<400> SEQUENCE: 13

Leu Glu His His His His His His
  1               5


<210> SEQ ID NO 14
<211> LENGTH: 545
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 14

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc atg aac gcc aac agc acc agc agc tca cat ttt cag ttg      273
Ser Gly Ser Met Asn Ala Asn Ser Thr Ser Ser Ser His Phe Gln Leu
         20                  25                  30
```

-continued

```
att tat aac ttg acg cta tgc gag ctg aat ggc aca gat tgg ctg gct      321
Ile Tyr Asn Leu Thr Leu Cys Glu Leu Asn Gly Thr Asp Trp Leu Ala
     35                  40                  45

gga aag ttt gat tgg gca gtg ctc gag cac cac cac cac cac cac          366
Gly Lys Phe Asp Trp Ala Val Leu Glu His His His His His His
 50                  55                  60

tgagatccgg ctgctaacaa agcccgaaag gaagctgagt tggctgctgc caccgctgag    426

caataactag cataacccct tggggcctct aaacgggtct tgaggggttt tttgctgaaa    486

ggaggaacta tatccggatt ggcgaatggg acgcgccctg tagcggcgca ttaagcgcg     545


<210> SEQ ID NO 15
<211> LENGTH: 108
<212> TYPE: DNA
<213> ORGANISM: Porcine reproductive and respiratory syndrome virus

<400> SEQUENCE: 15

atgaacgcca acagcaccag cagctcacat tttcagttga tttataactt gacgctatgc     60

gagctgaatg gcacagattg gctggctgga aagtttgatt gggcagtg                 108


<210> SEQ ID NO 16
<211> LENGTH: 64
<212> TYPE: PRT
<213> ORGANISM: Porcine reproductive and respiratory syndrome virus

<400> SEQUENCE: 16

Met Glu Gln Lys Leu Ile Ser Glu Glu Asp Leu Asn Arg Ser Met Asn
  1               5                  10                  15

Ser Ser Gly Ser Met Asn Ala Asn Ser Thr Ser Ser Ser His Phe Gln
             20                  25                  30

Leu Ile Tyr Asn Leu Thr Leu Cys Glu Leu Asn Gly Thr Asp Trp Leu
         35                  40                  45

Ala Gly Lys Phe Asp Trp Ala Val Leu Glu His His His His His His
     50                  55                  60


<210> SEQ ID NO 17
<211> LENGTH: 545
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 17

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc atg aac gcc agc aac gac agc agc tcc cat cta cag ctg      273
Ser Gly Ser Met Asn Ala Ser Asn Asp Ser Ser Ser His Leu Gln Leu
         20                  25                  30

att tac aac ttg acg cta tgt gag ctg aat ggc aca gat tgg cta gct      321
Ile Tyr Asn Leu Thr Leu Cys Glu Leu Asn Gly Thr Asp Trp Leu Ala
     35                  40                  45

aac aaa ttt gat tgg gca gtg ctc gag cac cac cac cac cac cac          366
```

-continued

```
Asn Lys Phe Asp Trp Ala Val Leu Glu His His His His His His
 50                  55                  60

tgagatccgg ctgctaacaa agcccgaaag gaagctgagt tggctgctgc caccgctgag    426

caataactag cataacccct tggggcctct aaacgggtct tgaggggttt tttgctgaaa    486

ggaggaacta tatccggatt ggcgaatggg acgcgccctg tagcggcgca ttaagcgcg     545


<210> SEQ ID NO 18
<211> LENGTH: 108
<212> TYPE: DNA
<213> ORGANISM: Porcine reproductive and respiratory syndrome virus

<400> SEQUENCE: 18

atgaacgcca gcaacgacag cagctcccat ctacagctga tttacaactt gacgctatgt     60

gagctgaatg gcacagattg gctagctaac aaatttgatt gggcagtg                 108


<210> SEQ ID NO 19
<211> LENGTH: 64
<212> TYPE: PRT
<213> ORGANISM: Porcine reproductive and respiratory syndrome virus

<400> SEQUENCE: 19

Met Glu Gln Lys Leu Ile Ser Glu Glu Asp Leu Asn Arg Ser Met Asn
  1               5                  10                  15

Ser Ser Gly Ser Met Asn Ala Ser Asn Asp Ser Ser Ser His Leu Gln
             20                  25                  30

Leu Ile Tyr Asn Leu Thr Leu Cys Glu Leu Asn Gly Thr Asp Trp Leu
         35                  40                  45

Ala Asn Lys Phe Asp Trp Ala Val Leu Glu His His His His His His
     50                  55                  60


<210> SEQ ID NO 20
<211> LENGTH: 596
<212> TYPE: DNA
<213> ORGANISM: Porcine reproductive and respiratory syndrome virus
<220> FEATURE:
<221> NAME/KEY: CDS
<222> LOCATION: (175)..(417)

<400> SEQUENCE: 20

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
            5                  10                  15

agt gga tcc atg aac gcc agc aac gac agc agc tcc cat cta cag ctg      273
Ser Gly Ser Met Asn Ala Ser Asn Asp Ser Ser Ser His Leu Gln Leu
        20                  25                  30

att tac aac ttg acg cta tgt gag ctg aat ggc aca gat tgg cta gct      321
Ile Tyr Asn Leu Thr Leu Cys Glu Leu Asn Gly Thr Asp Trp Leu Ala
    35                  40                  45

aac aaa ttt gat tgg gca gtg ctc gag gga gga ggc ggc agc ggg ttt      369
Asn Lys Phe Asp Trp Ala Val Leu Glu Gly Gly Gly Gly Ser Gly Phe
 50                  55                  60                  65

gtt cac ggg cgg tat gtc cta agt ctc gag cac cac cac cac cac cac      417
Val His Gly Arg Tyr Val Leu Ser Leu Glu His His His His His His
                70                  75                  80
```

-continued

```
tgagatccgg ctgctaacaa agcccgaaag gaagctgagt tggctgctgc caccgctgag    477

caataactag cataacccct tggggcctct aaacgggtct tgaggggttt tttgctgaaa    537

ggaggaacta tatccggatt ggcgaatggg acgcgccctg tagcggcgca ttaagcgcg     596


<210> SEQ ID NO 21
<211> LENGTH: 159
<212> TYPE: DNA
<213> ORGANISM: Porcine reproductive and respiratory syndrome virus

<400> SEQUENCE: 21

atgaacgcca gcaacgacag cagctcccat ctacagctga tttacaactt gacgctatgt     60

gagctgaatg gcacagattg gctagctaac aaatttgatt gggcagtgct cgagggagga    120

ggcggcagcg ggtttgttca cgggcggtat gtcctaagt                           159


<210> SEQ ID NO 22
<211> LENGTH: 81
<212> TYPE: PRT
<213> ORGANISM: Porcine reproductive and respiratory syndrome virus

<400> SEQUENCE: 22

Met Glu Gln Lys Leu Ile Ser Glu Glu Asp Leu Asn Arg Ser Met Asn
  1               5                  10                  15

Ser Ser Gly Ser Met Asn Ala Ser Asn Asp Ser Ser Ser His Leu Gln
             20                  25                  30

Leu Ile Tyr Asn Leu Thr Leu Cys Glu Leu Asn Gly Thr Asp Trp Leu
         35                  40                  45

Ala Asn Lys Phe Asp Trp Ala Val Leu Glu Gly Gly Gly Gly Ser Gly
     50                  55                  60

Phe Val His Gly Arg Tyr Val Leu Ser Leu Glu His His His His His
 65                  70                  75                  80

His


<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      Gly-Ser linker

<400> SEQUENCE: 23

Gly Gly Gly Gly Ser
  1               5


<210> SEQ ID NO 24
<211> LENGTH: 656
<212> TYPE: DNA
<213> ORGANISM: Porcine reproductive and respiratory syndrome virus
<220> FEATURE:
<221> NAME/KEY: CDS
<222> LOCATION: (175)..(477)

<400> SEQUENCE: 24

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1
```

-continued gaa caa aaa ctc atc tca gaa gag gat ctg aat cga tcc atg aat tct 225
Glu Gln Lys Leu Ile Ser Glu Glu Asp Leu Asn Arg Ser Met Asn Ser
5 10 15 agt gga tcc atg aag aat tgc atg tcc tgg cgc tac gcg tgt acc aga 273
Ser Gly Ser Met Lys Asn Cys Met Ser Trp Arg Tyr Ala Cys Thr Arg
20 25 30 tat acc aac ttt ctt ctg gac act aag ggc aga ctc tat cgt tgg cgg 321
Tyr Thr Asn Phe Leu Leu Asp Thr Lys Gly Arg Leu Tyr Arg Trp Arg
35 40 45 tcg cct gtc atc ata gag aaa agg ggc aaa gtt gag gtc gaa ggt cat 369
Ser Pro Val Ile Ile Glu Lys Arg Gly Lys Val Glu Val Glu Gly His
50 55 60 65 ctg atc gac ctc aaa aga gtt gtg ctt gat ggt tcc gtg gca acc cct 417
Leu Ile Asp Leu Lys Arg Val Val Leu Asp Gly Ser Val Ala Thr Pro
70 75 80 ata acc aga gtt tca gcg gaa caa tgg ggt cgt cct ctc gag cac cac 465
Ile Thr Arg Val Ser Ala Glu Gln Trp Gly Arg Pro Leu Glu His His
85 90 95 cac cac cac cac tgagatccgg ctgctaacaa agcccgaaag gaagctgagt 517
His His His His
100 tggctgctgc caccgctgag caataactag cataacccct tggggcctct aaacgggtct 577 tgaggggttt tttgctgaaa ggaggaacta tatccggatt ggcgaatggg acgcgccctg 637 tagcggcgca ttaagcgcg 656

<210> SEQ ID NO 25
<211> LENGTH: 219
<212> TYPE: DNA
<213> ORGANISM: Porcine reproductive and respiratory syndrome virus

<400> SEQUENCE: 25
atgaagaatt gcatgtcctg gcgctacgcg tgtaccagat ataccaactt tcttctggac 60
actaagggca gactctatcg ttggcggtcg cctgtcatca tagagaaaag gggcaaagtt 120
gaggtcgaag gtcatctgat cgacctcaaa agagttgtgc ttgatggttc cgtggcaacc 180
cctataacca gagtttcagc ggaacaatgg ggtcgtcct 219

<210> SEQ ID NO 26
<211> LENGTH: 101
<212> TYPE: PRT
<213> ORGANISM: Porcine reproductive and respiratory syndrome virus

<400> SEQUENCE: 26

Met Glu Gln Lys Leu Ile Ser Glu Glu Asp Leu Asn Arg Ser Met Asn
1 5 10 15

Ser Ser Gly Ser Met Lys Asn Cys Met Ser Trp Arg Tyr Ala Cys Thr
20 25 30

Arg Tyr Thr Asn Phe Leu Leu Asp Thr Lys Gly Arg Leu Tyr Arg Trp
35 40 45

Arg Ser Pro Val Ile Ile Glu Lys Arg Gly Lys Val Glu Val Glu Gly
50 55 60

His Leu Ile Asp Leu Lys Arg Val Val Leu Asp Gly Ser Val Ala Thr
65 70 75 80

Pro Ile Thr Arg Val Ser Ala Glu Gln Trp Gly Arg Pro Leu Glu His
85 90 95

His His His His His
100

-continued

```
<210> SEQ ID NO 27
<211> LENGTH: 656
<212> TYPE: DNA
<213> ORGANISM: Porcine reproductive and respiratory syndrome virus
<220> FEATURE:
<221> NAME/KEY: CDS
<222> LOCATION: (175)..(477)

<400> SEQUENCE: 27

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                             1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15

agt gga tcc atg aag aac tgc atg tcc tgg cgc tat tca tgt acc aga       273
Ser Gly Ser Met Lys Asn Cys Met Ser Trp Arg Tyr Ser Cys Thr Arg
         20                  25                  30

tac acc aac ttc ctc cta gac act aag ggc aga ctc tat cgt tgg cgg       321
Tyr Thr Asn Phe Leu Leu Asp Thr Lys Gly Arg Leu Tyr Arg Trp Arg
     35                  40                  45

tcg cct gtc att ata gag aaa ggg ggt aag gtt gag gtc gaa ggc cac       369
Ser Pro Val Ile Ile Glu Lys Gly Gly Lys Val Glu Val Glu Gly His
 50                  55                  60                  65

ctg atc gac ctc aaa aga gtt gtg ctt gat ggt tcc gtg gca aca cct       417
Leu Ile Asp Leu Lys Arg Val Val Leu Asp Gly Ser Val Ala Thr Pro
                 70                  75                  80

tta acc aga gtt tca gcg gaa caa tgg ggt cgt cct ctc gag cac cac       465
Leu Thr Arg Val Ser Ala Glu Gln Trp Gly Arg Pro Leu Glu His His
             85                  90                  95

cac cac cac cac tgagatccgg ctgctaacaa agcccgaaag gaagctgagt          517
His His His His
        100

tggctgctgc caccgctgag caataactag cataacccct tggggcctct aaacgggtct     577

tgaggggttt tttgctgaaa ggaggaacta tatccggatt ggcgaatggg acgcgccctg     637

tagcggcgca ttaagcgcg                                                  656


<210> SEQ ID NO 28
<211> LENGTH: 219
<212> TYPE: DNA
<213> ORGANISM: Porcine reproductive and respiratory syndrome virus

<400> SEQUENCE: 28

atgaagaact gcatgtcctg gcgctattca tgtaccagat acaccaactt cctcctagac      60

actaagggca gactctatcg ttggcggtcg cctgtcatta tagagaaagg gggtaaggtt     120

gaggtcgaag gccacctgat cgacctcaaa agagttgtgc ttgatggttc cgtggcaaca     180

cctttaacca gagtttcagc ggaacaatgg ggtcgtcct                            219


<210> SEQ ID NO 29
<211> LENGTH: 101
<212> TYPE: PRT
<213> ORGANISM: Porcine reproductive and respiratory syndrome virus

<400> SEQUENCE: 29

Met Glu Gln Lys Leu Ile Ser Glu Glu Asp Leu Asn Arg Ser Met Asn
  1               5                  10                  15
```

-continued

```
Ser Ser Gly Ser Met Lys Asn Cys Met Ser Trp Arg Tyr Ser Cys Thr
            20                  25                  30

Arg Tyr Thr Asn Phe Leu Leu Asp Thr Lys Gly Arg Leu Tyr Arg Trp
        35                  40                  45

Arg Ser Pro Val Ile Ile Glu Lys Gly Gly Lys Val Glu Val Glu Gly
    50                  55                  60

His Leu Ile Asp Leu Lys Arg Val Val Leu Asp Gly Ser Val Ala Thr
65                  70                  75                  80

Pro Leu Thr Arg Val Ser Ala Glu Gln Trp Gly Arg Pro Leu Glu His
                85                  90                  95

His His His His His
            100


<210> SEQ ID NO 30
<211> LENGTH: 700
<212> TYPE: DNA
<213> ORGANISM: Porcine reproductive and respiratory syndrome virus
<220> FEATURE:
<221> NAME/KEY: CDS
<222> LOCATION: (175)..(528)

<400> SEQUENCE: 30

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                            1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
            5                   10                  15

agt gga tcc atg aac gcc agc aac gac agc agc tcc cat cta cag ctg       273
Ser Gly Ser Met Asn Ala Ser Asn Asp Ser Ser Ser His Leu Gln Leu
        20                  25                  30

att tac aac ttg acg cta tgt gag ctg aat ggc aca gat tgg cta gct       321
Ile Tyr Asn Leu Thr Leu Cys Glu Leu Asn Gly Thr Asp Trp Leu Ala
    35                  40                  45

aac aaa ttt gat tgg gca gtg ctc gag gga gga ggc ggc agc ggg ttt       369
Asn Lys Phe Asp Trp Ala Val Leu Glu Gly Gly Gly Gly Ser Gly Phe
50                  55                  60                  65

gtt cac ggg cgg tat gtc cta agt gga gga ggc ggc agc atg ggg tcg       417
Val His Gly Arg Tyr Val Leu Ser Gly Gly Gly Gly Ser Met Gly Ser
                70                  75                  80

tcc tta gat gac ttc tgt cat gat agc acg gct cca caa aag gtg ctt       465
Ser Leu Asp Asp Phe Cys His Asp Ser Thr Ala Pro Gln Lys Val Leu
            85                  90                  95

gga gga ggc ggc agc gcg cac ttt cag agt aca aat aag ctc gag cac       513
Gly Gly Gly Gly Ser Ala His Phe Gln Ser Thr Asn Lys Leu Glu His
        100                 105                 110

cac cac cac cac cac tgagatccgg ctgctaacaa agcccgaaag gaagctgagt       568
His His His His His
    115

tggctgctgc caccgctgag caataactag cataacccct tggggcctct aaacgggtct     628

tgaggggttt tttgctgaaa ggaggaacta tatccggatt ggcgaatggg acgcgccctg     688

tagcggcgca tt                                                         700


<210> SEQ ID NO 31
<211> LENGTH: 270
```

-continued

<212> TYPE: DNA
<213> ORGANISM: Porcine reproductive and respiratory syndrome virus

<400> SEQUENCE: 31
atgaacgcca gcaacgacag cagctcccat ctacagctga tttacaactt gacgctatgt 60
gagctgaatg gcacagattg gctagctaac aaatttgatt gggcagtgct cgagggagga 120
ggcggcagcg ggtttgttca cgggcggtat gtcctaagtg gaggaggcgg cagcatgggg 180
tcgtccttag atgacttctg tcatgatagc acggctccac aaaaggtgct tggaggaggc 240
ggcagcgcgc actttcagag tacaaataag 270

<210> SEQ ID NO 32
<211> LENGTH: 118
<212> TYPE: PRT
<213> ORGANISM: Porcine reproductive and respiratory syndrome virus

<400> SEQUENCE: 32

Met Glu Gln Lys Leu Ile Ser Glu Glu Asp Leu Asn Arg Ser Met Asn
1 5 10 15

Ser Ser Gly Ser Met Asn Ala Ser Asn Asp Ser Ser Ser His Leu Gln
20 25 30

Leu Ile Tyr Asn Leu Thr Leu Cys Glu Leu Asn Gly Thr Asp Trp Leu
35 40 45

Ala Asn Lys Phe Asp Trp Ala Val Leu Glu Gly Gly Gly Gly Ser Gly
50 55 60

Phe Val His Gly Arg Tyr Val Leu Ser Gly Gly Gly Gly Ser Met Gly
65 70 75 80

Ser Ser Leu Asp Asp Phe Cys His Asp Ser Thr Ala Pro Gln Lys Val
85 90 95

Leu Gly Gly Gly Gly Ser Ala His Phe Gln Ser Thr Asn Lys Leu Glu
100 105 110

His His His His His His
115

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 33

His His His His His His
1 5

<210> SEQ ID NO 34
<211> LENGTH: 806
<212> TYPE: DNA
<213> ORGANISM: Porcine reproductive and respiratory syndrome virus
<220> FEATURE:
<221> NAME/KEY: CDS
<222> LOCATION: (175)..(627)

<400> SEQUENCE: 34
aggcgccagc aaccgcacct gtggcgccgg tgatgccggc cacgatgcgt ccggcgtaga 60
ggatcgagat ctcgatcccg cgaaattaat acgactcact ataggggaat tgtgagcgga 120
taacaattcc cctctagaaa taattttgtt taactttaag aaggagatat acat atg 177
Met
1

-continued gaa caa aaa ctc atc tca gaa gag gat ctg aat cga tcc atg aat tct 225
Glu Gln Lys Leu Ile Ser Glu Glu Asp Leu Asn Arg Ser Met Asn Ser
5 10 15 agt gga tcc atg cca aat aac aac ggc aag cag cag aag aga aag aag 273
Ser Gly Ser Met Pro Asn Asn Asn Gly Lys Gln Gln Lys Arg Lys Lys
20 25 30 ggg gat ggc cag cca gtc aat cag ctg tgc cag atg ctg ggt aag atc 321
Gly Asp Gly Gln Pro Val Asn Gln Leu Cys Gln Met Leu Gly Lys Ile
35 40 45 atc gct cag caa aac cag tcc aga ggc aag gga ccg gga aag aaa aat 369
Ile Ala Gln Gln Asn Gln Ser Arg Gly Lys Gly Pro Gly Lys Lys Asn
50 55 60 65 aag aag aaa aac ccg gag aag ccc cat ttt cct cta gcg act gaa gat 417
Lys Lys Lys Asn Pro Glu Lys Pro His Phe Pro Leu Ala Thr Glu Asp
70 75 80 gat gtc aga cat cac ttt acc cct agt gag cgg caa ttg tgt ctg tcg 465
Asp Val Arg His His Phe Thr Pro Ser Glu Arg Gln Leu Cys Leu Ser
85 90 95 tca atc cag acc gcc ttt aat caa ggc gct ggg act tgc acc ctg tca 513
Ser Ile Gln Thr Ala Phe Asn Gln Gly Ala Gly Thr Cys Thr Leu Ser
100 105 110 gat tca ggg agg ata agt tac act gtg gag ttt agt ttg cct acg cat 561
Asp Ser Gly Arg Ile Ser Tyr Thr Val Glu Phe Ser Leu Pro Thr His
115 120 125 cat act gtg cgc ctg atc cgc gtc aca gca tca ccc tca gca ctc gag 609
His Thr Val Arg Leu Ile Arg Val Thr Ala Ser Pro Ser Ala Leu Glu
130 135 140 145 cac cac cac cac cac cac tgagatccgg ctgctaacaa agcccgaaag 657
His His His His His His
150 gaagctgagt tggctgctgc caccgctgag caataactag cataacccct tggggcctct 717 aaacgggtct tgaggggttt tttgctgaaa ggaggaacta tatccggatt ggcgaatggg 777 acgcgccctg tagcggcgca ttaagcgcg 806

<210> SEQ ID NO 35
<211> LENGTH: 369
<212> TYPE: DNA
<213> ORGANISM: Porcine reproductive and respiratory syndrome virus

<400> SEQUENCE: 35
atgccaaata acaacggcaa gcagcagaag agaaagaagg gggatggcca gccagtcaat 60
cagctgtgcc agatgctggg taagatcatc gctcagcaaa accagtccag aggcaaggga 120
ccgggaaaga aaaataagaa gaaaaacccg gagaagcccc attttcctct agcgactgaa 180
gatgatgtca gacatcactt tacccctagt gagcggcaat tgtgtctgtc gtcaatccag 240
accgccttta atcaaggcgc tgggacttgc accctgtcag attcagggag gataagttac 300
actgtggagt ttagtttgcc tacgcatcat actgtgcgcc tgatccgcgt cacagcatca 360
ccctcagca 369

<210> SEQ ID NO 36
<211> LENGTH: 151
<212> TYPE: PRT
<213> ORGANISM: Porcine reproductive and respiratory syndrome virus

<400> SEQUENCE: 36

Met Glu Gln Lys Leu Ile Ser Glu Glu Asp Leu Asn Arg Ser Met Asn
1 5 10 15

-continued

```
Ser Ser Gly Ser Met Pro Asn Asn Asn Gly Lys Gln Gln Lys Arg Lys
            20                  25                  30

Lys Gly Asp Gly Gln Pro Val Asn Gln Leu Cys Gln Met Leu Gly Lys
        35                  40                  45

Ile Ile Ala Gln Gln Asn Gln Ser Arg Gly Lys Gly Pro Gly Lys Lys
    50                  55                  60

Asn Lys Lys Lys Asn Pro Glu Lys Pro His Phe Pro Leu Ala Thr Glu
65                  70                  75                  80

Asp Asp Val Arg His His Phe Thr Pro Ser Glu Arg Gln Leu Cys Leu
                85                  90                  95

Ser Ser Ile Gln Thr Ala Phe Asn Gln Gly Ala Gly Thr Cys Thr Leu
            100                 105                 110

Ser Asp Ser Gly Arg Ile Ser Tyr Thr Val Glu Phe Ser Leu Pro Thr
        115                 120                 125

His His Thr Val Arg Leu Ile Arg Val Thr Ala Ser Pro Ser Ala Leu
    130                 135                 140

Glu His His His His His His
145                 150


<210> SEQ ID NO 37
<211> LENGTH: 907
<212> TYPE: DNA
<213> ORGANISM: Porcine reproductive and respiratory syndrome virus
<220> FEATURE:
<221> NAME/KEY: CDS
<222> LOCATION: (175)..(735)

<400> SEQUENCE: 37

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                             1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
            5                   10                  15

agt gga tcc ggc agc ccg gtt tca tta ggc ggc gat gtc cct aac agt       273
Ser Gly Ser Gly Ser Pro Val Ser Leu Gly Gly Asp Val Pro Asn Ser
        20                  25                  30

tgg gaa gat ttg gct gtt agt agc ccc ttt gat ctc ccg acc cca cct       321
Trp Glu Asp Leu Ala Val Ser Ser Pro Phe Asp Leu Pro Thr Pro Pro
    35                  40                  45

gag ccg gca aca cct tca agt gag ctg gtg att gtg tcc tca ccg caa       369
Glu Pro Ala Thr Pro Ser Ser Glu Leu Val Ile Val Ser Ser Pro Gln
50                  55                  60                  65

tgc atc ttc agg ccg gcg aca ccc ttg agt gag ccg gct cca att ccc       417
Cys Ile Phe Arg Pro Ala Thr Pro Leu Ser Glu Pro Ala Pro Ile Pro
                70                  75                  80

gca cct cgc gga act gtg tct cga ccg gtg aca ccc ttg agt gag ccg       465
Ala Pro Arg Gly Thr Val Ser Arg Pro Val Thr Pro Leu Ser Glu Pro
            85                  90                  95

atc cct gtg ccc gca ccg cgg cgt aag ttt cag cag gtg aaa aga ttg       513
Ile Pro Val Pro Ala Pro Arg Arg Lys Phe Gln Gln Val Lys Arg Leu
        100                 105                 110

agt tcg gcg gcg gca atc cca ccg tac cag gac gag ccc ctg gat ttg       561
Ser Ser Ala Ala Ala Ile Pro Pro Tyr Gln Asp Glu Pro Leu Asp Leu
    115                 120                 125
```

-continued

```
tct gct tcc tca cag gct gaa tat gag gcc tct ccc cca gca ccg ccg      609
Ser Ala Ser Ser Gln Ala Glu Tyr Glu Ala Ser Pro Pro Ala Pro Pro
130                 135                 140                 145

cag agc ggg ggc gtt ctg gga gta gag ggg cat gaa gct gag gaa acc      657
Gln Ser Gly Gly Val Leu Gly Val Glu Gly His Glu Ala Glu Glu Thr
                150                 155                 160

ctg agt gaa atc tcg gac atg tcg ggt aac att aaa cct gcg tcc gtg      705
Leu Ser Glu Ile Ser Asp Met Ser Gly Asn Ile Lys Pro Ala Ser Val
            165                 170                 175

tca tca ctc gag cac cac cac cac cac cac tgagatccgg ctgctaacaa        755
Ser Ser Leu Glu His His His His His His
        180                 185

agcccgaaag gaagctgagt tggctgctgc caccgctgag caataactag cataacccct    815

tggggcctct aaacgggtct tgaggggttt tttgctgaaa ggaggaacta tatccggatt    875

ggcgaatggg acgcgccctg tagcggcgca tt                                  907


<210> SEQ ID NO 38
<211> LENGTH: 477
<212> TYPE: DNA
<213> ORGANISM: Porcine reproductive and respiratory syndrome virus

<400> SEQUENCE: 38

ggcagcccgg tttcattagg cggcgatgtc cctaacagtt gggaagattt ggctgttagt     60

agccccttg atctcccgac cccacctgag ccggcaacac cttcaagtga gctggtgatt    120

gtgtcctcac cgcaatgcat cttcaggccg gcgacaccct tgagtgagcc ggctccaatt    180

cccgcacctc gcggaactgt gtctcgaccg gtgacaccct tgagtgagcc gatccctgtg    240

cccgcaccgc ggcgtaagtt tcagcaggtg aaaagattga gttcggcggc ggcaatccca    300

ccgtaccagg acgagcccct ggatttgtct gcttcctcac aggctgaata tgaggcctct    360

cccccagcac cgccgcagag cgggggcgtt ctgggagtag aggggcatga agctgaggaa    420

accctgagtg aaatctcgga catgtcgggt aacattaaac ctgcgtccgt gtcatca       477


<210> SEQ ID NO 39
<211> LENGTH: 187
<212> TYPE: PRT
<213> ORGANISM: Porcine reproductive and respiratory syndrome virus

<400> SEQUENCE: 39

Met Glu Gln Lys Leu Ile Ser Glu Glu Asp Leu Asn Arg Ser Met Asn
  1               5                  10                  15

Ser Ser Gly Ser Gly Ser Pro Val Ser Leu Gly Gly Asp Val Pro Asn
             20                  25                  30

Ser Trp Glu Asp Leu Ala Val Ser Ser Pro Phe Asp Leu Pro Thr Pro
         35                  40                  45

Pro Glu Pro Ala Thr Pro Ser Ser Glu Leu Val Ile Val Ser Ser Pro
     50                  55                  60

Gln Cys Ile Phe Arg Pro Ala Thr Pro Leu Ser Glu Pro Ala Pro Ile
 65                  70                  75                  80

Pro Ala Pro Arg Gly Thr Val Ser Arg Pro Val Thr Pro Leu Ser Glu
                 85                  90                  95

Pro Ile Pro Val Pro Ala Pro Arg Arg Lys Phe Gln Gln Val Lys Arg
            100                 105                 110

Leu Ser Ser Ala Ala Ala Ile Pro Pro Tyr Gln Asp Glu Pro Leu Asp
        115                 120                 125

Leu Ser Ala Ser Ser Gln Ala Glu Tyr Glu Ala Ser Pro Pro Ala Pro
```

-continued

```
    130                 135                 140

Pro Gln Ser Gly Gly Val Leu Gly Val Glu Gly His Glu Ala Glu Glu
145                 150                 155                 160

Thr Leu Ser Glu Ile Ser Asp Met Ser Gly Asn Ile Lys Pro Ala Ser
                165                 170                 175

Val Ser Ser Leu Glu His His His His His His
            180                 185


<210> SEQ ID NO 40
<211> LENGTH: 532
<212> TYPE: DNA
<213> ORGANISM: Porcine reproductive and respiratory syndrome virus
<220> FEATURE:
<221> NAME/KEY: CDS
<222> LOCATION: (175)..(360)

<400> SEQUENCE: 40

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15

agt gga tcc gcg act gct aca gtc gct ggc cgc gct ttg tcc gtt cgt       273
Ser Gly Ser Ala Thr Ala Thr Val Ala Gly Arg Ala Leu Ser Val Arg
         20                  25                  30

gaa acc cgg cag gcc aag gag cac gag gtt gcc ggc gcc aac aag gct       321
Glu Thr Arg Gln Ala Lys Glu His Glu Val Ala Gly Ala Asn Lys Ala
     35                  40                  45

gag cac ctc aaa cac ctc gag cac cac cac cac cac cac tgagatccgg        370
Glu His Leu Lys His Leu Glu His His His His His His
 50                  55                  60

ctgctaacaa agcccgaaag gaagctgagt tggctgctgc caccgctgag caataactag     430

cataacccct tggggcctct aaacgggtct tgaggggttt tttgctgaaa ggaggaacta     490

tatccggatt ggcgaatggg acgcgccctg tagcggcgca tt                        532


<210> SEQ ID NO 41
<211> LENGTH: 102
<212> TYPE: DNA
<213> ORGANISM: Porcine reproductive and respiratory syndrome virus

<400> SEQUENCE: 41

gcgactgcta cagtcgctgg ccgcgctttg tccgttcgtg aaacccggca ggccaaggag      60

cacgaggttg ccggcgccaa caaggctgag cacctcaaac ac                        102


<210> SEQ ID NO 42
<211> LENGTH: 62
<212> TYPE: PRT
<213> ORGANISM: Porcine reproductive and respiratory syndrome virus

<400> SEQUENCE: 42

Met Glu Gln Lys Leu Ile Ser Glu Glu Asp Leu Asn Arg Ser Met Asn
  1               5                  10                  15

Ser Ser Gly Ser Ala Thr Ala Thr Val Ala Gly Arg Ala Leu Ser Val
            20                  25                  30

Arg Glu Thr Arg Gln Ala Lys Glu His Glu Val Ala Gly Ala Asn Lys
```

-continued

```
        35                  40                  45

Ala Glu His Leu Lys His Leu Glu His His His His His His
     50                  55                  60


<210> SEQ ID NO 43
<211> LENGTH: 538
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 43

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15

agt gga tcc gca aag att gac ctg tac ctc cgt ggt gca aca aat ctt       273
Ser Gly Ser Ala Lys Ile Asp Leu Tyr Leu Arg Gly Ala Thr Asn Leu
         20                  25                  30

gaa gaa tgc ttg gcc agg ctt gag aaa gcg cgc ccg cca cgc gta atc       321
Glu Glu Cys Leu Ala Arg Leu Glu Lys Ala Arg Pro Pro Arg Val Ile
     35                  40                  45

gac acc tcc ttt gat tgg gat ctc gag cac cac cac cac cac cac           366
Asp Thr Ser Phe Asp Trp Asp Leu Glu His His His His His His
 50                  55                  60

tgagatccgg ctgctaacaa agcccgaaag gaagctgagt tggctgctgc caccgctgag     426

caataactag cataacccct tggggcctct aaacgggtct tgaggggttt tttgctgaaa     486

ggaggaacta tatccggatt ggcgaatggg acgcgccctg tagcggcgca tt             538


<210> SEQ ID NO 44
<211> LENGTH: 108
<212> TYPE: DNA
<213> ORGANISM: Porcine reproductive and respiratory syndrome virus

<400> SEQUENCE: 44

gcaaagattg acctgtacct ccgtggtgca acaaatcttg aagaatgctt ggccaggctt      60

gagaaagcgc gcccgccacg cgtaatcgac acctcctttg attgggat                  108


<210> SEQ ID NO 45
<211> LENGTH: 64
<212> TYPE: PRT
<213> ORGANISM: Porcine reproductive and respiratory syndrome virus

<400> SEQUENCE: 45

Met Glu Gln Lys Leu Ile Ser Glu Glu Asp Leu Asn Arg Ser Met Asn
  1               5                  10                  15

Ser Ser Gly Ser Ala Lys Ile Asp Leu Tyr Leu Arg Gly Ala Thr Asn
             20                  25                  30

Leu Glu Glu Cys Leu Ala Arg Leu Glu Lys Ala Arg Pro Pro Arg Val
        35                  40                  45

Ile Asp Thr Ser Phe Asp Trp Asp Leu Glu His His His His His His
     50                  55                  60
```

-continued

```
<210> SEQ ID NO 46
<211> LENGTH: 526
<212> TYPE: DNA
<213> ORGANISM: Porcine reproductive and respiratory syndrome virus
<220> FEATURE:
<221> NAME/KEY: CDS
<222> LOCATION: (175)..(354)

<400> SEQUENCE: 46

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc atg ggg tcg tcc tta gat gac ttc tgt cat gat agc acg      273
Ser Gly Ser Met Gly Ser Ser Leu Asp Asp Phe Cys His Asp Ser Thr
         20                  25                  30

gct cca caa aag gtg ctt gga gga ggc ggc agc gcg cac ttt cag agt      321
Ala Pro Gln Lys Val Leu Gly Gly Gly Gly Ser Ala His Phe Gln Ser
     35                  40                  45

aca aat aag ctc gag cac cac cac cac cac cac tgagatccgg ctgctaacaa    374
Thr Asn Lys Leu Glu His His His His His His
 50                  55                  60

agcccgaaag gaagctgagt tggctgctgc caccgctgag caataactag cataacccct    434

tggggcctct aaacgggtct tgaggggttt tttgctgaaa ggaggaacta tatccggatt    494

ggcgaatggg acgcgccctg tagcggcgca tt                                  526


<210> SEQ ID NO 47
<211> LENGTH: 96
<212> TYPE: DNA
<213> ORGANISM: Porcine reproductive and respiratory syndrome virus

<400> SEQUENCE: 47

atggggtcgt ccttagatga cttctgtcat gatagcacgg ctccacaaaa ggtgcttgga     60

ggaggcggca gcgcgcactt tcagagtaca aataag                               96


<210> SEQ ID NO 48
<211> LENGTH: 60
<212> TYPE: PRT
<213> ORGANISM: Porcine reproductive and respiratory syndrome virus

<400> SEQUENCE: 48

Met Glu Gln Lys Leu Ile Ser Glu Glu Asp Leu Asn Arg Ser Met Asn
  1               5                  10                  15

Ser Ser Gly Ser Met Gly Ser Ser Leu Asp Asp Phe Cys His Asp Ser
             20                  25                  30

Thr Ala Pro Gln Lys Val Leu Gly Gly Gly Gly Ser Ala His Phe Gln
         35                  40                  45

Ser Thr Asn Lys Leu Glu His His His His His His
     50                  55                  60


<210> SEQ ID NO 49
<211> LENGTH: 694
<212> TYPE: DNA
<213> ORGANISM: Porcine reproductive and respiratory syndrome virus
<220> FEATURE:
<221> NAME/KEY: CDS
```

-continued

```
<222> LOCATION: (175)..(522)

<400> SEQUENCE: 49

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15

agt gga tcc tca gcc ata gaa acc tgg aaa ttc atc acc tcc aga tgc       273
Ser Gly Ser Ser Ala Ile Glu Thr Trp Lys Phe Ile Thr Ser Arg Cys
         20                  25                  30

cgt ttg tgc ttg cta ggc cgc aag tac att ctg gcc cct gcc cac cac       321
Arg Leu Cys Leu Leu Gly Arg Lys Tyr Ile Leu Ala Pro Ala His His
     35                  40                  45

gtt gaa agt gcc gca cgg ttt cat ccg att gcg gca aat gat aac cac       369
Val Glu Ser Ala Ala Arg Phe His Pro Ile Ala Ala Asn Asp Asn His
 50                  55                  60                  65

gca ttt gtc gtc cgg cgt ccc ggc tcc act acg gtc aac ggc aca ttg       417
Ala Phe Val Val Arg Arg Pro Gly Ser Thr Thr Val Asn Gly Thr Leu
                 70                  75                  80

gtg ccc ggg tta aaa agc ctc gtg ttg ggt ggc aga aaa gct gtt aaa       465
Val Pro Gly Leu Lys Ser Leu Val Leu Gly Gly Arg Lys Ala Val Lys
             85                  90                  95

cag gga gtg gta aac ctt gtc aaa tat gcc aaa ctc gag cac cac cac       513
Gln Gly Val Val Asn Leu Val Lys Tyr Ala Lys Leu Glu His His His
        100                 105                 110

cac cac cac tgagatccgg ctgctaacaa agcccgaaag gaagctgagt               562
His His His
    115

tggctgctgc caccgctgag caataactag cataacccct tggggcctct aaacgggtct     622

tgaggggttt tttgctgaaa ggaggaacta tatccggatt ggcgaatggg acgcgccctg     682

tagcggcgca tt                                                         694


<210> SEQ ID NO 50
<211> LENGTH: 264
<212> TYPE: DNA
<213> ORGANISM: Porcine reproductive and respiratory syndrome virus

<400> SEQUENCE: 50

tcagccatag aaacctggaa attcatcacc tccagatgcc gtttgtgctt gctaggccgc      60

aagtacattc tggcccctgc ccaccacgtt gaaagtgccg cacggtttca tccgattgcg     120

gcaaatgata accacgcatt tgtcgtccgg cgtcccggct ccactacggt caacggcaca     180

ttggtgcccg ggttaaaaag cctcgtgttg ggtggcagaa aagctgttaa acagggagtg     240

gtaaaccttg tcaaatatgc caaa                                            264


<210> SEQ ID NO 51
<211> LENGTH: 116
<212> TYPE: PRT
<213> ORGANISM: Porcine reproductive and respiratory syndrome virus

<400> SEQUENCE: 51

Met Glu Gln Lys Leu Ile Ser Glu Glu Asp Leu Asn Arg Ser Met Asn
  1               5                  10                  15
```

-continued

```
Ser Ser Gly Ser Ser Ala Ile Glu Thr Trp Lys Phe Ile Thr Ser Arg
            20                  25                  30

Cys Arg Leu Cys Leu Leu Gly Arg Lys Tyr Ile Leu Ala Pro Ala His
        35                  40                  45

His Val Glu Ser Ala Ala Arg Phe His Pro Ile Ala Ala Asn Asp Asn
    50                  55                  60

His Ala Phe Val Val Arg Arg Pro Gly Ser Thr Thr Val Asn Gly Thr
65                  70                  75                  80

Leu Val Pro Gly Leu Lys Ser Leu Val Leu Gly Gly Arg Lys Ala Val
                85                  90                  95

Lys Gln Gly Val Val Asn Leu Val Lys Tyr Ala Lys Leu Glu His His
            100                 105                 110

His His His His
        115


<210> SEQ ID NO 52
<211> LENGTH: 821
<212> TYPE: DNA
<213> ORGANISM: Porcine reproductive and respiratory syndrome virus
<220> FEATURE:
<221> NAME/KEY: CDS
<222> LOCATION: (175)..(642)

<400> SEQUENCE: 52

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
            5                   10                  15

agt gga tcc atg gcc ggt aaa aac cag agc cag aag aaa aag aaa agt       273
Ser Gly Ser Met Ala Gly Lys Asn Gln Ser Gln Lys Lys Lys Lys Ser
        20                  25                  30

aca gct ccg atg ggg aat ggc cag cca gtc aat caa ctg tgc cag ttg       321
Thr Ala Pro Met Gly Asn Gly Gln Pro Val Asn Gln Leu Cys Gln Leu
    35                  40                  45

ctg ggt gca atg ata aag tcc cag cgc cag caa cct agg gga gga cag       369
Leu Gly Ala Met Ile Lys Ser Gln Arg Gln Gln Pro Arg Gly Gly Gln
50                  55                  60                  65

gcc aaa aag aaa aag cct gag aag cca cat ttt ccc ctg gct gct gaa       417
Ala Lys Lys Lys Lys Pro Glu Lys Pro His Phe Pro Leu Ala Ala Glu
                70                  75                  80

gat gac atc cgg cac cac ctc acc cag act gaa cgc tcc ctc tgc ttg       465
Asp Asp Ile Arg His His Leu Thr Gln Thr Glu Arg Ser Leu Cys Leu
            85                  90                  95

caa tcg atc cag acg gct ttc aat caa ggc gca gga act gcg tcg ctt       513
Gln Ser Ile Gln Thr Ala Phe Asn Gln Gly Ala Gly Thr Ala Ser Leu
        100                 105                 110

tca tcc agc ggg aag gtc agt ttt cag gtt gag ttt atg ctg ccg gtt       561
Ser Ser Ser Gly Lys Val Ser Phe Gln Val Glu Phe Met Leu Pro Val
    115                 120                 125

gct cat aca gtg cgc ctg att cgc gtg act tct aca tcc gcc agt cag       609
Ala His Thr Val Arg Leu Ile Arg Val Thr Ser Thr Ser Ala Ser Gln
130                 135                 140                 145

ggt gca agt ctc gag cac cac cac cac cac cac tgagatccgg ctgctaacaa     662
Gly Ala Ser Leu Glu His His His His His His
                150                 155
```

-continued

```
agcccgaaag gaagctgagt tggctgctgc caccgctgag caataactag cataacccct    722

tggggcctct aaacgggtct tgaggggttt tttgctgaaa ggaggaacta tatccggatt    782

ggcgaatggg acgcgccctg tagcggcgca ttaagcgcg                           821


<210> SEQ ID NO 53
<211> LENGTH: 384
<212> TYPE: DNA
<213> ORGANISM: Porcine reproductive and respiratory syndrome virus

<400> SEQUENCE: 53

atggccggta aaaaccagag ccagaagaaa aagaaaagta cagctccgat ggggaatggc     60

cagccagtca atcaactgtg ccagttgctg ggtgcaatga taaagtccca gcgccagcaa    120

cctaggggag gacaggccaa aaagaaaaag cctgagaagc cacattttcc cctggctgct    180

gaagatgaca tccggcacca cctcacccag actgaacgct ccctctgctt gcaatcgatc    240

cagacggctt tcaatcaagg cgcaggaact gcgtcgcttt catccagcgg gaaggtcagt    300

tttcaggttg agtttatgct gccggttgct catacagtgc gcctgattcg cgtgacttct    360

acatccgcca gtcagggtgc aagt                                           384


<210> SEQ ID NO 54
<211> LENGTH: 156
<212> TYPE: PRT
<213> ORGANISM: Porcine reproductive and respiratory syndrome virus

<400> SEQUENCE: 54

Met Glu Gln Lys Leu Ile Ser Glu Glu Asp Leu Asn Arg Ser Met Asn
  1               5                  10                  15

Ser Ser Gly Ser Met Ala Gly Lys Asn Gln Ser Gln Lys Lys Lys Lys
             20                  25                  30

Ser Thr Ala Pro Met Gly Asn Gly Gln Pro Val Asn Gln Leu Cys Gln
         35                  40                  45

Leu Leu Gly Ala Met Ile Lys Ser Gln Arg Gln Gln Pro Arg Gly Gly
     50                  55                  60

Gln Ala Lys Lys Lys Lys Pro Glu Lys Pro His Phe Pro Leu Ala Ala
 65                  70                  75                  80

Glu Asp Asp Ile Arg His His Leu Thr Gln Thr Glu Arg Ser Leu Cys
                 85                  90                  95

Leu Gln Ser Ile Gln Thr Ala Phe Asn Gln Gly Ala Gly Thr Ala Ser
            100                 105                 110

Leu Ser Ser Ser Gly Lys Val Ser Phe Gln Val Glu Phe Met Leu Pro
        115                 120                 125

Val Ala His Thr Val Arg Leu Ile Arg Val Thr Ser Thr Ser Ala Ser
    130                 135                 140

Gln Gly Ala Ser Leu Glu His His His His His His
145                 150                 155


<210> SEQ ID NO 55
<211> LENGTH: 2336
<212> TYPE: DNA
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2134)..(2157)
```

-continued

```
<400> SEQUENCE: 55

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc gctgccggca aacgggctcg tgctaagcgt gccgctaaaa              274
Ser Gly Ser
         20

gtgagaagga ttcggctccc acccccaagg ttgccctgcc ggtccccacc tgtggaatta    334

ccacctactc tccaccgaca gacgggtctt gtggttggca tgtccttgcc gccataatga    394

accggatgat aaatggtgac ttcacgtccc ctctgactca gtacaacaga ccagaggatg    454

attgggcttc tgattatgat cttgttcagg cgattcaatg tctacgactg cctgctaccg    514

tggttcggaa tcgcgcctgt cctaacgcca agtaccttat aaaacttaac ggagttcact    574

gggaggtaga ggtgaggtct ggaatggctc ctcgctccct ttctcgtgaa tgtgtggttg    634

gcgtttgctc tgaaggctgt gtcgcaccgc cttatccagc agacgggcta cctaaacgtg    694

cactcgaggc cttggcgtct gcttacagac taccctccga ttgtgttagc tctggtattg    754

ctgactttct tgctaatcca cctcctcagg aattctggac cctcgacaaa atgttgacct    814

ccccgtcacc agagcggtcc ggcttctcta gtttgtataa attactatta gaggttgttc    874

cgcaaaaatg cggtgccacg gaaggggctt tcatctatgc tgttgagagg atgttgaagg    934

attgtccgag ctccaaacag gccatggccc ttctggcaaa aattaaagtt ccatcctcaa    994

aggccccgtc tgtgtccctg gacgagtgtt tccctacgga tgttttagcc gacttcgagc   1054

cagcatctca ggaaaggccc caaagttccg gcgctgctgt tgtcctgtgt tcaccggatg   1114

caaaagagtt cgaggaagca gccccggaag aagttcaaga gagtggccac aaggccgtcc   1174

actctgcact ccttgccgag ggtcctaaca atgagcaggt acaggtggtt gccggtgagc   1234

aactgaagct cggcggttgt ggtttggcag tcgggaatgc tcatgaaggt gctctggtct   1294

cagctggtct aattaacctg gtaggcggga atttgtcccc ctcagacccc atgaaagaaa   1354

acatgctcaa tagccgggaa gacgaaccac tggatttgtc ccaaccagca ccagcttcca   1414

caacgaccct tgtgagagag caaacacccg acaacccagg ttctgatgcc ggtgccctcc   1474

ccgtcaccgt tcgagaattt gtcccgacgg ggcctatact ctgtcatgtt gagcactgcg   1534

gcacggagtc gggcgacagc agttcgcctt tggatctatc tgatgcgcaa accctggacc   1594

agcctttaaa tctatccctg gccgcttggc cagtgagggc caccgcgtct gaccctggct   1654

gggtccacgg taggcgcgag cctgtctttg taaagcctcg aaatgctttc tctgatggcg   1714

attcagccct tcagttcggg gagctttctg aatccagctc tgtcatcgag tttgaccgga   1774

caaaagatgc tccggtggtt gacgccccctg tcgacttgac gacttcgaac gaggccctct   1834

ctgtagtcga tcctttcgaa tttgccgaac tcaagcgccc gcgtttctcc gcacaagcct   1894

taattgaccg aggcggtcca cttgccgatg tccatgcaaa aataaagaac cgggtatatg   1954

aacagtgcct ccaagcttgt gagcccggta gtcgtgcaac cccagccacc agggagtggc   2014

tcgacaaaat gtgggatagg gtggacatga aaacttggcg ctgcacctcg cagttccaag   2074

ctggtcgcat tcttgcgtcc ctcaaattcc tccctgacat gattcaagac acaccgcct    2133
```

-continued

```
ctc gag cac cac cac cac cac cac tgagatccgg ctgctaacaa agcccgaaag    2187
Leu Glu His His His His His His
                25

gaagctgagt tggctgctgc caccgctgag caataactag cataacccct tggggcctct   2247

aaacgggtct tgaggggttt tttgctgaaa ggaggaacta tatccggatt ggcgaatggg   2307

acgcgccctg tagcggcgca ttaagcgcg                                      2336
```

<210> SEQ ID NO 56
<211> LENGTH: 1899
<212> TYPE: DNA
<213> ORGANISM: Porcine reproductive and respiratory syndrome virus

<400> SEQUENCE: 56

```
gctgccggca aacgggctcg tgctaagcgt gccgctaaaa gtgagaagga ttcggctccc     60

acccccaagg ttgccctgcc ggtccccacc tgtggaatta ccacctactc tccaccgaca    120

gacgggtctt gtggttggca tgtccttgcc gccataatga accggatgat aaatggtgac    180

ttcacgtccc ctctgactca gtacaacaga ccagaggatg attgggcttc tgattatgat    240

cttgttcagg cgattcaatg tctacgactg cctgctaccg tggttcggaa tcgcgcctgt    300

cctaacgcca agtaccttat aaaacttaac ggagttcact gggaggtaga ggtgaggtct    360

ggaatggctc ctcgctccct ttctcgtgaa tgtgtggttg gcgtttgctc tgaaggctgt    420

gtcgcaccgc cttatccagc agacgggcta cctaaacgtg cactcgaggc cttggcgtct    480

gcttacagac taccctccga ttgtgttagc tctggtattg ctgactttct tgctaatcca    540

cctcctcagg aattctggac cctcgacaaa atgttgacct ccccgtcacc agagcggtcc    600

ggcttctcta gtttgtataa attactatta gaggttgttc cgcaaaaatg cggtgccacg    660

gaaggggctt tcatctatgc tgttgagagg atgttgaagg attgtccgag ctccaaacag    720

gccatggccc ttctggcaaa aattaaagtt ccatcctcaa aggccccgtc tgtgtccctg    780

gacgagtgtt tccctacgga tgttttagcc gacttcgagc cagcatctca ggaaaggccc    840

caaagttccg gcgctgctgt tgtcctgtgt tcaccggatg caaaagagtt cgaggaagca    900

gccccggaag aagttcaaga gagtggccac aaggccgtcc actctgcact ccttgccgag    960

ggtcctaaca atgagcaggt acaggtggtt gccggtgagc aactgaagct cggcggttgt   1020

ggtttggcag tcgggaatgc tcatgaaggt gctctggtct cagctggtct aattaacctg   1080

gtaggcggga atttgtcccc ctcagacccc atgaaagaaa acatgctcaa tagccgggaa   1140

gacgaaccac tggatttgtc ccaaccagca ccagcttcca caacgaccct tgtgagagag   1200

caaacacccg acaacccagg ttctgatgcc ggtgccctcc ccgtcaccgt tcgagaattt   1260

gtcccgacgg ggcctatact ctgtcatgtt gagcactgcg gcacggagtc gggcgacagc   1320

agttcgcctt tggatctatc tgatgcgcaa accctggacc agcctttaaa tctatccctg   1380

gccgcttggc cagtgagggc caccgcgtct gaccctggct gggtccacgg taggcgcgag   1440

cctgtctttg taaagcctcg aaatgctttc tctgatggcg attcagccct tcagttcggg   1500

gagctttctg aatccagctc tgtcatcgag tttgaccgga caaaagatgc tccggtggtt   1560

gacgcccctg tcgacttgac gacttcgaac gaggccctct ctgtagtcga tcctttcgaa   1620

tttgccgaac tcaagcgccc gcgtttctcc gcacaagcct taattgaccg aggcggtcca   1680

cttgccgatg tccatgcaaa aataaagaac cgggtatatg aacagtgcct ccaagcttgt   1740

gagcccggta gtcgtgcaac cccagccacc agggagtggc tcgacaaaat gtgggatagg   1800
```

-continued

```
gtggacatga aaacttggcg ctgcacctcg cagttccaag ctggtcgcat tcttgcgtcc   1860

ctcaaattcc tccctgacat gattcaagac acaccgcct                          1899


<210> SEQ ID NO 57
<211> LENGTH: 2588
<212> TYPE: DNA
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2386)..(2409)

<400> SEQUENCE: 57

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc gctggaaaga gagcaaggaa agcacgctct ggtatgacca              274
Ser Gly Ser
         20

ccacagtcgc tcaccgcgcc ttgcccgctc gtgaaatcca gcaagccaaa aagcacgagg    334

atgccggcgc tgataaggct gtgcatctca ggcactattc tccgcctgcc gacgggaact    394

gtggttggca ctgcatttcc gccatcgcca accgaatggt gaattccaaa tttgaaacta    454

ctcttcccga gagggtgaga ccttcagatg actgggctac tgacgaggac cttgtgaaca    514

ccatccaaat tctcaagctc cctgcggcct tggacaggaa cggtgcttgt gttggcgcca    574

aatacgtgct taagctggaa ggcgagcatt ggactgtctc tgtgaccctt gggatgtccc    634

cttctttgct ccccccttgaa tgtgttcagg gctgttgtga gcataagagc ggacttggtc   694

ccccagatgc ggtcgaagtt ttcggatttg accctgcctg ccttgaccga ctggctgagg    754

taatgcactt gcctagcagt gtcatcccag ctgctctggc cgaaatgtcc ggcgaccccca   814

actgtccggc ttccccggtc actactgtgt ggactgtttc acaattcttt gcccgccaca    874

gaggaggaga gcaccctgat caggtgcgct taggaaaaat catcagcctt tgtcaagttg    934

ttgaggaatg ctgttgccat cagaataaaa ccaaccgggc caccccggaa gaggttgcgg    994

caaggattga tcagtacctc catggtgcaa caagtcttga agaatgcttg attaggcttg   1054

agagggtttg cccgccgagc gctgcggaca ccttctttga ttggaatgtt gtgctccctg   1114

gggttggggc ttcaactcag acaaccaaac agctccatgt caaccagtgc cgcgctctgg   1174

ttcctgtcgt gactcaagag cctttggaca aagactcagt ccctctgacc gccttctcgc   1234

tgtccaattg ctactatcct gcacaaggtg acgaggttcg tcaccgtgag aggctaaact   1294

ccgtactctc taagctggag gggggttgttc gtgaggaata tgggctcacg ccaactgaac  1354

ctggcccgcg acccgcacta ccgaacgggc tcgtcgaact taaagaccag atggaggagg   1414

atctgctgaa actagtcaac gcccaggcaa cttcagaaat gatggcctgg gcagccgagc   1474

aggttgatct gaaagcttgg gtcaaaaact acccacggtg gacaccgcca ccccctccac   1534

caagagttca gcctcgaaaa acaaagtctg tcaagagctt gccagggaac aaacctgtcc   1594

ccgctccacg caggaaggtc agatctgatt gtggcagccc gattttgatg ggcgacaatg   1654
```

-continued

```
ttcctgacgg tcgggaagat ttgactgttg gtggccccct tgatctttcg acaccatccg   1714

agccgatgac acctctgagt gagcctgcac ttatgcccgc gttgcaatat atttctaggc   1774

cagtgacatc tttgagtgtg ctggccccag ttcctgcacc gcgtagaact gtgtcccgac   1834

cggtgacgcc cttgagtgag ccaatttttg tgtctgcacc gcgacacaaa tttcagcagg   1894

tggaagaagc gaatctggcg gcaacaacgc tgacgcacca ggacgaacct ctagatttgt   1954

ctgcatcctc acagactgaa tatgaggctt ctcccctaac accactgcag aacatgggta   2014

ttctggaggt ggggggcaa gaagctgagg aagttctgag tgaaatctcg gatacactga   2074

atgacatcaa ccctgcacct gtgtcatcaa gcagctccct gtcaagtgtt aagatcacac   2134

gcccaaaaca ctctgctcaa gccatcattg actcgggcgg gccctgcagt gggcatctcc   2194

gaagggaaaa agaagcatgc ctcagcatca tgcgtgaggc ttgtgatgcg gctaagctta   2254

gtgaccctgc cacgcaggaa tggctttctc gcatgtggga tagggttgac atgctgactt   2314

ggcgcaacac gtctgcttac caggcgttcc gcatcttaga tggtaggttt gagtttctcc   2374

caaagatgat a ctc gag cac cac cac cac cac cac tgagatccgg             2419
              Leu Glu His His His His His His
                                    25

ctgctaacaa agcccgaaag gaagctgagt tggctgctgc caccgctgag caataactag   2479

cataacccct tggggcctct aaacgggtct tgaggggttt tttgctgaaa ggaggaacta   2539

tatccggatt ggcgaatggg acgcgccctg tagcggcgca ttaagcgcg               2588


<210> SEQ ID NO 58
<211> LENGTH: 2151
<212> TYPE: DNA
<213> ORGANISM: Porcine reproductive and respiratory syndrome virus

<400> SEQUENCE: 58

gctggaaaga gagcaaggaa agcacgctct ggtatgacca ccacagtcgc tcaccgcgcc     60

ttgcccgctc gtgaaatcca gcaagccaaa aagcacgagg atgccggcgc tgataaggct    120

gtgcatctca ggcactattc tccgcctgcc gacgggaact gtggttggca ctgcatttcc    180

gccatcgcca accgaatggt gaattccaaa tttgaaacta ctcttcccga gagggtgaga    240

ccttcagatg actgggctac tgacgaggac cttgtgaaca ccatccaaat tctcaagctc    300

cctgcggcct tggacaggaa cggtgcttgt gttggcgcca aatacgtgct taagctggaa    360

ggcgagcatt ggactgtctc tgtgaccctt gggatgtccc cttctttgct ccccccttgaa    420

tgtgttcagg gctgttgtga gcataagagc ggacttggtc ccccagatgc ggtcgaagtt    480

ttcggatttg accctgcctg ccttgaccga ctggctgagg taatgcactt gcctagcagt    540

gtcatcccag ctgctctggc cgaaatgtcc ggcgaccccca actgtccggc ttccccggtc    600

actactgtgt ggactgtttc acaattcttt gcccgccaca gaggaggaga gcaccctgat    660

caggtgcgct taggaaaaat catcagcctt tgtcaagttg ttgaggaatg ctgttgccat    720

cagaataaaa ccaaccgggc cacccccggaa gaggttgcgg caaggattga tcagtacctc    780

catggtgcaa caagtcttga agaatgcttg attaggcttg agagggtttg cccgccgagc    840

gctgcggaca ccttctttga ttggaatgtt gtgctccctg ggggttggggc ttcaactcag    900

acaaccaaac agctccatgt caaccagtgc cgcgctctgg ttcctgtcgt gactcaagag    960

cctttggaca aagactcagt ccctctgacc gccttctcgc tgtccaattg ctactatcct   1020

gcacaaggtg acgaggttcg tcaccgtgag aggctaaact ccgtactctc taagctggag   1080
```

-continued

```
ggggttgttc gtgaggaata tgggctcacg ccaactgaac ctggcccgcg acccgcacta   1140

ccgaacgggc tcgtcgaact taaagaccag atggaggagg atctgctgaa actagtcaac   1200

gcccaggcaa cttcagaaat gatggcctgg gcagccgagc aggttgatct gaaagcttgg   1260

gtcaaaaact acccacggtg gacaccgcca cccccctccac caagagttca gcctcgaaaa   1320

acaaagtctg tcaagagctt gccagggaac aaacctgtcc ccgctccacg caggaaggtc   1380

agatctgatt gtggcagccc gattttgatg ggcgacaatg ttcctgacgg tcgggaagat   1440

ttgactgttg gtggcccccct tgatctttcg acaccatccg agccgatgac acctctgagt   1500

gagcctgcac ttatgcccgc gttgcaatat atttctaggc cagtgacatc tttgagtgtg   1560

ctggccccag ttcctgcacc gcgtagaact gtgtcccgac cggtgacgcc cttgagtgag   1620

ccaatttttg tgtctgcacc gcgacacaaa tttcagcagg tggaagaagc gaatctggcg   1680

gcaacaacgc tgacgcacca ggacgaacct ctagatttgt ctgcatcctc acagactgaa   1740

tatgaggctt ctcccctaac accactgcag aacatgggta ttctggaggt gggggggcaa   1800

gaagctgagg aagttctgag tgaaatctcg gatacactga atgacatcaa ccctgcacct   1860

gtgtcatcaa gcagctccct gtcaagtgtt aagatcacac gcccaaaaca ctctgctcaa   1920

gccatcattg actcgggcgg gccctgcagt gggcatctcc gaagggaaaa agaagcatgc   1980

ctcagcatca tgcgtgaggc ttgtgatgcg gctaagctta gtgaccctgc cacgcaggaa   2040

tggctttctc gcatgtggga tagggttgac atgctgactt ggcgcaacac gtctgcttac   2100

caggcgttcc gcatcttaga tggtaggttt gagtttctcc caaagatgat a            2151


<210> SEQ ID NO 59
<211> LENGTH: 907
<212> TYPE: DNA
<213> ORGANISM: Porcine reproductive and respiratory syndrome virus
<220> FEATURE:
<221> NAME/KEY: CDS
<222> LOCATION: (175)..(735)

<400> SEQUENCE: 59

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                              1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15

agt gga tcc ggc agc ccg att ttg atg ggc gac aat gtt cct gac ggt      273
Ser Gly Ser Gly Ser Pro Ile Leu Met Gly Asp Asn Val Pro Asp Gly
         20                  25                  30

cgg gaa gat ttg cct gtt ggt ggc ccc ctt gat ctt tcg aca cca tcc      321
Arg Glu Asp Leu Pro Val Gly Gly Pro Leu Asp Leu Ser Thr Pro Ser
     35                  40                  45

gag ccg atg aca cct ctg agt gag cct gca cct atg ccc gcg ttg caa      369
Glu Pro Met Thr Pro Leu Ser Glu Pro Ala Pro Met Pro Ala Leu Gln
 50                  55                  60                  65

tat att tct agg cca gtg aca cct ttg agt gag ctg gcc cca gta cct      417
Tyr Ile Ser Arg Pro Val Thr Pro Leu Ser Glu Leu Ala Pro Val Pro
                 70                  75                  80

gca ccg cgt aga act gtg tcc cga ccg gtg acg ccc ttg agt gag cca      465
Ala Pro Arg Arg Thr Val Ser Arg Pro Val Thr Pro Leu Ser Glu Pro
              85                  90                  95
```

-continued

```
att ttt gtg tct gca ccg cga cac aaa ttt cgg cag gtg gaa gaa gcg      513
Ile Phe Val Ser Ala Pro Arg His Lys Phe Arg Gln Val Glu Glu Ala
        100                 105                 110

aat ctg gcg gca aca atg ctg acg cac cag gac gaa cct cta gat ttg      561
Asn Leu Ala Ala Thr Met Leu Thr His Gln Asp Glu Pro Leu Asp Leu
    115                 120                 125

tct gca tcc tca cag act gaa tat gag gct tct ccc cta aca cca ctg      609
Ser Ala Ser Ser Gln Thr Glu Tyr Glu Ala Ser Pro Leu Thr Pro Leu
130                 135                 140                 145

cag aac atg ggt att ctt gag gtg ggg ggg caa gaa gct gag gaa gtt      657
Gln Asn Met Gly Ile Leu Glu Val Gly Gly Gln Glu Ala Glu Glu Val
                150                 155                 160

ctg agt gaa aac tcg gat aca ctg aat gac atc aac cct gca cct gtg      705
Leu Ser Glu Asn Ser Asp Thr Leu Asn Asp Ile Asn Pro Ala Pro Val
            165                 170                 175

tca tca ctc gag cac cac cac cac cac cac tgagatccgg ctgctaacaa        755
Ser Ser Leu Glu His His His His His His
        180                 185

agcccgaaag gaagctgagt tggctgctgc caccgctgag caataactag cataacccct    815

tggggcctct aaacgggtct tgaggggttt tttgctgaaa ggaggaacta tatccggatt    875

ggcgaatggg acgcgccctg tagcggcgca tt                                  907


<210> SEQ ID NO 60
<211> LENGTH: 477
<212> TYPE: DNA
<213> ORGANISM: Porcine reproductive and respiratory syndrome virus

<400> SEQUENCE: 60

ggcagcccga ttttgatggg cgacaatgtt cctgacggtc gggaagattt gcctgttggt     60

ggcccccttg atctttcgac accatccgag ccgatgacac ctctgagtga gcctgcacct    120

atgcccgcgt tgcaatatat ttctaggcca gtgacacctt tgagtgagct ggccccagta    180

cctgcaccgc gtagaactgt gtcccgaccg gtgacgccct tgagtgagcc aatttttgtg    240

tctgcaccgc gacacaaatt tcggcaggtg gaagaagcga atctggcggc aacaatgctg    300

acgcaccagg acgaacctct agatttgtct gcatcctcac agactgaata tgaggcttct    360

cccctaacac cactgcagaa catgggtatt cttgaggtgg gggggcaaga agctgaggaa    420

gttctgagtg aaaactcgga tacactgaat gacatcaacc ctgcacctgt gtcatca       477


<210> SEQ ID NO 61
<211> LENGTH: 187
<212> TYPE: PRT
<213> ORGANISM: Porcine reproductive and respiratory syndrome virus

<400> SEQUENCE: 61

Met Glu Gln Lys Leu Ile Ser Glu Glu Asp Leu Asn Arg Ser Met Asn
  1               5                  10                  15

Ser Ser Gly Ser Gly Ser Pro Ile Leu Met Gly Asp Asn Val Pro Asp
             20                  25                  30

Gly Arg Glu Asp Leu Pro Val Gly Gly Pro Leu Asp Leu Ser Thr Pro
         35                  40                  45

Ser Glu Pro Met Thr Pro Leu Ser Glu Pro Ala Pro Met Pro Ala Leu
     50                  55                  60

Gln Tyr Ile Ser Arg Pro Val Thr Pro Leu Ser Glu Leu Ala Pro Val
 65                  70                  75                  80

Pro Ala Pro Arg Arg Thr Val Ser Arg Pro Val Thr Pro Leu Ser Glu
                 85                  90                  95
```

-continued

```
Pro Ile Phe Val Ser Ala Pro Arg His Lys Phe Arg Gln Val Glu Glu
            100                 105                 110

Ala Asn Leu Ala Ala Thr Met Leu Thr His Gln Asp Glu Pro Leu Asp
        115                 120                 125

Leu Ser Ala Ser Ser Gln Thr Glu Tyr Glu Ala Ser Pro Leu Thr Pro
    130                 135                 140

Leu Gln Asn Met Gly Ile Leu Glu Val Gly Gly Gln Glu Ala Glu Glu
145                 150                 155                 160

Val Leu Ser Glu Asn Ser Asp Thr Leu Asn Asp Ile Asn Pro Ala Pro
                165                 170                 175

Val Ser Ser Leu Glu His His His His His His
            180                 185


<210> SEQ ID NO 62
<211> LENGTH: 644
<212> TYPE: DNA
<213> ORGANISM: Porcine reproductive and respiratory syndrome virus
<220> FEATURE:
<221> NAME/KEY: CDS
<222> LOCATION: (175)..(465)

<400> SEQUENCE: 62

aggcgccagc aaccgcacct gtggcgccgg tgatgccggc cacgatgcgt ccggcgtaga      60

ggatcgagat ctcgatcccg cgaaattaat acgactcact ataggggaat tgtgagcgga     120

taacaattcc cctctagaaa taattttgtt taactttaag aaggagatat acat atg       177
                                                            Met
                                                              1

gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15

agt gga tcc tgc atg gcc tgc cgc tat gcc cgt acc cgg ttt acc aac       273
Ser Gly Ser Cys Met Ala Cys Arg Tyr Ala Arg Thr Arg Phe Thr Asn
         20                  25                  30

ttc att gtg gac gac cgg ggg aga gtt cat cga tgg aag tct cca ata       321
Phe Ile Val Asp Asp Arg Gly Arg Val His Arg Trp Lys Ser Pro Ile
     35                  40                  45

gtg gta gaa aaa ttg ggc aaa gcc gaa gtc gat ggc aac ctc gtc acc       369
Val Val Glu Lys Leu Gly Lys Ala Glu Val Asp Gly Asn Leu Val Thr
 50                  55                  60                  65

atc aaa cat gtc gtc ctc gaa ggg gtt aaa gct caa ccc ttg acg agg       417
Ile Lys His Val Val Leu Glu Gly Val Lys Ala Gln Pro Leu Thr Arg
                 70                  75                  80

act tcg gct gag caa tgg gag gcc ctc gag cac cac cac cac cac cac       465
Thr Ser Ala Glu Gln Trp Glu Ala Leu Glu His His His His His His
             85                  90                  95

tgagatccgg ctgctaacaa agcccgaaag gaagctgagt tggctgctgc caccgctgag     525

caataactag cataacccct tggggcctct aaacgggtct tgaggggttt tttgctgaaa     585

ggaggaacta tatccggatt ggcgaatggg acgcgccctg tagcggcgca ttaagcgcg      644


<210> SEQ ID NO 63
<211> LENGTH: 207
<212> TYPE: DNA
<213> ORGANISM: Porcine reproductive and respiratory syndrome virus

<400> SEQUENCE: 63

tgcatggcct gccgctatgc ccgtacccgg tttaccaact tcattgtgga cgaccggggg      60

agagttcatc gatggaagtc tccaatagtg gtagaaaaat tgggcaaagc cgaagtcgat     120
```

-continued

```
ggcaacctcg tcaccatcaa acatgtcgtc ctcgaagggg ttaaagctca acccttgacg    180

aggacttcgg ctgagcaatg ggaggcc                                        207


<210> SEQ ID NO 64
<211> LENGTH: 97
<212> TYPE: PRT
<213> ORGANISM: Porcine reproductive and respiratory syndrome virus

<400> SEQUENCE: 64

Met Glu Gln Lys Leu Ile Ser Glu Glu Asp Leu Asn Arg Ser Met Asn
1               5                   10                  15

Ser Ser Gly Ser Cys Met Ala Cys Arg Tyr Ala Arg Thr Arg Phe Thr
            20                  25                  30

Asn Phe Ile Val Asp Asp Arg Gly Arg Val His Arg Trp Lys Ser Pro
        35                  40                  45

Ile Val Val Glu Lys Leu Gly Lys Ala Glu Val Asp Gly Asn Leu Val
    50                  55                  60

Thr Ile Lys His Val Val Leu Glu Gly Val Lys Ala Gln Pro Leu Thr
65                  70                  75                  80

Arg Thr Ser Ala Glu Gln Trp Glu Ala Leu Glu His His His His His
                85                  90                  95

His


<210> SEQ ID NO 65
<211> LENGTH: 694
<212> TYPE: DNA
<213> ORGANISM: Porcine reproductive and respiratory syndrome virus
<220> FEATURE:
<221> NAME/KEY: CDS
<222> LOCATION: (175)..(522)

<400> SEQUENCE: 65

aggcgccagc aaccgcacct gtggcgccgg tgatgccggc cacgatgcgt ccggcgtaga     60

ggatcgagat ctcgatcccg cgaaattaat acgactcact ataggggaat tgtgagcgga    120

taacaattcc cctctagaaa taattttgtt taactttaag aaggagatat acat atg      177
                                                            Met
                                                            1

gaa caa aaa ctc atc tca gaa gag gat ctg aat cga tcc atg aat tct      225
Glu Gln Lys Leu Ile Ser Glu Glu Asp Leu Asn Arg Ser Met Asn Ser
            5                   10                  15

agt gga tcc agc ttc aca gag tca tgg aag ttt atc act tcc aga tgc      273
Ser Gly Ser Ser Phe Thr Glu Ser Trp Lys Phe Ile Thr Ser Arg Cys
        20                  25                  30

aga ttg tgt tgc ctt ggc cgg cga tac att ctg gcc cct gcc cat cac      321
Arg Leu Cys Cys Leu Gly Arg Arg Tyr Ile Leu Ala Pro Ala His His
    35                  40                  45

gta gaa agt gct gca ggt ctc cat tca atc tca gcg tct ggt aac cga      369
Val Glu Ser Ala Ala Gly Leu His Ser Ile Ser Ala Ser Gly Asn Arg
50                  55                  60                  65

gca tac gct gtg aga aag ccc gga cta aca tca gtg aac ggc act cta      417
Ala Tyr Ala Val Arg Lys Pro Gly Leu Thr Ser Val Asn Gly Thr Leu
                70                  75                  80

gta cca gga ctt cgg agc ctc gtg ctg ggc ggc aaa cga gct gtt aaa      465
Val Pro Gly Leu Arg Ser Leu Val Leu Gly Gly Lys Arg Ala Val Lys
            85                  90                  95

cga gga gtg gtt aac ctc gtc aag tat ggc cgg ctc gag cac cac cac      513
Arg Gly Val Val Asn Leu Val Lys Tyr Gly Arg Leu Glu His His His
        100                 105                 110
```

-continued

```
cac cac cac tgagatccgg ctgctaacaa agcccgaaag gaagctgagt              562
His His His
    115

tggctgctgc caccgctgag caataactag cataacccct tggggcctct aaacgggtct    622

tgaggggttt tttgctgaaa ggaggaacta tatccggatt ggcgaatggg acgcgccctg    682

tagcggcgca tt                                                        694


<210> SEQ ID NO 66
<211> LENGTH: 264
<212> TYPE: DNA
<213> ORGANISM: Porcine reproductive and respiratory syndrome virus

<400> SEQUENCE: 66

agcttcacag agtcatggaa gtttatcact tccagatgca gattgtgttg ccttggccgg     60

cgatacattc tggcccctgc ccatcacgta gaaagtgctg caggtctcca ttcaatctca    120

gcgtctggta accgagcata cgctgtgaga aagcccggac taacatcagt gaacggcact    180

ctagtaccag gacttcggag cctcgtgctg ggcggcaaac gagctgttaa acgaggagtg    240

gttaacctcg tcaagtatgg ccgg                                           264


<210> SEQ ID NO 67
<211> LENGTH: 116
<212> TYPE: PRT
<213> ORGANISM: Porcine reproductive and respiratory syndrome virus

<400> SEQUENCE: 67

Met Glu Gln Lys Leu Ile Ser Glu Glu Asp Leu Asn Arg Ser Met Asn
  1               5                  10                  15

Ser Ser Gly Ser Ser Phe Thr Glu Ser Trp Lys Phe Ile Thr Ser Arg
             20                  25                  30

Cys Arg Leu Cys Cys Leu Gly Arg Arg Tyr Ile Leu Ala Pro Ala His
         35                  40                  45

His Val Glu Ser Ala Ala Gly Leu His Ser Ile Ser Ala Ser Gly Asn
     50                  55                  60

Arg Ala Tyr Ala Val Arg Lys Pro Gly Leu Thr Ser Val Asn Gly Thr
 65                  70                  75                  80

Leu Val Pro Gly Leu Arg Ser Leu Val Leu Gly Gly Lys Arg Ala Val
                 85                  90                  95

Lys Arg Gly Val Val Asn Leu Val Lys Tyr Gly Arg Leu Glu His His
            100                 105                 110

His His His His
        115


<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 68

aggtcgtgta ctgtcagtca                                                 20


<210> SEQ ID NO 69
<211> LENGTH: 20
<212> TYPE: DNA
<213> ORGANISM: Artificial Sequence
```

-continued

```
<220> FEATURE:
<223> OTHER INFORMATION: Description of Artificial Sequence: Synthetic
      nucleotide sequence

<400> SEQUENCE: 69

acgtggtgaa ctgccagtga                                                20


<210> SEQ ID NO 70
<211> LENGTH: 719
<212> TYPE: PRT
<213> ORGANISM: Porcine reproductive and respiratory syndrome virus

<400> SEQUENCE: 70

Ala Gly Lys Arg Ala Arg Lys Ala Arg Ser Gly Ala Thr Ala Thr Val
  1               5                  10                  15

Ala Gly Arg Ala Leu Ser Val Arg Glu Thr Arg Gln Ala Lys Glu His
             20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asn Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
        275                 280                 285

Asp Val Val Leu Pro Gly Val Glu Ala Ala Thr Gln Thr Thr Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335
```

-continued

```
Tyr Tyr Tyr Arg Ala Gln Gly Asp Glu Val Arg His Arg Glu Arg Leu
            340                 345                 350

Thr Ala Val Leu Ser Lys Leu Glu Gly Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Ala Thr Ser Asp Met Met Ala Trp Ala Ala Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Leu Leu Gly Gly Asn Val Pro Asn Ser Trp Glu Asp
465                 470                 475                 480

Leu Ala Val Gly Gly Pro Leu Asp Leu Pro Thr Pro Pro Glu Pro Ala
                485                 490                 495

Thr Pro Leu Ser Glu Pro Val Leu Val Ser Ala Pro Gln Cys Ile Phe
            500                 505                 510

Arg Pro Val Thr Pro Leu Ser Glu Pro Ala Pro Val Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Glu Arg Ala Asn Ser Ala
545                 550                 555                 560

Ala Ala Thr Pro Thr Tyr Gln Asp Glu Pro Leu Asp Leu Ser Ala Ser
                565                 570                 575

Ser Gln Thr Glu Tyr Glu Ala Ser Pro Leu Ala Pro Pro Gln Asn Gly
            580                 585                 590

Gly Val Leu Glu Val Glu Gly Gln Glu Ala Glu Glu Val Leu Ser Glu
        595                 600                 605

Ile Ser Asp Met Leu Gly Asp Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Ala Cys Leu Ser Ile Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Arg
    690                 695                 700

Thr Leu Asp Gly Arg Leu Lys Phe Leu Pro Lys Met Ile Leu Glu
705                 710                 715
```

<210> SEQ ID NO 71
<211> LENGTH: 719
<212> TYPE: PRT
<213> ORGANISM: Porcine reproductive and respiratory syndrome virus

<400> SEQUENCE: 71

-continued

```
Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Phe
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Pro Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
        355                 360                 365

Leu Met Pro Thr Lys Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Ala Glu Gln Val Asp
                405                 410                 415
```

-continued

```
Leu Lys Thr Trp Val Lys Asn Tyr Pro Arg Trp Thr Pro Pro Pro Pro
            420                 425                 430

Ser Pro Lys Val Gln Leu Arg Lys Thr Lys Pro Val Lys Ser Leu Pro
        435                 440                 445

Lys Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
                485                 490                 495

Ile Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Pro Ala Pro Pro Gln Ser Gly
            580                 585                 590

Gly Val Leu Gly Val Glu Gly His Glu Ala Glu Glu Thr Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Val Ile Cys
    690                 695                 700

Thr Leu Asp Gly Met Leu Lys Phe Leu Pro Lys Met Ile Leu Glu
705                 710                 715


<210> SEQ ID NO 72
<211> LENGTH: 719
<212> TYPE: PRT
<213> ORGANISM: Porcine reproductive and respiratory syndrome virus

<400> SEQUENCE: 72

Ala Gly Lys Arg Ala Arg Lys Ala Arg Ser Cys Ala Thr Ala Thr Val
  1               5                  10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80
```

-continued

```
Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Phe Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
                485                 490                 495
```

-continued

```
Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Pro Ala Pro Pro Gln Ser Gly
            580                 585                 590

Gly Val Leu Gly Val Glu Gly His Glu Ala Glu Glu Thr Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Cys
    690                 695                 700

Thr Leu Asn Gly Arg Leu Lys Phe Leu Pro Lys Met Ile Leu Glu
705                 710                 715


<210> SEQ ID NO 73
<211> LENGTH: 719
<212> TYPE: PRT
<213> ORGANISM: Porcine reproductive and respiratory syndrome virus

<400> SEQUENCE: 73

Ala Gly Lys Arg Ala Arg Lys Ala Arg Ser Cys Ala Thr Ala Thr Val
  1               5                  10                  15

Ala Gly Arg Ala Leu Ser Val Arg Glu Thr Arg Gln Ala Lys Glu His
             20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160
```

-continued

```
Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Phe Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

His Tyr Tyr Arg Ala Gln Gly Asp Glu Val Arg His Arg Glu Arg Leu
            340                 345                 350

Thr Ala Val Leu Ser Asn Leu Glu Lys Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
                485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575
```

-continued

```
Ser Gln Thr Glu Tyr Glu Ala Ser Pro Pro Ala Pro Pro Gln Ser Gly
            580                 585                 590

Gly Val Leu Gly Val Glu Gly His Glu Ala Glu Glu Thr Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Ala Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Cys
    690                 695                 700

Thr Leu Asp Gly Arg Leu Lys Phe Leu Pro Lys Met Ile Leu Glu
705                 710                 715


<210> SEQ ID NO 74
<211> LENGTH: 719
<212> TYPE: PRT
<213> ORGANISM: Porcine reproductive and respiratory syndrome virus

<400> SEQUENCE: 74

Ala Gly Lys Arg Ala Arg Lys Ala Arg Ser Cys Ala Thr Ala Thr Val
  1               5                  10                  15

Ala Gly Arg Ala Leu Ser Val Arg Glu Thr Arg Gln Ala Lys Glu His
             20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240
```

-continued

```
Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
                485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asp Glu Pro Leu Asp Leu Ser Ala Ser
                565                 570                 575

Ser Gln Thr Glu Tyr Glu Ala Ser Pro Pro Ala Pro Pro Gln Ser Gly
            580                 585                 590

Gly Val Leu Gly Val Glu Gly His Glu Ala Glu Glu Thr Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655
```

-continued

```
Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Cys
    690                 695                 700

Thr Leu Asp Gly Arg Leu Lys Phe Leu Pro Lys Met Ile Leu Glu
705                 710                 715


<210> SEQ ID NO 75
<211> LENGTH: 719
<212> TYPE: PRT
<213> ORGANISM: Porcine reproductive and respiratory syndrome virus

<400> SEQUENCE: 75

Ala Gly Lys Arg Ala Arg Lys Ala Arg Ser Cys Ala Thr Ala Thr Val
  1               5                  10                  15

Ala Gly Arg Ala Leu Ser Val Arg Glu Thr Arg Gln Ala Lys Glu His
            20                  25                  30

Glu Val Ala Gly Ala Asp Lys Ala Glu His Leu Lys His Tyr Ser Pro
        35                  40                  45

Pro Ala Glu Gly Asn Cys Gly Trp His Cys Ile Ser Ala Ile Ala Asn
     50                  55                  60

Arg Met Val Asn Ser Ile Phe Glu Thr Thr Leu Pro Glu Arg Val Arg
 65                  70                  75                  80

Pro Pro Asp Asp Trp Ala Thr Asp Asp Asp Leu Ala Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Ile Glu Val
145                 150                 155                 160

Ser Gly Phe Asp Pro Ala Cys Leu Asp Trp Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
        275                 280                 285

Asp Val Val Leu Pro Gly Val Glu Ala Ala Thr Gln Thr Asn Lys Leu
    290                 295                 300

Pro Gln Val Asn Gln Cys Arg Ala Leu Val Pro Val Val Thr Gln Lys
305                 310                 315                 320
```

-continued

```
Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Glu Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Arg Leu Ala Asn
385                 390                 395                 400

Ala Gln Ala Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Pro Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Leu Asp Leu Pro Thr Pro Pro Glu Pro Ala
                485                 490                 495

Thr Leu Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Val Pro Leu His Gln Asn Glu Pro Leu Asp Leu Ser Ala Ser
                565                 570                 575

Ser Gln Thr Glu Tyr Glu Ala Ser Pro Ser Ala Pro Pro Gln Ser Gly
            580                 585                 590

Gly Val Leu Gly Val Glu Gly His Glu Ala Glu Glu Thr Leu Ser Glu
        595                 600                 605

Ile Ser Asp Met Ser Gly Asn Ile Lys Pro Ala Ser Val Ser Ser Ser
    610                 615                 620

Ser Ser Leu Ser Ser Val Glu Ile Thr Arg Pro Lys Tyr Ser Ala Gln
625                 630                 635                 640

Ala Ile Ile Asp Ser Gly Gly Pro Cys Ser Gly His Leu Gln Gly Val
                645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Cys Gln Ala Ile Arg
    690                 695                 700

Thr Leu Asp Gly Arg Leu Lys Phe Leu Pro Lys Met Ile Leu Glu
705                 710                 715
```

<210> SEQ ID NO 76
<211> LENGTH: 719

-continued

<212> TYPE: PRT
<213> ORGANISM: Porcine reproductive and respiratory syndrome virus

<400> SEQUENCE: 76

```
Ala Gly Lys Arg Ala Arg Lys Ala Arg Ser Ser Ala Thr Ala Thr Val
  1               5                  10                  15

Ala Gly Arg Ala Leu Pro Val Arg Glu Thr Arg Gln Val Glu Glu His
             20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Gly Asn
     50                  55                  60

Arg Met Leu Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Ala Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Val Glu Val
145                 150                 155                 160

Pro Gly Phe Asp Pro Ala Cys Leu Asp Trp Leu Ala Glu Val Met His
                165                 170                 175

Leu Pro Ser Asn Ala Ile Pro Ala Ala Leu Ala Glu Met Ser Gly Asp
            180                 185                 190

Ser Asn Arg Pro Ala Ser Pro Val Thr Thr Val Trp Thr Val Ser Gln
        195                 200                 205

Phe Leu Ala Arg His Asn Gly Gly Asn His Pro Asp Gln Ile Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Met Asp Thr Ser Phe Asp Trp
        275                 280                 285

Asp Val Val Leu Pro Gly Val Glu Ala Ala Thr Gln Thr Thr Glu Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Gly Val Val Arg Glu Glu Tyr Gly
        355                 360                 365

Leu Met Pro Thr Gly Pro Gly Pro Arg Pro Thr Leu Pro Arg Gly Leu
    370                 375                 380

Asp Glu Leu Lys Asp Gln Met Glu Val Asp Leu Leu Lys Leu Ala Asn
385                 390                 395                 400
```

-continued

```
Ala Gln Met Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro Pro
            420                 425                 430

Pro Pro Ile Val Gln Pro Arg Lys Thr Lys Leu Val Lys Ser Leu Pro
        435                 440                 445

Glu Ser Lys Pro Val Pro Ala Pro Arg Arg Lys Val Arg Ser Asp Cys
    450                 455                 460

Asp Cys Pro Thr Leu Ser Gly Asn Asn Leu Pro Asp Ser Trp Glu Asp
465                 470                 475                 480

Leu Ala Val Gly Cys Pro Ser Asp Leu Pro Thr Ser Pro Glu Pro Val
                485                 490                 495

Thr Pro Leu Ser Glu Pro Ala Ser Val Ser Ala Pro Arg Arg Ser Phe
            500                 505                 510

Arg Pro Val Lys Pro Leu Ser Glu Pro Val Pro Val Pro Ala Pro Arg
        515                 520                 525

Lys Thr Val Ser Arg Pro Ala Thr Pro Leu Ser Glu Pro Ile Pro Val
    530                 535                 540

Pro Ala Pro Arg Arg Lys Phe Gln Gln Val Glu Lys Val Asn Pro Ala
545                 550                 555                 560

Ala Ala Thr Leu Gly Cys Gln Asp Glu Phe Pro Asp Leu Ser Ala Ser
                565                 570                 575

Ser His Thr Glu Tyr Glu Ala Ser Pro Leu Val Leu Pro Gln Asn Gly
            580                 585                 590

Asp Val Leu Glu Val Glu Glu Arg Glu Ala Glu Glu Ile Leu Ser Gly
        595                 600                 605

Ile Ser Asp Ile Leu Asp Ala Ile Lys Pro Ala Ser Ala Ser Ser Ser
    610                 615                 620

Ser Ser Leu Ser Ser Val Ala Ile Thr Arg Pro Lys Tyr Ser Ala Gln
625                 630                 635                 640

Ala Ile Ile Asp Ser Gly Gly Pro Tyr Ser Gly His Leu Gln Glu Val
                645                 650                 655

Lys Glu Thr Cys Leu Ser Ile Met Ser Glu Ala Cys Asp Val Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val His Gln Ala Ser Arg
    690                 695                 700

Thr Leu Asp Asp Arg Phe Lys Phe Leu Pro Lys Met Ile Leu Glu
705                 710                 715


<210> SEQ ID NO 77
<211> LENGTH: 719
<212> TYPE: PRT
<213> ORGANISM: Porcine reproductive and respiratory syndrome virus

<400> SEQUENCE: 77

Ala Gly Lys Arg Ala Arg Lys Ala Arg Ser Gly Met Thr Thr Thr Val
  1               5                  10                  15

Ala His Arg Ala Leu Pro Ala Arg Glu Ile Gln Gln Ala Lys Lys His
            20                  25                  30

Glu Asp Ala Gly Ala Asp Lys Ala Val His Leu Arg His Tyr Ser Pro
         35                  40                  45

Pro Ala Asp Gly Asn Cys Gly Trp His Cys Ile Ser Ala Ile Ala Asn
```

-continued

```
        50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Lys Leu Pro Ala Ala Leu Asp Arg Asn Gly Ala Cys Val Gly
            100                 105                 110

Ala Lys Tyr Val Leu Lys Leu Glu Gly Glu His Trp Thr Val Ser Val
        115                 120                 125

Thr Leu Gly Met Ser Pro Ser Leu Leu Pro Leu Glu Cys Val Gln Gly
    130                 135                 140

Cys Cys Glu His Lys Ser Gly Leu Gly Pro Pro Asp Ala Val Glu Val
145                 150                 155                 160

Phe Gly Phe Asp Pro Ala Cys Leu Asp Arg Leu Ala Glu Val Met His
                165                 170                 175

Leu Pro Ser Ser Val Ile Pro Ala Ala Leu Ala Glu Met Ser Gly Asp
            180                 185                 190

Pro Asn Cys Pro Ala Ser Pro Val Thr Thr Val Trp Thr Val Ser Gln
        195                 200                 205

Phe Phe Ala Arg His Arg Gly Gly Glu His Pro Asp Gln Val Arg Leu
    210                 215                 220

Gly Lys Ile Ile Ser Leu Cys Gln Val Val Glu Glu Cys Cys Cys His
225                 230                 235                 240

Gln Asn Lys Thr Asn Arg Ala Thr Pro Glu Glu Val Ala Ala Arg Ile
                245                 250                 255

Asp Gln Tyr Leu His Gly Ala Thr Ser Leu Glu Glu Cys Leu Ile Arg
            260                 265                 270

Leu Glu Arg Val Cys Pro Pro Ser Ala Ala Asp Thr Phe Phe Asp Trp
        275                 280                 285

Asn Val Val Leu Pro Gly Val Gly Ala Ser Thr Gln Thr Thr Lys Gln
    290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
        355                 360                 365

Leu Thr Pro Thr Glu Pro Gly Pro Arg Pro Ala Leu Pro Asn Gly Leu
    370                 375                 380

Val Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro Pro
            420                 425                 430

Pro Pro Arg Val Gln Pro Arg Lys Thr Lys Ser Val Lys Ser Leu Pro
        435                 440                 445

Gly Asn Lys Pro Val Pro Ala Pro Arg Arg Lys Val Arg Ser Asp Cys
    450                 455                 460

Gly Ser Pro Ile Leu Met Gly Asp Asn Val Pro Asp Gly Arg Glu Asp
465                 470                 475                 480
```

-continued

```
Leu Thr Val Gly Gly Pro Leu Asp Leu Ser Thr Pro Ser Glu Pro Met
                485                 490                 495

Thr Pro Leu Ser Glu Pro Ala Leu Met Pro Ala Leu Gln Tyr Ile Ser
            500                 505                 510

Arg Pro Val Thr Ser Leu Ser Val Leu Ala Pro Val Pro Ala Pro Arg
        515                 520                 525

Phe Thr Val Ser Arg Pro Val Thr Pro Leu Ser Glu Pro Ile Phe Val
    530                 535                 540

Ser Ala Pro Arg His Lys Phe Gln Gln Val Glu Glu Ala Asn Leu Ala
545                 550                 555                 560

Ala Thr Thr Leu Thr His Gln Asp Glu Pro Leu Asp Leu Ser Ala Ser
                565                 570                 575

Ser Gln Thr Glu Tyr Glu Ala Ser Pro Leu Thr Pro Leu Gln Asn Met
            580                 585                 590

Gly Ile Leu Glu Val Gly Gly Gln Glu Ala Glu Glu Val Leu Ser Glu
        595                 600                 605

Ile Ser Asp Thr Leu Asn Asp Ile Asn Pro Ala Pro Val Ser Ser Ser
    610                 615                 620

Ser Ser Leu Ser Ser Val Lys Ile Thr Arg Pro Lys His Ser Ala Gln
625                 630                 635                 640

Ala Ile Ile Asp Ser Gly Gly Pro Cys Ser Gly His Leu Arg Arg Glu
                645                 650                 655

Lys Glu Ala Cys Leu Ser Ile Met Arg Glu Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Phe Arg
    690                 695                 700

Ile Leu Asp Gly Arg Phe Glu Phe Leu Pro Lys Met Ile Leu Glu
705                 710                 715


<210> SEQ ID NO 78
<211> LENGTH: 719
<212> TYPE: PRT
<213> ORGANISM: Porcine reproductive and respiratory syndrome virus

<400> SEQUENCE: 78

Ala Gly Lys Arg Ala Arg Lys Ala Arg Ser Gly Met Thr Thr Thr Val
  1               5                  10                  15

Ala His Arg Ala Leu Pro Ala Arg Glu Ile Gln Gln Ala Lys Lys His
             20                  25                  30

Glu Asp Ala Gly Ala Asp Lys Ala Val His Leu Arg His Tyr Ser Pro
         35                  40                  45

Pro Ala Asp Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Lys Leu Pro Ala Ala Leu Asp Arg Asn Gly Ala Cys Val Gly
            100                 105                 110

Ala Lys Tyr Val Leu Lys Leu Glu Gly Glu His Trp Thr Val Ser Val
        115                 120                 125

Thr Leu Gly Met Ser Pro Ser Leu Leu Pro Leu Glu Cys Val Gln Gly
```

-continued

```
    130                 135                 140

Cys Cys Glu His Lys Ser Gly Leu Gly Pro Pro Asp Ala Val Glu Val
145                 150                 155                 160

Phe Gly Phe Asp Pro Ala Cys Leu Asp Arg Leu Ala Glu Val Met His
                165                 170                 175

Leu Pro Ser Ser Val Ile Pro Ala Ala Leu Ala Glu Met Ser Gly Asp
            180                 185                 190

Pro Asn Cys Pro Ala Ser Pro Val Thr Thr Val Trp Thr Val Ser Gln
        195                 200                 205

Phe Phe Ala Arg His Arg Gly Gly Glu His Pro Asp Gln Val Arg Leu
    210                 215                 220

Gly Lys Ile Ile Ser Leu Cys Gln Val Val Glu Glu Cys Cys Cys His
225                 230                 235                 240

Gln Asn Lys Thr Asn Arg Ala Thr Pro Glu Glu Val Ala Ala Arg Ile
                245                 250                 255

Asp Gln Tyr Leu His Gly Ala Thr Ser Leu Glu Glu Cys Leu Ile Arg
            260                 265                 270

Leu Glu Arg Val Cys Pro Pro Ser Ala Ala Asp Thr Phe Phe Asp Trp
        275                 280                 285

Asn Val Val Leu Pro Gly Val Gly Ala Ser Thr Gln Thr Thr Lys Gln
    290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
        355                 360                 365

Leu Thr Pro Thr Glu Pro Gly Pro Arg Pro Ala Leu Pro Asn Gly Leu
    370                 375                 380

Val Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro Pro
            420                 425                 430

Pro Pro Arg Val Gln Pro Arg Lys Thr Lys Ser Val Lys Ser Leu Pro
        435                 440                 445

Gly Asn Lys Pro Val Pro Ala Pro Arg Arg Lys Val Arg Ser Asp Cys
    450                 455                 460

Gly Ser Pro Ile Leu Met Gly Asp Asn Val Pro Asp Gly Arg Glu Asp
465                 470                 475                 480

Leu Thr Val Gly Gly Pro Leu Asp Leu Ser Thr Pro Ser Glu Pro Met
                485                 490                 495

Thr Pro Leu Ser Glu Pro Ala Leu Met Pro Ala Leu Gln Tyr Ile Ser
            500                 505                 510

Arg Pro Val Thr Ser Leu Ser Val Leu Ala Pro Val Pro Ala Pro Arg
        515                 520                 525

Arg Thr Val Ser Arg Pro Val Thr Pro Leu Ser Glu Pro Ile Phe Val
    530                 535                 540

Ser Ala Pro Arg His Lys Phe Gln Gln Val Glu Glu Ala Asn Leu Ala
545                 550                 555                 560
```

-continued

```
Ala Thr Thr Leu Thr His Gln Asp Glu Pro Leu Asp Leu Ser Ala Ser
                565                 570                 575

Ser Gln Thr Glu Tyr Glu Ala Ser Pro Leu Thr Pro Leu Gln Asn Met
            580                 585                 590

Gly Ile Leu Glu Val Gly Gly Gln Glu Ala Glu Glu Val Leu Ser Glu
        595                 600                 605

Ile Ser Asp Thr Leu Asn Asp Ile Asn Pro Ala Pro Val Ser Ser Ser
    610                 615                 620

Ser Ser Leu Ser Ser Val Lys Ile Thr Arg Pro Lys His Ser Ala Gln
625                 630                 635                 640

Ala Ile Ile Asp Ser Gly Gly Pro Cys Ser Gly His Leu Arg Arg Glu
                645                 650                 655

Lys Glu Ala Cys Leu Ser Ile Met Arg Lys Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Phe Arg
    690                 695                 700

Ile Leu Asp Gly Arg Phe Glu Phe Leu Pro Lys Met Ile Leu Glu
705                 710                 715


<210> SEQ ID NO 79
<211> LENGTH: 719
<212> TYPE: PRT
<213> ORGANISM: Porcine reproductive and respiratory syndrome virus

<400> SEQUENCE: 79

Ala Gly Lys Arg Ala Lys Lys Ala Arg Ser Gly Ala Thr Ala Thr Val
  1               5                  10                  15

Ala His Arg Ala Ser Pro Val Arg Glu Thr Gln Gln Ala Lys Lys His
             20                  25                  30

Glu Val Ala Asn Ala Asn Arg Ala Gly His Phe Lys Arg Tyr Ser Pro
         35                  40                  45

Pro Ala Asp Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Ala Ser
            100                 105                 110

Ala Lys Tyr Val Leu Lys Leu Glu Gly Glu His Trp Thr Val Ser Val
        115                 120                 125

Thr Pro Gly Thr Ser Pro Ser Leu Leu Pro Leu Glu Cys Val Gln Gly
    130                 135                 140

Cys Cys Glu His Lys Gly Gly Leu Gly Ser Pro Asp Ala Val Glu Ile
145                 150                 155                 160

Ser Gly Phe Asp Pro Ala Cys Leu Asp Arg Leu Ala Glu Ile Met His
                165                 170                 175

Leu Pro Ser Ser Val Ile Pro Ala Ala Leu Ala Glu Met Ser Gly Asp
            180                 185                 190

Pro Asn Arg Pro Ala Ser Pro Val Thr Thr Val Trp Thr Val Ser Gln
        195                 200                 205

Phe Phe Ala Arg His Arg Gly Gly Glu His Pro Asp Gln Val Arg Leu
```

-continued

```
    210                 215                 220

Gly Lys Ile Ile Ser Leu Cys Gln Val Ile Glu Glu Cys Cys Cys Arg
225                 230                 235                 240

Gln Asn Asp Thr Asn Arg Val Thr Pro Glu Glu Val Ala Val Lys Ile
                245                 250                 255

Asn Gln Tyr Leu Arg Gly Ala Thr Asn Leu Glu Glu Cys Leu Thr Arg
            260                 265                 270

Leu Glu Arg Ala Cys Pro Pro Ser Ala Ala Asp Thr Ser Phe Asp Trp
        275                 280                 285

Asn Val Val Leu Pro Gly Ile Glu Ala Ala Thr Gln Thr Thr Lys Gln
    290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
        355                 360                 365

Leu Thr Pro Thr Glu Pro Gly Pro Arg Pro Ala Leu Pro Asn Gly Leu
    370                 375                 380

Asp Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro Pro
            420                 425                 430

Pro Pro Arg Val Gln Pro Arg Lys Thr Lys Ser Val Lys Ser Leu Pro
        435                 440                 445

Gly Asp Lys Pro Val Pro Ala Pro Arg Arg Lys Val Arg Ser Asp Cys
    450                 455                 460

Gly Ser Pro Ile Leu Met Gly Asp Asn Asp Pro Asn Gly Arg Glu Asp
465                 470                 475                 480

Leu Thr Val Asp Gly Pro Leu Asp Leu Ser Thr Pro Ser Glu Pro Met
                485                 490                 495

Thr Pro Leu Gly Glu Pro Ala Leu Leu Pro Ala Leu Gln His Ile Ser
            500                 505                 510

Arg Pro Val Thr Ser Leu Ser Val Pro Ala Pro Val Pro Ala Pro Arg
        515                 520                 525

Arg Ala Val Ser Arg Pro Val Thr Pro Leu Ser Glu Pro Ile Phe Glu
    530                 535                 540

Ser Ala Pro Arg His Lys Leu Gln Gln Val Glu Glu Ala Asn Leu Val
545                 550                 555                 560

Ala Thr Thr Leu Thr His Gln Asp Glu Pro Leu Asp Leu Ser Ala Ser
                565                 570                 575

Ser Gln Thr Glu Tyr Glu Ala Ser Pro Leu Ala Pro Leu Gln Asn Met
            580                 585                 590

Gly Val Leu Glu Val Gly Gly Gln Glu Ala Glu Glu Val Leu Ser Glu
        595                 600                 605

Ile Ser Asp Ile Leu Asn Asp Ile Asn Pro Ala Pro Val Ser Ser Ser
    610                 615                 620

Ser Ser Leu Ser Ser Val Lys Ile Thr Arg Pro Lys Tyr Ser Ala Gln
625                 630                 635                 640
```

-continued

```
Ala Ile Ile Asp Ser Gly Gly Pro Cys Ser Gly His Leu Arg Arg Glu
                645                 650                 655

Lys Glu Ala Cys Leu Ser Ile Met Arg Lys Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Leu Arg
    690                 695                 700

Val Leu Asp Gly Arg Phe Gly Phe Leu Pro Lys Met Ile Leu Glu
705                 710                 715


<210> SEQ ID NO 80
<211> LENGTH: 725
<212> TYPE: PRT
<213> ORGANISM: Porcine reproductive and respiratory syndrome virus

<400> SEQUENCE: 80

Ala Gly Lys Arg Ala Arg Arg Ala Arg Ser Gly Ala Thr Ala Thr Val
  1               5                  10                  15

Ala His Cys Ala Leu Pro Ala Arg Glu Ala Gln Gln Ala Lys Lys Leu
             20                  25                  30

Glu Val Ala Ser Ala Asn Arg Ala Glu His Leu Lys Tyr Tyr Ser Pro
         35                  40                  45

Pro Ala Asp Gly Asn Cys Gly Trp His Cys Ile Ser Ala Ile Thr Asn
     50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Ala Gly
            100                 105                 110

Ala Lys Tyr Val Leu Lys Leu Glu Gly Glu His Trp Thr Val Ser Val
        115                 120                 125

Thr Pro Gly Met Thr Pro Ser Leu Leu Pro Leu Glu Cys Val Gln Gly
    130                 135                 140

Cys Cys Glu His Lys Ser Gly Leu Gly Phe Pro Asp Val Val Glu Val
145                 150                 155                 160

Ser Gly Phe Asp Pro Ala Cys Leu Asp Arg Leu Ala Glu Ile Met His
                165                 170                 175

Leu Pro Ser Ser Val Ile Pro Ala Ala Leu Ala Glu Met Ser Asp Asp
            180                 185                 190

Phe Asn Arg Leu Ala Ser Pro Ala Ala Thr Val Trp Thr Val Ser Gln
        195                 200                 205

Phe Phe Ala Arg His Arg Gly Gly Glu His Pro Asp Gln Val Cys Leu
    210                 215                 220

Gly Lys Ile Ile Asn Leu Cys Gln Val Ile Glu Glu Cys Cys Cys Ser
225                 230                 235                 240

Arg Asn Lys Ala Asn Arg Ala Thr Pro Glu Glu Val Ala Ala Lys Val
                245                 250                 255

Asp Gln Tyr Leu Arg Gly Ala Ala Ser Leu Gly Glu Cys Leu Ala Lys
            260                 265                 270

Leu Glu Arg Ala Arg Pro Pro Ser Ala Met Asp Thr Ser Phe Asp Trp
        275                 280                 285

Asn Val Val Leu Pro Gly Val Glu Thr Ala Asp Gln Thr Thr Lys Gln
```

-continued

```
    290                 295                 300

Leu His Val Asn Gln Cys Arg Ala Leu Val Pro Val Val Thr Gln Glu
305                 310                 315                 320

Pro Leu Asp Arg Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
        355                 360                 365

Leu Thr Pro Thr Gly Pro Gly Pro Arg Pro Ala Leu Pro Asn Gly Leu
    370                 375                 380

Asp Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro Pro
            420                 425                 430

Pro Pro Arg Val Gln Pro Arg Lys Thr Lys Ser Val Lys Ser Leu Leu
        435                 440                 445

Glu Asn Lys Pro Val Pro Ala Pro Arg Arg Lys Val Arg Ser Asp Tyr
    450                 455                 460

Gly Ser Pro Ile Leu Met Gly Asp Asn Val Pro Asn Gly Trp Glu Asp
465                 470                 475                 480

Ser Thr Val Gly Gly Pro Leu Asp Leu Ser Ala Pro Ser Glu Pro Met
                485                 490                 495

Thr Pro Leu Ser Glu Pro Val Leu Val Ser Ala Pro Gln Cys Ile Ser
            500                 505                 510

Arg Pro Val Thr Ser Leu Ser Val Pro Ala Pro Val Pro Ala Pro Arg
        515                 520                 525

Arg Ala Val Ser Arg Pro Met Thr Pro Ser Ser Glu Pro Ile Phe Val
    530                 535                 540

Ser Ala Leu Arg His Lys Phe Gln Gln Val Glu Lys Ala Asn Leu Ala
545                 550                 555                 560

Ala Ala Ala Pro Met Tyr Gln Asp Glu Pro Leu Asp Leu Ser Ala Ser
                565                 570                 575

Ser Gln Thr Glu Tyr Gly Ala Ser Pro Leu Thr Pro Pro Gln Asn Val
            580                 585                 590

Gly Ile Leu Glu Val Arg Gly Gln Glu Ala Glu Glu Val Leu Ser Glu
        595                 600                 605

Ile Ser Asp Ile Leu Asn Asp Thr Asn Pro Ala Pro Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Leu Gly Gly Pro Cys Ser Gly His Leu Gln Arg Glu
                645                 650                 655

Lys Glu Ala Cys Leu Arg Ile Met Arg Glu Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Phe Arg
    690                 695                 700

Thr Leu Asp Gly Arg Phe Gly Phe Leu Pro Lys Met Ile Leu Glu Thr
705                 710                 715                 720
```

-continued

```
Pro Pro Pro Tyr Pro
                725


<210> SEQ ID NO 81
<211> LENGTH: 719
<212> TYPE: PRT
<213> ORGANISM: Porcine reproductive and respiratory syndrome virus

<400> SEQUENCE: 81

Ala Gly Lys Arg Ala Arg Lys Ala Arg Ser Gly Ala Thr Thr Met Val
  1               5                  10                  15

Ala His Arg Ala Leu Ser Ala Arg Glu Thr Arg Gln Ala Lys Lys His
             20                  25                  30

Glu Gly Ala Asp Ala Asn Lys Ala Glu His Leu Glu His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Asn Phe Glu Thr Thr Leu Pro Glu Arg Ala Arg
 65                  70                  75                  80

Pro Leu Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Thr Ser
            100                 105                 110

Ala Lys Tyr Val Leu Arg Leu Glu Gly Glu His Trp Thr Val Ser Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Pro Val Asp
            180                 185                 190

Ser Asn Arg Pro Ala Ser Pro Val Thr Thr Ala Trp Thr Val Ser Gln
        195                 200                 205

Phe Tyr Ala Arg His Arg Gly Gly Asn His Arg Asp Gln Val Cys Leu
    210                 215                 220

Gly Lys Ile Ile Ser Leu Cys Gln Val Ile Glu Asp Cys Cys Cys His
225                 230                 235                 240

Gln Asn Lys Thr Asn Arg Ala Thr Pro Glu Glu Val Ala Ala Lys Ile
                245                 250                 255

Asp Gln Tyr Leu Arg Gly Ala Thr Ser Leu Glu Glu Cys Leu Ile Lys
            260                 265                 270

Leu Glu Arg Val Ser Pro Pro Ser Ala Ala Asp Thr Ser Phe Asp Trp
        275                 280                 285

Asn Val Val Leu Pro Gly Val Glu Ala Ala Asn Gln Thr Thr Lys Gln
    290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Leu Glu Glu Tyr Gly
```

-continued

```
        355                 360                 365

Leu Met Ser Thr Gly Leu Gly Pro Arg Pro Val Leu Pro Ser Gly Leu
    370                 375                 380

Asp Glu Leu Lys Asp Gln Met Glu Glu Asp Leu Leu Lys Leu Ala Asn
385                 390                 395                 400

Ala Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro Pro
            420                 425                 430

Pro Pro Arg Val Gln Pro Arg Lys Thr Lys Pro Val Lys Ser Leu Pro
        435                 440                 445

Glu Asn Lys Pro Val Pro Ala Pro Arg Arg Lys Val Gly Ser Asp Cys
    450                 455                 460

Gly Ser Pro Ile Leu Met Gly Asp Asn Val Pro Asn Gly Trp Glu Asp
465                 470                 475                 480

Phe Ala Val Gly Gly Pro Leu Asp Phe Pro Thr Pro Ser Glu Pro Met
                485                 490                 495

Thr Pro Leu Ser Glu Pro Val Leu Met Pro Ala Ser Gln His Ile Pro
            500                 505                 510

Arg Pro Val Thr Pro Leu Ser Gly Pro Ala Pro Val Pro Ala Pro Arg
        515                 520                 525

Arg Thr Val Ser Arg Pro Met Thr Pro Leu Ser Glu Pro Ile Phe Val
    530                 535                 540

Ser Ala Pro Arg His Lys Phe Gln Gln Val Glu Glu Ala Asn Pro Ala
545                 550                 555                 560

Ala Thr Thr Leu Thr Tyr Gln Asp Glu Pro Leu Asp Leu Ser Ala Phe
                565                 570                 575

Ser Gln Thr Glu Cys Glu Ala Ser Pro Leu Ala Pro Leu Gln Asn Met
            580                 585                 590

Gly Ile Leu Glu Ala Gly Gly Gln Glu Ala Glu Glu Val Leu Ser Gly
        595                 600                 605

Ile Ser Asp Ile Leu Asn Asp Ile Asn Pro Ala Pro Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Arg Glu
                645                 650                 655

Lys Glu Ala Cys Leu Ser Ile Met Arg Glu Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Leu His
    690                 695                 700

Thr Leu Asp Gly Arg Ser Gly Phe Leu Pro Lys Met Ile Leu Glu
705                 710                 715


<210> SEQ ID NO 82
<211> LENGTH: 200
<212> TYPE: PRT
<213> ORGANISM: Porcine reproductive and respiratory syndrome virus

<400> SEQUENCE: 82

Met Leu Gly Lys Cys Leu Thr Ala Gly Cys Cys Ser Arg Leu Leu Ser
  1               5                  10                  15
```

-continued

```
Leu Trp Cys Ile Val Pro Phe Cys Phe Ala Val Leu Ala Asn Ala Ser
            20                  25                  30

Asn Ser Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Pro
        195                 200


<210> SEQ ID NO 83
<211> LENGTH: 200
<212> TYPE: PRT
<213> ORGANISM: Porcine reproductive and respiratory syndrome virus

<400> SEQUENCE: 83

Met Leu Gly Lys Cys Leu Thr Ala Gly Trp Cys Ser Gln Leu Leu Ser
  1               5                  10                  15

Leu Gly Cys Ile Val Pro Phe Cys Phe Ala Val Leu Ala Asn Ala Ser
            20                  25                  30

Asn Asp Ser Ser Ser His Val Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190
```

-continued

```
Ser Ala Glu Gln Trp Gly Arg Pro
        195                 200


<210> SEQ ID NO 84
<211> LENGTH: 200
<212> TYPE: PRT
<213> ORGANISM: Porcine reproductive and respiratory syndrome virus

<400> SEQUENCE: 84

Met Leu Glu Lys Cys Leu Thr Ala Gly Cys Cys Ser Gln Leu Leu Ser
  1               5                  10                  15

Leu Trp Cys Ile Val Pro Phe Cys Phe Ala Val Leu Ala Asn Ala Ser
             20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 85
<211> LENGTH: 200
<212> TYPE: PRT
<213> ORGANISM: Porcine reproductive and respiratory syndrome virus

<400> SEQUENCE: 85

Met Leu Glu Lys Cys Leu Thr Ala Gly Cys Cys Ser Gln Leu Leu Ser
  1               5                  10                  15

Leu Trp Cys Ile Val Pro Phe Cys Phe Ala Val Leu Ala Asn Ala Ser
             20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110
```

-continued

```
Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 86
<211> LENGTH: 200
<212> TYPE: PRT
<213> ORGANISM: Porcine reproductive and respiratory syndrome virus

<400> SEQUENCE: 86

Met Leu Glu Lys Cys Leu Thr Ala Gly Cys Cys Ser Arg Leu Leu Ser
  1               5                  10                  15

Leu Trp Cys Ile Val Pro Phe Cys Phe Ala Val Leu Ala Asn Ala Ser
             20                  25                  30

Asn Asp Ser Ser Ser His Leu Gln Leu Ile Tyr Asn Leu Thr Leu Cys
         35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 87
<211> LENGTH: 200
<212> TYPE: PRT
<213> ORGANISM: Porcine reproductive and respiratory syndrome virus

<400> SEQUENCE: 87

Met Leu Glu Lys Cys Leu Thr Ala Gly Cys Cys Ser Arg Leu Leu Ser
  1               5                  10                  15

Leu Trp Cys Ile Val Pro Phe Cys Phe Ala Val Leu Ala Asn Ala Ser
             20                  25                  30
```

-continued

```
Asn Ser Ser Ser Ser His Leu Gln Leu Ile Tyr Asn Leu Thr Leu Cys
        35                  40                  45

Glu Leu Asn Gly Thr Asp Trp Leu Ala Asn Arg Phe Asp Trp Ala Val
    50                  55                  60

Glu Ser Phe Val Ile Phe Pro Val Leu Thr His Ile Val Ser Tyr Gly
 65                 70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200


<210> SEQ ID NO 88
<211> LENGTH: 200
<212> TYPE: PRT
<213> ORGANISM: Porcine reproductive and respiratory syndrome virus

<400> SEQUENCE: 88

Met Leu Gly Lys Cys Leu Thr Ala Gly Cys Cys Ser Arg Leu Leu Ser
  1               5                  10                  15

Phe Trp Cys Ile Val Pro Phe Cys Phe Ala Val Leu Val Asn Ala Ser
            20                  25                  30

Tyr Ser Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
 65                 70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Ser His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Pro
```

-continued 195 200

<210> SEQ ID NO 89
<211> LENGTH: 200
<212> TYPE: PRT
<213> ORGANISM: Porcine reproductive and respiratory syndrome virus

<400> SEQUENCE: 89

```
Met Leu Gly Arg Cys Leu Thr Ala Gly Cys Cys Ser Arg Leu Leu Ser
  1               5                  10                  15

Leu Trp Cys Ile Val Pro Phe Cys Phe Ala Ala Leu Val Asn Ala Asn
             20                  25                  30

Ser Asn Ser Ser Ser His Leu Gln Leu Ile Tyr Asn Leu Thr Leu Cys
         35                  40                  45

Glu Leu Asn Gly Thr Asp Trp Leu Lys Asp Lys Phe Asp Trp Ala Val
     50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200
```

<210> SEQ ID NO 90
<211> LENGTH: 200
<212> TYPE: PRT
<213> ORGANISM: Porcine reproductive and respiratory syndrome virus

<400> SEQUENCE: 90

```
Met Leu Gly Arg Cys Leu Thr Ala Gly Cys Cys Ser Arg Leu Leu Ser
  1               5                  10                  15

Leu Trp Cys Ile Val Pro Phe Cys Phe Ala Ala Leu Val Asn Ala Asn
             20                  25                  30

Ser Asn Ser Ser Ser His Leu Gln Leu Ile Tyr Asn Leu Thr Leu Cys
         35                  40                  45

Glu Leu Asn Gly Thr Asp Trp Leu Lys Asp Lys Phe Asp Trp Ala Val
     50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
```

-continued

```
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200


<210> SEQ ID NO 91
<211> LENGTH: 200
<212> TYPE: PRT
<213> ORGANISM: Porcine reproductive and respiratory syndrome virus

<400> SEQUENCE: 91

Met Leu Glu Lys Cys Leu Thr Ala Gly Cys Cys Leu Arg Leu Pro Ser
  1               5                  10                  15

Leu Trp Cys Ile Val Pro Phe Cys Phe Ala Val Leu Val Asn Ala Asn
             20                  25                  30

Asn Ser Ser Ser Ser His Phe Gln Ser Ile Tyr Asn Leu Thr Leu Cys
         35                  40                  45

Glu Leu Asn Gly Thr Glu Trp Leu Ser Glu Lys Phe Asp Trp Ala Val
     50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Leu His Arg Arg Tyr Val Leu Ser Ser Val Tyr
            100                 105                 110

Ala Val Cys Ala Leu Ala Ala Leu Ile Cys Phe Ile Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Lys Leu Tyr Arg Trp Arg Ser Pro Val Ile
145                 150                 155                 160

Ile Glu Lys Gly Gly Arg Val Glu Val Glu Gly His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Leu
        195                 200


<210> SEQ ID NO 92
<211> LENGTH: 200
<212> TYPE: PRT
<213> ORGANISM: Porcine reproductive and respiratory syndrome virus

<400> SEQUENCE: 92

Met Leu Gly Lys Cys Leu Thr Ala Gly Cys Cys Ser Arg Leu Leu Ser
  1               5                  10                  15

Leu Trp Cys Ile Val Pro Phe Cys Phe Ala Val Leu Gly Ser Ala Asn
             20                  25                  30

Ser Ser Ser Ser Ser His Phe Gln Leu Ile Tyr Asn Leu Thr Leu Cys
```

-continued

```
        35                  40                  45

Glu Leu Asn Gly Thr Asp Trp Leu Ala Glu Lys Phe Asp Trp Ala Val
     50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200


<210> SEQ ID NO 93
<211> LENGTH: 200
<212> TYPE: PRT
<213> ORGANISM: Porcine reproductive and respiratory syndrome virus

<400> SEQUENCE: 93

Met Leu Gly Lys Cys Leu Thr Thr Gly Cys Cys Ser Arg Leu Leu Ser
  1               5                  10                  15

Leu Trp Cys Ile Val Pro Phe Cys Phe Ala Val Leu Val Asn Ala Asn
             20                  25                  30

Ser Asn Ser Ser Ser His Phe Gln Leu Ile Tyr Asn Leu Thr Leu Cys
        35                  40                  45

Glu Leu Asn Gly Thr Asp Trp Leu Ala Asn Lys Phe Asp Trp Ala Val
     50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200
```

-continued

<210> SEQ ID NO 94
<211> LENGTH: 123
<212> TYPE: PRT
<213> ORGANISM: Porcine reproductive and respiratory syndrome virus

<400> SEQUENCE: 94

```
Met Pro Asn Asn Asn Gly Lys Gln Gln Lys Lys Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

<210> SEQ ID NO 95
<211> LENGTH: 123
<212> TYPE: PRT
<213> ORGANISM: Porcine reproductive and respiratory syndrome virus

<400> SEQUENCE: 95

```
Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

<210> SEQ ID NO 96
<211> LENGTH: 123
<212> TYPE: PRT
<213> ORGANISM: Porcine reproductive and respiratory syndrome virus

<400> SEQUENCE: 96

```
Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
```

-continued

```
        35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120


<210> SEQ ID NO 97
<211> LENGTH: 123
<212> TYPE: PRT
<213> ORGANISM: Porcine reproductive and respiratory syndrome virus

<400> SEQUENCE: 97

Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120


<210> SEQ ID NO 98
<211> LENGTH: 123
<212> TYPE: PRT
<213> ORGANISM: Porcine reproductive and respiratory syndrome virus

<400> SEQUENCE: 98

Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
        35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
```

-continued

```
        115                 120


<210> SEQ ID NO 99
<211> LENGTH: 123
<212> TYPE: PRT
<213> ORGANISM: Porcine reproductive and respiratory syndrome virus

<400> SEQUENCE: 99

Met Pro Asn Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120


<210> SEQ ID NO 100
<211> LENGTH: 123
<212> TYPE: PRT
<213> ORGANISM: Porcine reproductive and respiratory syndrome virus

<400> SEQUENCE: 100

Met Pro Asn Asn Asn Gly Lys Gln Gln Lys Lys Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Tyr Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120


<210> SEQ ID NO 101
<211> LENGTH: 123
<212> TYPE: PRT
<213> ORGANISM: Porcine reproductive and respiratory syndrome virus

<400> SEQUENCE: 101

Met Pro Asn Asn Asn Gly Lys Gln Gln Lys Lys Lys Arg Gly Asn Gly
  1               5                  10                  15

Gln Pro Val Asn Gln Leu Cys Gln Met Leu Gly Lys Ile Ile Ala Gln
             20                  25                  30
```

-continued

```
Gln Asn Gln Ser Arg Gly Lys Gly Pro Gly Lys Lys Ile Lys Asn Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Ser Ser Ala
        115                 120


<210> SEQ ID NO 102
<211> LENGTH: 123
<212> TYPE: PRT
<213> ORGANISM: Porcine reproductive and respiratory syndrome virus

<400> SEQUENCE: 102

Met Pro Asn Asn Asn Gly Lys Gln Gln Lys Lys Lys Arg Gly Asn Gly
  1               5                  10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Ile Lys Asn Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Ser Ser Ala
        115                 120


<210> SEQ ID NO 103
<211> LENGTH: 123
<212> TYPE: PRT
<213> ORGANISM: Porcine reproductive and respiratory syndrome virus

<400> SEQUENCE: 103

Met Pro Asn Asn Asn Gly Lys Gln Gln Lys Lys Lys Lys Gly Asn Gly
  1               5                  10                  15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Ile Lys Lys Lys
        35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110
```

-continued

```
Arg Leu Ile Arg Val Thr Ala Pro Pro Ser Ala
        115                 120


<210> SEQ ID NO 104
<211> LENGTH: 123
<212> TYPE: PRT
<213> ORGANISM: Porcine reproductive and respiratory syndrome virus

<400> SEQUENCE: 104

Met Pro Asn Asn Asn Gly Lys Gln Gln Lys Lys Lys Lys Gly Asn Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Ser Lys Lys Lys
         35                  40                  45

Asn Pro Glu Lys Pro His Phe Pro Leu Ala Thr Glu Asp Asp Val Arg
     50                  55                  60

His His Phe Thr Pro Gly Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120


<210> SEQ ID NO 105
<211> LENGTH: 123
<212> TYPE: PRT
<213> ORGANISM: Porcine reproductive and respiratory syndrome virus

<400> SEQUENCE: 105

Met Pro Asn Asn Asn Gly Lys Gln Arg Lys Lys Lys Lys Gly Asn Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Ser Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```